US007589232B2

(12) United States Patent
Swinnen et al.

(10) Patent No.: US 7,589,232 B2
(45) Date of Patent: Sep. 15, 2009

(54) ALKYNYL ARYL CARBOXAMIDES

(75) Inventors: Dominique Swinnen, Beaumont (FR); Patrick Gerber, Etoy (CH); Jerome Gonzalez, Annemasse (FR); Agnes Bombrun, Monnetier-Mornex (FR); Catherine Jorand-Lebrun, Contamine-Sarzin (FR)

(73) Assignee: Laboratories Serono S.A., Coinsins (CH)

( * ) Notice: Subject to any disclaimer, the term of this patent is extended or adjusted under 35 U.S.C. 154(b) by 473 days.

(21) Appl. No.: 10/565,538

(22) PCT Filed: Jul. 20, 2004

(86) PCT No.: PCT/EP2004/051557

§ 371 (c)(1),
(2), (4) Date: Jan. 23, 2006

(87) PCT Pub. No.: WO2005/012280

PCT Pub. Date: Feb. 10, 2005

(65) Prior Publication Data

US 2007/0105913 A1 May 10, 2007

Related U.S. Application Data

(60) Provisional application No. 60/517,993, filed on Nov. 6, 2003.

(30) Foreign Application Priority Data

Jul. 21, 2003 (EP) .................................. 03102235

(51) Int. Cl.
C07C 299/34 (2006.01)
A61K 31/195 (2006.01)
(52) U.S. Cl. .................. 562/455; 514/563; 514/403; 514/355; 514/443; 514/452; 514/453; 548/361.1; 546/316; 549/49; 549/232
(58) Field of Classification Search ................ 562/455; 514/563, 355, 403, 443, 452, 453; 548/361.1; 546/316; 549/49, 232
See application file for complete search history.

(56) References Cited

U.S. PATENT DOCUMENTS

| 7,053,245 | B2 * | 5/2006 | Jolidon et al. ............. 564/157 |
| 2005/0124656 | A1 | 6/2005 | Swinnen et al. |
| 2006/0189583 | A1 * | 8/2006 | Thomas et al. ............. 514/159 |

FOREIGN PATENT DOCUMENTS

| WO | 00/35859 | 6/2000 |
| WO | 02/18321 | 3/2002 |
| WO | 03/64376 | 8/2003 |

| WO | 2005/082347 | 9/2005 |

OTHER PUBLICATIONS

Rexford S. Ahima et al. "Leptin", Annu. Rev. Physiol., vol. 62, pp. 413-437 2000.
Gustave Bergnes, et al., "Generation of an ugi library of phosphate mimic-containing compounds and identification of novel dual specific phosphatase inhibitors", Bioorganic & Medicinal Chemistry Letters, vol. 9, pp. 2849-2854 1999.
Jeffrey D. Bjorge, et al., "Identification of protein-tyrosine phosphatase 1B as the major tyrosine phosphatase activity capable of dephosphorylating and activating c-Src in several human breast cancer cell lines", The Journal of Biological Chemistry, vol. 275, No. 52, pp. 41439-41446 2000.
Alan Cheng, et al., "Attenuation of leptin action and regulation of obesity by protein tyrosine phosphatase 1B", Developmental Cell, vol. 2, pp. 497-503 2002.
Ralph A. Defronzo, et al., "Insulin resistance: a multifaceted syndrome responsible for NIDDM, obesity, Hypertension, dyslipidemia, and atherosclerotic cardiovascular disease", Diabetes Care, vol. 14, No. 3, pp. 173-194 1991.

(Continued)

Primary Examiner—Shailendra Kumar
(74) Attorney, Agent, or Firm—Oblon, Spivak, McClelland, Maier & Neustadt, P.C.

(57) ABSTRACT

The present invention is related to alkynyl aryl carboxamides of Formula (I') and use thereof for the treatment and/or prevention of an inflammatory disorder, obesity and/or metabolic disorders mediated by insulin resistance or hyperglycemia, comprising diabetes type I and/or II, inadequate glucose tolerance, insulin resistance, hyperlipidemia, hypertriglyceridemia-hypercholesterolemia, polycystic ovary syndrome (PCOS). In particular, the present invention is related to the use of alkynyl aryl carboxamides of Formula (I') to modulate, notably to inhibit the activity of PTPs. (I') A is a $C_2$-$C_{15}$ alkynyl, $C_2$-$C_6$-alkynyl aryl, $C_2$-$C_6$-alkynyl heteroaryl. Cy is an aryl, heteroaryl, cycloalkyl or heterocycle group; n is either 0 or 1. Cy' is an aryl, which may optionally be fused by a 3-8 membered cycloalkyl. $R^1$ and $R^2$ are independently from each other is selected from the group consisting of hydrogen or ($C_1$-$C_6$)alkyl. $R^4$ and $R^5$ are each independently from each other selected from the group consisting of H, hydroxy. $C_1$-$C_6$ alkyl, carboxy, $C_1$-$C_6$ alkoxy, $C_1$-$C_3$ alkyl carboxy, $C_2$-$C_3$ alkenyl carboxy, $C_2$-$C_3$ alkynyl carboxy, amino or $R^4$ and $R^5$ may form an unsaturated or saturated heterocyclic ring, whereby at least one of $R^4$ or $R^5$ is not a hydrogen or $C_1$-$C_6$ alkyl.

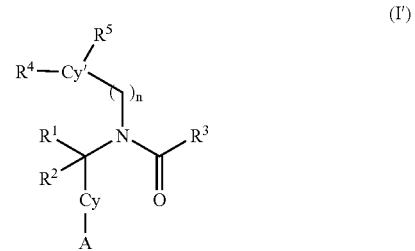

(I')

25 Claims, No Drawings

OTHER PUBLICATIONS

Evanthia Diamanti-Kandarakis, et al, "Therapeutic effects of metformin on insulin resistance and hyperandrogenism in polycystic ovary syndrome", European Journal of Endocrinology, vol. 138, pp. 269-274 1998.

Andrea Dunaif, "Insulin resistance and the polycystic ovary syndrome: mechanism and implications for pathogenesis", Endocrine Reviews, vol. 18, No. 6, pp. 774-800 1997.

Mounib Elchebly, et al., "Modulation of insulin signaling by protein tyrosine phosphatases", J. Mol. Med., vol. 78, pp. 473-482 2000.

R.J. Jarrett, "Cardiovascular disease and hypertension in diabetes mellitus", Diabetes/Metabolism Reviews, vol. 5, No. 7, pp. 547-558 1989.

Brian P. Kennedy, et al., "Protein tyrosine phosphatase-1B in diabetes", Biochemical Pharmacology, vol. 60, pp. 877-883 2000.

Lori D. Klaman, et al., "Increased energy expenditure, decreased adiposity, and tissue-specific insulin sensitivity in protein-tyrosine phosphatase 1B-deficient mice", Molecular and Cellular Biology, vol. 20, No. 15, pp. 5479-5489 2000.

Mary C. McGuire, et al., "Abnormal regulation of protein tyrosine phosphatase activities in skeletal muscle of insulin-resistant humans", Diabetes, vol. 40, pp. 939-942 1991.

Joseph Meyerovitch, et al, "Hepatic phosphotyrosine phosphatase activity and its alterations in diabetic rats", J. Clin. Invest., vol. 84 pp. 976-983 1989.

Niels Peter Hundahl Moller, et al., "Protein tyrosine phosphatases (PTPs) as drug targets: inhibitors of PTP-1B for the treatment of diabetes", Current Opinion in Drug Discovery & Development, vol. 3, No. 5, pp. 527-540 2000.

Purnima Pathre, et al., "PTP1B regulates neurite extension mediated by cell-cell and cell-matrix adhesion molecules", Journal of Neuroscience Research, vol. 63, pp. 143-150 2001.

Gerald M. Reaven, et al., "Nonketotic diabetes mellitus: insulin deficiency or insulin resistance?", The American Journal of Medicine, vol. 60, pp. 80-88 1976.

Lisa P. Shock, et al., "Protein tyrosine phosphatases expressed in developing brain and retinal Mueller glia", Molecular Brain Research, vol. 28, pp. 110-116 1995.

Janet Sredy, et al., "Insulin resistance is associated with abnormal dephosphorylation of a synthetic phosphopeptide corresponding to the major autophosphorylation sites of the insulin receptor", Metabolism, vol. 44, No. 8, pp. 1074-1081 1995.

Robert W. Stout, "Overview of the association between insulin and atherosclerosis", Metabolism, vol. 34, No. 12, suppl. 1, pp. 7-12 1985.

Sung Min Suhr et al., "Antisense oligodeoxynucleotide evidence that a unique osteoclastic protein-tyrosine phosphatase is essential for osteoclastic resorption", Journal of Bone and Mineral Research, vol. 16, No. 10, pp. 1795-1803 2001.

Zhong-Yin Zhang, "Protein tyrosine phosphatases: prospects for therapeutics", Current Opinion in Chemical Biology, vol. 5, pp. 416-423 2001.

Fiona J. Pixley, et al., "A heteromorphic protein-tyrosine phosphatase, PTPØ, is regulated by CSF-1 in macrophages", The Journal of Biological Chemistry, vol. 270, No. 45, pp. 27339-27347 1995.

Fiona J. Pixley, et al., "Protein tyrosine phosphatase φ regulates paxillin tyrosine phosphorylation and mediates colony-stimulating factor 1-induced morphological changes in macrophages", Molecular and Cellular Biology, vol. 21, No. 5, pp. 1795-1809 2001.

U.S. Appl. No. 10/565,538, filed Jan. 23, 2006, Swinnen, et al.

U.S. Appl. No. 10/565,557, filed Jan. 23, 2006, Thomas, et al.

* cited by examiner

ALKYNYL ARYL CARBOXAMIDES

This application is a 371 of PCT/EP04/51557 filed on Jul. 20, 2004, which claims benefit of 60/517,993 filed on Nov. 6, 2003.

FIELD OF THE INVENTION

The present invention is related to alkynyl aryl carboxamides of formula (I') & (I), in particular for the treatment and/or prevention of obesity and/or metabolic disorders mediated by insulin resistance or hyperglycemia, comprising diabetes type I and/or II, inadequate glucose tolerance, insulin resistance, hyperlipidemia, hypertriglyceridemia, hypercholesterolemia, polycystic ovary syndrome (PCOS). The compounds of this invention are particularly useful in the treatment of type II diabetes, obesity or the regulation of appetite. Specifically, the present invention is related to alkynyl aryl carboxamides for the modulation, notably the inhibition of the activity of PTPs, in particular of PTP1B.

BACKGROUND OF THE INVENTION

The prevalence of insulin resistance in glucose intolerant subjects is well known. Reaven et al (*American Journal of Medicine*, 60, 80 (1976)) used a continuous infusion of glucose and insulin (insulin/glucose clamp technique) and oral glucose tolerance tests to demonstrate that insulin resistance exists in a diverse group of non-obese, non-ketotic subjects. These subjects ranged from borderline glucose tolerant to overt, fasting hyperglycemia. The diabetic groups in these studies included both insulin dependent (IDDM) and non-insulin dependent (NIDDM) subjects.

Coincident with sustained insulin resistance is the more easily determined hyper-insulinemia, which may be measured by accurate determination of circulating plasma insulin concentration in the plasma of subjects. Hyperinsulinemia may be present as a result of insulin resistance, such as is in obese and/or diabetic (NIDDM) subjects and/or glucose intolerant subjects, or in IDDM subjects, as a consequence of over injection of insulin compared with normal physiological release of the hormone by the endocrine pancreas.

The association of hyperinsulinemia and insulin resistance with obesity and with ischemic diseases of the large blood vessels (e.g. atherosclerosis) has been well established by numerous experimental, clinical and epidemiological studios (Stout, *Metabolism*, 34, 7 (1985)). Statistically significant plasma insulin elevations at 1 and 2 hours after oral glucose load correlate with an increased risk of coronary heart disease.

Since most of these studies actually excluded diabetic subjects, data relating the risk of atherosclerotic diseases to the diabetic condition are not as numerous, but point in the same direction as for non-diabetic subjects. However, the incidence of atherosclerotic diseases in morbidity and mortality statistics in the diabetic population exceeds that of the nondiabetic population (Pyorala et al; Jarrett *Diabetes/Metabolism Reviews*, 5, 547 (1989)).

The association of hyperinsulinemia and insulin resistance with Polycystic Ovary Syndrome (PCOS) is also well acknowledged (Diamanti-Kandarakis et al.; Therapeutic effects of metformin on insulin resistance and hyperandrogenism in polycystic ovary syndrome; *European Journal of Endocrinology* 138, 269-274 (1998), Andrea Dunaif; Insulin Resistance and the Polycystic Ovary Syndrome: Mechanism and Implications for Pathogenesis; *Endocrine Reviews* 18(6), 774-800 (1997)).

The independent risk factors obesity and hypertension for atherosclerotic diseases are also associated with insulin resistance. Using a combination of insulin/glucose clamps, tracer glucose infusion and indirect calorimetry, it was demonstrated that the insulin resistance of essential hypertension is located in peripheral tissues (principally muscle) and correlates directly with the severity of hypertension (DeFronzo and Ferrminini, *Diabetes Care*, 14, 173 (1991)). In hypertension of obese people, insulin resistance generates hyper-insulinemia, which is recruited as a mechanism to limit further weight gain via thermogenesis, but insulin also increases renal sodium re-absorption and stimulates the sympathetic nervous system in kidneys, heart, and vasculature, creating hypertension.

It is assumed that insulin resistance is usually the result of a defect in the insulin receptor signaling system, at a site post binding of insulin to the receptor. Accumulated scientific evidence demonstrating insulin resistance in the major tissues which respond to insulin (muscle, liver, adipose), strongly suggests that a defect in insulin signal transduction resides at an early step in this cascade, specifically at the insulin receptor kinase activity, which appears to be diminished (Mounib Elchebly, Alan Cheng, Michel L. Tremblay; Modulation of insulin signaling by protein tyrosine phosphatases; *J. Mol. Med.* 78, 473-482 (2000)).

Protein-tyrosine phosphatases (PTPs) play an important role in the regulation of phosphorylation of proteins and represent the counterparts of kinases. Among classical PTPs, there are two types: (i) non-receptor or intracellular PTPs and (ii) receptor-like PTPs. Most intracellular PTPs contain one catalytic domain only, whereas most receptor-like enzymes contain two. The catalytic domain consists of about 250 amino acids (Niels Peter Hundahl Moller et al. Protein tyrosine phosphatases (PTPs) as drug targets: Inhibitors of PTP-1B for the treatment of diabetes; *Current Opinion in Drug Discovery & Development* 3(5), 527-540 (2000)).

The interaction of insulin with its receptor leads to phosphorylation of certain tyrosine molecules within the receptor protein, thus activating the receptor kinase. PTPs dephosphorylate the activated insulin receptor, attenuating the tyrosine kinase activity. PTPs can also modulate post-receptor signaling by catalyzing the dephosphorylation of cellular substrates of the insulin receptor kinase. The enzymes that appear most likely to closely associate with the insulin receptor and therefore, most likely to regulate the insulin receptor kinase activity, include PTP1B, LAR, PTP-alpha and SH-PTP2 (Lori Klaman et al.; Increased Energy Expenditure, Decreased Adiposity, and Tissue-specific insulin sensitivity in Protein-Tyrosine Phosphatase 1B-Deficient Mice; *Molecular and Cellular Biology*, 5479-5489 (2000)).

PTP1B is a member of the PTP family. This 50 kDa protein contains a conserved phosphatase domain at residues 30-278 and is localized to the cytoplasmic face of the endoplasmic reticulum by its C-terminal 35 residues. Its interactions with other proteins are mediated by proline-rich regions and SH2 compatible sequence. PTP1B is believed to act as a negative regulator in insulin signaling.

McGuire et al. (*Diabetes*, 40, 939 (1991)) demonstrated that non-diabetic glucose intolerant subjects possessed significantly elevated levels of PTP activity in muscle tissue vs. normal subjects, and that insulin infusion failed to suppress PTP activity as it did in insulin sensitive subjects.

Meyerovitch et al. (*J. Clinical Invest.*, 84, 976 (1989)) observed significantly increased PTP activity in the livers of two rodent models of IDDM, the genetically diabetic BB rat, and the STZ-induced diabetic rat. Sredy et al. (*Metabolism*, 44, 1074, (1995)) observed similar increased PTP activity in the livers of obese, diabetic ob/ob mice, which represent a typical rodent model of NIDDM.

Zhang et al (*Curr. Opin. Chem. Biol.*, 5(4), 416-23 (2001)) found that PTPs are also implicated in a wide variety of other disorders, including cancer. Bjorge, J. D. et al. (*J. Biol. Chem.*, 275(52), 41439-46 (2000)) indicates that PTP1B is the primary protein-tyrosine phosphatase capable of dephosphorylating c-Src in several human breast cancer cell lines and suggests a regulatory role for PTP1B in the control of c-Src kinase activity.

Pathre et at (*J. Neurosci. Res.*, 63(2), 143-150 (2001)) describes that PTP1B regulates neurite extension mediated by cell-cell and cell-matrix adhesion molecules. Further, Shock L. P et al. (*Mol. Brain. Res.*, 28(1), 110-16 (1995)) demonstrates that a distinct overlapping set of PTPs is expressed in the developing brain and retinal Mueller glia, including 2 novel PTPs that may participate in neural cell communication.

The insulin receptor (IR) is a prototypical tyrosine kinase receptor whose ligand binding and dimerization results in auto-phosphorylation on multiple tyrosines. This is followed by the recruitment and phosphorylation of IRS1-4 (depending on the tissue) and PI3K. Although vanadium-containing compounds have been known since the $19^{th}$ century to alleviate diabetes, it was understood only recently that these inhibitors stimulate the insulin signaling pathway by blocking PTP action. Evidence for the involvement of the IR (insulin receptor) and IRS-1 in this phenotype was that both proteins show increased tyrosine phosphorylation in the PTP1B-mutated mice. The available data strongly suggest that in particular PTP1B is a promising target for the development of drugs to treat diabetes and obesity (Brian P. Kennedy and Chidambaram Ramachandran; Protein Tyrosine Phosphatase-1B in Diabetes; *Biochemical Pharmacology*, Vol. 60, 877-883, (2000)).

A further protein involved in obesity is Leptin. Leptin is a peptide hormone that plays a central role in feeding and adiposity (Leptin, *Annu. Rev. Physiol.* 62 p. 413-437 (2000) by Ahima R. S. et al.). Recently, it has been suggested that PTP1B negatively regulates leptin signaling, and provides one mechanism by which it may regulate obesity. Further, it is known that pharmacological inhibitors of PTP1B hold promise as an alternative or a supplement to leptin in the treatment of obesity due to leptin resistance (*Developmental Cell.*, vol. 2, p. 497-503 (2002)).

Recent findings suggest that inhibitors of Glepp-1 (PTP-phi) would be useful in the treatment of inflammatory disorders (Suhr et al. *J. Bone Miner. Res.* 16(10): 1795; 2001; Pixley et al *Mol. Cell. Biol.* 21(5): 1795-809; Pixley et al. *J. Biol. Chem.* 270(45):27339-47).

Also recently it was found that PTP1B inhibitors are useful in the treatment of cardiovascular disorders (EP-04100778.2).

In numerous patent application small molecules have been proposed as inhibitors of PTPs.

Substituted aryl and heteroaryl derivatives of benzamidines and their use as anti-thrombotics are described in WO 00/35859.

Further compounds are described by G. Bergnes et al., in *Bioorganic Medicinal Chemistry Letters* 9(19) p. 2849-5 (1999).

SUMMARY OF THE INVENTION

The present invention relates to alkynyl aryl carboxamides of formula (I').

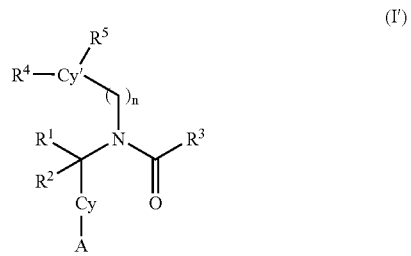

Such compounds are suitable for the treatment and/or prevention of obesity, cardiovascular disorders inflammatory diseases and metabolic disorders mediated by insulin resistance or hyperglycemia, comprising diabetes type I and/or II, inadequate glucose tolerance, insulin resistance, hyperlipidemia, hypertriglyceridemia, hypercholesterolemia, polycystic ovary syndrome (PCOS). The compounds of this invention are inhibitors of PTPs.

DETAILED DESCRIPTION OF THE INVENTION

The following paragraphs provide definitions of the various chemical moieties that make up the compounds according to the invention and are intended to apply uniformly through-out the specification and claims unless an otherwise expressly set out definition provides a broader definition.

"PTPs" are protein tyrosine phosphatases and include for instance PTP1B, TC-PTP, PTP-β, PTP-H1, DEP-1, LAR, SHP-1, SHP-2, GLEPP-1, PTP-µ, VHR hVH5, LMW-PTP, PTEN.

"$C_1$-$C_6$-alkyl" refers to alkyl groups having 1 to 6 carbon atoms. This term is exemplified by groups such as methyl, ethyl, n-propyl, isopropyl, n-butyl, isobutyl, tert-butyl, n-pentyl, n-hexyl and the like.

"Aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl, phenantrenyl and the like.

"$C_1$-$C_6$-alkyl aryl" refers to $C_1$-$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, phthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_6$-alkyl heteroaryl" refers to $C_1$-$C_6$-alkyl groups having a heteroaryl substituent, including 2-furylmethyl, 2-thienylmethyl, 2-(1H-indol-3-yl)ethyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH═CH$_2$), n-2-propenyl (allyl, —Ch$_2$CH═CH$_2$) and the like.

"C$_2$-C$_6$-alkenyl aryl" refers to C$_2$-C$_6$-alkenyl groups having an aryl substituent, including 2-phenylvinyl and the like.

"C$_2$-C$_6$-alkenyl heteroaryl" refers to C$_2$-C$_6$-alkenyl groups having a heteroaryl substituent, including 2-(3-pyridinyl)vinyl and the like.

"C$_2$-C$_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—CH$_2$C≡CH), and the like.

"C$_2$-C$_6$-alkynyl aryl" refers to C$_2$-C$_6$-alkynyl groups having an aryl substituent, including phenylethynyl and the like.

"C$_2$-C$_6$-alkynyl heteroaryl" refers to C$_2$-C$_6$-alkynyl groups having a heteroaxyl substituent, including 2-thienylethynyl and the like.

"C$_3$-C$_8$-cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopentyl, cyclohexyl, norbornyl and the like.

"C$_1$-C$_6$-alkyl cycloalkyl" refers to C$_1$-C$_6$-alkyl groups having a cycloalkyl substituent, including cyclohexylmethyl, cyclopentylpropyl, and the like.

"heterocycloalkyl" refers to a C$_3$-C$_8$-cycloalkyl group according to the definition above, in which 1 to 3 carbon atoms are replaced by hetero atoms chosen from the group consisting of O, S, NR, R being defined as hydrogen or C$_1$-C$_6$ alkyl. Preferred heterocycloalkyl include pyrrolidine, piperidine, piperazine, 1-methylpiperazine, morpholine, and the like.

"C$_1$-C$_6$-alkyl heterocycloalkyl" refers to C$_1$-C$_6$-alkyl groups having a heterocycloalkyl substituent, including 2-(1-pyrrolidinyl)ethyl, 4-morpholinylmethyl, (1-methyl-4-piperidinyl)methyl and the like.

"Carboxy" refers to the group —C(O)OH.

"C$_1$-C$_6$-alkyl carboxy" refers to C$_1$-C$_6$-alkyl groups having a carboxy substituent, including 2-carboxyethyl and the like.

"Acyl" refers to the group —C(O)R where R includes H, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alky cycloalkyl", "C$_1$-C$_6$-alkyl heterocycloalkyl".

"C$_1$-C$_6$-alkyl acyl" refers to C$_1$-C$_6$-alkyl groups having an acyl substituent, including 2-acetylethyl and the like.

"Aryl acyl" refers to aryl groups having an acyl substituent, including 2-acetylphenyl and the like.

"Heteroaryl acyl" refers to hetereoaryl groups having an acyl substituent, including 2-acetylpyridyl and the like.

"C$_3$-C$_8$-(hetero)cycloalkyl acyl" refers to 3 to 8 membered cycloalkyl or heterocycloalkyl groups having an acyl substituent.

"Acyloxy" refers to the group —OC(O)R where R includes H, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl acyloxy" refers to C$_1$-C$_6$-alkyl groups having an acyloxy substituent, including 2-(acetyloxy)ethyl and the like.

"Alkoxy" refers to the group —O—R where R includes "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl alkoxy" refers to C$_1$-C$_6$-alkyl groups having an alkoxy substituent, including 2-ethoxyethyl and the like.

"Alkoxycarbonyl" refers to the group —C(O)OR where R includes "C$_1$-C$_6$-alkyl". "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl alkoxycarbonyl" refers to C$_1$-C$_6$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen, "C$_1$-C$_6$-alkyl", "C$_2$-C$_6$-alkenyl", "C$_2$-C$_8$-alkynyl", "C$_3$-C$_8$-cycloalkyl", "heterocycloalkyl", "aryl", "heteroaryl", "C$_1$-C$_6$-alkyl aryl" or "C$_2$-C$_6$-alkyl heteroaryl", C$_2$-C$_6$-alkenyl aryl", "C$_2$-C$_6$-alkenyl heteroaryl", "C$_2$-C$_6$-alkynyl aryl"; "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl aminocarbonyl" refers to C$_1$-C$_6$-alkyl groups having an aminocarbonyl substituent, including 2-(dimethylaminocarbonyl)ethyl and the like.

"Acylamino" refers to the group —NRC(O)R' where each R, R' is independently hydrogen, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_8$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl acylamino" refers to C$_1$-C$_6$-alkyl groups having an acylamino substituent, including 2-(propionylamino) ethyl and the like.

"Ureido" refers to the group —NRC(O)NR'R'' where each R, R', R'' is independently hydrogen, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl", and where R' and R'', together with the nitrogen atom to which they are attached, can optionally form a 3-8-membered heterocycloalkyl ring.

"C$_1$-C$_6$-alkyl ureido" refers to C$_1$-C$_6$-alkyl groups having an ureido substituent, including 2-(N'-methylureido)ethyl and the like.

"Carbamate" refers to the group —NRC(O)OR' where each R, R' is independently hydrogen, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"Amino" refers to the group —NRR' where each R, R' is independently hydrogen, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "$C_2$-$C_8$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R and R', together with the nitrogen atom to which they are attached, can optionally form a 3-8-membered heterocycloalkyl ring.

"$C_1$-$C_6$-alkyl amino" refers to $C_1$-$C_6$-alkyl groups having an amino substituent, including 2-(1-pyrrolidinyl)ethyl and the like.

"Ammonium" refers to a positively charged group —N'RR'R", where each R, R', R" is independently, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R and R', together with the nitrogen atom to which they are attached, can optionally form a 3-8-membered heterocycloalkyl ring.

"$C_1$-$C_6$-alkyl ammonium" refers to $C_1$-$C_6$-alkyl groups having an ammonium substituent, including 2-(1-pyrrolidinyl)ethyl and the like.

"Halogen" refers to fluoro, chloro, bromo and iodo atoms.

"Sulfonyloxy" refers to a group —OSO$_2$—R wherein R is selected from H, "$C_1$-$C_6$-alkyl", "$C_1$-$C_6$-alkyl" substituted with halogens, e.g., an —OSO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonyloxy" refers to $C_1$-$C_6$-alkyl groups having a sulfonyloxy substituent, including 2-(methylsulfonyloxy)ethyl and the like.

"Sulfonyl" refers to group "—SO$_2$—R" wherein R is selected from H, "aryl", "heteroaryl", "$C_1$-$C_6$-alkyl", "$C_1$-$C_6$-alkyl" substituted with halogens, e.g., an —SO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonyl" refers to $C_1$-$C_6$-alkyl groups having a sulfonyl substituent, including 2-(methylsulfonyl)ethyl and the like.

"Sulfinyl" refers to a group "—S(O)—R" wherein R is selected from H, "$C_1$-$C_6$-alkyl", "$C_1$-$C_6$-alkyl" substituted with halogens, e.g., an —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfinyl" refers to $C_1$-$C_6$-alkyl groups having a sulfinyl substituent, including 2-(methylsulfinyl)ethyl and the like.

"Sulfanyl" refers to groups —S—R where R includes H, "$C_1$-$C_6$-alkyl", "$C_1$-$C_6$-alkyl" optionally substituted with halogens, e.g. a —S—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl". Preferred sulfanyl groups include methylsulfanyl, ethylsulfanyl, and the like.

"$C_1$-$C_6$-alkyl sulfanyl" refers to $C_1$-$C_6$-alkyl groups having a sulfanyl substituent, including 2-(ethylsulfanyl)ethyl and the like.

"Sulfonylamino" refers to a group —NRSO$_2$—R' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonylamino" refers to $C_1$-$C_6$-alkyl groups having a sulfonylamino substituent, including 2-(ethylsulfonylamino)ethyl and the like.

"Aminosulfonyl" refers to a group —SO$_2$—NRR' where each R, R' includes independently hydrogen, "$C_1$-$C_6$-alkyl", "$C_2$-$C_6$-alkenyl", "$C_2$-$C_6$-alkynyl", "$C_3$-$C_6$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl aminosulfonyl" refers to $C_1$-$C_6$-alkyl groups having an aminosulfonyl substituent, including 2-(cyclohexylaminosulfonyl)ethyl and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "$C_1$-$C_6$-alkyl", "$C_2$-$C_6$-alkenyl", "$C_2$-$C_6$-alkynyl", "cycloalkyl", "heterocycloalkyl", "$C_1$-$C_6$-alkyl aryl", "$C_1$-$C_6$-alkyl heteroaryl", "$C_1$-$C_6$-alkyl cycloalkyl", "$C_1$-$C_6$-alkyl heterocycloalkyl", "amino", "ammonium", "acyl", "acyloxy", "acylamino", "aminocarbonyl", "alkoxycarbonyl", "ureido", "carbamate", "aryl", "heteroaryl", "sulfinyl", "sulfonyl", "alkoxy", "sulfanyl", "halogen", "carboxy", trihalomethyl, cyano, hydroxy, mercapto, nitro, and the like. Alternatively said substitution could also comprise situations where neighbouring substituents have undergone ring closure, notably when vicinal functional substituents are involved, thus forming, e.g., lactams, lactons, cyclic anhydrides, but also acctals, thioacetals, animals formed by ring closure for instance in an effort to obtain a protective group.

"Pharmaceutically acceptable salts or complexes" refers to salts or complexes of the below-specified compounds of formula (I) & (I'). Examples of such salts include, but are not restricted, to base addition salts formed by reaction of compounds of formula (I) & (I') with organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amino salts derived from methylamine, dimethylamine, trimethylamine, ethylamine, diethylamine, triethylamine, morpholine, N—Me-D-glucamine, N,N'-bis(phenylmethyl)-1,2-ethanediamine, tromethamine, ethanolamine, diethanolamine, ethylenediamine, N-methylmorpholine, procaine, piperidine, piperazine and the like are contemplated being within the scope of the instant invention.

Also comprised are salts which are formed from to acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid.

"Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism. Said prodrug is comprised of the active drug compound itself and a chemical masking group. Such masking group may be an ester moiety.

"Enantiomeric excess" (ee) refers to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded.

Said formula also comprises its tautomers, its geometrical isomers, its optically active forms as enantiomers, diastereoisomers and its racemate forms, as well as pharmaceutically acceptable salts thereof. Preferred pharmaceutically acceptable salts of the formula (I) or (I'), are base addition salts formed by reaction of compounds of formula (I) or (I') with pharmaceutically acceptable bases like N-methyl-D-glucamine, tromethamine, sodium, potassium or calcium salts of carbonates, bicarbonates or hydroxides.

The alkynyl aryl carboxamides according to the present invention are those of formulae (I) or (I'):

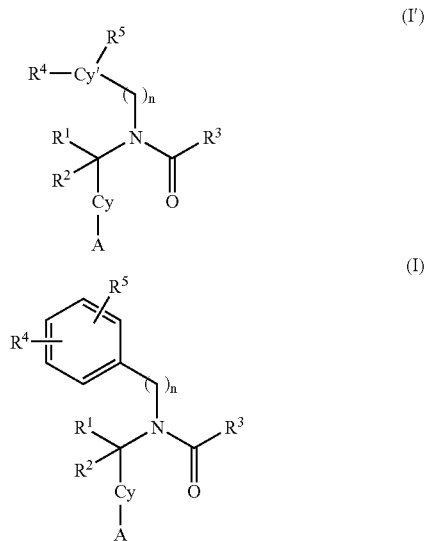

Formula (I) or (I') comprises also the geometrical isomers, the optically active forms, including enantiomers, diastereomers and its racemate forms, as well as pharmaceutically acceptable salts and pharmaceutically active derivatives thereof.

The substituents $R^1$, $R^2$, $R^3$, $R^4$, $R^5$, n, Cy' and Cy within Formulae (I) and (I') are defined as follows:

A is a substituted or unsubstituted $C_2$-$C_{15}$ alkynyl, substituted or unsubstituted $C_2$-$C_6$-alkynyl aryl, substituted or unsubstituted $C_2$-$C_6$-alkynyl heteroaryl.

n is either 0 or 1.

Cy is a substituted or unsubstituted aryl, substituted or unsubstituted heteroaryl, substituted or unsubstituted cycloalkyl or substituted or unsubstituted heterocycle group.

Cy' is an aryl, which may optionally be fused by a 3-8 membered cycloalkyl (e.g. Cy' may be a tetrahydronaphthyl, dihydroindenyl, tetrahydrobenzocycloheptenyl).

Said aryl or heteroaryl moieties Cy include phenyl, naphthyl, phenantrenyl, pyrrolyl, furyl, thienyl, imidazolyl, pyridyl, oxazolyl, isoxazolyl, thiazolyl, isothiazolyl, pyrazolyl, 1,2,3-triazolyl, 1,2,4-triazolyl, 1,2,3-oxadiazolyl, benzo(1,2,5)oxadiazolyl, 1,2,4-oxadiazolyl, 1,2,5-oxadiazolyl, 1,3,4-oxadiazolyl, tetrazolyl, 1,3,4-triazinyl, 1,2,3-triazinyl, benzopyrimidinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, benzothiazolyl, benzoxazolyl, pyridazinyl, pyrimidyl, quinolizinyl, quinazolinyl, pthalazinyl, quinoxalinyl, cinnolinyl, napthyridinyl, quinolyl, isoquinolyl, tetrazolyl, 5,6,7,8-tetrahydroquinolyl, 5,6,7,8-tetrahydroisoquinolyl, purinyl, pteridinyl, xanthenyl, benzoquinolyl, oxolanyl, pyrolidinyl, pyrazolidinyl, 2H-benzo[d]1,3-dioxolenyl, indanyl, imidazolidinyl, 1,2,4-oxadiazolidinyl, 1,2,5-oxadiazolidinyl, 1,3,4-oxadiazolidinyl or isoxazolidinyl.

According to one embodiment of formula (I), Cy is a substituted or unsubstituted phenyl. Also comprised are diaryl (e.g. biphenyl), or di-heteroaryl, or aryl-heteroaryl (e.g. phenyl-thiazolyl, or heteroaryl-aryl (e.g. thiazolyl-phenyl) moieties.

$R^1$ and $R^2$ are independently selected from each other from the group consisting of hydrogen or substituted or unsubstituted $(C_1$-$C_6)$alkyl. According to one embodiment both $R^1$ and $R^2$ are hydrogen.

$R^3$ is selected from the group consisting of substituted or unsubstituted $C_1$-$C_6$-alkyl, substituted or unsubstituted $C_2$-$C_6$-alkenyl, substituted or unsubstituted $C_2$-$C_6$-alkynyl, substituted or unsubstituted $C_1$-$C_6$-alkoxy, substituted or unsubstituted $C_1$-$C_6$-alkyl amino, substituted or unsubstituted $C_1$-$C_6$-alkyl alkoxy, substituted or unsubstituted $C_1$-$C_6$-alkyl carboxy, substituted or unsubstituted aryl, substituted or unsubstituted heteroaryl, substituted or unsubstituted saturated or unsaturated 3-8-membered cycloalkyl, substituted or unsubstituted 3-8-membered heterocycloalkyl, substituted or unsubstituted $C_1$-$C_6$-alkyl aryl, substituted or unsubstituted $C_1$-$C_6$-alkyl heteroaryl, substituted or unsubstituted $C_2$-$C_6$-alkenyl aryl, substituted or unsubstituted $C_2$-$C_6$-alkenyl heteroaryl, substituted or unsubstituted $C_2$-$C_6$-alkynyl aryl, substituted or unsubstituted $C_2$-$C_6$-alkynyl heteroaryl, substituted or unsubstituted $C_1$-$C_6$-alkyl cycloalkyl, substituted or unsubstituted $C_1$-$C_6$-alkyl heterocycloalkyl, substituted or unsubstituted $C_2$-$C_6$-alkenyl cycloalkyl, substituted or unsubstituted $C_2$-$C_6$-alkenyl heterocycloalkyl, substituted or unsubstituted $C_2$-$C_6$-alkynyl cycloalkyl, substituted or unsubstituted $C_2$-$C_6$-alkynyl heterocycloalkyl.

$R^4$ and $R^5$ are each independently from each other selected from the group consisting of H, hydroxy, fluoro, substituted or unsubstituted $C_1$-$C_6$ alkyl, carboxy, substituted or unsubstituted $C_1$-$C_6$ alkoxy, substituted or unsubstituted $C_1$-$C_3$ alkyl carboxy, substituted or unsubstituted $C_2$-$C_3$ alkenyl carboxy, substituted or unsubstituted $C_2$-$C_3$ alkynyl carboxy.

At any rate, at least one of the substituents $R^4$ or $R^5$ is not a hydrogen or a $C_1$-$C_6$ alkyl. At least one of $R^4$ or $R^5$ must be a hydroxy, fluoro, carboxy, $C_1$-$C_6$ alkoxy, $C_1$-$C_3$ alkyl carboxy, $C_2$-$C_3$ alkenyl carboxy, $C_2$-$C_3$ alkynyl carboxy.

In one embodiment A is a moiety of the formula —C≡C—$R^6$ wherein $R^6$ is a substituted or unsubstituted $C_6$-$C_{12}$ alkyl, a substituted or unsubstituted 3-8 membered cycloalkyl, substituted or unsubstituted $C_1$-$C_6$ alkyl-(3-8 membered)cycloalkyl, substituted or unsubstituted $C_2$-$C_6$-alkenyl, substituted or unsubstituted $C_2$-$C_6$-alkynyl, phenyl, substituted or unsubstituted $C_1$-$C_{12}$ alkyl phenyl, substituted or unsubstituted $C_2$-$C_6$-alkenyl phenyl, substituted or unsubstituted $C_2$-$C_6$-alkynyl phenyl.

More specific alkynyl aryl carboxamide derivatives of the present invention have either of the formulae (Ia), (Ib), (Ic), (Id), (Ie) or (If):

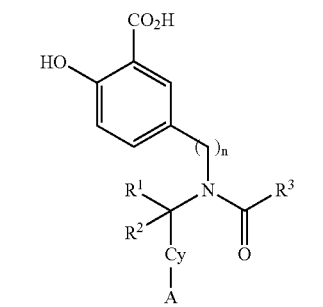
(Ia)

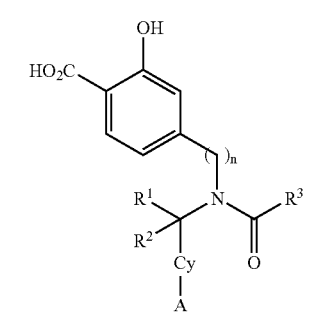
(Ib)

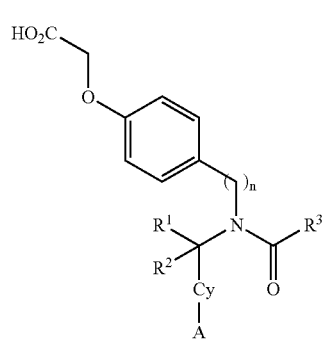
(Ic)

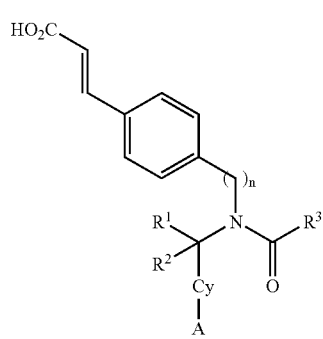
(Id)

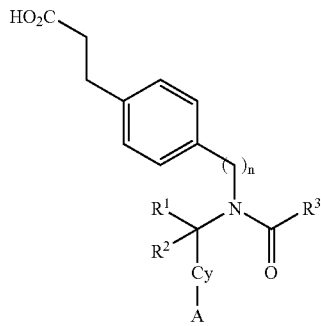
(Ie)

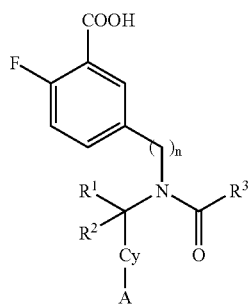
(If)

wherein A, Cy, n. R', $R^2$ and $R^3$ are as above defined.

Specific alkynyl aryl carboxamide derivatives according to formula (I) or (I') comprise the following:

5-[(3-Cyclopentylpropanoyl)(4-dec-1-ynylbenzyl)amino]-2-hydroxybenzoic acid

5-[(3-Cyclopentylpropanoyl)(4-dec-1-ynylbenzyl)amino]-2-hydroxybenzoic acid, N-methyl-D-glucamine (i.e. 1-deoxy-1-(methylamino)glucitol) salt 5-[{4-[(4-Butylphenyl)ethynyl]benzyl}(3-cyclopentylpropanoyl)amino]-2-hydroxybenzoic acid 5-[{4-[(4-Butylphenyl)ethynyl]benzyl}(3-cyclopentylpropanoyl)amino]-2-hydroxybenzoic acid, N-methyl-D-glucamine (i.e. 1-deoxy-1-(methylamino)glucitol) salt 5-[Acetyl(4-dec-1-ynylbenzyl)amino]-2-hydroxybenzoic acid 5-[(4-Dec-1-ynylbenzyl)(pyridin-3-ylcarbonyl)amino]-2-hydroxybenzoic acid 5-[(4-Dec-1-ynylbenzyl)(isonicotinoyl)amino]-2-hydroxybenzoic acid 5-{(4-Dec-1-ynylbenzyl)[(2E)-3-phenylprop-2-enoyl]amino}-2-hydroxybenzoic acid 5-[(4-Dec-1-ynylbenzyl)(thien-2-ylacetyl)amino]-2-hydroxybenzoic acid 5-((4-Dec-1-ynylbenzyl){(2E)-3-[3-(trifluoromethyl)phenyl]prop-2-enoyl}amino)-2-hydroxybenzoic acid 5-[(4-Dec-1-ynylbenzyl)(phenoxyacetyl)amino]-2-hydroxybenzoic acid

[4-({(4-Dec-1-ynylbenzyl)[(2E)-3-phenylprop-2-enoyl]amino}methyl)phenoxy]acetic acid (4-{([(3-Cyclopentylpropanoyl)(4-dec-1-ynylbenzyl)amino]methyl}phenoxy)acetic acid (4-{[(4-Dec-1-ynylbenzyl)(hexanoyl)amino]methyl}phenoxy)acetic acid (4-{[Acetyl(4-dec-1-ynylbenzyl)amino]methyl}phenoxy) acetic acid 2-(Carboxymethoxy)-5-({(4-dec-1-ynylbenzyl)[(2E)-3-phenylprop-2-enoyl]amino}methyl)benzoic acid 2-(Carboxymethoxy)-5-{[[(3-cyclopentylpropanoyl)(4-dec-1-ynylbenzyl)amino]methyl}benzoic acid 5-{[Acetyl(4-dec-1-ynylbenzyl)amino]methyl}-2-(carboxymethoxy)benzoic acid (2E)-3-(4-{[(4-Dec-1-ynylbenzyl)(3-phenylpropanoyl)amino]methyl}phenyl)acrylic acid (2E)-3-{4-[(4-Dec-1-ynylbenzyl)(3-phenylpropanoyl)amino]phenyl}acrylic acid (2E)3-{4-[Acetyl(4-dec-1-ynylbenzyl)amino]phenyl}acrylic acid 3-(4-{[([(3-Cyclopentylpropanoyl)(4-dec-1-ynylbenzyl)amino]methyl}phenyl)propanoic acid 5-[{4-[(4-Butylphenyl)ethynyl]benzyl}(cyclohexylcarbonyl)amino]-2-hydroxybenzoic acid 5-[{4-[(4-Butylphenyl)ethynyl]benzyl}(hexanoyl)amino]-2-hydroxybenzoic acid, N-methyl-D-glucamine (i.e. 1-deoxy-1-(methylamino)glucitol) salt 5-((4-tert-Butylbenzoyl){4-[(4-butylphenyl)ethynyl]benzyl}amino)-2-hydroxybenzoic acid, N-methyl-D-glucamine (i.e. 1-deoxy-1-(methylamino)glucitol) salt 5-((Biphenyl-4-ylcarbonyl){4-[(4-butylphenyl)ethynyl]benzyl}amino)-2-hydroxybenzoic acid 5-[{4-[(4-Butylphenyl)ethynyl]benzyl}(3,3-dimethylbutanoyl)amino]-2-hydroxybenzoic acid 5-[{4-[(4-Butylphenyl)ethynyl]benzyl}(2,3-dihydro-1-benzofuran-5-ylcarbonyl)amino]-2-hydroxybenzoic acid 5-[{4-[(4-Butylphenyl)ethynyl]benzyl}(7-carboxyheptanoyl)amino]-2-hydroxybenzoic acid 5-((1,3-Benzodioxol-5-ylcarbonyl){4-[(4-butylphenyl)ethynyl]benzyl}amino)-2-hydroxybenzoic acid 5-[{4-[(4-Butylphenyl)ethynyl]benzyl}(2,2-dimethylpropanoyl)amino]-2-hydroxybenzoic acid 5-([(Benzyloxy)acetyl]{4-[(4-butylphenyl)ethynyl]benzyl}amino)-2-hydroxybenzoic acid 5-[{4-[(4-Butylphenyl)ethynyl]benzyl}(4-hexylbenzoyl)amino]-2-hydroxybenzoic acid 5-[{4-[(4-Butylphenyl)ethynyl]benzyl}(2-naphthoyl)amino]-2-hydroxybenzoic acid 5-((1-Benzothien-2-ylcarbonyl){4-[(4-butylphenyl)ethynyl]benzyl}amino)-2-hydroxybenzoic acid, N-methyl-D-glucamine (i.e. 1-deoxy-1-(methylamino)glucitol) salt 4-[{4-[(4-Butylphenyl)ethynyl]benzyl}(3-cyclopentylpropanoyl)amino]-2-hydroxybenzoic acid, N-methyl-D-glucamine (i.e. 1-deoxy-1-(methylamino)glucitol) salt 5-{[{4-[(4-Butylphenyl)ethynyl]benzyl}(3-cyclopentylpropanoyl)amino]methyl}-2-hydroxybenzo acid, N-methyl-D-glucamine (i.e. 1-deoxy-1-(methylamino)glucitol) salt 5-{[{4-[(4-Butylphenyl)ethynyl]benzyl}(hexanoyl)amino]methyl}-2-hydroxybenzoic acid (4-{[{4-[(4-Butylphenyl)ethynyl]benzyl}(hexanoyl)amino]methyl}phenoxy)acetic acid, N-methyl-D-glucamine (i.e. 1-deoxy-1-(methylamino)glucitol) salt (4-{[{4-[(4-Butylphenyl)ethynyl]benzyl}(cyanoacetyl)amino]methyl}phenoxy)acetic acid (4-{[{4-[(4-Butylphenyl)ethynyl]benzyl}(1H-indazol-3-ylcarbonyl)amino]methyl}-phenoxy)acetic acid (4-{[{4-[(4-Butylphenyl)ethynyl]benzyl}(pent-4-ynoyl)amino]methyl}phenoxy)acetic acid

[4-({{4-[(4-Butylphenyl)ethynyl]benzyl}[(6-hydroxypyridin-3-yl)carbonyl]amino}methyl-phenoxy]acetic acid

[4-({{4-[(4-Butylphenyl)ethynyl]benzyl}[(2-methoxyethoxy)acetyl]amino}methyl)-phenoxy]acetic acid (4-{[{4-[(4-Butylphenyl)ethynyl]benzyl}(1H-pyrazol-4-ylcarbonyl)amino]-methyl}phenoxy)acetic acid 3-[(3-Cyclopentylpropanoyl)(4-dec-1-yn-1-ylbenzyl)amino]benzoic acid, N-methyl-D-glucamine (i.e. 1-deoxy-1-(methylamino)glucitol) salt 3-[(4-Dec-1-yn-1-ylbenzyl)(hexanoyl)amino]benzoic acid 4-{[{4-[(4-Butylphenyl)ethynyl]benzyl}(3-cyclopentylpropanoyl)amino]methyl}benzoic acid 4-{[{4-[(4-Butylphenyl)ethynyl]benzyl}(hexanoyl)amino]methyl}benzoic acid 4-[((4-tert-Butylbenzoyl){4-[(4-butylphenyl)ethynyl]benzyl}amino)methyl]benzoic acid 4-[{(4-[(4-Butylphenyl)ethynyl]benzyl}(hexanoyl)amino]benzoic acid 4-[{4-[(4-Butylphenyl)ethynyl]benzyl}(3-cyclopentylpropanoyl)amino]benzoic acid 8-[{4-[(4-Butylphenyl)ethynyl]benzyl}(3-cyclopentylpropanoyl)amino]-5,6,7,8-tetrahydronaphthalene-2-carboxylic acid, N-methyl-D-glucamine (i.e. 1-deoxy-1-(methylamino)glucitol) salt 5-[{4-[(4-Chlorophenyl)ethynyl]benzyl}(3-cyclopentylpropanoyl)amino]-2-hydroxybenzoic acid, N-methyl-D-glucamine (i.e. 1-deoxy-1-(methylamino)glucitol) salt 5-[{4-[(4-Chlorophenyl)ethynyl]benzyl}(4-heptylbenzoyl)amino]-2-hydroxybenzoic acid 5-[{4-[(4-Chlorophenyl)ethynyl]benzyl}(isoxazol-5-ylcarbonyl)amino]-2-hydroxybenzoic acid 5-[{4-[(4-Chlorophenyl)ethynyl]benzyl}(2-thienylacetyl)amino]-2-hydroxybenzoic acid 5-[{(4-[(4-Chlorophenyl)ethynyl]benzyl}(3-phenylpropanoyl)amino]-2-hydroxybenzoic acid, N-methyl-D-glucamine (i.e. 1-deoxy-1-(methylamino)glucitol) salt 5-[{4-[(4-Chlorophenyl)ethynyl]benzyl}(4-methoxybenzoyl)amino]-2-hydroxybenzoic acid, N-methyl-D-glucamine (i.e. 1-deoxy-1-(methylamino)glucitol) salt 5-[{4-[(4-Chlorophenyl)ethynyl]benzyl}(3-fluorobenzoyl)amino]-2-hydroxybenzoic acid, N-methyl-D-glucamine (i.e. 1-deoxy-1-(methylamino)glucitol) salt 5-[{4-[(4-Chlorophenyl)ethynyl]benzyl}(cyclohexylcarbonyl)amino]-2-hydroxybenzoic acid, N-methyl-D-glucamine (i.e. 1-deoxy-1-(methylamino)glucitol) salt 5-(acetyl{4-[(4-Chlorophenyl)ethynyl]benzyl}amino)-2-hydroxybenzoic acid, N-methyl-D-glucamine (i.e. 1-deoxy-1-(methylamino)glucitol) salt 5-[{4-[(4-Butylphenyl)ethynyl]-2-fluorobenzyl}(3-cyclopentylpropanoyl)amino]-2-hydroxybenz acid, N-methyl-D-glucamine (i.e. 1-deoxy-1-(methylamino)glucitol) salt 8-((3-Cyclopentylpropanoyl){4-[(4-fluorophenyl)ethynyl]benzyl}amino)-5,6,7,8-tetrahydronaphthalene-2-carboxylic acid, N-methyl-D-glucamine (i.e. 1-deoxy-1-(methylamino)glucitol) salt 5-[({6-[(4-Butylphenyl)ethynyl]pyridin-3-yl}methyl)(3-cyclopentylpropanoyl)amino]-2-hydroxybenzoic acid, N-methyl-D-glucamine (i.e. 1-deoxy-1-(methylamino)glucitol) salt 5-[{4-[(4-Butylphenyl)ethynyl]benzyl}(3-cyclopentylpropanoyl)amino]-2-fluorobenzoic acid, N-methyl-D-glucamine (i.e. 1-deoxy-1-(methylamino)glucitol) salt 5-[{4-[(4-Butylphenyl)ethynyl]benzyl}(3,3-dimethylbutanoyl)amino]-2-fluorobenzoic acid, N-methyl-D-glucamine (i.e. 1-deoxy-1-(methylamino)glucitol) salt 5-[{4-[(4-Butylphenyl)ethynyl]benzyl}(2-thienylacetyl)amino]-2-fluorobenzoic acid, N-methyl-D-glucamine (i.e. 1-deoxy-1-(methylamino)glucitol) salt 4-[{4-[(4-Butylphenyl)ethynyl]benzyl}(3,3-dimethylbutanoyl)amino]-2-hydroxybenzoic acid, N-methyl-D-glucamine (i.e. 1-deoxy-1-(methylamino)glucitol) salt 3-[{4-[(4-Butylphenyl)ethynyl]benzyl}(3-cyclopentylpropanoyl)amino]-4-fluorobenzoic acid 4-[{4-[(4-Chlorophenyl)ethynyl]benzyl}(3-cyclopentylpropanoyl)amino]-2-hydroxybenzoic acid, N-methyl-D-glucamine (i.e. 1-deoxy-1-(methylamino)glucitol) salt 4-(Acetyl{4-[(4-butylphenyl)ethynyl]benzyl}amino)-2-hydroxybenzoic acid, N-methyl-D-glucamine (i.e. 1-deoxy-1-(methylamino)glucitol) salt 4-[{4-[(4-Butylphenyl)ethynyl]benzyl}(cyclohexylcarbonyl)amino]-2-hydroxybenzoic acid, N-methyl-D-glucamine (i.e. 1-deoxy-1-(methylamino)glucitol) salt 4-[{4-[(4-Butylphenyl)ethynyl]benzyl}(hexanoyl)amino]-2-hydroxybenzoic acid, N-methyl-D-glucamine (i.e. 1-deoxy-1-(methylamino)glucitol) salt 4-[{4-[(4-Butylphenyl)ethynyl]benzyl}(3-cyclopentylpropanoyl)amino]-2-fluorobenzoic acid, N-methyl-D-glucamine (i.e. 1-deoxy-1-(methylamino)glucitol) salt 4-[{4-[(4-Butylphenyl)ethynyl]benzyl}(2,2-dimethylpropanoyl)amino]-2-hydroxybenzoic acid, N-methyl-D-glucamine (i.e. 1-deoxy-1-(methylamino)glucitol) salt 4-((3-Cyclopentylpropanoyl){4-[(4-methoxyphenyl)ethynyl]benzyl}amino)-2-hydroxybenzoic acid, N-methyl-D-glucamine (i.e. 1-deoxy-1-(methylamino)glucitol) salt 4-[{4-[(4-tert-Butylphenyl)ethynyl]benzyl}(3-cyclopentylpropanoyl)amino]-2-hydroxybenzoic acid, N-methyl-D-glucamine (i.e. 1-deoxy-1-(methylamino)glucitol) salt 4-((3-Cyclopentylpropanoyl){4-[(4-propoxyphenyl)ethynyl]benzyl}amino)-2-hydroxybenzoic acid, N-methyl-D-glucamine (i.e. 1-deoxy-1-(methylamino)glucitol) salt 4-((3-Cyclopentylpropanoyl){4-[(4-propylphenyl)ethynyl]benzyl}amino)-2-hydroxybenzoic acid, N-methyl-D-glucamine (i.e. 1-deoxy-1-(methylamino)glucitol) salt 4-{(3-Cyclopentylpropanoyl)[4-(5-phenylpent-1-yn-1-yl)benzyl]amino}-2-hydroxybenzoic acid, N-methyl-D-glucamine (i.e. 1-deoxy-1-(methylamino)glucitol) salt The compounds of formula (I) or (I') are useful in the treatment and/or prevention of cardiovascular diseases (e.g. heart failure), inflammatory disorders, osteoporosis, obesity and/or metabolic disorders mediated by insulin resistance or hyperglycemia, comprising diabetes type I and/or II, inadequate glucose tolerance, insulin resistance, hyperlipidemia, hypertriglyceridemia, hypercholesterolemia or polycystic ovary syndrome (PCOS).

In one embodiment the compounds according to formula (I) or (I') are particularly useful in the treatment and/or prevention of diabetes type II, obesity and for the regulation of appetite in mammals.

In a further embodiment the compounds according to formula (I) or (I') are suitable for the modulation of the activity of PTPs, in particular of PTP1B and/or GLEPP-1. It is therefore believed that the compounds of the present invention are therefore useful for the treatment and/or prevention of disorders which are mediated by PTPs, in particular of PTP1B. Said treatment involves the modulation—notably the down regulation or the inhibition—of PTPs, particularly of PTP1B and/or GLEPP-1.

A further aspect of the present invention is related to a pharmaceutical composition comprising a alkynyl aryl carboxamide according to Formula (I) or (I') and at least one further drug (in particular an anti-diabetes agent). In one embodiment the further diabetes agents are selected from the group comprising or consisting of insulin (or insulin mimicks), aldose reductase inhibitors, alpha-glucosidase inhibitors, sulfonyl urea agents, biguanides (e.g. metformin), thiazolidinediones (e.g. pioglitazone, rosiglitazone, cf. WO 02/100396) or PPARs agonists, or c-Jun Kinase or GSK-3 inhibitors.

Insulins useful with the method of the present invention include rapid acting insulins, intermediate acting insulins, long acting insulins and combination of intermediate and rapid acting insulins.

Aldose reductase inhibitors useful in the method of this invention include those known in the art. These include the non-limiting list of:

a) the spiro-isoquinoline-pyrrolidine tetrone compounds disclosed in U.S. Pat. No. 4,927,831 (Malamas), the contents of which are incorporated herein by reference, which includes ARI-509, also known as minalrestat or Spiro[isoquinoline-4(1H), 3'-pyrrolidine]-1,2',3,5' (2H)-tetrone, and analogs thereof, b) 2-[(4-bromo-2-fluorophenyl)methyl]-6-fluoro-(9CI);

c) the compounds of U.S. Pat. No. 4,439,617, the contents of which are incorporated herein by reference, which includes Tolrestat, also known as Glycine, N-[[6-metloxy-5-(trifluoromethyl)-1-naphtalenyl]thioxomethyl]-N-methyl-(9CI) or AY-27773 and analogs thereof;

d) Sorbinil (Registra No. 68367-52-2) also known as Spiro [4H-1-benzopyran4,4'-imidazoline]-2',5'-dione, 6-fluoro-2,3-dihydro-, (4S)-(9CI) or CP 45634;

e) Methosorbinil;

f) Zopolrestat, which is 1-Phtalazineacetic acid, 3,44-dihydro-4-oxo-3-[[5-(trifluoromethyl)-2-benzothiazolyl] methyl]-(9CI) (Registry No. 110703-94-i1);

g) Epalrestat, which is 3-Thiazolidineacetic acid, 5-[(2E)-2-methyl-3-phenyl-2-propcnylidene]4-oxo-2-thioxo-, (5Z)-(9CI) (Registry No. 82150-09-9);

h) Zenarestat (Registry No. 112733-40-6) or 3-[(4-bromo-2-fluorophenyl)-methyl]-7-chloro-3,4-dihydro-2,4-di-oxo-1(2H)-quinazoline acetic acid;

i) Imirestat, also known as 2,7-difluorospiro(9H-fluorene-9,4'-imidazolidine)-2',5'-dione;

j) Ponalrestat (Registry No. 72702-95-5), which is 1-Phtalazineacetic acid, 3-[(4-bromo-2-fluorophenyl)methyl] 3,4-dihydro-4-oxo-(9CI) and also known as Stalil or Statyl;

k) ONO-2235, which is 3-Thiazolidineacetic acid, 5-[(2E)-2-methyl-3-phenyl-2-propenylidene-4-oxo-2-thioxo-, (5Z)-(9CI);

l) GP-1447, which is {3-[(4,5,7-trifluorobenzothiazol-2-yl)methyl]-5-methylphenylacetic acid};

m) CT-112, which is 5-(3-ethoxy-4-pentyloxyphenyl)-2,4-thiazolidinedione;

n) BAL-ARI 8, which is Glycine, N[(7-fluoro-9-oxo-9H-xanthen-2-yl)sulfonyl]-N-methyl-)9CI), Reg. No. 124066-40-6));

o) AD-5467, which is 2,3-dihydro-2,8-bis(1-methylethyl)-3-thioxox-4H-1,4-benzoxazine-4-acetic acid of the chloride salt form (4H-1,4-Benzoxazine-4-acetic acid, 2,3-dihydro-2,8-bis(1-methylethyl)-3-thioxo-(9CI):

p) ZD5522, which is (3',5'-dimethyl-4'-nitromethylsulfonyl-2-(2-tolyl)acetanilide);

q) 3,4-dihydro-2,8-diisopropyl-3-thioxo-2H-1,4-benzoxazine-4-acetic acid;

r) 1-[(3-bromo-2-benzofuranyl)sulfonyl]-2,4-imidazolidinedione (M-16209), s) NZ-314, which is 1-Imidazolidineacetic acid, 3-[(3-nitrophenyl)methyl]-2,4,5-trioxo-9(CI) (Registry No. 128043-99-2), t) 1-phtalazineacetic acid, 3,4-dihydro-4-oxo-3-[(5-trifluoromethyl)-2-benzothiazolyl]-methyl];

u) M-79175, which is Spiro[4H-1-benzopyran-4,4'-imidazolidine]-2',5'-dione; 6-fluoro-2,3-dihydro-2-methyl-, (2R,4S)-(9CI);

v) SPR-210, which is 2H-1,4-Benzothiazine-2-acetic acid, 3,4-dihydro-3-oxo-4-[(4,5,7-trifluoro-2-benzothiazolyl)methyl]-(9CI);

w) Spiro[pyrrolidine-3,6'(5'H)-pyrrolo[1,2,3-de][1,4]benzoxazine]-2,5,5'-trione, 8'-chloro-2'-3'-dihydro-(9CI)

(also known as AND 138 or 8-chloro-2',3'-dihydrospiro[pyrolizine-3,6'(5H)-pyrrolo-[1,2,3-de]-[1,4]benzoxazine]2,5,5'-trione);

x) 6-fluoro-2,3-dihydro-2',5'-dioxo-(2S-cis)-spiro[4H-1-benzopyran-4,4'-imidazolidine]-2-carboxamide (also known as SNK-860);

or a pharmaceutically acceptable salt form of one or more of these compounds.

Among the more preferred aldose reductase inhibitors of this invention are minalrestat, Tolrestat, Sorbinil, Methosorbinil, Zopolrestat, Epalrestat, Zenarestat, Imirestat and Ponairestat or the pharmaceutically acceptable salt forms thereof.

The alpha-glucosidase inhibitors useful for the method of the present invention include miglitol or acarbose, or the pharmaceutically acceptable salt form thereof.

Sulfonylurea agents useful with the method of the present invention include glipizide, Glyburide (Glibenclamide) Clorpropamide, Tolbutamide, Tolazamide and Glimepiride, or the pharmaceutically acceptable salt forms thereof.

Preferably, said supplementary pharmaceutically active agent is selected from the group consisting of a rapid acting insulin, an intermediate acting insulin, a long acting insulin, a combination of intermediate and rapid acting insulins, Inalrestat, Tolrestat, Sorbinil, Methosorbinil, Zopoirestat, Epairestat, Zenarestat, Imirestat, Ponalrestat, ONO-2235, GP-1447, CT-112, BAL-ARI 8, AD-5467, ZD5522, M-16209, NZ-314, M-79175, SPR-210, ADN 138, or SNK-860, Miglitol, Acarbose, Glipizide, Glyburide, Clorpropamide, Tolbutamide, Tolazamide, or Glimepiride.

Still a further object of the invention is a process for preparing alkynyl aryl carboxamides according to formula (I) or (I').

The alkynyl aryl carboxamides of the present invention may be prepared from readily available starting materials using the below general methods and procedures. It will be appreciated that where typical or preferred experimental conditions (i.e. reaction temperatures, time, moles of reagents, solvents, etc.) are given, other experimental conditions may also be used, unless otherwise stated. Optimum reaction conditions may vary with the particular reactants or solvents used, but such conditions can be determined by one skilled in the art by routine optimisation procedures.

By the following set out general methods and procedures compounds of formula (I) or (I') are obtained.

Generally, substituted alkynyl aryl carboxamide derivatives according to the general formula (I) or (I') may be obtained by several processes, using both solution-phase and solid-phase chemistry protocols. Depending on the nature of Cy', Cy, $R^1$, $R^2$, $R^3$, $R^4$, $R^5$, n, and A, some processes will be preferred to others, this choice of the most suitable process being assumed by the practitioner skilled in the art.

Generally, alkynyl aryl carboxamide derivatives of formula (I) or (I') may be obtained by the initial deprotection of the precursors (Z), wherein Cy', Cy, $R^3$ are as above defined and the moiety FG is A (as above defined) and wherein $R^4$ and $R^5$ can be independently from each other the protected or the non-protected form of $R^4$ and $R^5$ (as above defined) (see Scheme 1 below). For example, when $R^4$ or $R^5$ is a hydroxy group, $R^{4'}$ or $R^{5'}$ can be an ether protecting group such as OBn, OMe or an ester protecting group such as OAc. When $R^4$ or $R^5$ contains a carboxy group, the carboxy groups of $R^{4'}$ or $R^{5'}$ can be an ester such as $CO_2Me$, $CO_2Bn$ or $CO_2tBu$. When $R^4$ (or $R^5$) is a carboxy group and when $R^5$ (or $R^4$) is a hydroxy group, both $R^{4'}$ and $R^{5'}$ groups can be member of a heterocycle such as a substituted 2,2-dimethyl-4-oxo-4H-1,3-benzodioxin-4-one.

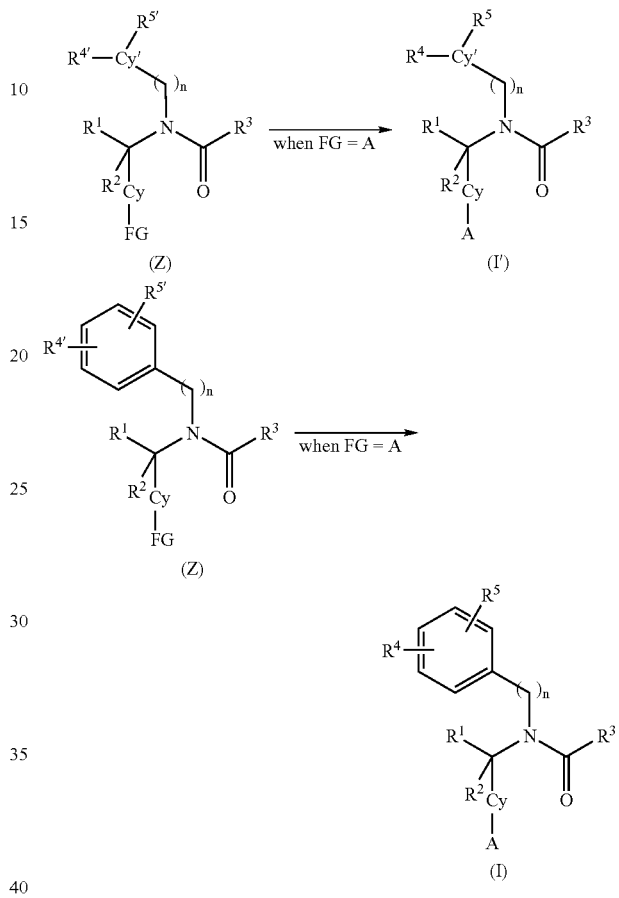

Scheme 1

In one embodiment Cy' is phenyl (cf. second part of Scheme 1), however, Cy' may also be a tetrahydronaphthyl, dihydroindenyl, tetrahydrobenzocycloheptenyl moiety.

It is recognized by those skilled in the art of organic synthesis that the successful use of these methods and of the methods described below is dependent upon the compatibility of substituents on other parts of the molecules. Protecting groups and/or changes in the order of steps described herein may be required.

Those skilled in the art will recognize that certain reactions are best carried out when potentially reactive functionality on the molecule is masked or protected, thus avoiding side reactions and/or increasing the yield of the reaction. Examples of protecting group moieties may be found in Philip J. Kocienski, "Protecting Groups", Georg Thieme Verlag Stuttgart, New York, 1994 and in Theodora W. Greene and Peter G. M. Wuts "Protective Groups in Organic Synthesis", $3^{rd}$ edition, John Wiley & Sons Inc., 1999 (New York). The need and choice of protecting groups for a particular reaction is known to those skilled in the art and depends on the nature of the functional group to be protected (hydroxy, amino, carboxy, etc.), the structure and the stability of the molecule of which the substituent is part of the reaction conditions.

In the following, the general preparation of alkynyl aryl carboxamide derivatives of formula (Z), wherein Cy', Cy, $R^1$, $R^2$, $R^3$ and n are as above-defined, wherein $R^{4'}$, $R^{5'}$ may be independently from each other the protected or the non-protected form of $R^4$ and $R^5$ and the moiety FG is A or a leaving group such as Br, Cl, I, OMs or OTf shall be illustrated.

Substituted alkynyl aryl carboxamide derivatives of formula (Z) may be prepared by coupling the corresponding amine of formula (II), wherein P is H and wherein Cy', Cy, $R^1$, $R^2$, $R^3$, F, n, $R^{4'}$ and $R^{5'}$ are as define above, with a carboxylic acid derivatives LG-CO—$R^3$ of formula (III) wherein $R^3$ is as above defined and LG is a suitable leaving group—including OH, Cl, O-alkyl or O-alkylaryl (see Scheme 2 below). A general protocol for such preparation is given below in the Examples, using conditions and methods well known to those skilled in the art to prepare an amide bond from an amine and a carboxylic acid or carboxylic acid derivative (e.g. acyl chloride), with or without standard coupling agents, such as e.g. DIC, EDC, TBTU, DECP, DCC, PyBOP®, Isobutyl chloroformate or others in the presence or not of bases such as TEA, DIEA, NMM in a suitable solvent such as DCM, THF or DMF.

In one embodiment Cy' is phenyl (cf. second part of Scheme 1), however, Cy' may also be a tetrahydronaphthyl, dihydroindenyl, tetrahydrobenzocycloheptenyl moiety.

The precursor compounds of formula (II) wherein P is H may be obtained by deprotection of their corresponding protected forms, wherein P is a protecting group such as e.g. Boc or Fmoc.

The precursor compounds of formula (II) wherein P is H or a suitable protecting group, may be prepared from the corresponding precursors of formulae (IV), (V) or (VI), using a variety of synthetic strategies for which some examples are indicated in the below Scheme 3.

Compounds of formula (II)—wherein $R^2$ is H—may for instance be prepared by alkylation of the amines (VII)—wherein $R^{4'}$ and $R^{5'}$ are as above-defined and wherein P is H or a suitable protecting group with the carbonyl derivatives (IV), wherein $R^1$, Cy', Cy and FG are as above defined (see Scheme 3, Method A). The reaction may be performed in the presence of a suitable reducing agent including $NaBH(OAc)_3$, $NaBH_3CN$, $NaBH_4$ or hydrogen and an appropriate catalyst such as Pd/C or $PtO_2$.

Alternatively, compounds of formula (II) may be prepared by alkylation of amines of formula (VII)—wherein $R^{4'}$ and $R^{5'}$ are as above-defined and wherein P is H or a suitable protecting group such as e.g. Boc or Fmoc—with the derivatives of formula (V), wherein $LG^1$ is a suitable leaving group including Cl, Br, I, OH, OMS, OTs and wherein $R^1$, $R^2$, Cy', Cy and FG are as above-defined (see Scheme 3, Method B).

Also, compounds of formula (II) may be prepared by alkylation of amines of formula (VI), with the alkylating agents of formula (VIII) wherein $LG^1$ is the above-mentioned leaving group (see Scheme 3, Method C).

Still a further alternative is set out in Scheme 3 (Method D). This embodiment illustrates the preparation of compounds of formula (II) by alkylation of the amines of formula (VI) with carbonyl derivatives (IX) in the presence of a reducing agent such as e.g. $NaBH(OAc)_3$, $NaBH_3CN$, NaBH4 or hydrogen with an appropriate catalyst such, as e.g. Pd/C or $PtO_2$, in order to provide compounds of formula (II), wherein n is 1.

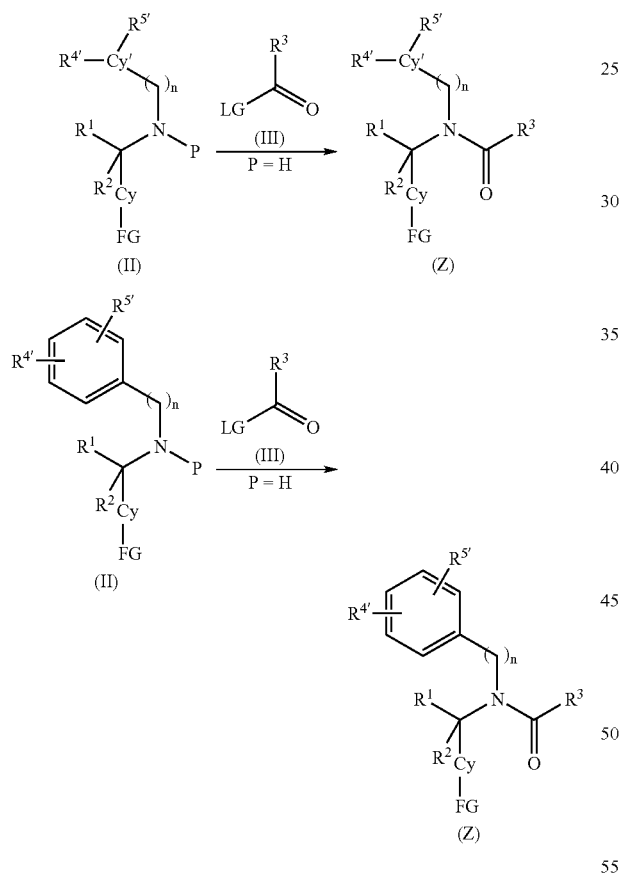

Scheme 2

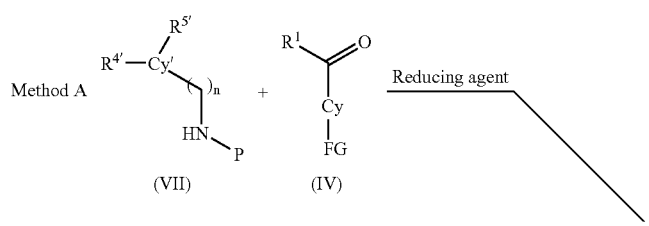

Scheme 3

-continued

Method B 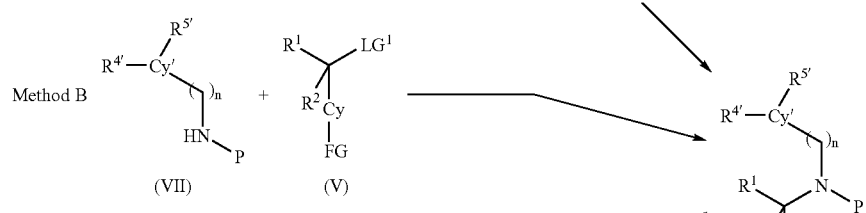

Method C 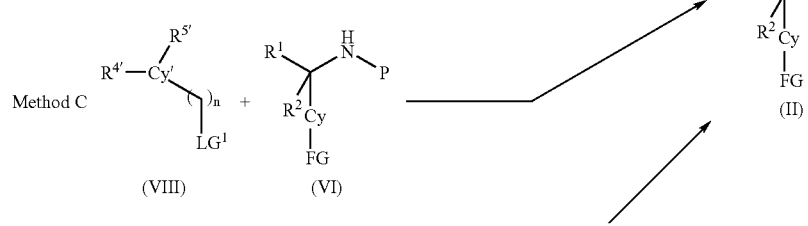

Method D 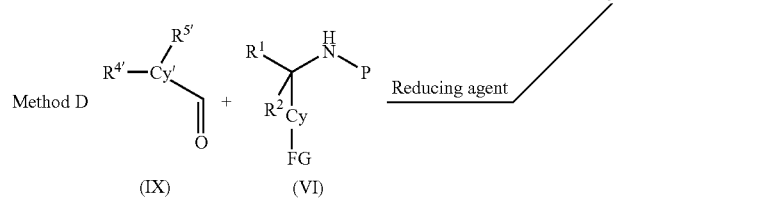

Method A 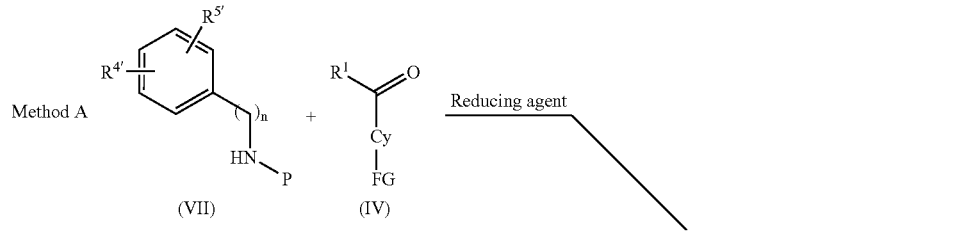

Method B 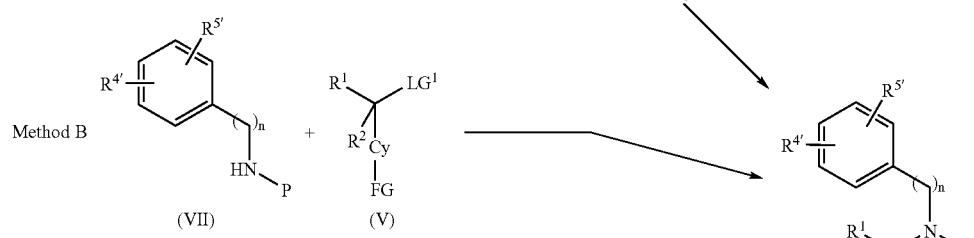

Method C 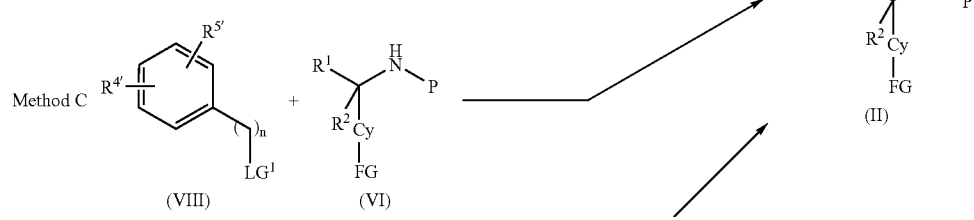

Method D 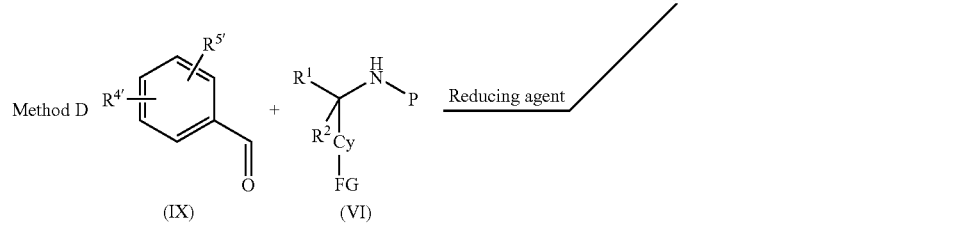

The precursor compounds of formulae (IV), (V), (VI), (VII), (VIII) or (IX) are either commercially available or readily accessible from commercial starting materials. General protocols for such preparation are given below in the Examples, using conditions and methods well known to those skilled in the art.

The transformation of the moiety FG of the precursors of formulae (Z), (II), (IV), (V) and (VI) wherein $R^1$, $R^2$, Cy, Cy', n, P, $R^{4'}$ and $R^{5'}$ are as above defined and wherein FG is a leaving group such as Br, Cl, I, OMs or OTf, into the precursors of formulae (Z), (II), (IV), (V) and (VI) wherein the moiety FG is A (as above defined) can be performed at any stage of the preparation of substituted alkynyl aryl carboxamide derivatives according to the general formula (I) or (I') (see Scheme 4 below). It is recognized by those skilled in the art of organic synthesis that the successful use of these methods is dependent upon the compatibility of substituents on other part of the molecules. Protecting group and/or changes in the order of steps described herein may be required.

Scheme 4

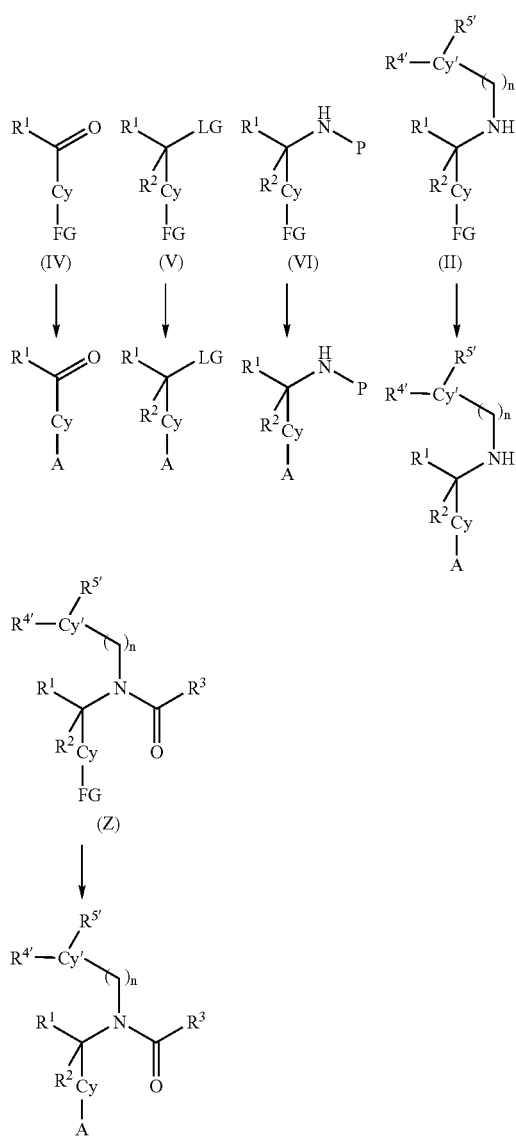

Preferred intermediate compounds (II) are selected from the group consisting of:
6-[(4-Dec-1-ynylbenzyl)amino)-2,2-dimethyl-4H-1,3-benzodioxin-4-one
6-({4-[(4-Butylphenyl)ethynyl]benzyl}amino)-2,2-dimethyl-4H-1,3-benzodioxin-4-one
Methyl(4-{[(4-dec-1-ynylbenzyl)amino]methyl}phenoxy)acetate
Methyl 5-{[(4-dec-1-ynylbenzyl)amino]methyl}-2-(2-methoxy-2-oxoethoxy)benzoate, hydrochloride salt
Methyl(2E)-3-(4-{[(4-dec-1-ynylbenzyl)amino]methyl}phenyl)-acrylate
Ethyl (2E)-3-{4-[(4-dec-1-ynylbenzyl)amino]phenyl}acrylate
Methyl 3-(4-{[(4-dec-1-ynylbenzyl)amino]methyl}phenyl)propanoate
7-({4-[(4-Butylphenyl)ethynyl]benzyl}amino)-2,2-dimethyl-4H-1,3-benzodioxin-4-one
6-[({4-[(4-Butylphenyl)ethynyl]benzyl}amino)methyl]-2,2-dimethyl-4H-1,3-benzodioxin-4-one
Methyl 3-[(4-dec-1-yn-1-ylbenzyl)amino]benzoate hydrochloride
Methyl 4-[({4-[(4-butylphenyl)ethynyl]benzyl}amino)methyl]benzoate
Ethyl 4-({4-[(4-butylphenyl)ethynyl]benzyl}amino)benzoate
Methyl 8-({4-[(4-butylphenyl)ethynyl]benzyl}amino)-5,6,7,8-tetrahydronaphthalene-2-carboxylate
6-({4-[(4-Chlorophenyl)ethynyl]benzyl}amino)-2,2-dimethyl-4H-1,3-benzodioxin-4-one
4-[(4-Butylphenyl)ethynyl]-2-fluorobenzaldehyde
Methyl 8-({4-[(4-fluorophenyl)ethynyl]benzyl}amino)-5,6,7,8-tetrahydro-2-naphthalenecarboxylate
6-[(4-Butylphenyl)ethynyl]nicotinaldehyde
Methyl 5-({4-[(4-butylphenyl)ethynyl]benzyl}amino)-2-fluorobenzoate
Ethyl 3-({4-[(4-butylphenyl)ethynyl]benzyl}amino)-4-fluorobenzoate
7-[((E)-{4-[(4-Chlorophenyl)ethynyl]phenyl}methylidene)amino]-2,2-dimethyl-4H-1,3-benzodioxin-4-one
Methyl 4-({4-[(4-butylphenyl)ethynyl]benzyl}amino)-2-fluorobenzoate
7-({4-[(4-Methoxyphenyl)ethynyl]benzyl}amino)-2,2-dimethyl-4H-1,3-benzodioxin-4-one Thus, precursors of formulae (Z), (II), (IV), (V) or (VI) wherein FG is a leaving group such as Br, Cl, I, OMs or OTf can be reacted with a substituted alkyne, e.g. of formula HC≡C—$R^6$, wherein $R^6$ is as above defined, optionally in the presence of additives, such as copper (I) salts in conjunction with palladium catalysts, (e.g. palladium tetrakis (triphenylphosphine), and amines (e.g. triethylamine). Preferred conditions imply use of copper(I) bromide, palladium tetrakis (triphenyl-phosphine) in triethylamine at e.g. at 90° C.

A preferred process for preparing compounds of formula (II) is sot out in the above Scheme 3, Method A. Therein, the reductive animation of carbonyl compounds of formula (IV) wherein the moiety FG is A (as above defined), with the amines of formula (VII) (P is H) is performed by refluxing them in a suitable solvent (such as toluene with the azeotropic removal of water) to form the intermediate imine followed by its reduction with a reducing agent such as $NaBH_4$ in a suitable solvent such as MeOH. The process thus affords the amino of formula (II) wherein P is H.

According to the methods described in Scheme 2, the resulting amine (II) is coupled with a carboxylic acid derivative (III) such as LG—CO—$R^3$, wherein $R^3$ is as above defined and LG preferably Cl in the presence of a base such as DIEA in an aprotic solvent (such as e.g. DCM or THF), thus affording substituted alkynyl aryl carboxamide derivatives of formula (Z). Subsequent deprotection of $R^{4'}$ and $R^{5'}$ using standard methods and protocols as described below in the Examples affords the desired substituted alkynyl aryl carboxamide derivatives of formula (I) or (I'). For example, compounds of formula (Z) wherein $R^{4'}$ and/or $R^{5'}$ contain an ester group, may be hydrolysed to yield compounds of formula (I) or (I') of this invention by their treatment with hydroxide such as e.g. NaOH in an appropriate protic solvent (such as e.g. EtOH), followed by acidification of the reaction mixture.

According to a further preferred process of preparing compounds of formula (I) & (I') wherein $R^4$ is OH and $R^5$ is $CO_2H$, compounds of formula (Z), wherein $R^{4'}$ and $R^{5'}$ are members of a heterocycle such as a substituted 2,2-dimethyl-4-oxo-4H-1,3-benzodioxin-4-one, may be hydrolysed to yield compounds of formula (I) & (I') of this invention by their treatment with hydroxide such as e.g. NaOH in an appropriate protic solvent (such as e.g. EtOH) at 70° C., followed by acidification of the reaction mixture.

Basic salts of the compounds of formula (I) or (I') are prepared in a conventional manner as is known by those skilled in the art. In particular the N—Me—D-glucamine (i.e. 1-deoxy-1-(methylamino)glucitol), the tromethamine (i.e. 2-amino-2-(hydroxymethyl)-1,3-propanediol) and lysine salts of this invention provide more soluble derivatives in solvents such as water, PBS, PEG or CMC (carboxy methyl cellulose).

The methods of preparation of the substituted methylene amides of formula (I) or (I') of this invention according to the above protocols have the specific advantage of being convenient and economic in the sense that they involve only a few steps.

When employed as pharmaceuticals, alkynyl aryl carboxamides of the present invention are typically administered in the form of a pharmaceutical composition. Hence, pharmaceutical compositions comprising a compound of formula (I) or (I') and a pharmaceutically acceptable carrier, diluent or excipient therefore are also within the scope of the present invention. A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals; alkynyl aryl carboxamides of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of these inventions can be administered by a variety of routes including oral, rectal, transdermal, subcutaneous, intravenous, intramuscular, and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the alkynyl aryl carboxamide according to the invention is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, alkynyl aryl carboxamides of formula (I) or (I') in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 5 of *Remington's Pharmaceutical Sciences*, 20$^{th}$ Edition, 2000, Marck Publishing Company, Easton, Pa., which is incorporated herein be reference.

The compounds of this invention can also be administered in sustained release forms or from sustained release drug delivery systems. A description of representative sustained release materials can also be found in the incorporated materials in *Remington's Pharmaceutical Sciences*.

In the following the present invention shall be illustrated by means of some examples which are not construed to be viewed as limiting the scope of the invention. The following abbreviations are hereinafter used in the accompanying examples: h (hour), g (grain), mg (milligram), mmol (millimole), m.p. (melting point), eq (equivalents), mL (milliliter), μL (microliters), ESI (Electro-spray ionization), L (liters), EtOAc (Ethyl acetate), Boc (tert-Butoxycarbonyl), CDCl$_3$ (deuterated chloroform), CD$_3$OD (Deuterated methanol), CH$_3$CN (Acetonitrile). DBU (Diazabicyclo[5.4.0]undee-7-ene), DCC (Dicyclohexyl carbodiimide), DCM (Dichloromethane), DIC (Diisopropyl carbodiimide), DIEA (Diisopropylethyl-amine), DMAP (4-Dimethylaminopyridine), DMF (Dimethylformamide), DMSO (Dimethylsulfoxide), DMSO-d$_6$, (Deuterated dimethylsulfoxide), EDC (1-(3-Dimethyl-amino-propyl)-3-ethylcarbodiimide), c-Hex (Cyclohexane), EtOAc (EtOAc), Et$_2$O (Diethyl ether), EtOH (Ethanol), Fmoc (9-Fluorenylmethoxycarbonyl), i-PrOH (2-propanol), K$_2$CO$_3$ (Potassium carbonate), MeOH (Methanol), MgSO$_4$ (Magnesium sulfate), min. (minute), MTBE (Methyl tert-butyl ether), NaHCO$_3$ (Sodium bicarbonate), NaBH, (Sodium borohydride), NaBH₃CN (Sodium cyanoborohydride), NaBH(OAc)₃ (Sodium triacetoxy-borohydride), NMM (N-methyl-morpholine), Pd(PPh₃)₄ (Tetrakis triphenylphosphine palladium), PetEther (Petroleum ether), rt (room temperature), PyBOP® (Benzotriazole-1-yl-oxy-tris-pyrrolidino-phosphonium hexafluorophosphate), Rt (retention time), SPE (solid phase extraction), TBTU (2-(1-H-benzotriazole-1-yl)-1,1,3,3-tetramethyluromium tetrafluoroborate), TEA (Triethylamine), TFA (Trifluoroacetic acid), TFAA (Trifluoro-acetic acid anhydride), THF (Tetrahydrofuran).

The HPLC data provided in the examples described below were obtained as followed. HPLC: Waters Symmetry C₈ column 50 mm×4.6 mm; UV detection (maxplot); flow: 2 mL/min; Conditions: 8 min gradient from 0.1% TFA in H₂O to 0.07% TFA in CH₃CN. The MS data provided in the examples described below were obtained as followed: Mass spectrum: LC/MS Waters ZMD (ESI). The NMR data provided in the examples described below were obtained as followed: ¹H-NMR: Bruker DPX-300 MHz.

EXAMPLES

Intermediate I 7-amino-2,2-dimethyl-4H-1,3-benzodioxin-4-one

Step a) Formation of 4-{[(benzyloxy)carbonyl]amino}-2-hydroxybenzoic acid

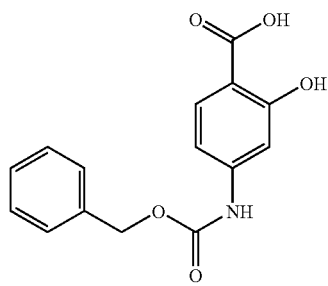

To a solution of sodium-p-aminosalicylate (100 g, 0.65 mol) in 10% aqueous NaOH solution (1 L) was added a 50% wt solution of benzyl chloroformate (670 g, 1.96 mol in toluene) at 0° C. and stirred at rt for 48 h. The reaction mixture was cooled and acidified with a 10% aqueous HCl at 0° C. The solid obtained was filtered and washed with cold water and dried. The solid was treated with PetEther and filtered to give the title compound (129 g, 68%) used in the next steps without further purification.

Step b) Formation of benzyl 2,2-dimethyl)-4-oxo-4H-1,3-benzodioxin-7-ylcarbamate

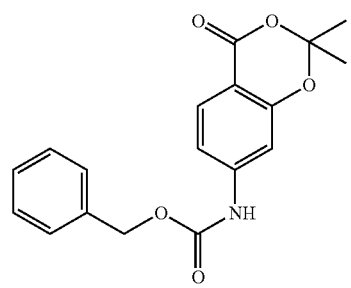

To a suspension of 4-{[(benzyloxy)carbonyl]amino}-2-hydroxybenzoic acid (25 g, 0.087 mol) in TFA (108 mL) was added trifluoroacetic anhydride (TFAA, 35 mL, 0.249 mol) at rt with stirring. To this was added 60 mL of dry acetone in portions (each 4 h interval) and the reaction mixture was refluxed at 60° C. for 24 h. Excess TFA and TFAA was removed under vacuum to give crude product. The crude was purified by column chromatography over silica gel (treated with triethylamine) using CH₂Cl₂ as an eluent to give mixture of two compounds: benzyl 2,2-dimethyl-4-oxo-4H-1,3-benzodioxin-7-ylcarbamate (3.5 g) and 7-amino-2,2-dimethyl-4H-1,3-benzodioxin-4-one (1.6 g).

Step c) Formation of 7-amino-2,2-dimethyl-4H-1,3-benzodioxin-4-one

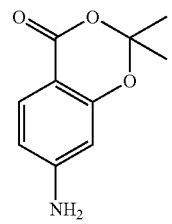

To a solution of benzyl 2,2-dimethyl-4-oxo-4H-1,3-benzodioxin-7-ylcarbamate (3.5 g) in methanol (250 mL) was added Pd/C (350 mg) and hydrogenated under 2 Kg of pressure for 24 h. The reaction mixture was filtered through a bed of celite and concentrated to give the title compound (1.6 g).

Intermediate II 6-amino-2,2-dimethyl-4H-1,3-benzodioxin-4-one

Step a) Formation of 2,2-dimethyl-6-nitro-4H-1,3-benzodioxin-4-one

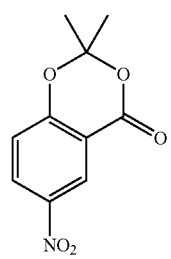

A mixture of 2-hydroxy-5-nitrobenzoic acid (50.0 g. 0.27 mol), acetone (40 mL, 0.54 mol) and trifluoroacetic anhydride (100 mL, 0.71 mol) in TFA (300 mL) was heated at reflux. After 1 hour, a supplementary amount of acetone (60 mL, 0.82 mol) was added and the reaction mixture was refluxed for 48 hours. The solvents were evaporated under reduced pressure. The residual brown solid was dissolved in DCM (800 mL) and washed with a mixture of saturated aqueous NaHCO₃ (400 mL) and water (400 mL). The aqueous layer was extracted with DCM (2×400 mL). The combined organic layers were dried over MgSO₄ and the solvent was removed under reduced pressure. The residual brown oil was taken up in cold pentane (300 mL, 0° C.) and a yellow solid precipitated off. Filtration and washing with pentane gave 53.8 g (88%) of the title compound as a yellow solid.

HPLC, Rt: 2.9 min (purity: 99.8%). $^1$H NMR (CDCl$_3$) δ: 8.88 (d, J=2.8 Hz, 1H), 8.44 (dd, J=9.0, 2.8 Hz, 1H), 7.14 (d, J=9.0 Hz, 1H), 1.80 (s, 6H).

Step b) Formation of
6-amino-2,2-dimethyl-4H-1,3-benzodioxin-4-one

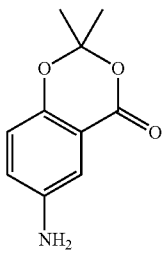

To a solution of 6-nitro-2,2-dimethyl-4H-1,3-benzodioxin-4-one (4.1 g) in EtOH (30 mL) was added Pd/C (1.947 g) under nitrogen atmosphere and then hydrogenated for 12 h at rt. The reaction mixture was filtered through a bed of celite, washed with EtOH and THF. The filtrates were concentrated under vacuum to give the title compound as pale yellow solid (3.5 g, 98%). $^1$H NMR (CDCl$_3$) δ 7.71 (d, J=8.7 Hz, 1H), 7.15 (d, J=2.6 Hz, 1H), 6.83 (dd, J=8.7 Hz, 2.6 Hz, 1H), 3.44 (brs, 2H), 2.63 (s, 6H).

Intermediate III 6-(aminomethyl)-2,2-dimethyl-4H-1,3-benzodioxin-4-one

Step a) Formation of methyl-5-bromosalicylate

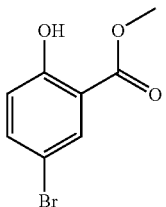

To a solution of 5-bromosalicylic acid (200 g, 0.92 mol) in methanol (2 L) was added thionylchloride (440 g, 3.7 mol) at 0° C. with stirring and then allowed to reflux at 70° C. for 40 h. Excess solvent was distilled off and to the crude residue was added EtOAc (2 L). The organic layer was washed with 10% cold aqueous NaHCO$_3$ solution (2×1 L), brine and dried. The solvent was removed under vacuum to give the title compound as a low melting point solid (190 g, 89%). TLC: PetEther/EtOAc, 7:3, R$_f$: 0.6

Step b) Formation of methyl-5-cyano salicylate

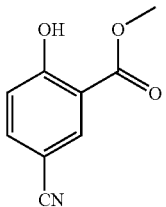

To a solution of methyl-5-bromosalicylate (190 g, 0.822 mol) in dry DMF (1.75 L) was added CuCN (175 g, 1.94 mol) and the reaction mixture was heated to 140° C. with stirring under N$_2$ for 20 h. The reaction mixture was cooled, quenched with water (4 L) and stirred for 45 min. The product was extracted with EtOAc (3×1.5 L), dried and concentrated to give crude product. The aqueous layer was acidified with 1.5 N HCl to pH 3 and further extracted with EtOAc (2×1 L). The combined organic layer was dried and concentrated. The crude product was treated with 10% chloroform in PetEther (200 mL) and the solid filtered off. The solid was further washed with 3% EtOAc in PetEther (200 mL) and dried to give the title compound (80 g, 55%). TLC: PetEther/EtOAc, 8:2. R$_f$: 0.6

Step c) Formation of 5-cyano salicylic acid

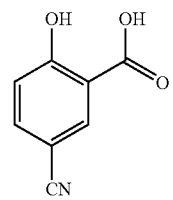

To a suspension of methyl-5-cyano salicylate (80 g, 0.45 mol) in methanol (400 mL), THF (400 mL) and water (200 mL) was added LiOH (32 g, 1.35 mol) and stirred at rt for 20 h. The reaction mixture was concentrated under vacuum, acidified with 1.5 N HCl to pH 3 and the solid obtained filtered off. The solid was dried by azeotropic removal of water using toluene to give the title compound (60 g, 81%). TLC: PetEther/EtOAc, 7:3, R$_f$: 0.1

Step d) Formation of 2,2-dimethyl-4-oxo-4H-1,3-benzodioxine-6-carbonitrile

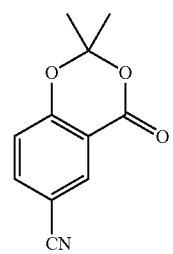

To a suspension of 5-cyano salicylic acid (60 g, 0.368 mol) in TFA (134 mL, 1.76 mol) and TFAA (45 mL, 0.32 mol) was added dry acetone (20 mL) and heated to reflux. After each 1 h interval was added 15 mL of dry acetone for 4 times and the reflux continued for 20 h. The reaction mixture was concentrated under vacuum and crude purified by flash column chromatography over silica gel (230-400 mesh) using CH$_2$Cl$_2$ as an eluent to give the title compound as a white solid (12 g, 15%). TLC: CH$_2$Cl$_2$ (100%), R$_f$: 0.5

Step e) Formation of 6-(aminomethyl)-2,2-dimethyl-4H-1,3-benzodioxin-4-one acetate

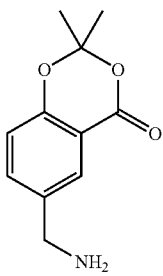

To a solution of 2,2-dimethyl-4-oxo-4H-1,3-benzodioxine-6-carbonitrile (12 g, 0.06 mol) in methanol (500 mL) was added glacial acetic acid (3.5 g, 0.059 mol) and passed $N_2$ for 30 min. To this was added Pd/C (2.4 g, 20%) and hydrogenated under 2 Bars of pressure for 22 h. The reaction mixture was filtered through celite and filtrate concentrated under vacuum. To the solid was added EtOAc (200 mL), stirred for 20 h and filtered. The solid was dried under vacuum to give 6-(aminomethyl)-2,2-dimethyl-4H-1,3-benzodioxin-4-one acetate (6 g, 38%). TLC:CHCl$_3$/MeOH, 9:1, $R_f$: 0.15

Intermediate IV methyl [4-(aminomethyl)phenoxy]acetate, acetate salt

Step a) Formation of methyl (4.formylphenoxy)acetate

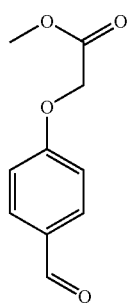

To a solution of 4-hydroxybenzaldehyde (100 g, 0.818 mol) in dry DMF (1 L) was added potassium carbonate (260 g, 1.88 mol) and KI (10 g) with stirring at rt. The reaction mixture was slowly heated to 40° C. and added methylbromoacetate (104 g, 0.67 mol) with stirring and heated to 70° C. for 4 h. The reaction mixture was cooled to rt, filtered off the solid and filtrate was diluted with water (1.5 L). The aqueous mixture was extracted with EtOAc (3×750 mL), washed with 2.5% aqueous NaOH solution (2×400 mL), water and dried. The solvent was removed under vacuum to give the title compound a slight yellow solid (112 g).

Step b) Formation of methyl {4-[(hydroxyimino)methyl]phenoxy}acetate

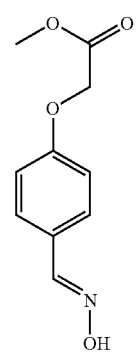

A solution of methyl-(4-formylphenoxy)acetate (100 g, 0.515 mol) in methanol (500 mL) was cooled to 0-5° C. To this was added a solution of hydroxylamine hydrochloride (54 g) and sodium acetate (64 g) in water (500 mL) drop-wise and stirred at rt for 6 h. The reaction mixture diluted with water and filtered off the solid. The solid was washed with water and dried under vacuum to give the title compound (80 g, 74%).

Step c) Formation of methyl [4-(aminomethyl)phenoxy]acetate, acetate salt

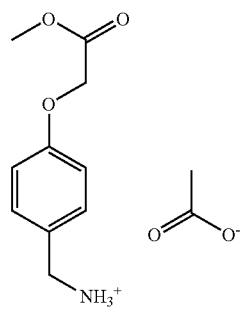

To a solution of methyl {4-[(hydroxyimino)methyl]phenoxy}acetate (30 g, 0.14 mol) in methanol (650 mL) was added glacial acetic acid (6.8 g) and passed $N_2$ for 30 min. To this was added Pd/C (10%, 3 g) and hydrogenated under 2 bars of pressure for 12 h. The reaction mixture was concentrated under vacuum. The crude product was treated with EtOAc (500 mL) and the white product filtered off The solid was dried under vacuum to give the title compound (29 g, 81%).

Intermediate V methyl 5-(aminomethyl)-2-(2-methoxy-2-oxoethoxy)benzoate, acetate salt

Step a) formation of methyl 5-cyano-2-(2-methoxy-2-oxoethoxy)benzoate

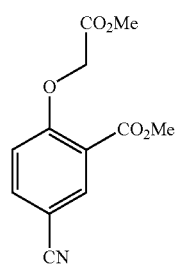

To a suspension of methyl-5-cyano salicylate (40 g, 0.22 mol) and potassium carbonate (41.4 g, 0.300 mol) in DMF (300 mL)) was added methylbromoacetate (34.4 g, 0.225 mol) and the reaction mixture heated to 80° C. for 15 h. The reaction mass was cooled and potassium carbonate was filtered off. The filtrate was diluted with water (1.5 L) and the product was extracted into EtOAc (3×200 mL). The combined organic layers were washed with brine, dried and evaporated to give the title compound as a liquid (52 g, 92%). TLC: PetEther/EtOAc, 8:2, Rf: 0.8

Step b) Formation of methyl 5-(aminomethyl)-2-(2-methoxy-2-oxoethoxy)benzoate, acetate salt

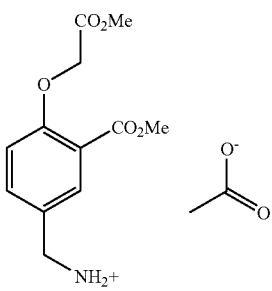

To a solution of methyl-5-cyano-2-(2-methoxy-2-oxoethoxy)benzoate (5 g, 0.02 mol) in methanol (1 L) was added glacial acetic acid (1.1 g, 0.02 mol) and passed $N_2$ for 30 min. To this was added Pd/C (1.5 g, 35%) and hydrogenated under 2.5 Kg of pressure for 24 h. The reaction mixture was filtered and filtrate concentrated under vacuum (temp. 38° C. under $N_2$). To the crude residue was added 100 mL of EtOAc and again removed under vacuum at same temp. The solid was treated with 100 mL EtOAc, stirred for 2 h, filtered and dried to give the title compound as a white powder (2.25 g, 35%). TLC: chloroform/methanol, 9:1, $R_f$: 0.15

Intermediate VI methyl (2E)-3-[4-(aminomethyl)phenyl]acrylate, hydrochloride salt

Step a) Formation of methyl-(4-aminomethyl)benzoate

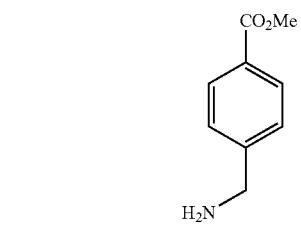

To a solution of (4-aminomethyl)benzoic acid (125 g, 0.83 mol) in methanol (1.5 L) was added thionylchloride (350 g, 3 eq.) at 0° C. with stirring and then allowed to stir at rt for overnight and finally refluxed at 60° C. for 12 h for the completion of the reaction. The reaction mixture was concentrated and crude hydrochloric salt was neutralized using 10% aqueous $NaHCO_3$ solution to pH 8. The aqueous layer was concentrated and kept at 0° C. overnight. The solid obtained was filtered, washed with cold water and dried under suction to give the title compound (112 g, 82%).

Step b) Formation of methyl (N-Boc-4-aminomethyl)benzoate

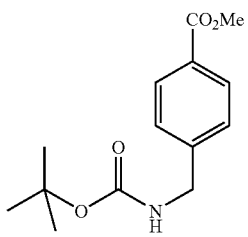

To a solution of methyl-(4-aminomethyl)benzoate (112 g, 0.678 mol) in methanol (2 L) was added DMAP (16.5 g, 0.13 mol) and Boc-anhydride (236 g, 1.08 mol) at rt and allowed to stir for 16 h. The reaction mixture was concentrated under vacuum and crude diluted with $CH_2Cl_2$ (500 mL). The residue was filtered off and filtrate washed with citric acid (10%, 2×250 mL), brine (200 mL) and dried. The solvent was removed under vacuum to give the title compound (118 g, 71%).

Step c) Formation of N-Boc-(4-hydroxymethyl)benzylamine

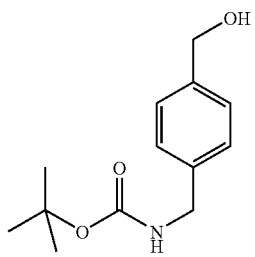

To a suspension of LAH (8.6 g, 0.226 mol) in dry THF (700 mL) was added a solution of methyl (N-Boc-4-aminomethyl) benzoate (50 g, 0.188 mol) in THF (300 mL) at −40° C. with stirring and stirred for 6 h. The reaction mixture was quenched with an aqueous NaOH solution (10% of 40 mL) at −30° C. The reaction mixture was filtered, washed with THF and concentrated under vacuum to give, the title compound as white solid (41 g, 91%)

Step d) Formation of (N-Boc-4-aminomethyl)benzaldehyde

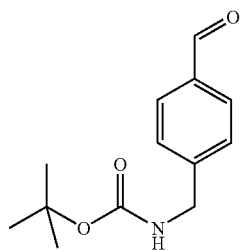

To a suspension of $MnO_2$ (600 g) in dry DCM (3 L) was added a solution of N-Boc-(4-hydroxymethyl)benzylamine (90 g) in 500 mL of DCM at rt over 30 min and allowed to stir 3 h. The reaction mixture was filtered and filtrate concentrated under vacuum to give the title compound (88 g, 97%).

Step e) Formation of 4-(N-Boc aminomethyl) cinnamic acid

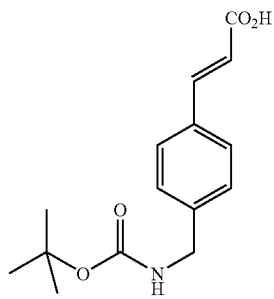

To a solution of (N-Boc-4-aminomethyl)benzaldehyde (50 g, 0.212 mol) in pyridine (600 mL) was added malonic acid (55 g. 0.53 mol) and piperidine (5 mL) with stirring at rt. The reaction mixture was allowed to reflux at 105° C. for 3 h. The reaction mixture was cooled and concentrated under vacuum. The solid residue obtained was treated with 10% aqueous citric acid solution. The solid was filtered, washed with cold water (2 L) and dried to give the title compound (58 g, 97%).

Step f) Formation of methyl (2E)-3-[4-(aminomethyl)pentyl]acrylate, hydrochloride salt

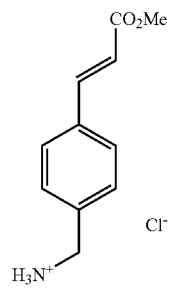

To a mixture of 4-(N-Boc-aminomethyl) cinnamic acid (5 g, 0.018 mol) in methanol (200 mL) was added thionylchloride (11 g) at 0° C. and slowly heated to reflux for 3 h. The reaction mixture was concentrated to give solid product. The solid hydrochloride salt was washed with EtOAc and filtered off to give the title compound (3.5 g, 86%).

Intermediate VII methyl 3-[4-(aminomethyl)phenyl]propanoate, hydrochloride salt

Step a) Formation of methyl (2E)-3-(4-cyanophenyl)acrylate

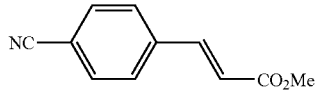

To a solution of 4-bromobenzonitrile (25 g, 0.136 mol) and methylacrylate (58.6 g, 0.682 mol) in dry DMF (250 mL) was added $PPh_3$ (2.8 g, 0.0106 mol), $Pd(OAc)_2$ (1.3 g, 0.00579 mol), sodium bicarbonate (18 g, 0.214 mol) and triethylamine (25 mL). The reaction mixture was heated to 100° C. for 16 h under nitrogen. The reaction mixture was cooled and the solid was filtered off. The filtrate was diluted with water (1 L) and the product was extracted with diethyl ether (4×200 ml). The combined organic layer was washed with water, brine, dried and evaporated to yield the crude product which was purified by chromatography ($SiO_2$, PetEther/EtOAc (9.5/0.5) as eluent) to yield the title compound as a liquid (18 g, 71%). TLC: PetEther/EtOAc (9.5/0.5); $R_f$: 0.75

Step b) Formation of methyl 3-[4-(aminomethyl)phenyl]propanoate

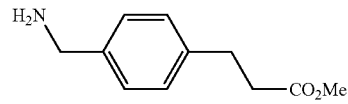

To solution of methyl (2E)-3-(4-cyanophenyl)acrylate (18 g, 0.096 mol) in methanol (200 ml) was added Pd/C (1.8 g) and hydrogenated under a pressure of 50 psi of hydrogen for 12 h. The catalyst was filtered off and the filtrate was concentrated to a residue. The residue was purified by chromatography (SiO$_2$, chloroform/methanol 9/1) to yield the title compound as a liquid (16 g, 86%). TLC:CHCl$_3$/MeOH (9/1); R$_f$: 0.3

Intermediate VIII methyl 8-amino-5,6,7,8-tetrahydronaphthalene-2-carboxylate.AcOH Step a) Formation of methyl 8-oxo-5,6,7,8-tetrahydronaphthalene-2-carboxylate

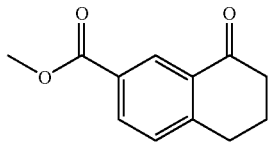

To a solution of 8-oxo-5,6,7,8-tetrahydronaphthalene-2-carboxylic acid (16 g, 0.084 mol) in MeOH was added thionylchloride (23 g, 0.2 mol). The mixture was then stirred at rt for 12 h. The solvent was removed under vacuum and the residue was taken up in EtOAc (200 ml). The organic layer was washed with a 10% aqueous solution of NaHCO$_3$, dried over MgSO$_4$ and evaporated to give 16 g (94%) of the titled compound as a liquid. TLC: Chloroform/MeOH (9/1), R$_f$=0.9.

Step b) Formation of methyl(8E)-8-(hydroxyimino)-5,6,7,8-tetrahydronaphthalene-2-carboxylate

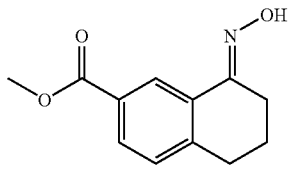

To a solution of methyl 8-oxo-5,6,7,8-tetrahydronaphthalene-2-carboxylate (10 g, 0.048 mol) in MeOH (100 ml) was added hydroxylamine hydrochloride (5 g, 0.07 mol), followed by sodium acetate (6 g, 0.072 mol). The reaction mixture was stirred at rt for 1 h and heated to 50° C. for 15 h. The solvent was removed under vacuum and the residue was diluted with water. The product was extracted with EtOAc (2×150 ml), dried and evaporated to yield 10 g (93%) of the titled compound as a solid. TLC-Chloroform/MeOH (9/1), R$_f$=0.3.

Step c) methyl 8-amino-5,6,7,8-tetrahydronaphthalene-2-carboxylate.AcOH

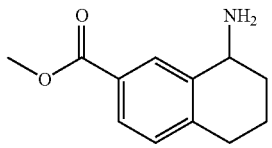

To a mixture of methyl (8E)-8-(hydroxyimino)-5,6,7,8-tetrahydronaphthalene-2-carboxylate (10 g, 0.045 mol) and Pd-C (1 g) in MeOH (250 ml) was added acetic acid (2.75 g, 0.045 mol). Hydrogenation was then performed under pressure of 30 psi of hydrogen for 20 h. The catalyst was filtered off and the filtrated evaporated to yield 8.5 g (71%) of the titled compound as a solid. TLC-Chloroform/MeOH (8/2), R$_f$=0.2. $^1$H NMR (DMSO-$d_6$) δ: 8.12 (d, J=1.4 Hz, 1H), 7.70 (dd, J=1.8, 7.9 Hz, 1H), 7.20 (d, J=8.0 Hz. 1H), 5.66 (brs, 2H). 3.96 (m, 1H), 3.82 (s, 3H), 2.75 (m, 2H), 1.86-1.96 (m, 5H), 1.64 (m, 2H).

Procedure A: Reductive Animation (Scheme 3, Method A)

A solution of aldehyde (0.90-1.1 eq.) and amine (0.90-1.1 eq.) in toluene (0.1-1 M) was heated at reflux for 1 to 24 h with azeotropic removal of water (1 eq of DIEA was added with amine being used as an acetic acid or hydrochloride salt). The toluene was evaporated off under reduced pressure. The residue was taken up in methanol (0.1-1 M) and cooled to 0° C. An appropriate volume of anhydrous THF was added to improve solubility if necessary. NaBH$_4$ (1-8 eq.) was added portionwise and the reaction mixture was stirred at 0° C. for 1-5 h. The reaction mixture was poured into water (0.1-1 M) and extracted with Et$_2$O. The organic layers were washed with brine, combined and dried over MgSO$_4$. The solvent was removed under reduced pressure to give the crude product. The product was purified either by flash chromatography on silicagel, by crystallization from an appropriate solvent (e.g. MeOH) or by precipitation of the hydrochloride salt in ether, MeOH or i-PrOH.

Procedure B: Formation of the Amides

To a cold (0° C.) solution of amine (1.0 eq.) and DIEA or TEA (1.0-1.2 eq. when the amine is used as a free base, or 2.0-3.0 eq. when the amine is used as a salt) in anhydrous DCM (0.1-1 M) was added a (0.1-1 M) DCM solution of the acyl chloride (1.0-1.2 eq.). The mixture was stirred 1-3 h at 0° C. then 1-14 h at rt. Water was added and the resulting mixture partitioned. The aqueous layer was extracted with DCM. The combined organic layers were washed with an aqueous solution of HCl 1N, a saturated aqueous solution of NaHCO$_3$, brine, dried over MgSO$_4$, filtered and evaporated to give the crude product. The product was then purified by flash chromatography on silicagel.

Procedure C: Deprotection of the Lactone (i.e. the 2,2-dimethyl-4H-1,3-benzodioxin-4-one moiety)

To a solution of lactone in EtOH or MeOH (0.1-1 M) was added an aqueous solution of NaOH (1N or 5N, 5 eq.) and the resulting mixture was stirred at 70° C. for 3-7 h (reaction followed by HPLC). After completion of the reaction, an aqueous solution of HCl (1N) was added and the resulting mixture was extracted with Et$_2$O or EtOAc. The combined organic layers were dried over MgSO$_4$, filtered and evaporated to give the desired product. The is product was used without further purification or purified by crystallization from appropriate solvent (e.g. MeOH).

Procedure D: Formation of an Ammonium Salt

To a solution of the acid (1.0 eq.) in EtOH, MeOH or THF (0.1-1 M), was added the amine (e.g. tris (hydroxymethyl) amino methane or N-methyl-D-glucamine) (1.0 eq) neat or as a water solution (0.1-1M). The resulting mixture was stirred until a homogeneous solution was obtained. The solvent was removed in vacuum and the residue was dissolved in a 9/1 mixture of H$_2$O/EtOH. The resulting solution was then lyophilized to afford the title compound as a powder.

Procedure E: Formation of the Amides with Polymer-Supported Tertiary Amines

To a cold (0° C.) solution of amine (1.0 eq.) was added the morpholinomethyl polystyrene resin (Novabiochem, HL, 3.8 mmol/g, 1.0-1.5 eq.) in anhydrous DCM or THF (0.01-0.1 M). Then a (0.1-1 M) DCM or THF solution of the acyl chloride (1.0-1.2 eq.) was added. The mixture was shaken for 1 h at 0° C. then overnight a rt. Then PL-AMS-Resin (Polymer Laboratories, 1.93 mmol/g, 1.0-1.5 eq.) was added and the mixture was shaken overnight at rt. Filtration of the resins gave the desired product after evaporation. Purification by flash chromatography on silicagel was performed if necessary.

Procedure F: Hydrolysis of Esters

To a solution of ester in MeOH or THF (0.01-0.2M) was added all aqueous solution of NaOH (1N or 5N, 1-25 eq.) or LiOH (1-10 eq) and the resulting mixture was stirred at rt or 70° C. for 0.5-24 h (reaction followed by HPLC or TLC). After completion of the reaction, an aqueous solution of HCl (1N) was added and the resulting mixture was extracted with $Et_2O$ or EtOAc. The combined organic layers were dried over $MgSO_4$ or $Na_2SO_4$, filtered and evaporated to give the desired compound.

Procedure G: Formation of the Amides in Pyridine

To a cold (0° C.) solution of amine (1.0 eq.) in pyridine (0.1-1M) was added neat the acyl chloride (1.5 eq). The resulting mixture was stirred at 0° C. for 1-5 h. Then PL-AMS-Resin (Polymer Laboratories, 1.93 mmol/g, 1.0-1.5 eq.) was added and the mixture was stirred at rt for 1-15 h. After filtration of the resin, the mixture was diluted with aqueous HCl (1N) and extracted with DCM. The combined organic layers were dried over $MgSO_4$, filtered and concentrated under reduced pressure. The residue was purified by flash chromatography on silicagel to give the desired compound.

Procedure H: Formation of the Amides with Polymer-Supported Reagents

To a solution of the carboxylic acid (1.5-3.0 eq) and HOBT (2.0-3.0 eq) in DCM (0.05-0.5 M) (an appropriate volume of DMF could be added for a total dissolution) was added PS-carbodimide (1.5-2.0 eq). After 15 min at rt, the amine (1.0 eq) was added and the resulting mixture was stirred at rt for 10-15 hours. The resin was removed by filtration and rinsed with DCM. Trisamine resin (5-10 eq) was added to the filtrate and stirred at rt for six additional hours. Then the resin was removed by filtration and rinsed by DCM. The solvent was evaporated under reduced pressure to give the crude product. The product was used without further purification or purified by flash chromatography.

Procedure I: Formation of the Amides Under Microwave Conditions

A solution of amine (1.0 eq), acyl chloride (2 eq) and DIEA (3 eq) in anhydrous THF (0.1-1.0M) was heated at 130° C. for 15-60 min under microwave conditions. An aqueous solution of HCl 1N was added and the resulting mixture was extracted with $Et_2O$. The combined organic layers were dried over $MgSO_4$, filtered and evaporated to give the crude product. Purification was performed by flash chromatography or by crystallization in appropriate solvent (e.g. MeOH).

Procedure J: Formation of the Amides Using Polymer-Supported Scavengers

To a solution of the amine (1.0 eq) and DIEA (1.0-1.2 eq when the amine was used as a free base, or 2.0-3.0 eq when the amine was used as a salt) in anhydrous DCM (0.1-1M) was added the acyl chloride (1.0-1.2 eq)). The mixture was stirred at rt for 1-12 hours. Then PL-AMS resin (Polymer Laboratories, 1.93 mmol/g, 1.0-1.5 eq) was added and stirred for 5 additional hours. The resin was removed by filtration. The filtrate was washed with an aqueous solution of HCl 1N, dried over $Na_2SO_4$ and the solvent was removed under reduced pressure to give the crude product. The product was used without further purification or purified by flash chromatography.

Procedure K: Formation of the Amides Using Polymer-Supported Scavengers

To a solution of the amine (1.0 eq) and DIEA (1.0-1.2 eq when the amine was used as a free base or 2.0-3.0 eq when the amine was used as a salt) in anhydrous DCM (0.1-1M) was added the acyl chloride (1.0-1.2 eq)). The mixture was stirred at rt for 1-12 hours. Then PL-AMS resin (Polymer Laboratories, 1.93 mmol/g, 1.0-1.5 eq) was added and stirred for 5 additional hours. The resin was removed by filtration through a SPE column (International Sorbent Technology, Isolute SCX) using $Et_2O$ as eluant. The solvents were evaporated under reduced pressure to give the crude product. The product was used without further purification or purified by flash chromatography.

Procedure L: Reductive Animation with Sodium Triacetoxyborohydride

A solution of the amine (1.0 eq), aldehyde (1.0 eq), acetic acid (1.5 eq) and sodium triacetoxyborohydride (1.5 eq) in DCE (0.1-1M) was stirred at rt for 6-12 hours. The reaction mixture was diluted with DCM and washed with a saturated aqueous solution of $NaHCO_3$, brine and dried over $MgSO_4$. The solvents were removed under reduced pressure to give crude product, which was used without further purification or purified by flash chromatography.

Procedure M: Formation of the Amides in THF

To a solution of amine (1.0 eq.) and DIEA (1.0-2.0 eq. when the amine is used as a free base, or 2.0-3.0 eq. when the amine is used as a salt) in anhydrous THF (0.1-1 M) was added the acyl chloride (1.0-2.0 eq.). Then the reaction mixture was stirred 1-18 h at reflux. The reaction mixture was diluted with $Et_2O$ and washed with an aqueous solution of HCl 1N and saturated aqueous solution of $NaHCO_3$. The aqueous layers were extracted with $Et_2O$ (2×). The combined organic layers were dried over $MgSO_4$, filtered and evaporated to give the crude product. The product was then purified by flash chromatography on silicagel or by crystallization from an appropriate solvent (e.g. $Et_2O$/pentane).

Procedure N: Alcynes coupling reaction

To a solution of the aryl bromide (1.0 eq) and TEA (3.0 eq) in degassed anhydrous THF (0.1-1.0 M) was added a catalytic amount of tetrakis(triphenylphosphine)palladium and CuBr in a ration 1:3. The reaction mixture was heated at 70° C. After 5 min, the alcyne was added. After 1-15 h at 70° C., the reaction mixture was diluted with an aqueous solution of HCl 5N and extracted with Et2O. The combined organic layers were dried over Na2SO4, filtered and evaporated to give the crude product. The product was then purified by flash chromatography on silicagel or by crystallization in appropriate solvent (e.g. MTBE).

Example 1

5-[(3-cyclopentylpropanoyl)(4-dec-1-ynylbenzyl)amino]-2-hydroxybenzoic acid

Step a) Formation of 4-dec-1-ynylbenzaldehyde

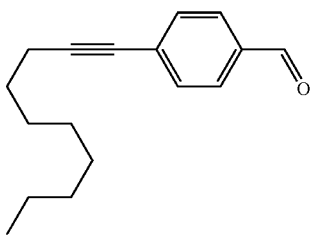

To a solution of 4-bromobenzaldehyde (30.0 g, 162.2 mmol), 1-decyne (26.9 g, 35 mL, 194.6 mmol), CuI (309 mg, 1.62 mmol) and of Et₃N (68 mL) in anhydrous THF (450 mL) were added PPh₃ (1.7 g, 6.49 mmol) and Pd(OAc)₂ (728 mg). The reaction mixture was refluxed under argon for 1 hour. After cooling to rt, the solution was concentrated under reduced pressure and the residual oil was dissolved in hexane (480 mL). The solution was washed with an aqueous solution of HCl (0.1N, 1×), brine (2×), water (2×), dried over MgSO₄, filtered and concentrated under reduced pressure to give a brown oil. Purification by chromatography on silicagel (c-Hex/EtOAc 20/1) gave the title compound as a yellow solid (34.7 g, 88%). $^1$H NMR (CDCl₃) δ 9.97 (s, 1H), 7.78 (d, J=8.7 Hz, 2H), 7.51 (d, J=8.3 Hz, 2H), 2.42 (t, J=7.0 Hz, 2H), 1.67-1.55 (m, 2H), 1.50-1.38 (m, 2H), 1.36-1.21 (m, 8H), 0.87 (m, 3H). HPLC, Rt: 5.50 min (purity: 93.2%).

Step b) Formation of 6-[(4-dec-1-ynylbenzyl)amino]-2,2-dimethyl-4H-1,3-benzodioxin-4-one

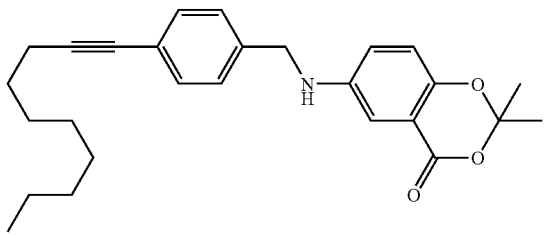

The title compound was prepared following the procedure A using 4-dec-1-ynylbenzaldehyde and 6-amino-2,2-dimethyl-4H-1,3-benzodioxin-4-one (purification by flash chromatography on SiO₂, EtOAc/c-Hex 10/90 up to 40/60 in 45 min.) as a colorless oil (55%). HPLC, Rt: 5.9 min (purity: 99.4%). $^1$H NMR (CDCl₃) δ 7.29 (d, J=8.3 Hz, 2H), 7.19 (d, J=8.3 Hz, 2H), 7.09 (d, J=2.6 Hz, 1H), 6.79-6.67 (m, 2H), 4.21 (s, 2H), 4.18 (brs, 1H), 2.31 (t, J=7.2 Hz, 2H), 1.62 (s, 6H), 1.57-1.45 (m, 2H), 1.43-1.31 (m, 3H), 1.30-1.12 (m, 7H), 0.80 (t, J=7.2 Hz, 3H)

Step c) Formation of 3-cyclopentyl-N-(4-dec-1-ynylbenzyl)-N-(2,2-dimethyl-4-oxo-4H-1,3-benzodioxin-6-yl)propanamide

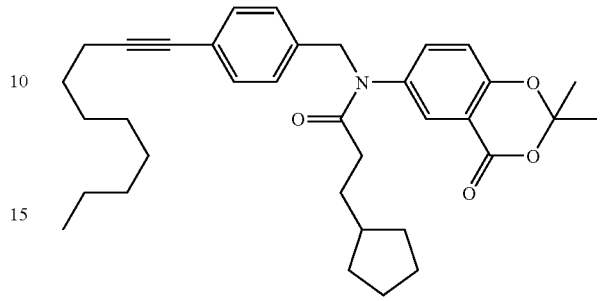

The title compound was prepared following the procedure B using 6-[(4-dec-1-ynylbenzyl)amino]-2,2-dimethyl-4H-1,3-benzodioxin-4-one and 3-cyclopentylpropanoyl chloride (purification by flash chromatography on SiO₂ EtOAc/c-Hex 20/80) as a colorless oil (97%). $^1$H NMR (CDCl₃) δ: 7.68 (d, J=2.3 Hz, 1H), 7.30 (d, J=7.7 Hz, 2H), 7.09 (d, J=7.7 Hz, 2H), 7.06-6.99 (m, 1H), 6.90 (d, J=8.7 Hz, 1H), 4.85 (s, 2H), 2.39 (t, J=7.2 Hz, 2H), 2.13-2.01 (m, 2H), 1.75 (s, 6H), 1.70-1.20 (m, 21H), 1.04-0.83 (m, 5H). HPLC, Rt: 6.6 min (purity: 99.7%).

Step d) Formation of 5-[(3-cyclopentylpropanoyl)(4-dec-1-ynylbenzyl)amino]-2-hydroxybenzoic acid

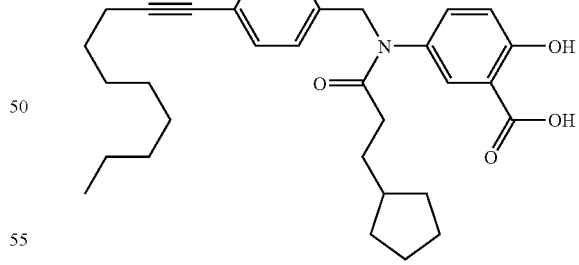

The title compound was prepared following the procedure C using 3-cyclopentyl-N-(4-dec-1-ynylbenzyl)-N-(2,2-dimethyl-4-oxo-4H-1,3-benzodioxin-6-yl)propanamide as a colorless oil (97%). $^1$H NMR (CDCl₃) δ: 10.70 (s, 1H), 7.51 (d, J=2.3 Hz, 1H), 7.23 (d, J=7.9 Hz, 2H), 7.03 (d, J=8.3 Hz, 2H), 6.95-6.80 (m, 2H), 4.77 (s, 2H), 2.31 (t, J=6.8 Hz, 2H), 2.40 (t, J=7.2 Hz, 2H), 1.65-1.15 (m, 21H), 0.95-0.74 (m, 5H). M$^-$ (ESI): 502.3; M$^+$ (ESI): 504.2. HPLC, Rt: 6.1 min (purity: 99.8%).

Example 2

5-[(3-cyclopentylpropanoyl)(4-dec-1-ynylbenzyl)amino]-2-hydroxybenzoic acid. N-methyl-D-glucamine (i.e. 1-deoxy-1-(methylamino)glucitol) salt

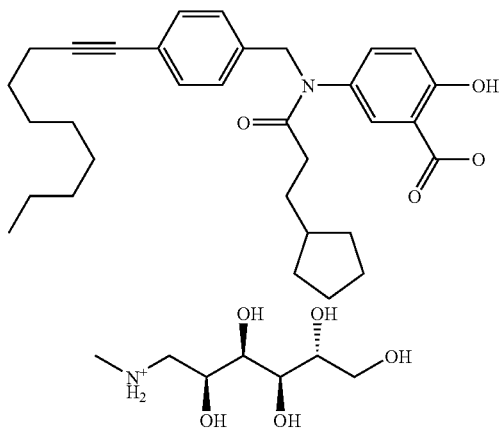

The title compound was prepared following the procedure D using 5-[(3-cyclopentyl-propanoyl)(4-dec-1-ynylbenzyl)amino]-2-hydroxybenzoic acid and N-methyl-D-glucamine as a white powder (93%). M⁺ (ESI): 504.1; M⁻ (ESI): 502.3. HPLC, Rt: 6.1 min (purity: 98.1%)

Example 3

5-[{4-[(4-butylphenyl)ethynyl]benzyl}(3-cyclopentylpropanoyl)amino]-2-hydroxybenzoic acid Step a) Formation of 4-[(4-butylphenyl)ethynyl]benzaldehyde

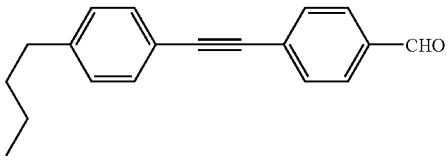

A solution of p-bromobenzaldehyde (50 g, 270 mmol), 1-butyl-4-ethynylbenzene (47.0 g, 297 mmol), Et₃N (540 mmol, 75 mL), CuI (0.52 g, 2.70 mmol), and PPh₃ (1.42 g, 5.40 mmol) in 500 mL dry THF was degassed for 15 min by passing a stream of N₂ through the solution. Pd(OAc)₂ (1.21 g, 5.40 mmol) was then added and the black solution was stirred at rt for 17 hours. 1-butyl-4-ethynylbenzene (4.3 g) was added and the reaction stirred for an additional 3 hours. The reaction was filtered and 20 g of activated charcoal was added to the combined filtrates. This suspension was stirred for 2 hours at rt and was filtered over a pad of celite and reduced to a dark brown solid. The solid was taken up in DCM and added 100 g silica gel and removed the solvent. The product, now disposed on silica gel, was added to the top of a silica gel plug, preconditioned with 5% EtOAc in c-Hex, and filtered using 5% EtOAc in c-Hex, then up to 50%. The fractions containing the product were concentrated to a dark solid. The solid was taken up in 500 mL EtOAc and reduced to half volume. The solution was allowed to stand at rt and solids appeared. Then 200 mL pentane was added and cooled to 0° C. This was allowed to stand overnight. The solids were filtered and washed with 10% MTBE in pentane. The solids were still very dark. This material was further purified by flash chromatography on SiO₂ (10/90 EtOAc/c-Hex). The combined pure fractions were evaporated to give a light brown solid. This solid was crystallized by dissolving in 100/150 EtOAc/MTBE with slight heating. Upon cooling to rt, solids appeared. 400 mL of pentane were added and the resulting mixture was then cooled to 0° C. and allowed to stand overnight. The solids were filtered and washed with 750 mL 1/3 MTBE/Pentane to give the title compound as a slightly off-white colored solids (a plate like crystal) (41.0 g, 58%). ¹H NMR (CDCl₃) δ: 10.03 (s, 1H), 7.87 (d, J=8.3 Hz, 2H), 7.67 (d, J=8.3 Hz, 2H), 7.49 (d, J=8.3 Hz, 2H), 7.21 (d, J=8.3 Hz, 2H), 2.66 (t, J=7.9 Hz, 2H), 1.71-1.56 (m, 2H), 1.46-1.31 (m, 2H), 0.98 (t, J=7.2 Hz, 3H). HPLC, Rt: 5.3 min (purity: 100%).

Step b) Formation of 6-({4-[(4-butylphenyl)ethynyl]benzyl}amino)-2,2-dimethyl-4H-1,3-benzodioxin-4-one

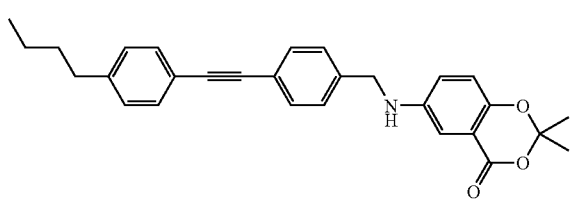

The title compound was prepared following the procedure A using 4-[(4-butylphenyl)-ethynyl]benzaldehyde and 6-amino-2,2-dimethyl-4H-1,3-benzodioxin-4-one (purification by flash chromatography on SiO₂, EtOAc/c-Hex 15/85) as a yellowish solid (53%). ¹H NMR (CDCl₃) δ: 7.45 (d, J=8.3 Hz, 2H), 7.39 (d, J=8.3 Hz, 2H), 7.28 (d, J=8.3 Hz, 2H), 7.15-7.06 (m, 3H), 6.80-6.70 (m, 2H), 4.20 (s, 2H), 4.04 (brs, 1H), 2.57 (t, J=7.7 Hz, 2H), 1.65 (s, 6H), 1.61-1.49 (m, 2H), 1.37-1.23 (m, 2H), 0.88 (t, J=7.3 Hz, 3H). HPLC, Rt: 6.3 min (purity: 92.2%).

Step c) Formation of N-{4-[(4-butylphenyl)ethynyl]benzyl}-3-cyclopentyl-N-(2,2-dimethyl-4-oxo-4H-1,3-benzodioxin-6-yl)propanamide

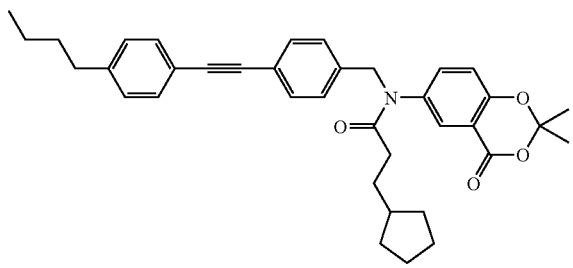

The title compound was prepared following the procedure B using 6-({4-[(4-butylphenyl)-ethynyl]benzyl}amino)-2,2-dimethyl-4H-1,3-benzodioxin-4-one and 3-cyclopentyl-propanoyl chloride (purification by flash chromatography on SiO₂, EtOAc/c-Hex 15/85) as a colorless oil (86%). ¹H NMR (CDCl₃) δ: 7.71 (s, 1H), 7.44 (d, J=8.1 Hz, 4H), 7.17 (d, J=8.1 Hz, 4H), 7.06 (d, J=8.7 Hz, 1H), 9.92 (d. J=8.7 Hz, 1H), 4.89 (s, 2H), 2.63 (t, J=7.9 Hz, 2H), 2.09 (t, J=7.2 Hz, 2H), 1.75 (s, 6H), 1.72-1.22 (m, 19H), 1.04-0.85 (m, 5H). M⁺ (ESI): 564.1. HPLC, Rt: 6.2 min (purity: 99.9%).

Step d) Formation of 5-[{4-[(4-butylphenyl)ethynyl]benzyl}(3-cyclopentylpropanoyl)amino]-2-hydroxybenzoic acid

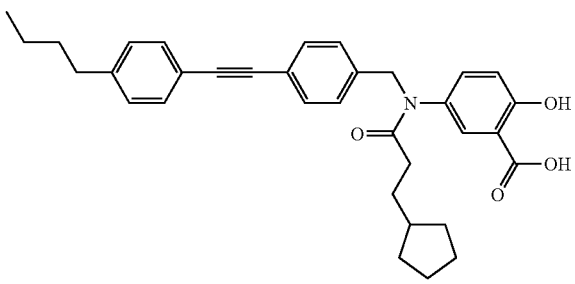

The title compound was prepared following the procedure C using N-{4-[(4-butylphenyl)ethynyl]benzyl}-3-cyclopentyl-N-(2,2-dimethyl-4-oxo-4H-1,3-benzodioxin-6-yl)propanamide as a colorless oil (89%). $^1$H NMR (DMSO-$d_6$) δ: 7.58-7.45 (m, 5H), 7.38-7.21 (m, 5H), 6.94 (d, J=8.7 Hz, 1H), 4.83 (s, 2H), 3.50 (brs, 1H), 2.60 (t, J=7.9 Hz, 2H), 2.05 (t, J=7.2 Hz, 2H), 1.68-1.17 (m, 14H), 0.97-0.81 (m, 5H). M$^+$ (ESI): 524.2; M$^-$ (ESI): 522.4. HPLC, Rt: 5.9 min (purity: 99.8%).

Example 4

5-[{4-[(4-butylphenyl)ethynyl]benzyl}(3-cyclopentylpropanoyl)amino]-2-hydroxybenzoic acid, N-methyl-D-glucamine (i.e. 1-deoxy-1-(methylamino)glucitol) salt

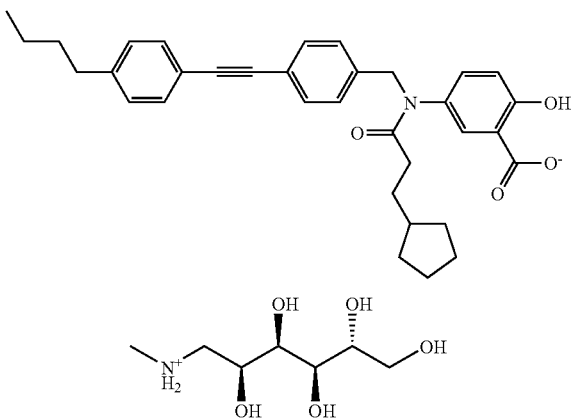

The title compound was prepared following the procedure D using N-{4-[(4-butylphenyl)ethynyl]benzyl}-3-cyclopentyl-N-(2,2-dimethyl-4-oxo-4H-1,3-benzodioxin-6-yl)propanamide and N-methyl-D-glucamine (89%). M$^-$ (ESI): 522.2. HPLC, Rt: 5.8 min (purity: 99.9%).

Example 5

5-[acetyl(4-dec-1-ynylbenzyl)amino]-2-hydroxybenzoic acid

Step a) Formation of N-(4-dec-1-ynylbenzyl)-N-(2,2-dimethyl-4-oxo-4H-1,3-benzodioxin-6-yl)acetamide

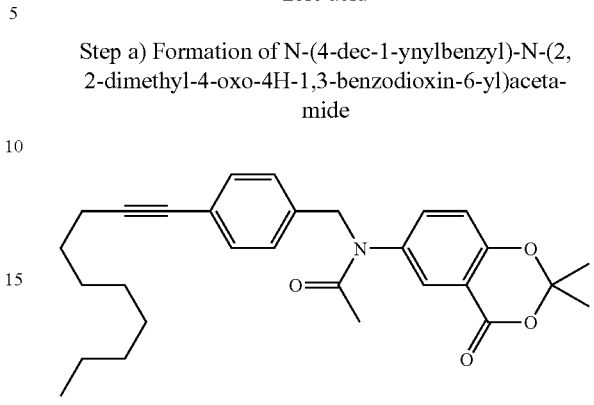

The title compound was prepared following the procedure E using 6-[(4-dec-1-ynylbenzyl)amino]-2,2-dimethyl-4H-1,3-benzodioxin-4-one and acetyl chloride. HPLC, Rt: 5.8 min (purity: 99.9%).

Step b) Formation of 5-[acetyl(4-dec-1-ynylbenzyl)amino]-2-hydroxybenzoic acid

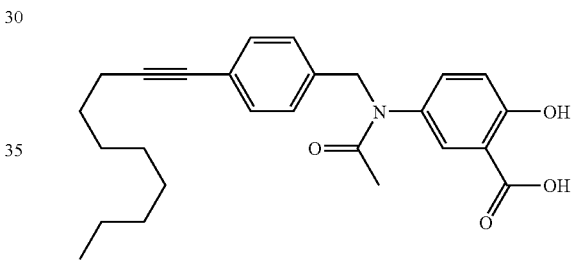

The title compound was prepared following the procedure C using N-(4-dec-1-ynylbenzyl)-N-(2,2-dimethyl-4-oxo-4H-1,3-benzodioxin-6-yl)acetamide as a white solid. $^1$H NMR (DMSO-$d_6$) δ: 10.91 (s, 1H), 7.52 (d, J=2.6 Hz, 1H), 7.23 (d, J=8.3 Hz, 2H), 7.04 (d, J=8.3 Hz, 2H), 6.95-6.80 (m, 2H), 4.79 (s, 2H), 2.3 (t, J=7.2 Hz, 2H), 1.88 (s, 3H), 1.59-1.44 (m, 2H), 1.43-1.29 (m, 2H), 1.29-1.10 (m, 8H), 0.80 (t, J=7.0 Hz, 3H). M$^+$ (ESI): 422.3; M$^-$ (ESI): 420.4. HPLC, Rt: 5.3 min (purity: 95.6%).

Example 6

5-[(4-dec-1-ynylbenzyl)(pyridin-3-ylcarbonyl)amino]-2-hydroxybenzoic acid

Step a) Formation of N-(4-dec-1-ynylbenzyl)-N-(2,2-dimethyl-4-oxo-4H-1,3-benzodioxin-6-yl)nicolinamide Step b) Formation of 5-[(4-dec-1-ynylbenzyl)(pyridin-3-ylcarbonyl)amino]-2-hydroxybenzoic acid

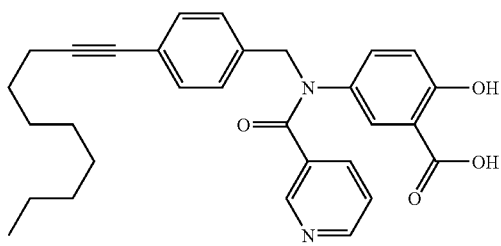

The title compound was prepared following the procedure C using N-(4-dec-1-ynylbenzyl)-N-(2,2-dimethyl-4-oxo-4H-1,3-benzodioxin-6-yl)nicolinamide as a brown solid. M+ (ESI): 485.6; M− (ESI): 483.1. HPLC, Rt: 4.6 min (purity: 82.2%).

Example 7

5-[(4-dec-1-ynylbenzyl)(isonicotinoyl)amino]-2-hydroxybenzoic acid

Step a) Formation of N-(4-dec-1-ynylbenzyl)-N-(2,2-dimethyl-4-oxo-4H-1,3-benzodioxin-6-yl)isonicolinamide

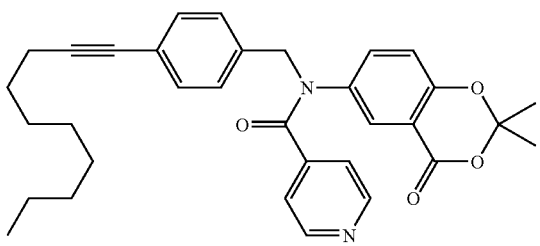

The title compound was prepared following the procedure E using 6-[(4-dec-1-ylnylbenzyl)amino]-2,2-dimethyl-4H-1,3-benzodioxin-4-one and isonicotinyl chloride hydrochloride. HPLC, Rt: 4.9 min (purity: 99.7%).

Step b) Formation of 5-[(4-dec-1-ynlbenzyl)(isonicotinoyl)amino]-2-hydroxybenzoic acid

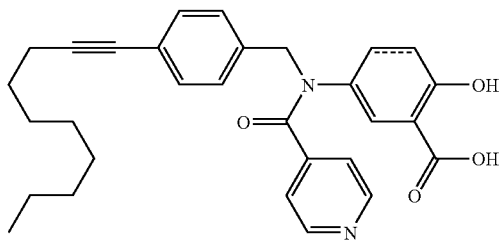

The title compound was prepared following the procedure C using N-(4-dec-1-ynylbenzyl)-N-(2,2-dimethyl-4-oxo4H-1,3-benzodioxin-6-yl)isonicotinamide as a yellow solid. M+ (ESI): 485.3; M− (ESI): 483.2. HPLC, Rt: 4.5 min (purity: 90.1%). -

Example 8

5-{(4-dec-1-ynylbenzyl)[(2E)-3-phenylprop-2-enoyl]amino}-2-hydroxybenzoic acid

Step a) Formation of (2E)-N-(4-dec-1-ynylbenzyl)-N-(2,2-dimethyl-4-oxo-4H-1,3-benzodioxin-6-yl)-3-phenylacrylamide

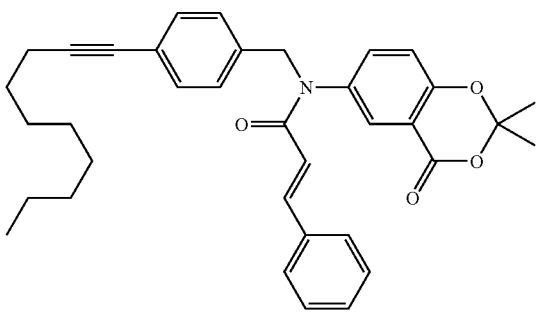

The title compound was prepared following the procedure E using 6-[(4-dec-1-ynylbenzyl)amino]-2,2-dimethyl-4H-1,3-benzodioxin-4-one and (2E)-3-phenylacryloyl chloride. HPLC, Rt: 6.3 min (purity: 95.5%).

Step b) Formation of 5-{(4-dec-1-ynylbenzl)[(2E)-3-phenylprop-2-enoyl]amino}-2-hydroxybenzoic acid

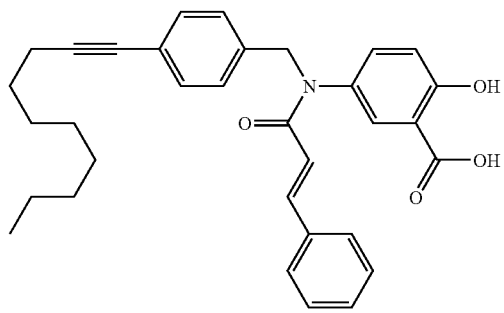

The title compound was prepared following the procedure C using (2E)-N-(4-dec-1-ynylbenzyl)-N-(2,2-dimethyl-4-oxo-4H-1,3-benzodioxin-6-yl)-3-phenylacrylamide as a white solid. M+ (ESI): 510.7; M− (ESI): 508.3. HPLC, Rt: 5.9 min (purity: 91.7%). $^1$H NMR (CDCl$_3$) δ: 10.87 (s, 1H), 7.73 (d, J=15.5 Hz, 1H), 7.62 (m, 1H), 7.19 (m, 2H), 7.32-7.17 (m, 6H), 7.12-7.06 (m, 2H), 7.09-6.95 (m, 1H), 6.88 (m, 1H), 6.23 (m, J=15.5 Hz, 1H), 4.92 (brs, 2H), 2.31 (t, J=7.0 Hz, 2H), 1.57-1.45 (m, 2H), 1.41-1.15 (m, 10H), 0.81 (m, 3H)

Example 9

5-[(4-dec-1-ynylbenzyl)(thien-2-ylacetyl)amino]-2-hydroxybenzoic acid

Step c) Formation of N-(4-dec-1-ynylbenzyl)-N-(2,2-dimethyl-4-oxo-4H-1,3-benzodioxin-6-yl)-2-thien-2-ylacetamide

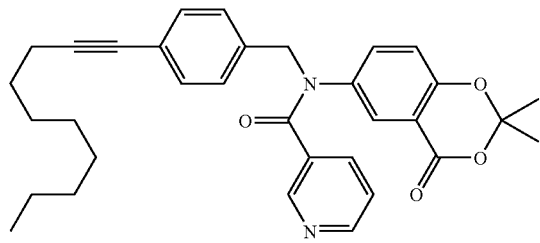

The title compound was prepared following the procedure E using 6-[(4-dec-1-ynylbenzyl)amino]-2,2-dimethyl-4H-1,3-benzodioxin-4-one and nicotinyl chloride hydrochloride. HPLC, Rt: 5.2 min (purity: 79.9%).

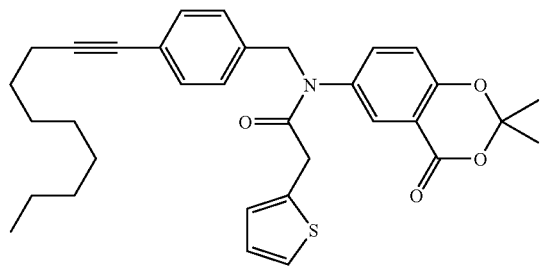

The title compound was prepared following the procedure E using 6-[(4-dec-1-ynylbenzyl)amino]-2,2-dimethyl-4H-1,3-benzodioxin-4-one and thien-2-ylacetyl chloride. HPLC, Rt: 6.1 min (purity: 82.6%).

Step d) Formation of 5-[(4-dec-1-ynylbenzyl)(thien-2-ylacetyl)amino]-2-hydroxybenzoic acid

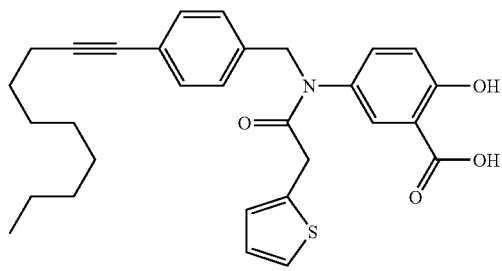

The title compound was prepared following the procedure C using N-(4-dec-1-ynylbenzyl)-N-(2,2-dimethyl-4-oxo-4H-1,3-benzodioxin-6-yl)-2-thien-2-ylacetamide as a brown solid. M$^+$ (ESI): 504.2; M$^-$ (ESI): 502.1. HPLC, Rt: 5.7 min (purity: 87.8%). $^1$H NMR (CDCl$_3$) δ 10.72 (s, 1H), 7.46 (s, 1H), 7.23-7.19 (m, 2H), 7.10-6.99 (m, 3H), 6.85-6.75 (m, 3H), 6.63 (m, 1H), 4.89 (brs, 2H), 3.62 (s, 2H), 2.30 (t, J=7.1 Hz, 2H), 1.57-1.45 (m, 2H), 1.40-1.15 (m, 10H), 0.81 (m, 3H).

Example 10

5-((4-dec-1-ynylbenzyl){(2E)-3-[3-(trifluoromethyl)phenyl]prop-2-enoyl}amino)-2-hydroxybenzoic acid Step a) Formation of (2E)-N-(4-dec-1-ynylbenzyl)-N-(2,2-dimethyl-4-oxo-4H-1,3-benzodioxin-6-yl)-3-[3-(trifluoromethyl)phenyl]acrylamide

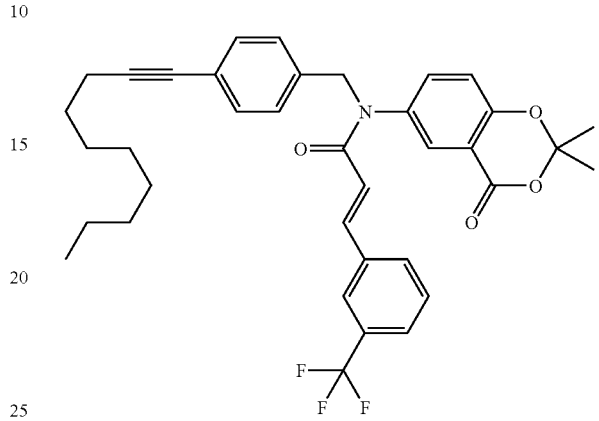

The title compound was prepared following the procedure E using 6-[(4-dec-1-ynylbenzyl)amino]-2,2-dimethyl-4H-1,3-benzodioxin-4-one and (2E)-3-[3-(trifluoromethyl)phenyl]acryloyl chloride. HPLC, Rt: 6.6 min (purity: 87.4%).

Step b) Formation of 5-((4-dec-1-ynylbenzyl){(2E)-3-[3-(trifluoromethyl)phenyl]prop-2-enoyl}amino)-2-hydroxybenzoic acid

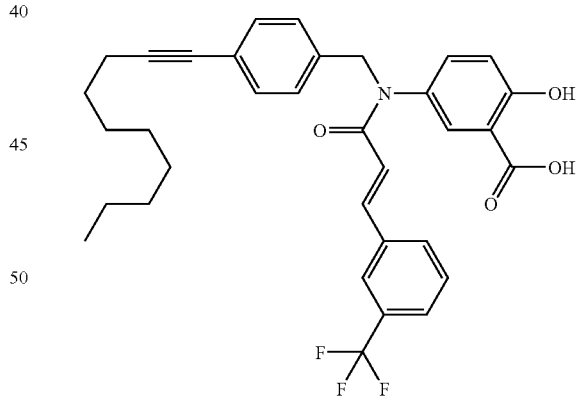

The title compound was prepared following the procedure C using (2E)-N-(4-dec-1-ynylbenzyl)-N-(2,2-dimethyl-4-oxo-4H-1,3-benzodioxin-6-yl)-3-[3-(trifluoromethyl)phenyl]acrylamide as a brown solid. M$^+$ (ESI): 578.5; M$^-$ (ESI): 576.0. HPLC, Rt: 6.1 min (purity: 88.4%). $^1$H NMR (CDCl$_3$) δ: 10.79 (s, 1H), 7.74 (d, J=15.4 Hz, 1H), 7.60 (m, 1H), 7.50-7.30 (m, 5H), 7.24 (d, J=8.3 Hz, 2H), 7.08 (d, J=8.1 Hz, 2H), 7.02-6.96 (m, 1H), 6.88 (m, 1H), 6.28 (d, J=15.4 Hz, 1H), 4.92 (brs, 2H), 2.30 (t, J=7.1 Hz, 2H), 1.57-1.44 (m, 2H), 1.40-1.12 (m, 10H), 0.80 (m, 3H).

Example 11

5-[(4-dec-1-ynylbenzyl)(phenoxyacetyl)amino]-2-hydroxybenzoic acid

Step a) Formation of N-(4-dec-1-ynylbenzyl)-N-(2,2-dimethyl-4-oxo-4H-1,3-benzodioxin-6-yl)-2-phenoxyacetamide

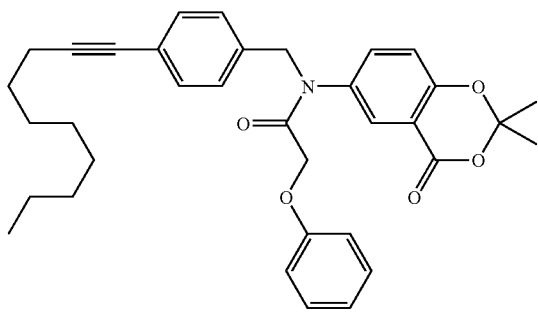

The title compound was prepared following the procedure E using 6-[(4-dec-1-ynylbenzyl)amino]-2,2-dimethyl-4H-1,3-benzodioxin-4-one and phenoxyacetyl chloride. HPLC, Rt: 6.1 min (purity: 99.70%).

Step b) Formation of 5-[(4-dec-1-ynylbenzyl)(phenoxyaceoyl)amino]-2-hydroxybenzoic acid

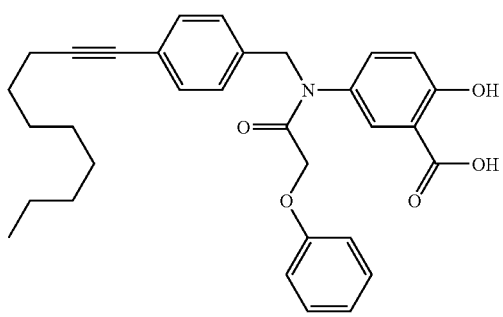

The title compound was prepared following the procedure C using N-(4-dec-1-ynylbenzyl)-N-(2,2-dimethyl-4-oxo-4H-1,3-benzodioxin-6-yl)-2-phenoxyacetamide as a yellow solid. M$^+$ (ESI): 514.2; M$^-$ (ESI): 512.7. HPLC, Rt: 5.7 min (purity: 93.4%).

Example 12

[4-({(4-dec-1-ynylbenzyl)[(2E)-3-phenylprop-2-enoyl]amino}methyl)-phenoxy]acetic acid Step a) Formation of methyl (4-{[(4-dec-1-ynylbenzyl)amino]methyl}phenoxy)acetate

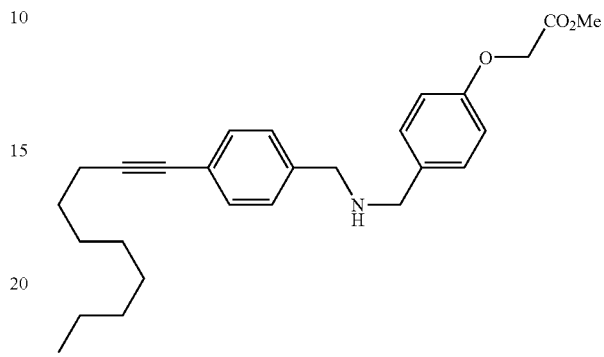

The title compound was prepared following the procedure A using 4-dec-1-ynylbenzaldehyde, methyl [4-(aminomethyl)phenoxy]acetate, acetate salt and DIEA (1 eq.) (purification by flash chromatography on SiO$_2$, DCM/MeOH 95:5) as a pale yellow oil (63%). M$^+$ (ESI): 422.2. HPLC, Rt: 4.3 min (purity: 96.4%). $^1$H NMR (CDCl$_3$) δ: 7.37 (d, J=8.3 Hz, 2H), 7.28 (m, 4H), 6.88 (d, J=8.6 Hz, 2H), 4.63 (s, 2H), 3.78 (m, 7H), 2.40 (t, J=7.0 Hz, 2H), 1.61 (m, 2H), 1.44 (m, 2H), 1.30 (brs, 8H), 0.90 (t, J=6.8 Hz, 3H).

Step b) Formation of methyl [4-({(4-dec-1-ynylbenzyl)[(2E)-3-phenylprop-2-enoyl]amino}methyl)phenoxy]acetate

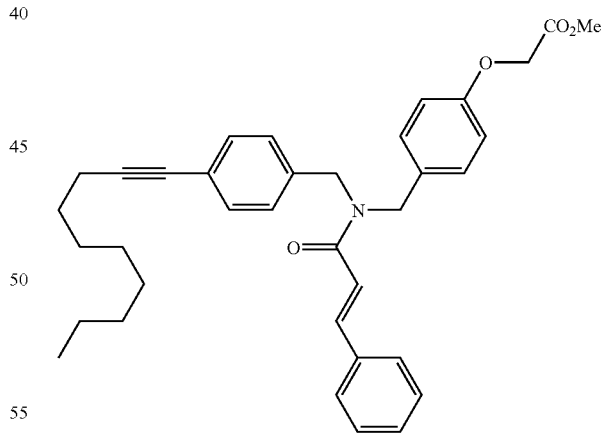

The title compound was prepared following the procedure E using methyl (4-{[(4-dec-1-ynylbenzyl)amino]methyl}phenoxy)acetate and (2E)-3-phenylacryloyl chloride (purification by flash chromatography on SiO$_2$-c-Hex/EtOAc 9:1) as a colorless oil (64%). M$^+$ (ESI): 552.1. HPLC, Rt: 6.1 min (purity: 99.5%). $^1$H NMR (CDCl$_3$) δ: 7.85 (m, 1H), 7.47-7.12 (m, 11H), 6.90 (m, 3H), 4.65-4.52 (m, 6H), 3.82 (s, 3H), 2.41 (t, J=7.0 Hz, 2H), 1.61 (m, 2H), 1.45 (m, 2H), 1.30 (m, 8H), 0.89 (t, J=6.8 Hz, 3H).

Step c) Formation of [4-({(4-dec-1-ynylbenzyl)[(2E)-3-phenylprop-2-enoyl]amino}methyl)-phenoxy]acetic acid

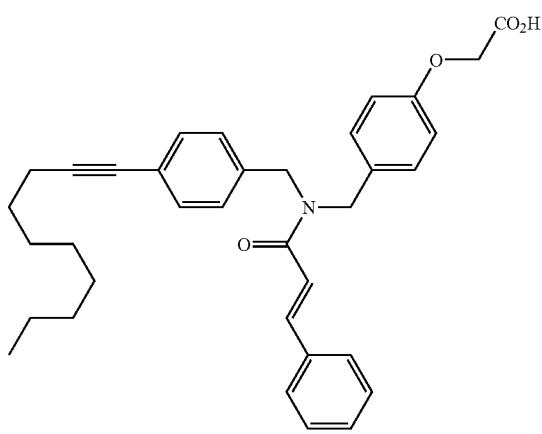

The title compound was prepared following the procedure F using methyl [4-({(4-dec-1-ynylbenzyl)[(2E)-3-phenylprop-2-enoyl]amino}methyl)phenoxy]acetate as a white solid (82%). M⁺ (ESI): 538.2; M⁻ (ESI): 536.1. HPLC, Rt: 5.7 min (purity: 99.9%). ¹H NMR (CDCl₃) δ: 7.87 (d, J=15.5 Hz, 1H), 7.47-7.14 (m, 11H), 6.89 (m, 3H), 4.69-4.54 (m, 6H), 2.41 (t, J=7.0 Hz, 2H), 1.61 (m, 2H), 1.44-1.31 (m, 10H), 0.89 (t, J=6.8 Hz, 3H).

Example 13

(4-{[(3-cyclopentylpropanoyl)(4-dec-1-ynylbenzyl)amino]methyl}phenoxy)-acetic acid Step a) Formation of methyl (4-{([(3-cyclopentylpropanoyl)(4-dec-1-ynylbenzyl)amino]-methyl}phenoxy)acetate

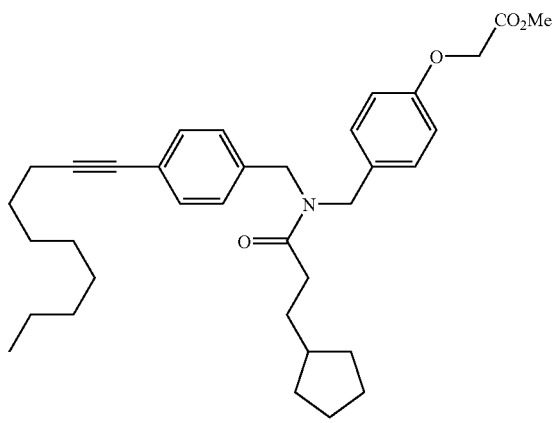

The title compound was prepared following the procedure G using methyl (4-{[(4-dec-1-ynylbenzyl)amino]methyl}phenoxy)acetate and 3-cyclopentylpropanoyl chloride (purification by flash chromatography on SiO₂, c-Hex/EtOAc 9:1) as a colorless oil (77%). M⁺ (ESI): 546.1. HPLC, Rt: 6.4 min (purity: 100%). ¹H NMR (CDCl₃) δ: 7.40 (d, J=8.3 Hz, 1H), 7.34 (d, J=8.0 Hz, 1H), 7.16-7.05 (m, 4H), 6.91 (d, J=8.7 Hz, 1H), 6.85 (d, J=8.3 Hz, 1H), 4.66 (s, 1H), 4.63 (s, 1H), 4.54 (s, 1H), 4.51 (s, 1H), 4.40 (s, 1H), 4.36 (s, 1H), 3.83 (s, 1.5H), 3.82 (s, 1.5H), 2.41 (m, 4H), 1.74-1.08 (m, 23H), 0.90 (t, J=6.4 Hz, 3H).

Step b) Formation of (4-{[(3-cyclopentylpropanoyl)(4-dec-1-ynylbenzyl)amino]methyl}-phenoxy)acetic acid

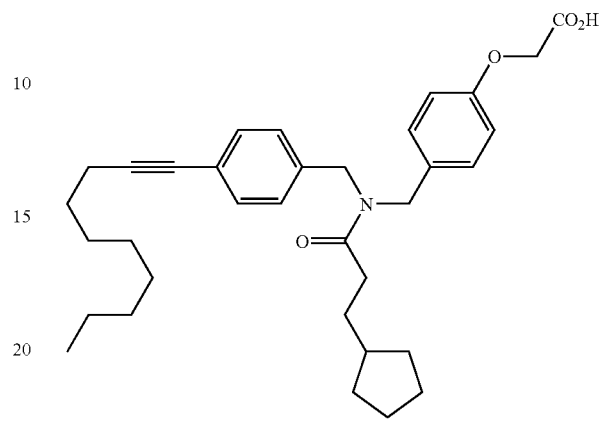

The title compound was prepared following the procedure F using methyl (4-{[(3-cyclopentylpropanoyl) (4-dec-1-ynylbenzyl)amino]methyl}phenoxy)acetate as a colorless oil (99%). M⁺ (ESI): 532.3; M⁻ (ESI): 530.3. HPLC, Rt: 6.0 min (purity: 99.9%). ¹H NMR (CDCl₃) δ: 7.40 (d, J=7.9 Hz, 1H), 7.34 (d, J=8.0 Hz, 1H), 7.17-7.05 (m, 4H), 6.90 (m, 2H), 4.69 (s, 1H), 4.67 (s, 1H), 4.55 (s, 1H), 4.53 (s, 1H), 4.42 (s, 1H), 4.37 (s, 1H), 2.41 (m, 4H), 1.73-1.09 (m, 23H), 0.90 (t, J=6.4 Hz, 3H).

Example 14

(4-{[(4-dec-1-ynylbenzyl)(hexanoyl)amino]methyl}phenoxy)acetic acid

Step a) Formation of methyl (4-{[(4-dec-1-ynylbenzyl) (hexanoyl)amino]methyl}phenoxy)acetate

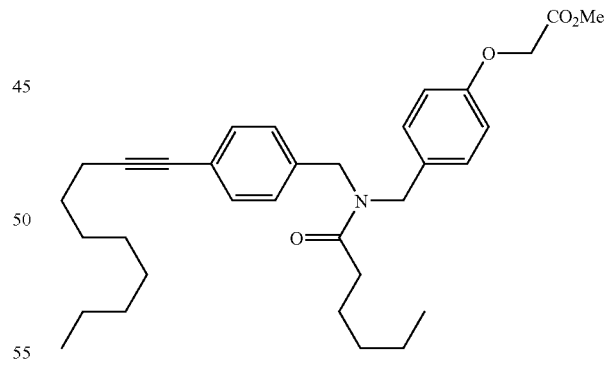

The title compound was prepared following the procedure G using methyl (4-{[(4-dec-1-ynylbenzyl)amino]methyl}phenoxy)acetate and hexanoyl chloride (purification by flash chromatography on SiO₂, c-Hex/EtOAc 9:1) as a colorless oil (63%). M⁺ (ESI): 520.6. HPLC, Rt: 6.2 min (purity: 99.30%). ¹H NMR (CDCl₃) δ: 7.39 (d, J=8.3 Hz, 1H), 7.34 (d, J=7.9 Hz, 1H), 7.16-7.05 (m, 4H), 6.91 (d, J=8.7 Hz, 1H), 6.85 (d, J=8.7 Hz, 1H), 4.65 (s, 1H), 4.63 (s, 1H), 4.54 (s, 1H), 4.52 (s, 1H), 4.40 (s, 1H), 4.36 (s, 1H), 3.83 (s, 1.5H), 3.82 (s, 1.5H), 2.41 (m, 4H), 1.70 (m, 2H), 1.61 (m, 2H), 1.45 (m, 2H), 1.31 (brs, 12H), 0.90 (m, 6H).

Step b) Formation of (4-{[(4-dec-1-ynylbenzyl)(hexanoyl)amino]methyl}phenoxy)acetic acid

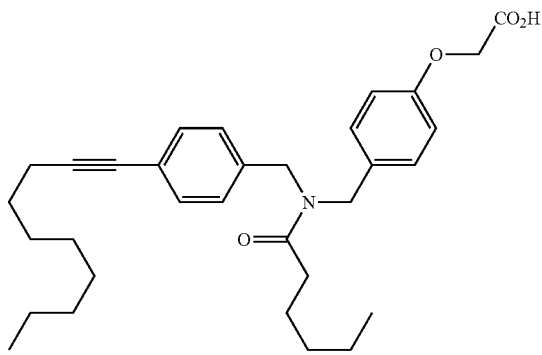

The title compound was prepared following the procedure F using methyl (4-{[(4-dec-1-ynylbenzyl) (hexanoyl)amino]methyl}phenoxy)acetate as a yellow oil (78%). M⁺ (ESI): 506.0. M⁻ (ESI): 504.0. HPLC, Rt: 5.8 min (purity: 99.9%). ¹H NMR (CDCl₃) δ: 7.40 (d, J=7.9 Hz, 1H), 7.34 (d, J=8.0 Hz, 1H), 7.16-7.04 (m, 4H), 6.92 (d, J=7.9 Hz, 1H), 4.37 (s, J=7.9 Hz, 1H), 4.69 (s, 1H), 4.66 (s, 1H), 4.55 (s, 1H), 4.53 (s, 1H), 4.41 (s, 1H), 4.37 (s, 1H), 2.41 (m, 4H), 1.70 (m, 2H), 1.61 (m, 2H), 1.35 (m, 14H), 0.89 (m, 6H).

Example 15

(4-{[acetyl(4-dec-1-ynylbenzyl)amino]methyl}phenoxy)acetic acid

Step a) Formation of methyl (4-{[acetyl(4-dec-1-ynylbenzyl)amino]methyl}phenoxy)acetate

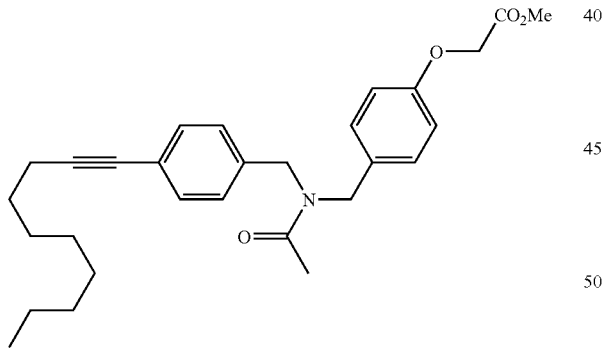

The title compound was prepared following the procedure G using methyl (4-{[(4-dec-1-ynylbenzyl)amino]methyl}phenoxy)acetate and acetyl chloride (purification by flash chromatography on SiO₂, c-Hex/EtOAc 9:1) as a colorless oil (26%). M⁺ (ESI): 464.3. HPLC, Rt: 5.6 min (purity: 100%). ¹H NMR (CDCl₃) δ: 7.40 (d, J=7.9 Hz, 1H), 7.34 (d, J=7.9 Hz, 1H), 7.17-7.05 (m, 4H), 6.91 (d, J=8.7 Hz. 1H), 6.86 (d, J=8.3 Hz, 1H), 4.65 (s, 1H), 4.63 (s, 1H), 4.54 (s, 1H), 4.51 (s, 1H), 4.40 (s, 1H), 4.35 (s, 1H), 3.83 (s, 1.5H), 3.82 (s, 1.5H), 2.41 (t, J=7.2 Hz, 1H), 2.40 (t, J=7.2 Hz, 1H), 2.22 (s, 1.5H), 2.18 (s, 1.5 H), 1.61 (m, 2H), 1.45 (m, 2H), 1.30 (brs, 8H), 0.90 (t, J=6.6 Hz, 3H).

Step b) Formation of (4-{[acetyl(4-dec-1-ynylbenzyl)amino]methyl}phenoxy)acetic acid

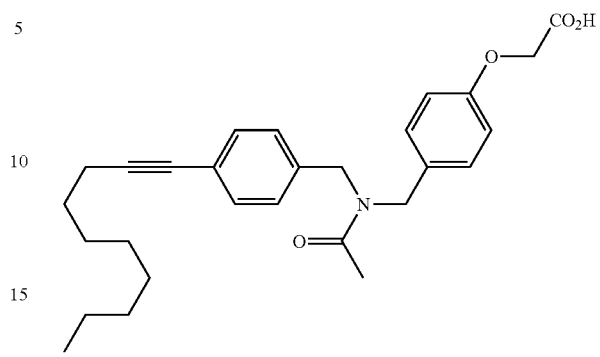

The title compound was prepared following the procedure F using methyl (4-{[acetyl(4-dec-1-ynylbenzyl)amino]methyl}phenoxy)acetate as a yellow oil (99%). M⁺ (ESI): 450.0; M⁻ (ESI): 448.0. HPLC, Rt: 5.2 min (purity: 98.8%). ¹H NMR (CDCl₃) δ: 7.37 (m, 2H), 7.14 (m, 4H), 6.91 (m, 2H), 4.69 (m, 2H), 4.55 (m, 2H), 4.40 (m, 2H), 2.41 (m, 2H), 2.24 (brs, 3H), 1.61 (m, 2H), 1.44 (m, 2H), 1.27 (m, 8H), 0.90 (m, 3H).

Example 16

2-(carboxymethoxy)-5-({{(4-dec-1-ynylbenzyl)[(2E)-3-3-phenylprop-2-enoyl]amino}methyl)benzoic acid Step a) Formation of methyl 5-{[(4-dec-1-ynylbenzyl)amino]methyl}-2-(2-methoxy-2-oxoethoxy)benzoate, hydrochloride salt

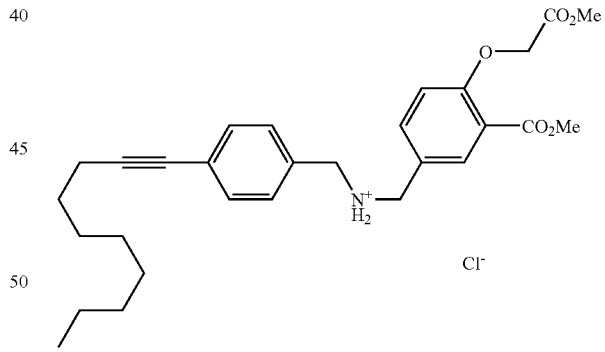

The title compound was prepared following the procedure A using 4-dec-1-ynylbenzaldehyde, methyl 5-(aminomethyl)-2-(2-methoxy-2-oxoethoxy)benzoate acetate and DIEA (1 eq.) (purification by flash chromatography on SiO₂, DCM/MeOH 95:5, followed by precipitation of the hydrochloride salt in i-PrOH) as a white solid (50%). M⁺ (ESI): 480.1. HPLC, Rt: 4.3 min (purity: 99.1%). ¹H NMR (DMSO-d₆) δ: 9.53 (brs, 2H), 7.84 (d, J=1.5 Hz, 1H), 7.66 (dd, J=8.7, 1.5 Hz, 1H), 7.49 (d, J=8.3 Hz, 2H), 7.41 (d, J=8.3 Hz, 2H), 7.10 (d, J=8.7 Hz, 1H), 4.92 (s, 2H), 4.12 (s, 4H), 3.80 (s, 3H), 3.68 (s, 3H), 2.41 (t, J=6.6 Hz, 2H), 1.52 (m, 2H), 1.39 (m, 2H), 1.26 (brs, 8H), 0.85 (t, J=6.4 Hz, 3H).

Step b) Formation of methyl 5-({(4-dec-1-ynylbenzyl)[(2E)-3-phenylprop-2-enoyl]amino}-methyl)-2-(2-methoxy-2-oxoethoxy)benzoate

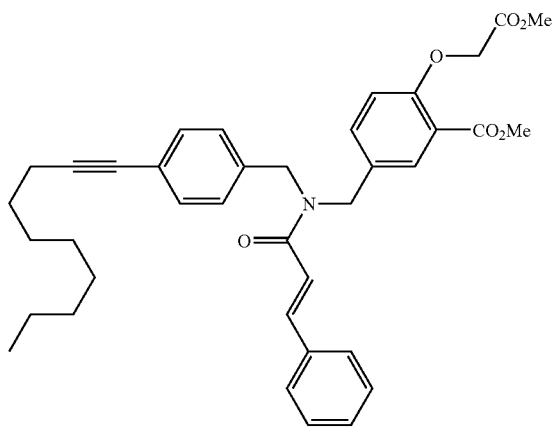

The title compound was prepared following the procedure G using the hydrochloride salt of methyl 5-{[(4-dec-1-ynylbenzyl)amino]methyl}-2-(2-methoxy-2-oxoethoxy)benzoate and (2E)-3-phenylacryloyl chloride (purification by flash chromatography on $SiO_2$, DCM/MeOH 98:2) as a pale yellow oil (82%). $M^+$ (ESI): 610.0. HPLC, Rt: 6.0 min (purity: 99.5%). $^1$H NMR ($CDCl_3$) δ: 7.85 (d, J=15.4 Hz, 1H), 7.70 (m, 1H), 7.47-7.12 (m, 10H), 6.86 (m, 2H), 4.74 (s, 2H), 4.61 (m, 4H), 3.90 (s, 3H), 3.81 (s, 3H), 2.41 (t, J=7.0 Hz, 2H), 1.61 (m, 2H), 1.45 (m, 2H), 1.30 (m, 8H), 0.89 (t, J=6.8 Hz, 3H).

Step c) Formation of 2-(carboxymethoxy)-5-({(4-dec-1-ynylbenzyl)[(2E)-3-phenylprop-2-enoyl]amino}methyl)benzoic acid

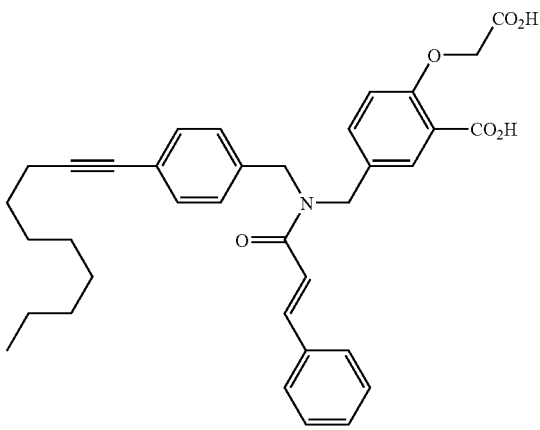

The title compound was prepared following the procedure F using methyl 5-({(4-dec-1-ynylbenzyl)[(2E)-3-phenylprop-2-enoyl]amino}methyl)-2-(2-methoxy-2-oxoethoxy)benzoate as a pale yellow foam (83%). $M^+$ (ESI): 581.9; $M^-$ (ESI): 580.6. HPLC, Rt: 5.5 min (purity: 98.8%). $^1$H NMR ($CD_3OD$) δ: 7.84 (m, 1H), 7.76 (d, J=15.4 Hz, 1H), 7.60 (m, 2H), 7.52-7.34 (m, 6H), 7.27-7.08 (m, 4H), 4.86 (s, 2E), 4.79 (s, 2H), 4.73 (m, 2H), 2.43 (t, J=6.8 Hz, 2H), 1.63 (m, 2H), 1.51 (m, 2H), 1.37 (brs, 8H), 0.94 (m, 3H).

Example 17

2-(carboxymethoxy)-5-{[(3-cyclopentylpropanoyl)(4-dec-1-ynylbenzyl)-amino]methyl}benzoic acid Step a) Formation of methyl 5-{[(3-cyclopentylpropanoyl)(4-dec-1-ynylbenzyl)amino]-methyl}-2-(2-methoxy-2-oxoethoxy)benzoate

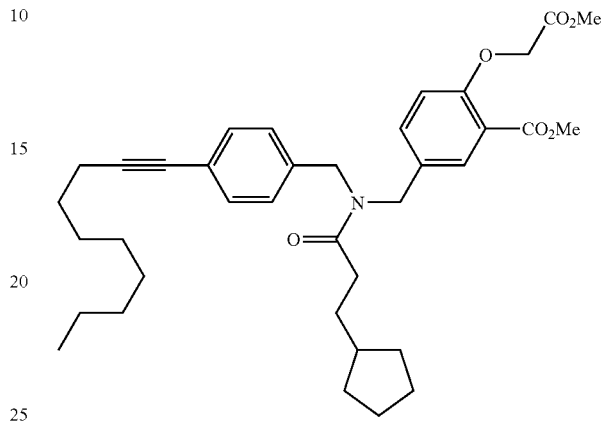

The title compound was prepared following the procedure G using the hydrochloride salt of methyl 5-{[(4-dec-1-ynylbenzyl)amino]methyl}-2-(2-methoxy-2-oxoethoxy)benzoate and 3-cyclopentylpropanoyl chloride (purification by flash chromatography on $SiO_2$, chloroform/MeOH 99:1) as a colorless oil (70%). $M^+$ (ESI): 604.0. HPLC, Rt: 6.2 min purity: 100%). $^1$H NMR ($CDCl_3$) δ: 7.61 (m, 1H), 7.41-7.05 (m, 5H), 6.85 (m, 1H), 4.75 (s, 1H), 4.72 (s, 1H), 4.56 (m, 2H), 4.42 (m, 2H), 3.92 (s, 1.5H), 3.90 (s, 1.5H), 3.82 (s, 1.5H), 3.81 (s, 1.5H), 2.41 (m, 4H), 1.74-1.09 (m, 23H), 0.90 (t, J=6.6 Hz, 3H).

Step b) Formation of 2-(carboxymethoxy)-5-{[(3-cyclopentylpropanoyl)(4-dec-1-ynylbenzl)amino]methyl}benzoic acid

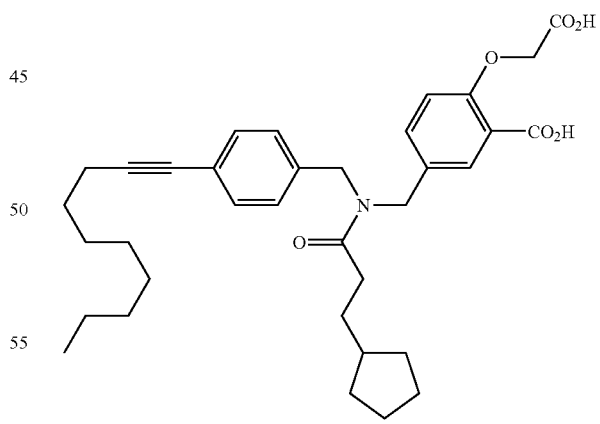

The title compound was prepared following the procedure F using methyl 5-{[(3-cyclopentylpropanoyl) (4-dec-1-ynylbenzyl)amino]methyl}-2-(2-methoxy-2-oxoethoxy)benzoate as a pale yellow solid (55%). $M^+$ (ESI): 576.1; $M^-$ (ESI): 574.0. HPLC, Rt: 5.7 min (purity: 96.6%). $^1$H NMR ($CDCl_3$) δ: 7.92 (m, 1H), 7.49-6.93 (m, 6H), 4.85 (m, 2H): 4.60-4.45 (m, 4H), 2.43 (m, 4H), 1.73-1.07 (m, 23H), 0.90 (t, J=7.1 Hz, 3H).

Example 18

5-{[acetyl(4-dec-1-ynylbenzyl)amino]methyl}-2-(carboxymethoxy)benzoic acid

Step a) Formation of methyl 5-{[acetyl(4-dec-1-ynylbenzyl)amino]methyl}-2-(2-methoxy-2-oxoethoxy)benzoate

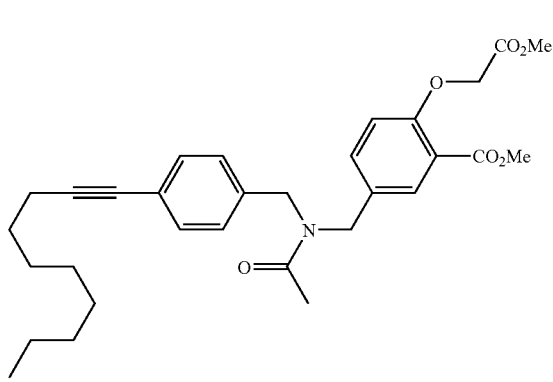

The title compound was prepared following the procedure G using the hydrochloride salt of methyl 5-{[(4-dec-1-ynylbenzyl)amino]methyl}-2-(2-methoxy-2-oxoethoxy)benzoate and acetyl chloride (purification by flash chromatography on $SiO_2$, chloroform/MeOH 99:1 to 90:10) as a colorless oil (72%). $M^+$ (ESI): 521.9. HPLC, Rt: 5.4 min (purity: 100%). $^1$H NMR ($CDCl_3$) δ: 7.62 (m, 1H), 7.41-7.05 (m, 5H), 6.85 (m, 1H), 4.75 (s, 1H), 4.73 (s, 1H), 4.55 (s, 1H), 4.53 (s, 1H), 4.41 (s, 1H), 4.38 (s, 1H), 3.92 (s, 1.5H), 3.90 (s, 1.5H), 3.82 (s, 1.5H), 3.81 (s, 1.5H), 2.41 (m, 2H), 2.21 (s, 1.5H), 2.20 (s, 1.5H), 1.62 (m, 2H), 1.45 (m, 2H), 1.31 (brs, 8H), 0.90 (t, J=6.6 Hz, 3H).

Step b) Formation of 5-{[acetyl(4-dec-1-ynylbenzyl)amino]methyl}-2-(carboxymethoxy)-benzoic acid

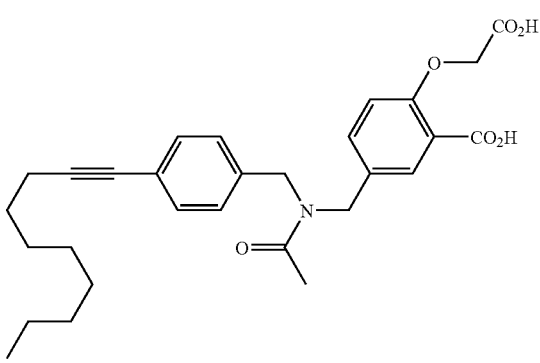

The title compound was prepared following the procedure F using methyl 5-{[acetyl(4-dec-1-ynylbenzyl)amino]methyl}-2-(2-methoxy-2-oxoethoxy)benzoate as a pale yellow solid (36%). $M^+$ (ESI): 494.1; $M^-$ (ESI): 492.1. HPLC, Rt: 4.9 min (purity: 85.0%). $^1$H NMR ($CDCl_3$) δ: 7.97 (m, 1H), 7.50-6.94 (m, 6H), 4.85 (m, 2H), 4.58-4.45 (m, 4H), 2.41 (m, 2H), 2.26 (brs, 3H), 1.62 (m, 2H), 1.44 (m, 2H), 1.30 (m, 8H), 0.90 (m, 3H).

Example 19

(2E)-3-(4-{[(4-dec-1-ynylbenzyl)(3-phenylpropanoyl)amino]methyl}phenyl)-acrylic acid Step a) Formation of methyl (2E)-3-(4-{[(4-dec-1-ynylbenzyl)amino]methyl}phenyl)-acrylate

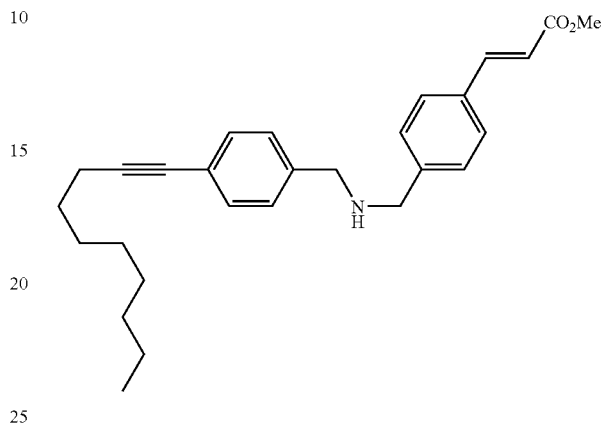

The title compound was prepared following the procedure A using 4-dec-1-ynylbenz-aldehyde and methyl (2E)-3-[4-(aminomethyl)phenyl]acrylate. (purification by flash chromatography on $SiO_2$, EtOAc/c-Hex 20/80 to 50/50 for about 30 min.) as a white solid (73%). $^1$H NMR ($CDCl_3$) δ: 7.56 (d, 1H, J=16.2 Hz), 7.36 (d, 2H, J=8.3 Hz), 7.23 (m, 4H), 7.12 (m, 2H), 6.29 (d, 1H, J=15.8 Hz), 3.69-3.63 (m, 7E), 2.26 (m, 2H), 1.56-1.40 (m, 2H), 1.38-1.10 (m, 10H), 0.76 (m, 3H). $M^+$ (ESI): 418.3. HPLC, Rt: 4.5 min (purity: 100%).

Step b) Formation of methyl (2E)-3-(4-{[(4-dec-1-ynylbenzl)(3-phenylpropanoyl)amino]-methyl}phenyl)acrylate

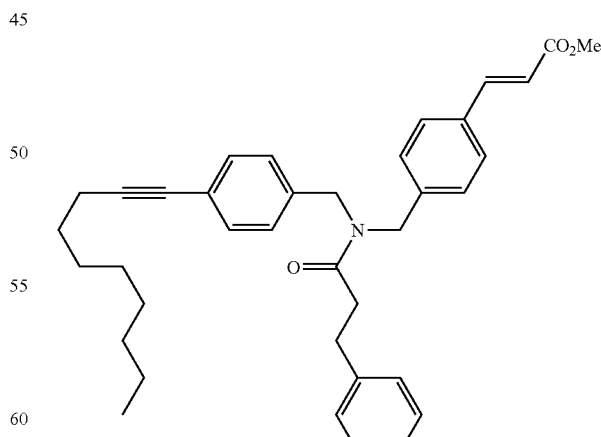

The title compound was prepared following the procedure E using methyl (2E)-3-(4-{[(4-dec-1-ynylbenzyl)amino] methyl}phenyl)acrylate and 3-phenylpropanoyl chloride (84%). $M^+$ (ESI): 550.0. HPLC, Rt: 6.4 min (purity: 98.2%).

Step c) Formation of (2E)-3-(4-{[(4-dec-1-ynylbenzyl)(3-phenylpropanoyl)amino]methyl}-phenyl)acrylic acid

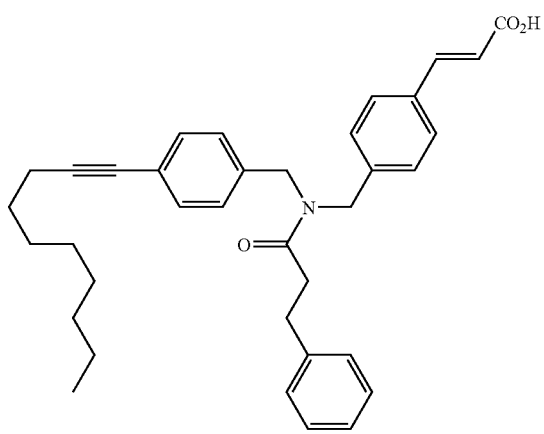

The title compound was prepared following the procedure F using methyl (2E)-3-(4-{[(4-dec-1-ynylbenzyl)(3-phenylpropanoyl)amino]methyl}phenyl)acrylate as a colorless oil (62%). $^1$H NMR (CDCl$_3$) δ: 7.69 (d, J=15.8 Hz, 1H), 7.42 (m, 2H), 7.31-7.07 (m, 8H), 7.00 (d, 2H, J=7.7 Hz). 6.90 (d, 1H, J=8.1 Hz), 6.42-6.32 (m, 1H), 4.52 and 4.50 (2s, 2H), 4.26 (brs, 2H), 2.98 (m, 2H), 2.70-2.55 (m, 2H), 2.32 (t, J=7.1 Hz, 2H), 1.59-1.46 (m, 2H), 1.43-1.15 (m, 10H), 0.81 (m, 3H). M$^+$ (ESI): 536.7; M$^−$ (ESI): 534.6. HPLC, Rt: 5.9 min (purity: 97.6%).

Example 20

(2E)-3-{4-[(4-dec-1-ynylbenzyl)(3-phenylpropanoyl)amino]phenyl}acrylic acid

Step a) Formation of ethyl (2E)-3-{4-[(4-dec-1-ynylbenzyl)amino]phenyl}acrylate

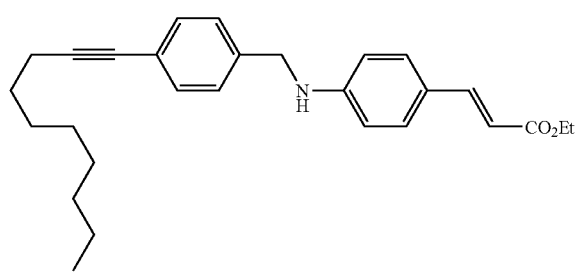

The title compound was prepared following the procedure A using 4-dec-1-ynyl-benzaldehyde and ethyl (2E)-3-(4-aminophenyl)acrylate. (purification by flash chromatography on SiO$_2$, EtOAc/c-Hex 1/7 to 1/6 in about 30 min.) as a yellow solid (61%). $^1$H NMR (CDCl$_3$) δ: 7.59 (d, J=15.8 Hz, 1H), 7.36 (m, 4H), 7.26 (m, 2H), 6.57 (d, J=8.7 Hz, 2H), 6.21 (d, J=15.8 Hz, 1H), 4.35 (s, 2H), 4.23 (dd, J1=7.2 Hz, J2=14.3 Hz, 2H), 2.39 (t, J=7.2 Hz, 2H), 1.66-1.52 (m, 2H), 1.50-1.39 (m, 2H), 1.38-1.24 (m, 11H), 0.87 (m, 3H). M$^+$ (ESI): 418.1; M$^−$ (ESI): 416.2. HPLC, Rt: 6.1 min (purity: 98.7%).

Step b) Formation of ethyl (2E)-3-{4-[(4-dec-1-ynylbenzyl)(3-phenylpropanoyl)-amino]phenyl}acrylate The title compound was prepared following the procedure E using of ethyl (2E)-3-{4-[(4-dec-1-ynylbenzyl)amino]phenyl}acrylate and 3-phenylpropanoyl chloride (58%). M$^+$ (ESI): 560.6. HPLC, Rt: 6.4 min (purity: 98.7%).

Step c) Formation of (2E)-3-{4-[(4-dec-1-ynylbenzyl)(3-phenylpropanoyl)amino])phenyl}-acrylic acid

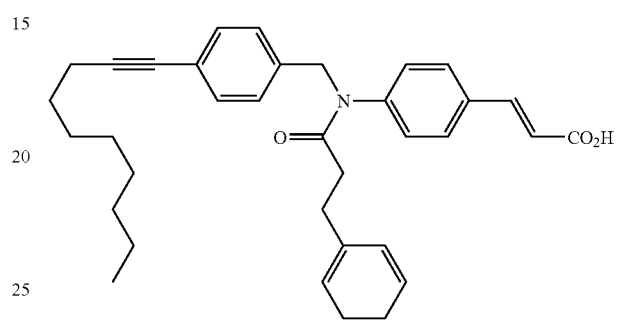

The title compound was prepared following the procedure F using ethyl (2E)-3-{4-[(4-dec-1-ynylbenzyl)(3-phenylpropanoyl)amino]phenyl}acrylate as a yellow oil (84%). $^1$H NMR (CDCl$_3$) δ: 7.71 (d, J=16.0 Hz, 1H), 7.42 (d, J=8.3 Hz, 2H), 7.31-7.16 (m, 5H), 7.08 (m, 2H), 7.02 (d, J=8.3 Hz, 2H), 6.82-6.72 (m, 2H), 6.40 (d, J=16.0 Hz, 1H), 4.84 (s, 2H), 2.95 (t, J=7.4 Hz, 2H), 2.39 (m, 4H), 1.66-1.54 (m, 2H), 1.50-1.24 (m, 10H), 0.88 (m, 3H). M$^+$ (ESI): 522.1; M$^−$ (ESI): 520.1. HPLC, Rt: 5.8 min (purity: 98.2%).

Example 21

(2E)-3-{4-[acetyl(4-dec-1-ynylbenzyl)amino]phenyl}acrylic acid

Step a) Formation of ethyl (2E)-3-{4-[acetyl(4-dec-1-ynylbenzyl)amino]phenyl}acrylate

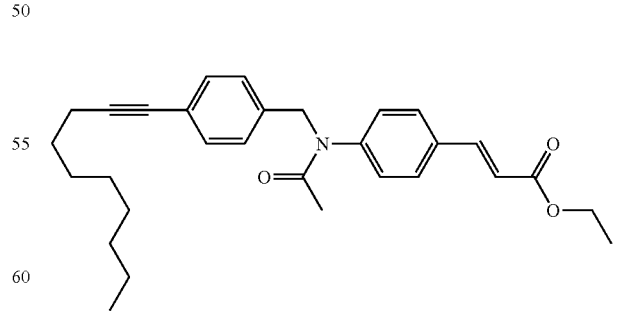

The title compound was prepared following the procedure E using ethyl (2E)-3-{4-[(4-dec-1-ynylbenzyl)amino]phenyl}acrylate and acetyl chloride as a yellow oil (97%). M$^+$ (ESI): 460.2. HPLC, Rt: 6.0 min (purity: 98.8%).

Step b) Formation of (2E)-3-{4-[acetyl(4-dec-1-ynylbenzyl)amino]phenyl}acrylic acid

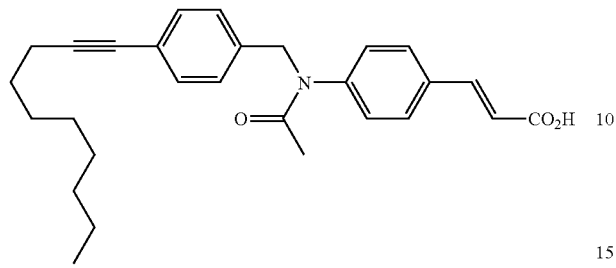

The title compound was prepared following the procedure F ethyl (2E)-3-{4-[acetyl(4-dec-1-ynylbenzyl)amino]phenyl}acrylate as a colorless oil (76%). $^1$H NMR (CDCl$_3$) δ: 7.66 (d, J=16 Hz, 1H), 7.44 (d, J=8.4 Hz, 2H), 7.23 (d, J=8.1 Hz, 2H), 7.03 (d, J=7.3 Hz, 2H), 6.94 (d, J=8.1 Hz, 2H), 6.36 (d, J=16 Hz, 1H), 5.22 and 5.80 (2 s, 3H), 2.31 (t, J=6.6 Hz, 2H), 1.85 (brs, 2H). 1.59-1.45 (m, 2H), 1.43-1.30 (m, 2H), 1.30-1.10 (m, 8H), 0.81 (t, J=6.6 Hz, 3H). M$^+$ (ESI): 432.1; M$^-$ (ESI): 430.2. HPLC, Rt: 5.3 min (purity: 99.0%).

Example 22

3-(4-{[(3-cyclopentylpropanoyl)(4-dec-1-ynylbenzyl)amino]methyl}phenyl)-propanoic acid

Step a) Formation of methyl 3-(4-{[(4-dec-1-ynylbenzyl)amino]methyl}phenyl)propanoate

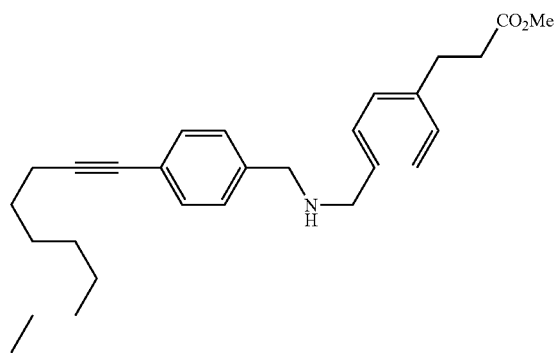

The title compound was prepared following the procedure A using 4-dec-1-ynylbenz-aldehyde and methyl 3-[4-(aminomethyl)phenyl]propanoate (purification by flash chromatography on SiO$_2$, EtOAc/c-Hex 20/80) as a yellow oil (53%). $^1$H NMR (CDCl$_3$) δ: 7.28 (d, J=8.3 Hz, 2H), 7.23-7.13 (m, 4H), 7.08 (d, J=7.9 Hz, 2H), 3.70 (s, 2H), 3.66 (s, 2H), 3.59 (s, 3H), 2.86 (t, J=8.3 Hz, 2H), 2.55 (t, J=7.2 Hz, 2H), 2.32 (t, J=7.2 Hz, 2H), 1.56-1.46 (m, 2H), 1.43-1.31 (m, 2H), 0.86-0.76 (m, 3H). M$^+$ (ESI): 420.4. HPLC, Rt: 4.5 min (purity: 99.5%).

Step b) Formation of methyl 3-(4-{[(3-cyclopentyl-propanoyl)(4-dec-1-ynylbenzyl)-amino]methyl}phenyl)propanoate

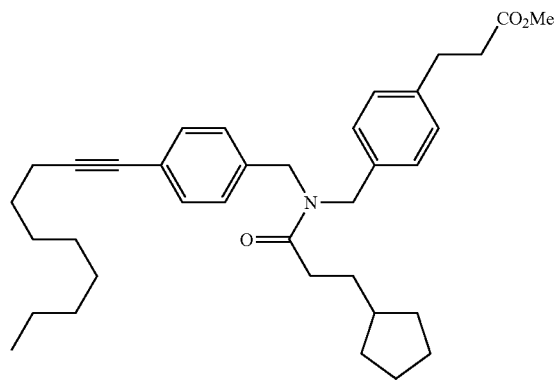

The title compound was prepared following the procedure E using of methyl 3-(4-{[(4-dec-1-ynylbenzyl)amino]methyl}phenyl)propanoate and 3-cyclopentylpropanoyl chloride (purification by flash chromatography on SiO$_2$. EtOAc/c-Hex 1/1) as a colorless oil (81%). $^1$H NMR (CDCl$_3$) δ: 7.35-6.93 (m, 8H), 4.47 (s, 2H), 4.34 (s, 1H), 4.31 (s, 1H), 3.61 and 3.60 (2 s, 3H) 2.88 (q, J=7.9 Hz, 2H), 2.55 (q, J=7.2 Hz, 2H), 2.41-2.20 (m, 4H), 1.78-1.12 (m, 21H), 1.10-0.91 (m, 2H), 0.88-0.75 (m, 3H). M$^+$ (ESI): 544.1. HPLC, Rt: 6.6 min (purity: 93.8%).

Step c) Formation of 3-(4-{[(3-cyclopentylpropanoyl)(4-dec-1-ynylbenzyl)amino]methyl}-phenyl)propanoic acid

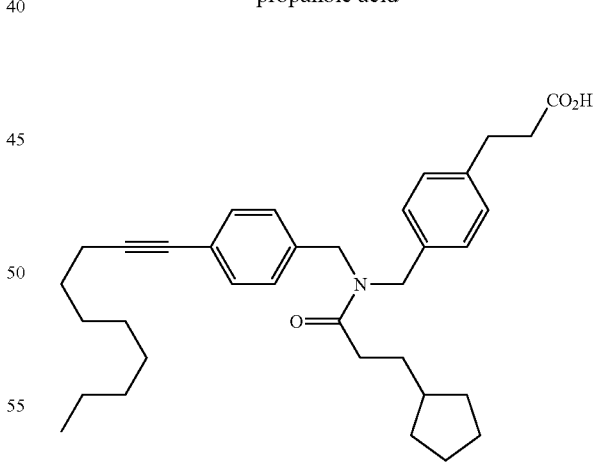

The title compound was prepared following the procedure F using methyl 3-(4-{[(3-cyclopentylpropanoyl) (4-dec-1-ynylbenzyl)amino]methyl}phenyl)propanoate as a colorless oil (69%). $^1$H NMR (CDCl$_3$) δ: 7.36-6.93 (m, 8H), 4.47 (s, 2H), 4.34 (s, 1H), 4.31 (s, 1H), 2.88 (q. J=7.5 Hz, 2H), 2.67-2.54 (m, 2H), 2.42-2.23 (m, 4H), 1.79-1.10 (m, 21H), 1.09-0.90 (m, 2H), 0.88-0.73 (m, 3H). HPLC, Rt: 6.2 min (purity: 94.7%). M$^+$ (ESI): 530.0; M$^-$ (ESI): 528.0.

Example 23

5-[{4-[(4-butylphenyl)ethynyl]benzyl}(cyclohexyl-carbonyl)amino]-2-hydroxybenzoic acid Step a) Formation of N-{4-[(4-butylphenyl)ethynyl]benzyl}-N-(2,2-dimethyl-4-oxo-4H-1,3-benzo-dioxin-6-yl)cyclohexanecarboxamide

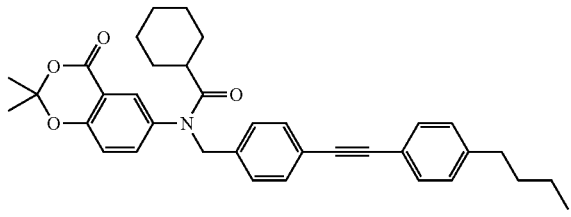

The titled compound was prepared following the procedure J using 6-({4-[(4-butylphenyl)ethynyl]benzyl}amino)-2,2-dimethyl-4H-1,3-benzodioxin-4-one hydrochloride and cyclohexanecarbonyl chloride as a colorless oil (86%). $^1$H NMR (CDCl$_3$, 300 MHz) δ 7.70 (d, J=2.3 Hz, 1H), 7.43 (m, 4H), 7.15 (m, 4H), 7.04 (dd, J=8.7, 2.3 Hz, 1H), 6.91 (d, J=8.7 Hz, 1H), 4.86 (s, 2H), 2.63 (t, J=7.7 Hz, 2H), 2.10 (m, 1H), 1.76 (s, 6H), 1.75-1.56 (m, 10H), 1.42-0.97 (m, 4H), 0.94 (t, J=7.4 Hz, 3H). M$^+$ (ESI): 550.8. HPLC, Rt: 6.45 min (Purity: 100%).

Step b) Formation of 5-[{4-[(4-butylphenyl)ethynyl]benzyl}(cyclohexylcarbonyl)amino]-2-hydroxybenzoic acid

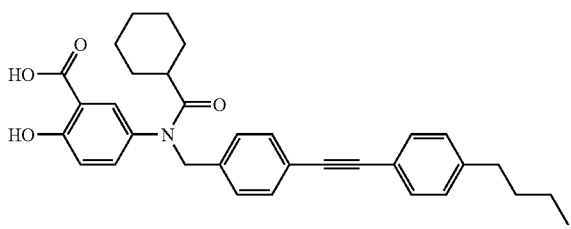

The titled compound was prepared following the procedure C using N-{4-[(4-butylphenyl)ethynyl]benzyl}-N-(2,2-dimethyl-4-oxo-4H-1,3-benzodioxin-6-yl)cyclohexanecarboxamide and NaOH (1N) in the presence of EtOH as a white powder (42%). $^1$H NMR (DMSO-d$_6$, 300 MHz) δ 7.44 (m, 5H), 7.27-7.16 (m, 5H), 6.95 (d, J=8.7 Hz, 1H), 4.79 (s, 2H), 2.59 (t, J=7.8 Hz, 2H), 2.12 (m, 1H), 1.63-0.89 (m, 14H), 0.88 (t, J=7.4 Hz, 3H). M$^-$ (ESI): 508.3; M$^+$ (ESI): 509.7. HPLC, Rt: 5.58 min (Purity: 99.8%).

Example 24

5-[{4-[(4-butylphenyl)ethynyl]benzyl}(hexanoyl)amino]-2-hydroxybenzoic acid. N-methyl-D-glu-camine (i.e. 1-deoxy-1-(methylamino)glucitol) salt Step a) Formation of N-{4-[(4-butylphenyl)ethynyl]benzyl}-N-(2,2-dimethyl-4-oxo-4H-1,3-benzo-dioxin-6-yl)hexanamide

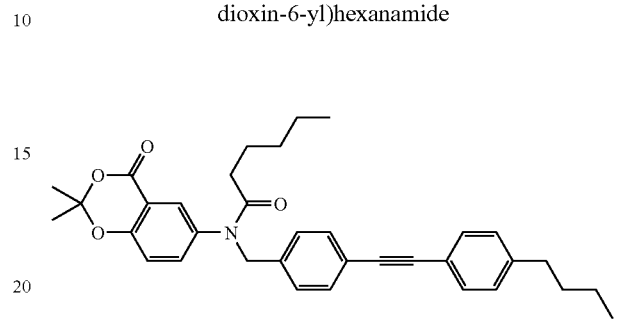

The titled compound was prepared following the procedure B using 6-({4-[(4-butylphenyl)ethynyl]benzyl}amino)-2,2-dimethyl-4H-1,3-benzodioxin-4-one hydrochloride and hexanoyl chloride as a colorless oil (88%). $^1$H NMR (CDCl$_3$, 300 MHz) δ 7.70 (d, J=2.3 Hz, 1H), 7.44 (m, 4H), 7.16 (m, 4H), 7.05 (dd, J=8.6, 2.3 Hz, 1H), 6.91 (d, J=8.6 Hz, 1H) 4.88 (s, 2H), 2.63 (t, J=7.7 Hz, 2H), 2.06 (t, J=7.5 Hz. 2H), 1.75 (s, 6H), 1.61 (m, 4H), 1.36 (m, 2H), 1.23 (m, 4H), 0.94 (t, J=7.3 Hz, 3H), 0.85 (t, J=6.8 Hz, 3H). M$^+$ (ESI): 538.4 HPLC, Rt: 5.95 min (Purity: 98.2%).

Step b) Formation of 5-[{4-[(4-butylphenyl)ethynyl]benzyl}(hexanoyl)amino]-2-hydroxybenzoic acid

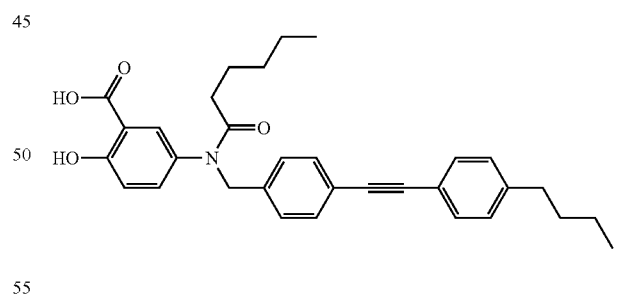

The titled compound was prepared following the procedure C using N-{4-[(4-butylphenyl)ethynyl]benzyl}-N-(2,2-dimethyl-4-oxo-4H-1,3-benzodioxin-6-yl)hexanamide and NaOH 5N aq in the presence of EtOH as a white foam (87%). $^1$R NMR (CDCl$_3$, 300 MHz) δ 10.72 (s, 1H), 7.56 (d, J=2.5 Hz, 1H), 7.43 (m, 4H), 7.17 (m, 4H), 7.04 (dd, J=8.8, 2.5 Hz, 1H), 6.95 (d, J=8.8 Hz, 1H), 4.88 (s, 2H), 2.62 (t, J=7.7 Hz, 2H), 2.10 (t, J=7.6 Hz, 2H), 1.61 (m, 4H), 1.36 (m, 2H), 1.22 (m, 4H), 0.93 (t, J=7.3 Hz, 3H), 0.84 (t, J=6.7 Hz, 3H). M$^-$ (ESI): 496.4; M$^+$ (ESI): 498.4. HPLC, Rt: 5.84 min (Purity: 100%).

Step c) Formation of 5-[{4-[(4-butylphenyl)ethynyl]benzyl}(hexanoyl)amino]-2-hydroxybenzoic acid, N-methyl-D-glucamine (i.e. 1-deoxy-1-(methylamino)glucitol) salt

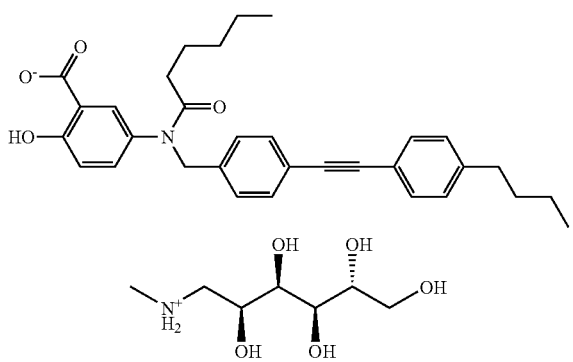

The titled compound was prepared following the procedure D using 5-[{4-[(4-butylphenyl)ethynyl]benzyl}(hexanoyl)amino]-2-hydroxybenzoic acid and N-methyl-D-glucamine in the presence of MeOH as a white powder (85%). M⁻ (ESI): 496.4; M⁺ (ESI): 498.4. HPLC, Rt: 5.81 min (Purity: 100%).

Example 25

5-((4-tert-butylbenzoyl){4-[(4-butylphenyl)ethynyl]benzyl}amino)-2-hydroxybenzoic acid, N-methyl-D-glucamine (i.e. 1-deoxy-1-(methylamino)glucitol) salt Step a) Formation of 4-tert-butyl-N-{4-[(4-butylphenyl)ethynyl]benzyl}-N-(2,2-dimethyl-4-oxo-4H-1,3-benzodioxin-6-yl)benzamide

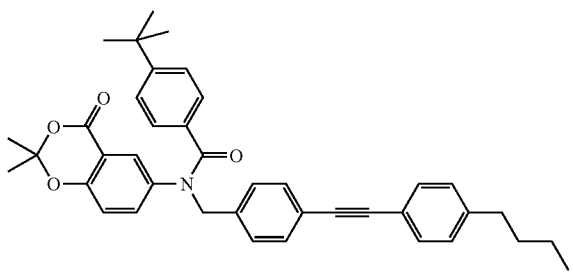

The titled compound was prepared following the procedure J using 6-({4-[(4-butylphenyl)ethynyl]benzyl}amino)-2,2-dimethyl-4H-1,3-benzodioxin-4-one hydrochloride and 4-tert-butylbenzoyl chloride as a colorless oil (76%). ¹H NMR (CDCl₃, 300 MHz) δ 7.65 (d, J=2.3 Hz, 1H), 7.46 (m, 4H), 7.30-7.16 (m, 8H), 7.01 (dd, J=8.7, 2.3 Hz, 1H), 6.74 (d, J=8.7 Hz, 1H), 5.14 (s, 2H), 2.64 (t, J=7.7 Hz, 2H), 1.68 (s, 6H), 1.62 (m, 2H), 1.38 (m, 2H), 1.25 (s, 9H), 0.95 (t, J=7.2 Hz, 3H). HPLC, Rt: 6.12 min (Purity: 97%).

Step b) Formation of 5-((4-tert-butylbenzoyl){4-[(4-butylphenyl)ethynyl]benzyl}amino)-2-hydroxybenzoic acid

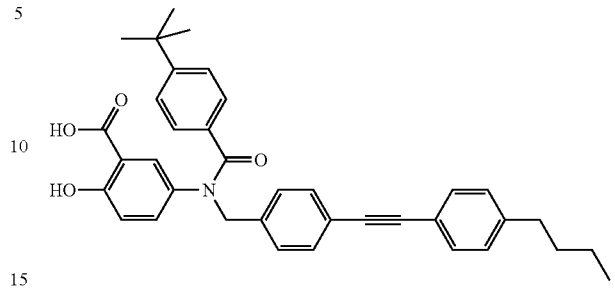

The titled compound was prepared following the procedure C using 4-tert-butyl-N-{4-[(4-butylphenyl)ethynyl]benzyl}-N-(2,2-dimethyl-4-oxo-4H-1,3-benzodioxin-6-yl)benzamide and NaOH 1M aq. in the presence of EtOH as a white powder (61%). ¹H NMR (McOD, 300 MHz) δ 7.63 (d, J=2.3 Hz, 1H), 7.46 (d, J=8.3 Hz, 2H), 7.43 (d, J=8.3 Hz, 2H), 7.33 (m, 6H), 7.22 (d, J=8.3 Hz, 2H), 6.85 (brd, J=8.7 Hz, 1H), 6.62 (d, J=8.7 Hz, 1H), 5.13 (s, 2H), 2.66 (t, J=7.5 Hz, 2H), 1.64 (m, 2H), 1.41 (m, 2H), 1.26 (s, 9H), 0.97 (t, J=7.3 Hz, 3H). M⁻ (ESI): 558.3. HPLC, Rt: 5.72 min (Purity: 97.9%).

Step c) Formation of 5-((4-tert-butylbenzoyl){4-[(4-butylphenyl)ethynyl]benzyl}amino)-2-hydroxybenzoic acid, N-methyl-D-glucamine (i.e. 1-deoxy-1-(methylamino)glucitol) salt The titled compound was prepared following the procedure D using 5-((4-tert-butylbenzoyl){4-[(4-butylphenyl)ethynyl]benzyl}amino)-2-hydroxybenzoic acid and N-methyl-D-glucamine as a pale pink powder (95%). M⁻ (ESI): 558.3; M⁺ (ESI): 560.1. HPLC, Rt: 5.94 min (Purity: 100%).

Example 26

5-((biphenyl-4-ylcarbonyl){4-[(4-butylphenyl)ethynyl]benzyl}amino)-2-hydroxybenzoic acid Step a) Formation of N-{4-[(4-butylphenyl)ethynyl]benzyl}-N-(2,2-dimethyl-4-oxo-4H-1,3-benzodioxin-6-yl)biphenyl-4-carboxamide

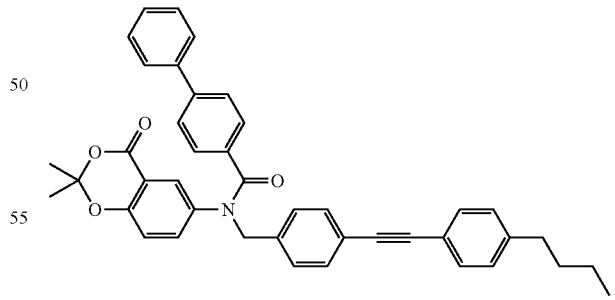

The titled compound was prepared following the procedure J using 6-({4-[(4-butylphenyl)ethynyl]benzyl}amino)-2,2-dimethyl-4H-1,3-benzodioxin-4-one hydrochloride and biphenyl-4-carbonyl chloride as a pale yellow oil (43%). ¹H NMR (CDCl₃, 300 MHz) δ 7.72 (brs, 1H), 7.53-7.27 (m, 15H), 7.17 (d, J=8.3 Hz, 2H), 6.98 (brd, J=8.7 Hz, 1H), 6.73 (d, J=8.7 Hz, 1H), 5.15 (s, 2H), 2.63 (t, J=7.5 Hz, 2H), 1.67 (s, 6H), 1.61 (m, 2H), 1.37 (m, 2H), 0.94 (t, J=7.2 Hz, 3H). HPLC, Rt: 6.07 min (Purity: 99.8%).

Step b) Formation of 5-((biphenyl-4-ylcarbonyl){4-[(4-butylphenyl)ethynyl]benzyl}amino)-2-hydroxybenzoic acid

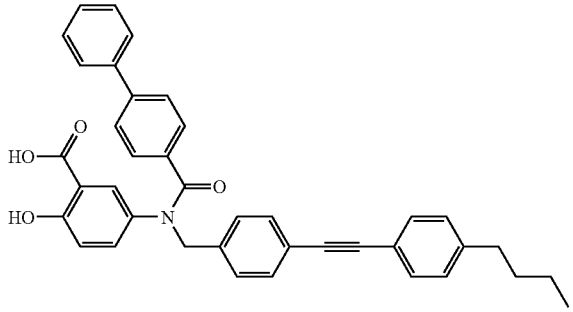

The titled compound was prepared following the procedure C using N-{4-[(4-butylphenyl)ethynyl]benzyl}-N-(2,2-dimethyl-4-oxo-4H-1,3-benzodioxin-6-yl)biphenyl-4-carboxamide and NaOH 1M aq. in the presence of EtOH as a pale yellow powder (41%).

$^1$H NMR (MeOD, 300 MHz) δ 7.66 (brs, 1H), 7.59 (d, J=7.2 Hz, 2H), 7.54-7.32 (m, 13H), 7.23 (d, J=8.3 Hz, 2H), 6.93 (brd, J=8.7 Hz, 1H), 6.67 (d, J=8.7 Hz, 1H), 5.18 (s, 2H), 2.67 (t, J=7.5 Hz, 2H), 1.65 (m, 2H), 1.41 (m, 2H), 0.98 (t, J=7.3 Hz, 3H). M$^-$ (ESI): 579.6 HPLC, Rt: 5.67 min (Purity: 99.4%).

Example 27

5-[{4-[(4-butylphenyl)ethynyl]benzyl}(3,3-dimethylbutanoyl)amino]-2-hydroxybenzoic acid Step a) Formation of N-{4-[(4-butylphenyl)ethynyl]benzyl}-N-(2,2-dimethyl-4-oxo-4H-1,3-benzodioxin-6-yl)-3,3-dimethylbutanamide

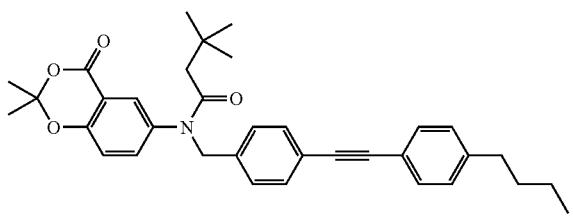

The titled compound was prepared following the procedure J using 6-({4-[(4-butylphenyl)ethynyl]benzyl}amino)-2,2-dimethyl-4H-1,3-benzodioxin-4-one hydrochloride and 4-hexylbenzoyl chloride as a colorless oil (95%). $^1$H NMR (CDCl$_3$, 300 MHz) δ 7.67 (brs, 1H), 7.43 (m, 4H), 7.16 (m, 4H), 7.01 (brd, J=8.7 Hz, 1H), 6.90 (d, J=8.7 Hz, 1H), 4.89 (s, 2H), 2.62 (t, J=7.6 Hz, 2H), 2.02 (s, 2H), 1.75 (s, 6H), 1.61 (m, 2H), 1.37 (m, 2H), 1.00 (s, 9H), 0.93 (t, J=7.2 Hz, 3H). M$^+$ (ESI): 538.1. HPLC, Rt: 5.97 min (Purity: 99.9%)

Step b) Formation of 5-[{4-[(4-butylphenyl)ethynyl]benzyl}(3,3-dimethylbutanoyl)amino]-2-hydroxybenzoic acid

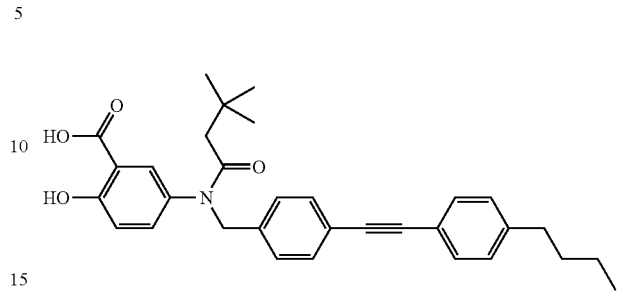

The titled compound was prepared following the procedure C using N-{4-[(4-butylphenyl)ethynyl]benzyl}-N-(2,2-dimethyl-4-oxo-4H-1,3-benzodioxin-6-yl)-3,3-dimethylbutanamide and aqueous NaOH (1M) in the presence of EtOH as a white powder (36%). $^1$H NMR (McOD, 300 MHz) δ 7.53 (d, J=2.4 Hz, 1H), 7.45 (d, J=8.0 Hz, 2H), 7.43 (d, J=8.0 Hz, 2H), 7.24 (d, J=8.0 Hz, 2H), 7.22 (d, J=8.0 Hz, 2H), 7.09 (dd, J=8.8, 2.4 Hz, 1H), 6.92 (d, J=8.8 Hz, 1H). 4.91 (s, 2H), 2.66 (t, J=7.7 Hz, 2H), 2.13 (s, 2H), 1.64 (m, 2H), 1.40 (m, 2H), 1.01 (s, 9H), 0.97 (t, J=7.5 Hz, 3H). M$^-$ (ESI): 496.4. HPLC, Rt: 5.56 min (Purity: 100%).

Example 28

5-[{4-[(4-butylphenyl)ethynyl]benzyl}(2,3-dihydro-1-benzofuran-5-ylcarbonyl)amino]-2-hydroxybenzoic acid Step a) Formation of N-{4[(4-butylphenyl)ethynyl]benzyl}-N-(2,2-dimethyl-4-oxo-4H-1,3-benzodioxin-6-yl)-2,3-dihydro-1-benzofuran-5-carboxamide

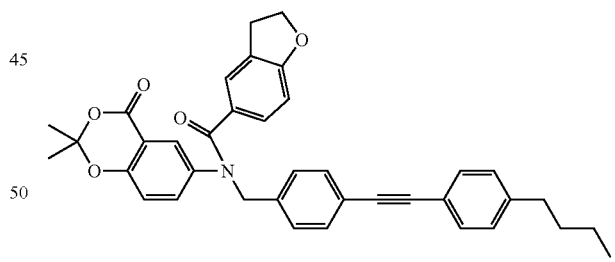

The titled compound was prepared following the procedure J using 6-({4-[(4-butylphenyl)ethynyl]benzyl}amino)-2,2-dimethyl-4H-1,3-benzodioxin-4-one hydrochloride and 2,3-dihydro-1-benzofuran-5-carbonyl chloride as a colorless oil (92%). $^1$H NMR (CDCl$_3$, 300 MHz) δ 7.66 (d, J=2.7 Hz, 1H), 7.44 (m, 4H), 7.34 (brs, 1H), 7.26 (d, J=8.3 Hz, 2H), 7.16 (d, J=8.0 Hz, 2H), 7.02 (m, 1H), 6.97 (dd, J=8.6, 2.7 Hz, 1H), 6.74 (d, J=8.6 Hz, 1H), 6.52 (d, J=8.3 Hz, 1H), 5.12 (s, 2H), 4.55 (t, J=8.9 Hz, 2H), 3.12 (t, J=8.9 Hz, 2H), 2.62 (t, J=7.8 Hz, 2H), 1.69 (s, 6H), 1.61 (m, 2H), 1.36 (m, 2H), 0.93 (t, J=7.4 Hz, 3H). M$^+$ (ESI): 586.4. HPLC, Rt: 6.05 min (Purity: 100%).

71

Step b) Formation of 5-[{4-[(4-biphenyl)ethynyl]benzyl}(2,3-dihydro-1-benzofuran-5-ylcarbonyl)amino]-2-hydroxybenzoic acid

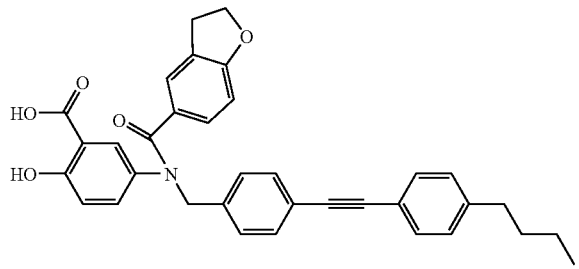

The titled compound was prepared following the procedure C using N-{4-[(4-butylphenyl)ethynyl]benzyl}-N-(2,2-dimethyl-4-oxo-4H-1,3-benzodioxin-6-yl)-2,3-dihydro-1-benzofuran-5-carboxamide and NaOH 1M aq in the presence of EtOH as a white powder (44%). $^1$H NMR (MeOD, 300 MHz) δ 7.51 (d, J=2.6 Hz, 1H), 7.47 (d, J=8.1 Hz, 2H), 7.43 (d, J=8.1 Hz, 2H), 7.33 (d, J=8.1 Hz, 2H), 7.28 (s, 1H), 7.22 (d, J=8.1 Hz, 2H), 7.13 (m, 2H), 6.79 (d, J=8.7 Hz, 1H), 6.59 (d, J=8.3 Hz, 1H), 5.12 (s, 2H), 4.54 (t, J=8.9 Hz, 2H), 3.12 (t, J=8.9 Hz, 2H), 2.66 (t, J=7.7 Hz, 2H), 1.64 (m, 2H), 1.40 (m, 2H), 0.97 (t, J=7.3 Hz, 3H). M$^-$ (ESI): 544.3; M$^+$ (ESI): 546.3. HPLC, Rt: 5.3 min (Purity: 99.8%).

Example 29

5-[{4-[(4-butylphenyl)ethynyl]benzyl}(7-carboxyheptanoyl)amino]-2-hydroxybenzoic acid Step a) Formation of methyl 8-[{4-[(4-butylphenyl)ethynyl]benzyl}(2,2-dimethyl-4-oxo-4H-1,3-benzodioxin-6-yl)amino]-8-oxooctanoate

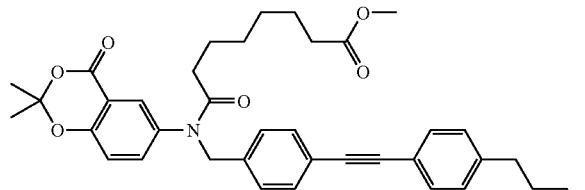

The titled compound was prepared following the procedure J using 6-({4-[(4-butylphenyl)ethynyl]benzyl}amino)-2,2-dimethyl-4H-1,3-benzodioxin-4-one hydrochloride and methyl 8-chloro-8-oxooctanoate as a colorless oil (97%). $^1$H NMR (CDCl$_3$, 300 MHz) δ 7.69 (br s, 1H), 7.44 (m, 4H), 7.18 (m, 4H), 7.04 (m, 1H), 6.92 (d, J=8.7 Hz, 1H), 4.88 (s, 2H), 3.66 (s, 3H). 2.63 (t, J=7.5 Hz, 2H), 2.28 (t, J=7.3 Hz, 2H), 2.05 (t, J=7.3 Hz, 2H), 1.75 (s, 6H), 1.61 (m, 6H), 1.38 (m, 2H), 1.26 (m, 4H), 0.94 (t, J=7.3 Hz, 3H). M$^+$ (ESI): 610.2. HPLC, Rt: 5.81 min (Purity: 100%).

72

Step b) Formation of 5-[{4-[(4-butylphenyl)ethynyl]benzyl}(7-carboxyheptanoyl)amino]-2-hydroxybenzoic acid

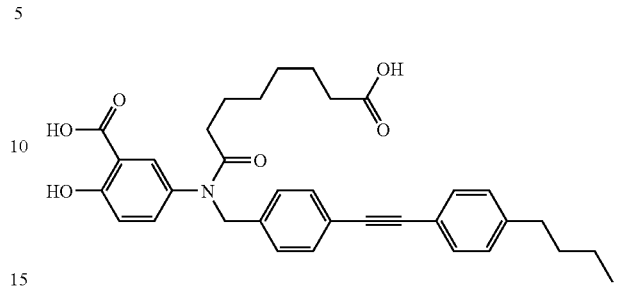

The titled compound was prepared following the procedure C using methyl 8-[{4-[(4-butylphenyl)ethynyl]benzyl}(2,2-dimethyl-4-oxo-4H-1,3-benzodioxin-6-yl)amino]-8-oxooctanoate and NaOH 1M aq in the presence of EtOH as a white powder (35%). $^1$H NMR (CDCl$_3$, 300 MHz) δ 10.69 (br s, 1H), 7.57 (d, J=2.3 Hz, 1H), 7.43 (m, 4H), 7.16 (m, 4H), 7.02 (dd, J=8.7, 2.3 Hz, 1H), 6.94 (d, J=8.7 Hz, 1H), 4.87 (s, 2H), 2.62 (t. J=7.5 Hz, 2H), 2.30 (t, J=7.4 Hz, 2H), 2.11 (t, J=7.3 Hz, 2H), 1.60 (m, 6H), 1.36 (m, 2H), 1.25 (m, 4H), 0.93 (t, J=7.3 Hz, 3H). M$^-$ (ESI): 554.3, M$^+$ (ESI): 556.4. HPLC, Rt: 5.03 min (Purity: 99%).

Example 30

5-((1,3-benzodioxol-5-ylcarbonyl){4-[(4-butylphenyl)ethynyl]benzyl}amino)-2-hydroxybenzoic acid Step a) Formation of N-{4-[(4-butylphenyl)ethynyl]benzyl}-N-(2,2-dimethyl-4-oxo-4H-1,3-benzodioxin-6-yl)-1,3-benzodioxole-5-carboxamide

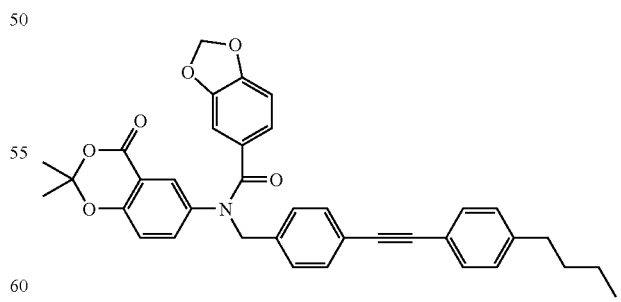

The titled compound was prepared following the procedure K using 6-({4-[(4-butylphenyl)ethynyl]benzyl}amino)-2,2-dimethyl-4H-1,3-benzodioxin-4-one hydrochloride and 1,3-benzodioxole-5-carbonyl chloride as a pale yellow oil (94%). M$^+$ (ESI): 588.3. HPLC, Rt: 5.69 min (Purity: 99.4%).

Step b) Formation of 5-((1,3-benzodioxol-5-ylcarbonyl){4-[(4-butylphenyl)ethynyl]-benzyl}amino)-2-hydroxybenzoic acid

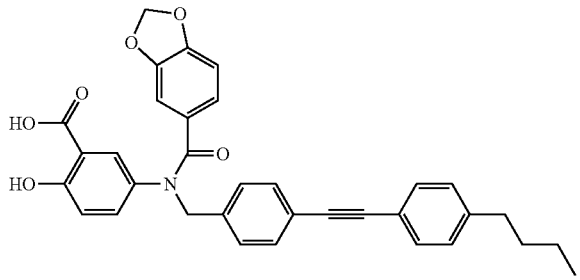

The titled compound was prepared following the procedure C using N-{4-[(4-butylphenyl)ethynyl]benzyl}-N-(2,2-dimethyl-4-oxo-4H-1,3-benzodioxin-6-yl)-1,3-benzodioxole-5-carboxamide and NaOH 5M aq. in the presence of EtOH as a pale yellow powder (55%). $^1$H NMR (CDCl$_3$, 300 MHz) δ 10.47 (s, 1H), 7.44 (m, 5H), 7.26 (d, J=8.2 Hz, 2H), 7.16 (d, J=8.0 Hz, 2H), 6.97 (m, 1H), 6.86 (m, 2H), 6.80 (d, J=9.1 Hz, 1H), 6.62 (d, J=8.6 Hz, 1H), 5.93 (s, 2H), 5.07 (s, 2H), 2.62 (t, J=7.8 Hz, 2H), 1.61 (m, 2H), 1.36 (m, 2H), 0.93 (t, J=7.2 Hz, 3H). M$^-$ (ESI): 546.2; M$^+$ (ESI): 548: HPLC, Rt: 5.23 min (Purity: 98.3%)

Step b) Formation of 5-[{4-[(4-butylphenyl)ethynyl]benzyl}(2,2-dimethylpropanoyl)amino]-2-hydroxybenzoic acid

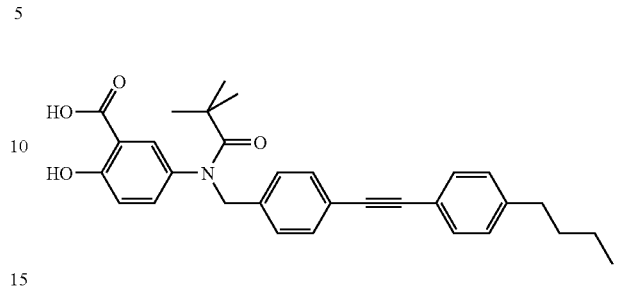

The titled compound was prepared following the procedure C using N-{4-[(4-butylphenyl)ethynyl]benzyl}-N-(2,2-dimethyl-4-oxo-4H-1,3-benzodioxin-6-yl)-2,2-dimethylpropionamide and NaOH 5M aq. in the presence of EtOH as a white powder (70%). $^1$H NMR (CDCl$_3$, 300 MHz) δ 10.62 (s, 1H), 7.55 (d, J=2.6 Hz, 1H), 7.43 (m, 4H), 7.15 (m, 4H), 7.08 (dd, J=8.7, 2.6 Hz, 1H), 6.93 (d, J=8.7 Hz, 1H), 4.83 (s, 2H), 2.62 (t, J=7.8 Hz, 2H), 1.61 (m, 2H), 1.36 (m, 2H, 1.08 (s, 9H), 0.93 (t, J=7.4 Hz, 3H). M$^-$ (ESI): 482.4; M$^+$ (ESI): 484.3. HPLC, Rt: 5.39 min (Purity: 100%).

Example 31

5-[{4-[(4-butylphenyl)ethynyl]benzyl}(2,2-dimethylpropanoyl)amino]-2-hydroxybenzoic acid Step a) Formation of N-{4-[(4-butylphenyl)ethynyl]benzyl}-N-(2,2-dimethyl-4-oxo-4H-1,3-benzodioxin-6-yl)-2,2-dimethylpropionamide

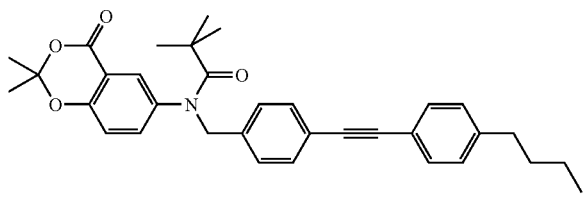

The titled compound was prepared following the procedure K using 6-({4-[(4-butylphenyl)ethynyl]benzyl}amino)-2,2-dimethyl-4H-1,3-benzodioxin-4-one hydrochloride and 2,2-dimethylpropanoyl chloride as a colorless oil (88%). $^1$H NMR (CDCl$_3$, 300 MHz) δ 7.72 (d, J=2.5 Hz, 1H), 7.43 (m, 4H), 7.15 (m, 4H), 7.06 (dd, J=8.7, 2.5 Hz, 1H), 6.87 (d, J=8.7 Hz, 1H), 4.84 (s, 2H), 2.63 (t, J=7.7 Hz, 2H), 1.75 (s, 6H), 1.61 (m, 2H), 1.36 (m, 2H), 1.07 (s, 9H), 0.94 (t, J=7.4 Hz, 3H). M$^+$ (ESI): 524.2. HPLC, Rt: 5.85 min (Purity: 99.5

Example 32

5-([(benzyloxy)acetyl]{4-[(4-butylphenyl)ethynyl]benzyl}amino)-2-hydroxybenzoic acid Step a) Formation of 2-(benzyloxy)-N-{4-[(4-butylphenyl)ethynyl]benzyl}-N-(2,2-dimethyl-4-oxo-4H-1,3-benzodioxin-6-yl)acetamide

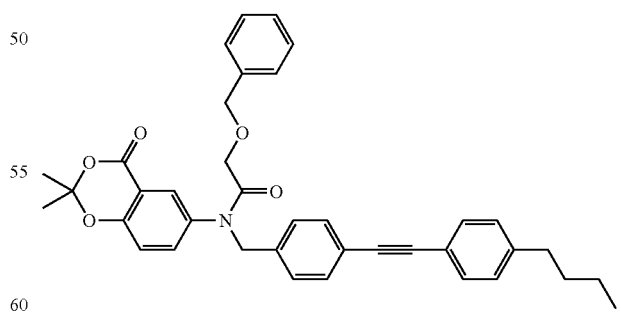

The titled compound was prepared following the procedure K using 6-({4-[(4-butylphenyl)ethynyl]benzyl}amino)-2,2-dimethyl-4H-1,3-benzodioxin-4-one hydrochloride and (benzyloxy)acetyl chloride as a yellow oil (88%). M$^+$ (ESI): 588.5. HPLC, Rt: 5.76 min (Purity: 100%).

Step b) Formation of 5-([(benzyloxy)acetyl]{4-[(4-butylphenyl)ethynyl]benzyl}amino)-2-hydroxybenzoic acid

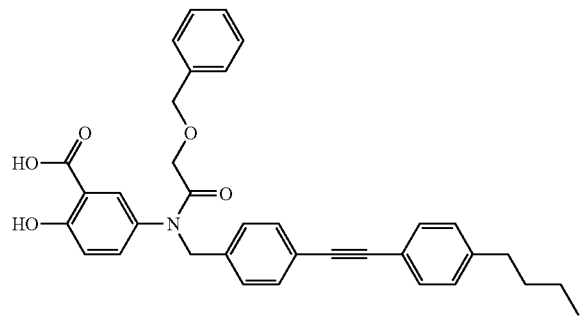

The titled compound was prepared following the procedure C using 2-(benzyloxy)-N-{4-[(4-butylphenyl)ethynyl]benzyl}-N-(2,2-dimethyl-4-oxo-4H-1,3-benzodioxin-6-yl)acetamide and NaOH 5M aq. in die presence of EtOH as a beige powder (67%). $^1$H NMR (CDCl$_3$, 300 MHz) δ 10.76 (s, 1H), 7.53 (m, 1H), 7.43 (m, 4H), 7.28 (m, 5H), 7.17 (m, 4H), 6.98 (m, 1H), 6.90 (d, J=8.7 Hz, 1H), 4.88 (s, 2H), 4.56 (s, 2H), 3.91 (s, 2H), 2.62 (t, J=7.7 Hz, 2H), 1.61 (m, 2H), 1.37 (m, 2H), 0.93 (t, J=7.4 Hz, 3H). M$^-$ (ESI): 546.2; M$^+$ (ESI): 548.3. HPLC, Rt; 5.33 min (Purity: 99%).

Example 33

5-[{4-[(4-butylphenyl)ethynyl]benzyl}(4-hexylbenzoyl)amino]-2-hydroxybenzoic acid

Step a) Formation of N-{4-[(4-butylphenyl)ethynyl]benzyl}-N-(2,2-dimethyl-4-oxo-4H-1,3-benzodioxin-6-yl)-4-hexylbenzamide

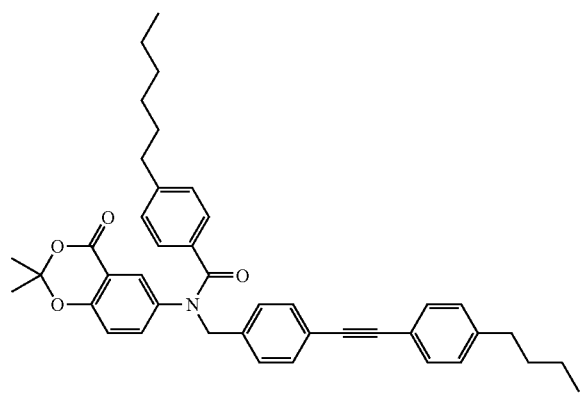

The titled compound was prepared following the procedure K using 6-({4-[(4-butylphenyl)ethynyl]benzyl}amino)-2,2-dimethyl-4H-1,3-benzodioxin-4-one hydrochloride and 4-hexylbenzoyl chloride as a yellow oil (85%). HPLC, Rt: 6.45 min (Purity: 99.8%).

Step b) Formation of 5-[{4-[(4-butylphenyl)ethynyl]benzyl}(4-hexylbenzoyl)amino]-2-hydroxybenzoic acid

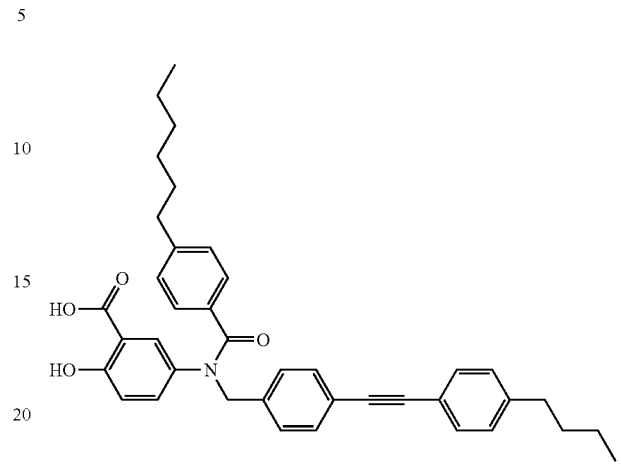

The titled compound was prepared following the procedure C using N-{4-[(4-butylphenyl)ethynyl]benzyl}-N-(2,2-dimethyl-4-oxo-4H-1,3-benzodioxin-6-yl)-4-hexylbenzamide and NaOH 5M aq. in the presence of EtOH as a grey powder (43%). $^1$H NMR (CDCl$_3$, 300 MHz) δ 10.46 (s, 1H), 7.46 (m, 5H), 7.27 (m, 4H), 7.16 (d, J=7.9 Hz, 2H), 7.00 (m, 3H), 6.76 (d, J=9.0 Hz, 1H), 5.10 (s, 2H), 2.62 (t, J=7.6 Hz, 2H), 2.52 (t, J=7.7 Hz, 2), 1.58 (m, 4H), 1.36 (m, 2H), 1.24 (brs, 6H), 0.93 (t, J=7.2 Hz, 3H), 0.85 (t, J=6.8 Hz, 3H). M$^-$ (ESI): 586.3; M$^1$(ESI): 588.2. HPLC, Rt: 6.04 min (Purity: 98.3%).

Example 34

5-[{4-[(4-butylphenyl)ethynyl]benzyl}(2-naphthoyl)amino]-2-hydroxybenzoic acid

Step a) Formation of N-{4-[(4-butylphenyl)ethynyl]benzyl}-N-(2,2-dimethyl-4-oxo-4H-1,3-benzodioxin-6-yl)-2-naphthamide

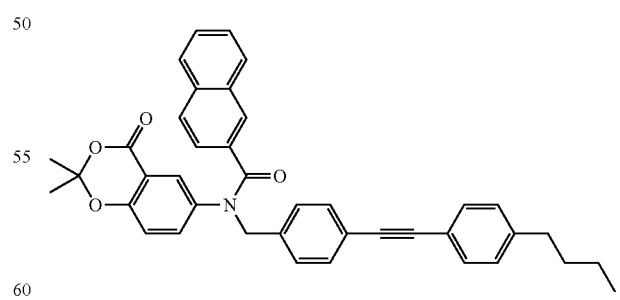

The titled compound was prepared following the procedure K using 6-({4-[(4-butylphenyl)ethynyl]benzyl}amino)-2,2-dimethyl-4H-1,3-benzodioxin-4-one hydrochloride and 2-naphthoyl chloride as a colorless oil (93%). M$^+$ (ESI): 594.4. HPLC, Rt: 5.96 min (Purity: 93.2%).

Step b) Formation of 5-[{4-[(4-butylphenyl)ethynyl]benzyl}(2-naphthoyl)amino]-2-hydroxybenzoic acid

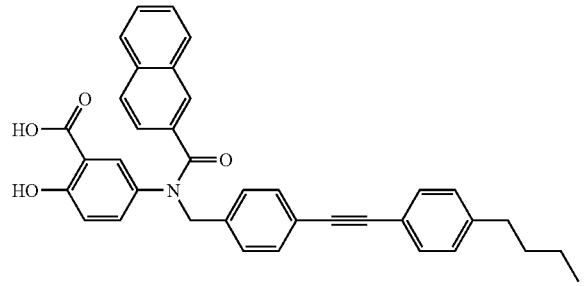

The titled compound was prepared following the procedure C using N-{4-[(4-butylphenyl)ethynyl]benzyl}-N-(2,2-dimethyl-4-oxo-4H-1,3-benzodioxin-6-yl)-2-naphthamide and NaOH 5M aq. in the presence of EtOH as a white powder (51%). $^1$H NMR (CDCl$_3$/MeOD 35:1, 300 MHz) δ 7.92 (s, 1H), 7.73 (d, J=8.7 Hz, 2H), 7.62 (d, J=8.7 Hz, 1H), 7.54 (s, 1H), 7.45 (m, 6H), 7.32 (m, 3H), 7.16 (d, J=7.9 Hz, 2H), 6.94 (d, J=8.3 Hz, 1H), 6.68 (d, J=8.6 Hz, 1H), 5.13 (s, 2H), 2.62 (t, J=7.7 Hz, 2H), 1.60 (m, 2H), 1.35 (m, 2H), 0.93 (t, J=7.2 Hz, 3H). M$^-$ (ESI): 552.3; M$^+$ (ESI): 554.2. HPLC, Rt: 5.53 min (Purity: 98.9%).

Example 35

5-((1-benzothien-2-ylcarbonyl){4-[(4-butylphenyl)ethynyl]benzyl}amino)-2-hydroxybenzoic acid, N-methyl-D-glucamine (i.e. 1-deoxy-1-(methylamino)glucitol) salt Step a) Formation of N-{4-[(4-butylphenyl)ethynyl]benzyl}-N-(2,2-dimethyl-4-oxo-4H-1,3-benzodioxin-6-yl)-1-benzothiophene-2-carboxamide

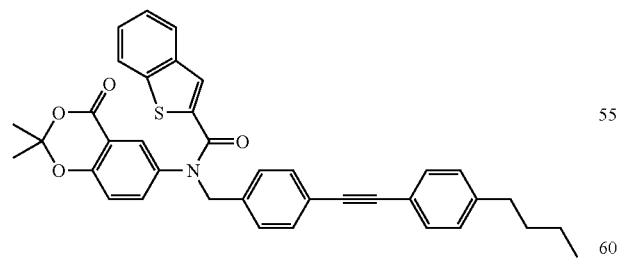

The titled compound was prepared following the procedure K using 6-({4-[(4-butylphenyl)ethynyl]benzyl}amino)-2,2-dimethyl-4H-1,3-benzodioxin-4-one hydrochloride and 1-benzothiophene-2-carbonyl chloride as a yellow oil (95%). HPLC, Rt: 6.04 min (Purity: 92.1%).

Step b) Formation of 5-((1-benzothien-2-ylcarbonyl){4-[(4-butylphenyl)ethynyl]benzyl}amino)-2-hydroxybenzoic acid

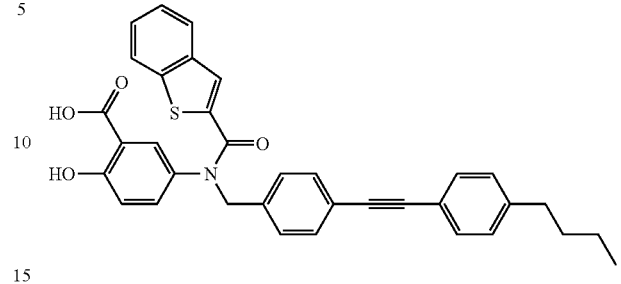

The titled compound was prepared following the procedure C using N-{4-[(4-butylphenyl)ethynyl]benzyl}-N-(2,2-dimethyl-4-oxo-4H-1,3-benzodioxin-6-yl)-1-benzothiophene-2-carboxamide and NaOH 5M aq. in the presence of EtOH as a beige powder (37%). $^1$H NMR (CDCl$_3$/MeOD 35:1, 300 MHz) δ 7.67 (m, 3H), 7.45-7.24 (m, 9H) 7.11 (m, 3H), 6.91 (d, J=9 Hz, 1H) 5.05 (s, 2H), 2.61 (t, J=7.5 Hz, 2H), 1.58 (m, 2H), 1.34 (m, 2H), 0.91 (t, J=7.2 Hz, 3H). M$^-$ (ESI): 558.3; M$^+$ (ESI): 560.1 HPLC, Rt: 5.62 min (Purity: 99.2%).

Step c) Formation of 5-((1-benzothien-2-ylcarbonyl){4-[(4-butylphenyl)ethynyl]benzyl}amino)-2-hydroxybenzoic acid, N-methyl-D-glucamine (i.e. 1-deoxy-1-(methylamino)glucitol) salt The titled compound was prepared following the procedure D using 5-((1-benzothien-2-ylcarbonyl){4-[(4-butylphenyl)ethynyl]benzyl}amino)-2-hydroxybenzoic acid and N-methyl-D-glucamine as a white powder (88%). M$^-$ (ESI): 558.2; M$^+$ (ESI); 560.1. HPLC, Rt: 5.59 min (Purity: 98%).

Example 36

4-[{4-[(4-butylphenyl)ethynyl]benzyl}(3-cyclopentylpropanoyl)amino]-2-hydroxybenzoic acid, N-methyl-D-glucamine (i.e. 1-deoxy-1-(methylamino)glucitol) salt Step a) Formation of 7-({4-[(4-butylphenyl)ethynyl]benzyl}amino)-2,2-dimethyl-4H-1,3-benzodioxin-4-one

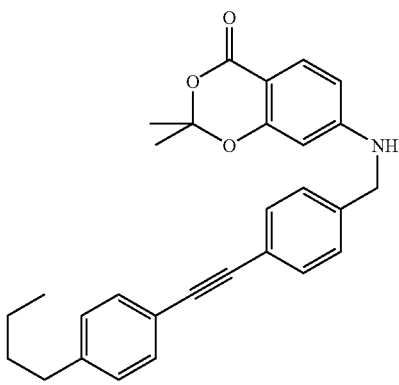

The titled compound was prepared following the procedure A using 4-[(4-butylphenyl)ethynyl]benzaldehyde and 7-amino-2,2-dimethyl-4H-1,3-benzodioxin-4-one as a yellow powder (66%). ¹H NMR (CDCl₃, 300 MHz) δ 7.71 (d, J=8.6 Hz, 1H), 7.50 (d, J=8.3 Hz, 2H), 7.42 (d, J=8.3 Hz, 2H), 7.29 (d, J=8.3 Hz, 2H), 7.14 (d, J=7.9 Hz, 2H), 6.32 (m, 1H), 6.10 (m, 1H), 4.38 (s, 2H), 2.61 (t, J=7.7 Hz, 2H), 1.68 (s, 6H), 1.68-1.52 (m, 2H), 1.41-1.25 (m, 2H), 0.92 (t, J=7.3 Hz, 3H).

Step b) Formation of N-{4-[(4-butylphenyl)ethynyl]benzyl}-3-cyclopentyl-N-(2,2-dimethyl-4-oxo-4H-1,3-benzodioxin-7-yl)propanamide

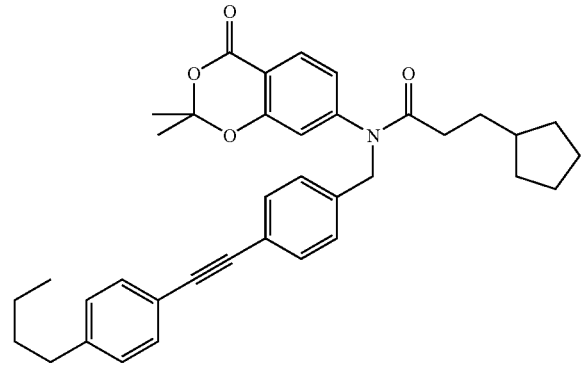

The titled compound was prepared following the procedure I using 7-({4-[(4-butylphenyl)ethynyl]benzyl}amino)-2,2-dimethyl-4H-1,3-benzodioxin-4-one and 3-cyclopentylpropanoyl chloride as a white powder (44%). ¹H NMR (CDCl₃, 300 MHz) δ 7.92 (d, J=8.3 Hz, 1H), 7.42 (m, 4H), 7.14 (m, 4H), 6.77 (m, 1H), 6.60 (br s, 1H), 4.89 (s, 2H), 2.61 (t, J=7.5 Hz, 2H), 2.16 (m, 2H), 1.71 (s, 6H), 1.68-1.28 (m, 13H), 1.03-0.88 (m, 5H). HPLC, Rt: 6.24 min (Purity: 99%).

Step c) Formation of 4-[{4-[(4-butylphenyl)ethynyl]benzyl}(3-cyclopentylpropanoyl)amino]-2-hydroxybenzoic acid

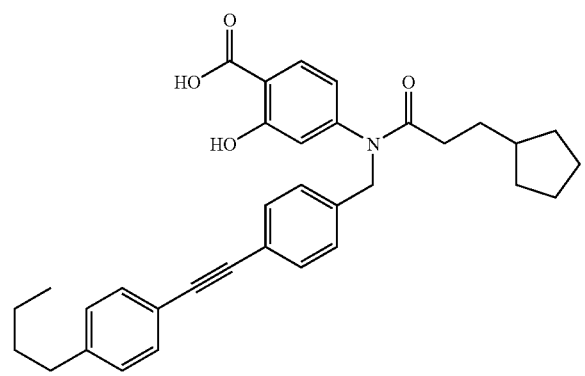

The titled compound was prepared following the procedure C using N-{4-[(4-butylphenyl)ethynyl]benzyl}-3-cyclopentyl-N-(2,2-dimethyl-4-oxo-4H-1,3-benzodioxin-7-yl)propanamide and NaOH as a yellow powder (74%). ¹H NMR (DMSO-d₆, 300 MHz) δ 7.76 (d, J=8.3 Hz, 1H), 7.45 (m, 4H), 7.23 (m, 4H) 6.84 (m, 1H), 6.77 (m, 1H), 4.92 (s, 2H), 2.60 (t, J=7.6 Hz, 2H), 2.20 (t, J=7.3 Hz, 2H), 1.70-1.21 (m, 13H), 1.00-0.84 (m, 5H). HPLC, Rt: 5.84 min (Purity: 100%).

Step d) Formation of 4-[{-4-[(4-butylphenyl)pentynyl]benzyl}3-cyclopentylpropanoyl)amino]-2-hydroxybenzoic acid, N-methyl-D-glucamine (i.e. 1-deoxy-1-(methylamino)glucitol) salt The titled compound was prepared following the procedure D using 4-[{4-[(4-butylphenyl)ethynyl]benzyl}(3-cyclopentylpropanoyl)amino]-2-hydroxybenzoic acid and N-methyl-D-glucamine as a white powder (96%). HPLC, Rt: 5.88 min (Purity: 100%).

Example 37

5-{[{4-[(4-butylphenyl)ethynyl]benzyl}(3-cyclopentylpropanoyl)amino]methyl}-2-hydroxybenzoic acid, N-methyl-D-glucamine (i.e. 1-deoxy-1-(methylamino)glucitol) salt Step a) Formation of 6-[({4-[(4-butylphenyl)ethynyl]benzyl}amino)methyl]-2,2-dimethyl-4H-1,3-benzodioxin-4-one

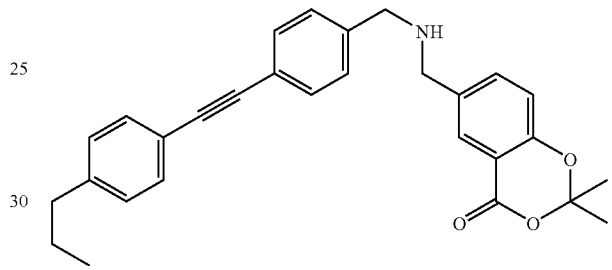

The titled compound was prepared following the procedure A using 4-[(4-butylphenyl)ethynyl]benzaldehyde and 6-(aminomethyl)-2,2-dimethyl-4H-1,3-benzodioxin-4-one acetate as a yellow oil (83%). ¹H NMR (CDCl₃, 300 MHz) δ 7.91 (s, 1H), 7.55 (m, 1H), 7.47 (d, J=7.9 Hz, 2H), 7.42 (d, J=7.9 Hz, 2H), 7.30 (d, J=8.3 Hz, 2H), 7.14 (m, 2H), 6.92 (d, J=8.3 Hz, 1H), 3.80 (s, 2H), 3.77 (s, 2H), 2.61 (m, 2H), 1.72 (s, 6H), 1.65-1.54 (m, 2H), 1.43-1.10 (m, 2H), 0.92 (m, 3H). M⁺ (ESI): 454.4. HPLC, Rt: 4.23 min (Purity: 100%).

Step b) Formation of N-{4-[(4-butylphenyl)ethynyl]benzyl}-3-cyclopentyl-N-[(2,2-dimethyl-4-oxo-4H-1,3-benzodioxin-6-yl)methyl]propanamide

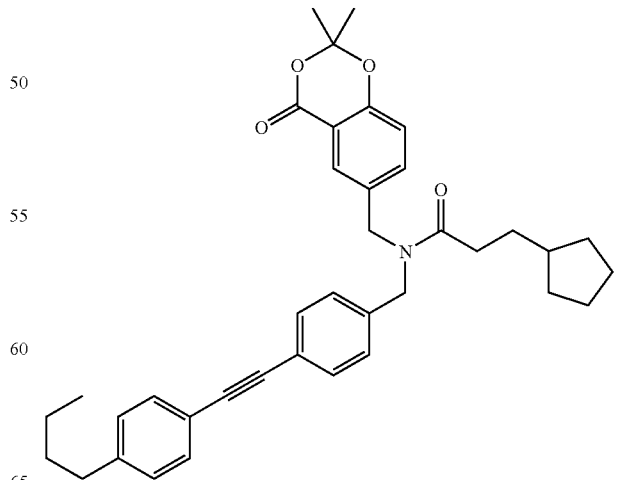

The titled compound was prepared following the procedure B using 6-[({4-[(4-butylphenyl)ethynyl]benzyl}amino)

methyl]-2,2-dimethyl-4H-1,3-benzodioxin-4-one and 3-cyclopentylpropanoyl chloride as a colorless oil (72%). $^1$H NMR (CDCl$_3$, 300 MHz) δ 7.74 (m, 1H), 7.50 (m, 2H), 7.43 (m, 2H), 7.35-7.21 (m, 1H), 7.20-6.85 (m, 5H), 4.56 (m, 2H), 4.52-4.40 (m, 2H), 2.61 (t, J=7.5 Hz, 2H), 2.42 (m, 2H), 1.80-1.62 (m, 11H), 1.61-1.30 (m, 8H). 1.18-1.00 (m, 2H), 0.92 (t, J=7.2 Hz, 3H). HPLC, Rt: 6.11 min (Purity; 98.7%).

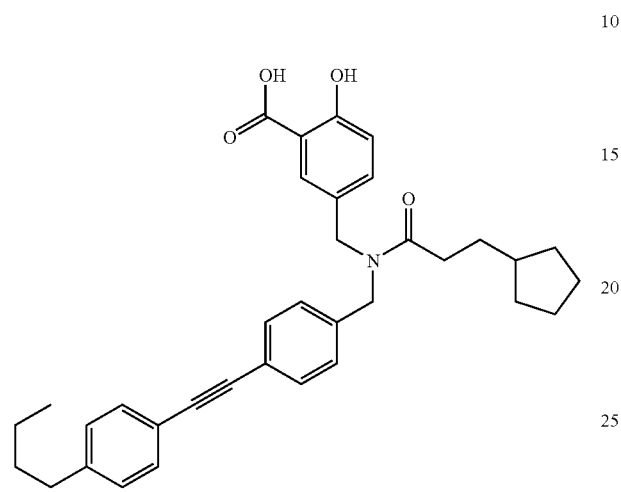

Step c) Formation of 5-{[{4-[(4-butylphenyl)ethynyl]benzyl}(3-cyclopentylpropanoyl)-amino]methyl}-2-hydroxybenzoic acid The titled compound was prepared following the procedure C using N-{4-[(4-butylphenyl)ethynyl]benzyl}-3-cyclopentyl-N-[(2,2-dimethyl-4-oxo-4H-1,3-benzodioxin-6-yl)methyl]propanamide acid NaOH as a colorless oil (94%). $^1$H NMR (CDCl$_3$, 300 MHz) 10.87 (s, 1H), 7.89 (s, 0.6H), 7.67 (s, 0.4H), 7.57-7.39 (m, 4H), 7.33-6.85 (m, 7H), 4.65-4.35 (m, 4H), 2.67-2.56 (m. 2H), 2.54-2.40 (m, 2H), 1.85-1.25 (m, 12H), 1.20-1.00 (m, 2H), 0.98-0.85 (t, J=7.4 Hz, 3H). HPLC, Rt: 6 min (Purity: 99.9%).

Step d) Formation of 5-{[{4-[(4-butylphenyl)ethynyl]benzyl}(3-cyclopentylpropanoyl)amino]methyl}-2-hydroxybenzoic acid, N-methyl-D-glucamine (i.e. 1-deoxy-1-(methylamino)glucitol) salt The titled compound was prepared following the procedure D using 5-{[{4-[(4-butylphenyl)ethynyl]benzyl}(3-cyclopentylpropanoyl)amino]methyl}-2-hydroxybenzoic acid and N-methyl-D-glucamine as a white powder (93%). M$^-$ (ESI): 536.1; M$^+$ (ESI): 538.2. HPLC, Rt: 5.74 min (Purity: 100%).

Example 38

5-{[{4-[(4-butylphenyl)ethynyl]benzyl}(hexanoyl)amino]methyl}-2-hydroxybenzoic acid Step a) Formation of N-{4-[(4-butylphenyl)ethynyl]benzyl}-N-[(2,2-dimethyl-4-oxo-4H-1,3-benzodioxin-6-yl)methyl]hexamine

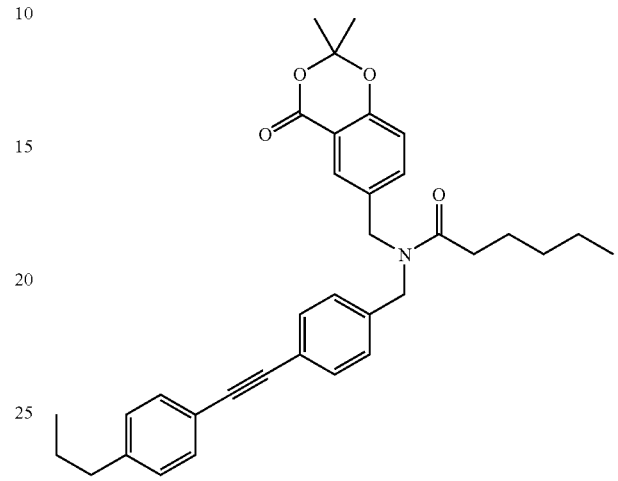

The titled compound was prepared following the procedure B using 6-[({4-[(4-butylphenyl)ethynyl]benzyl}amino)methyl]-2,2-dimethyl-4H-1,3-benzodioxin-4-one and hexanoyl chloride as a yellow oil (97%). $^1$H NMR (CDCl$_3$, 300 MHz) δ 8.03 (s, 1H), 7.75 (m, 1H, 7.49 (m, 4H), 7.15 (m, 4H), 6.95 (m, 1H), 4.60 (s, 1H) 4.58 (s, 1H), 4.51 (s, 1H), 4.44 (s, 1H), 2.63 (t J=7.7 Hz, 2H), 2.42 (m, 2H), 1.75 (s, 3H), 1.73 (s, 3H), 1.61 (m, 4H), 1.33 (m, 6H), 0.94 (t, J=7.4 Hz, 3H), 0.90 (m, 3H). M$^+$ (ESI): 552.5. HPLC, Rt: 6.2 min (Purity: 99.4%).

Step b) Formation of 5-{[{4-[(4-butylphenyl)ethynyl]benzyl}(hexanoyl)amino]methyl}-2-hydroxybenzoic acid

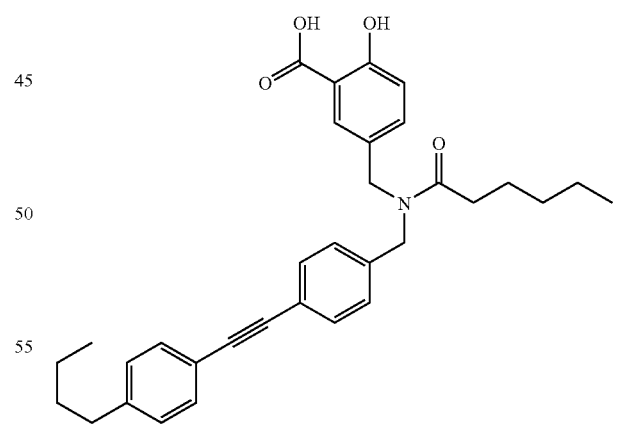

The titled compound was prepared following the procedure C using N-{4-[(4-butylphenyl)ethynyl]benzyl}-N-[(2,2-dimethyl-4-oxo-4H-1,3-benzodioxin-6-yl)methyl]hexanamide and NaOH 5N in the presence of EtOH as a yellow powder (79%). $^1$H NMR (CDCl$_3$, 300 MHz) δ 10.85 (s, 1H), 7.90-6.95 (m, 11H), 4.64-4.43 (m, 4H), 2.64 (t, J=7.5 Hz, 2H), 2.48 (m, 2H), 1.75 (m, 2H), 1.62 (m, 2H), 1.33 (m, 6H), 0.94 (t, J=7.2 Hz, 3H), 0.88 (m, 3H). M$^-$ (ESI): 510.3; M$^+$ (ESI): 512.4. HPLC, Rt: 5.6 min (Purity: 99%).

Example 39

(4-{[{4-[(4-butylphenyl)ethynyl]benzyl}(hexanoyl) amino]methyl}-phenoxy)acetic acid. N-methyl-D-glucamine (i.e. 1-deoxy-1-(methylamino)glucitol) salt

Step a) Formation of methyl {4-[({4-[(4-butylphenyl)ethynyl]benzyl}amino)methyl]phenoxy}acetate

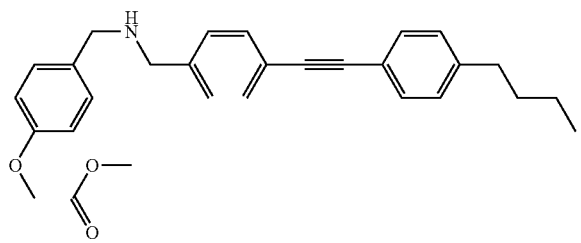

The titled compound was prepared following the procedure A using methyl [4-(aminomethyl)phenoxy]acetate acetate and 4-[(4-butylphenyl)ethynyl]benzaldehyde as a pale yellow oil (36%). $^1$H NMR (CDCl$_3$, 300 MHz) δ 7.46 (d, J=8.1 Hz, 2H), 7.42 (d, J=8.3 Hz, 2H), 7.29 (d, J=8.3 Hz, 2H), 7.25 (d, J=8.7 Hz, 2H), 7.13 (d, J=8.3 Hz, 2H), 6.86 (d, J=8.7 Hz, 2H), 4.60 (s, 2H), 3.79 (s, 3H), 3.78 (s, 2H), 3.72 (s, 2H), 2.59 (t, J=7.7 Hz, 2H), 1.58 (m, 2H), 1.34 (m, 2H), 0.91 (t, J=7.2 Hz, 3H). M$^+$ (ESI): 442.3. HPLC, Rt: 4.17 min (Purity: 94.9%).

Step b) Formation of methyl (4-{[{4-[(4-butylphenyl)ethynyl]benzyl}(hexanoyl)amino]methyl}phenoxy)acetate

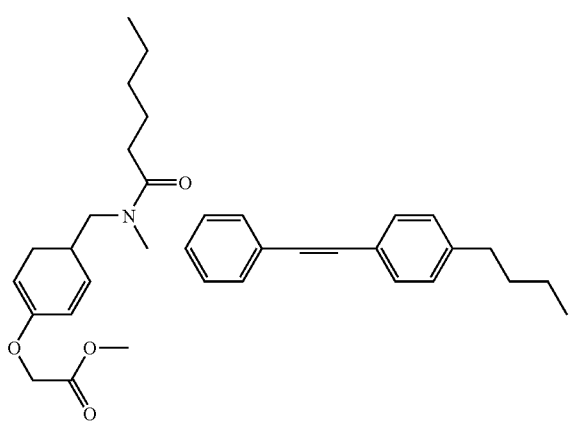

The titled compound was prepared following the procedure B using methyl {4-[({4-[(4-butylphenyl)ethynyl]benzyl}amino)methyl]phenoxy}acetate and hexanoyl chloride as a colorless oil (79%). $^1$H NMR (CDCl$_3$, 300 MHz) δ 7.41-7.50 (m, 4H), 7.03-7.16 (m, 6H), 6.85 (m, 2H), 4.62 (s, 1H), 4.60 (s, 1H), 4.55 (s, 1H), 4.51 (s, 1H), 4.41 (s, 1H), 4.36 (s, 1H), 3.80 (s, 1.5H), 3.79 (s, 1.51, 2.60 (t, J=7.6 Hz, 2H), 2.38 (m, 2H), 1.56-1.67 (m, 4H), 1.30-1.37 (m, 6H), 0.91 (m, 6H). M$^+$ (ESI): 540.4. HPLC, Rt: 5.85 min (Purity: 99.3%).

Step c) Formation of (4-{[{4-[(4-butylphenyl)ethynyl]benzyl}(hexanoyl)amino]methyl}phenoxy)acetic acid

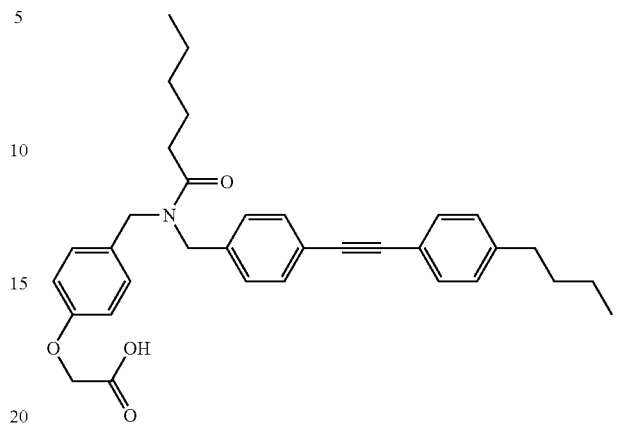

The titled compound was prepared following the procedure F using methyl (4-{[{4-[(4-butylphenyl)ethynyl]benzyl}(hexanoyl)amino]methyl}phenoxy)acetate and NaOH 1 N in the presence of MeOH/THF as a colorless oil (86%). $^1$H NMR (MeOD, 300 MHz) δ 7.39-7.47 (m, 4H), 7.10-7.20 (m, 6H), 6.91 (m, 2H), 4.65 (s, 1H), 4.64 (s, 1H), 4.54 (m, 4H), 2.63 (t, J=7.6 Hz, 2H), 2.45 (m, 2H), 1.62 (m, 4H), 1.23-1.40 (m, 6H), 0.90-0.97 (m, 6H), M$^-$ (ESI): 524.4; M$^+$ (ESI): 526.4. HPLC, Rt: 5.47 min (Purity: 98.7%).

Step d) Formation of (4-{[{4-[(4-butylphenyl)ethynyl]benzyl}(hexanoyl)amino]methyl}phenoxy)acetic acid, N-methyl-D-glucamine (i.e. 1-deoxy-1-(methylamino)glucitol) salt The titled compound was prepared following the procedure D using (4-{[{4-[(4-butylphenyl)ethynyl]benzyl}(hexanoyl)amino]methyl}phenoxy)acetic acid and N-methyl-D-glucamine in the presence of MeOH/H$_2$O as a white powder (98%). M$^-$ (ESI): 524.3; M$^+$ (ESI): 526.3. HPLC, Rt: 5.51 min (Purity: 99%).

Example 40

(4-{[{4-[(4-butylphenyl)ethynyl]benzyl}(cyanoacetyl)amino]methyl}phenoxy)acetic acid

Step a) Formation of methyl (4-{[{4-[(4-butylphenyl)ethynyl]benzyl}(cyanoacetyl)amino]methyl}phenoxy)acetate

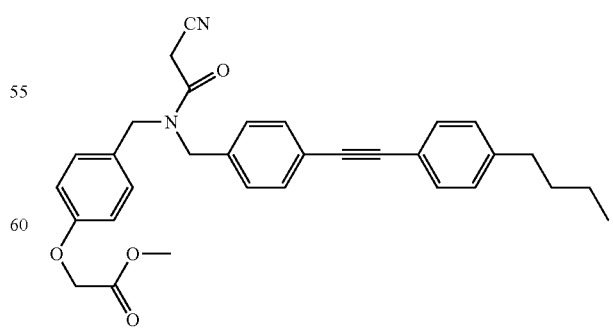

The titled compound was prepared following the procedure H using methyl {4-[({4-[(4-butylphenyl)ethynyl]benzyl}amino)methyl]phenoxy}acetate and cyanoaceticacid, as a pale yellow oil (96%). M⁻ (ESI): 507.4; M⁺ (ESI): 509.4. HPLC, Rt: 5.22 min (Purity: 86.2%).

Step b) Formation of (4-{[{4-[(4-butylphenyl)ethynyl]benzyl}(cyanoacetyl)amino]methyl}phenoxy) acetic acid

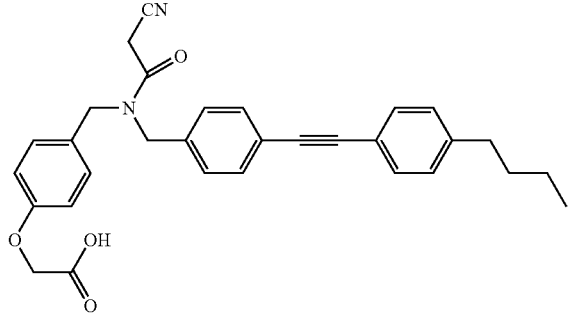

The titled compound was prepared following the procedure F using methyl (4-{[{4-[(4-butylphenyl)ethynyl]benzyl}(cyanoacetyl)amino]methyl}phenoxy)acetate and NaOH 1 N in the presence of DMF, as a white powder (20%). M⁻ (ESI): 493.3; M⁺ (ESI): 495.3. HPLC, Rt: 5.01 min (Purity: 80.6%).

Example 41

(4-{[{4-[(4-butylphenyl)ethynyl]benzyl}(1H-indazol-3-ylcarbonyl)amino]methyl}phenoxy)acetic acid Step a) Formation of methyl (4-{[{4-[(4-butylphenyl)ethynyl]benzyl}(1H-indazol-3-ylcarbonyl)amino]methyl}phenoxy)acetate

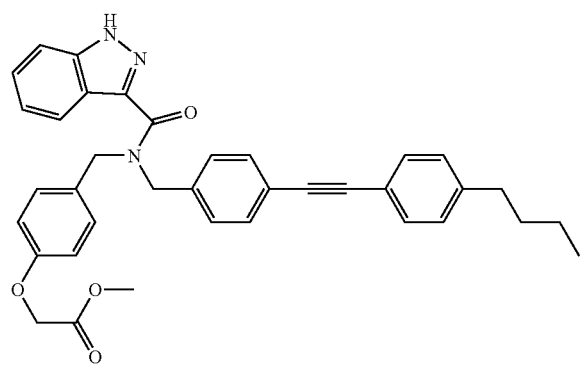

The titled compound was prepared following the procedure H using methyl {4-[({4-[(4-butylphenyl)ethynyl]benzyl}amino)methyl]phenoxy}acetate and 1H-indazole-3-carboxylic acid as a yellow oil (55%). ¹H NMR (MeOD, 300 MHz) δ 8.05 (m, 1H), 7.17-7.56 (m, 13H), 6.88 (m, 2H), 5.06 (s, 1H), 5.02 (s, 1H), 4.68 (m, 4H), 3.76 (s, 3H), 2.62 (t, J=7.4 Hz, 2H), 1.60 (m, 2H), 1.34 (m, 2H), 0.94 (t, J=7.4 Hz, 3H). M⁻ (ESI): 584.4; M⁺ (ESI): 5.86.3. HPLC, Rt: 5.49 min (Purity: 84.1%).

Step b) Formation of (4-{[{4-[(4-butylphenyl)ethynyl]benzyl}(1H-indazol-3-ylcarbonyl)amino]methyl}phenoxy)acetic acid

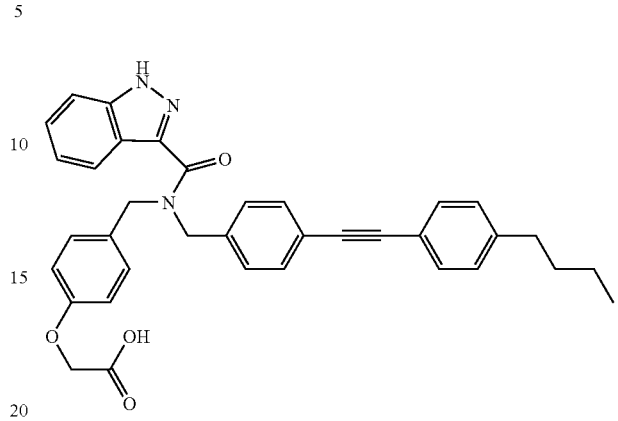

The titled compound was prepared following the procedure F using methyl (4-{[{4-[(4-butylphenyl)ethynyl]benzyl}(1H-indazol-3-ylcarbonyl)amino]methyl}phenoxy)acetate and NaOH 1N in the presence of MeOH/THF, as a yellow oil (75%). ¹H NMR (MeOD, 300 MHz) δ 8.09 (m, 1H), 7.17-7.64 (m, 13H), 6.90 (m, 2H), 5.07 (s, 1H), 5.02 (s, 1H), 4.67 (m, 4H), 2.62 (t, J=7.6 Hz, 2H), 1.61 (m, 2H), 1.35 (m, 2H), 0.95 (t, J=7.3 Hz, 3H). M⁻ (ESI): 570.3; M⁺ (ESI): 572.3. HPLC, Rt: 5.16 min (Purity: 94.1%).

Example 42

(4-{[{4-[(4-butylphenyl)ethynyl]benzyl}(pent-4-ynoyl)amino]methyl}phenoxy) acetic acid Step a) Formation of methyl (4-{[{4-[4-butylphenyl)ethynyl]benzyl}(pent-4-ynoyl)amino]methyl}phenoxy)acetate

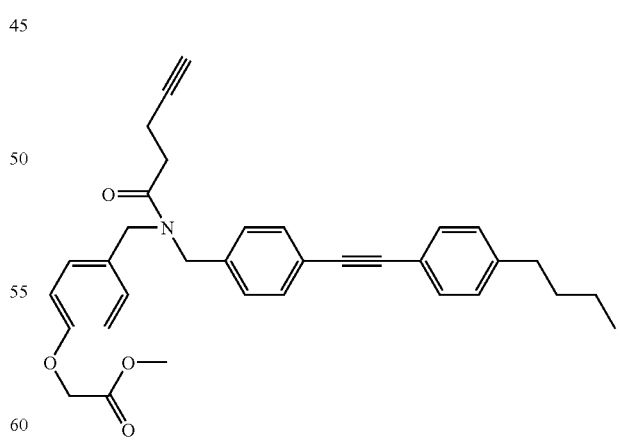

The titled compound was prepared following the procedure H using methyl {4-[({4-[(4-butylphenyl)ethynyl]benzyl}amino)methyl]phenoxy}acetate and pent-4-ynoic acid as a yellow oil (99%). HPLC, Rt: 5.63 min (Purity: 98.6%).

Step b) Formation of (4-{[{4-[(4-butylphenyl)ethynyl]benzyl}(pent-4-ynoyl)amino]methyl}phenoxy) acetic acid

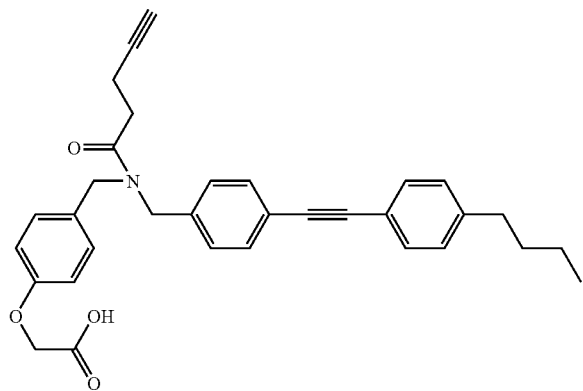

The titled compound was prepared following the procedure F using methyl (4-{[{4-[(4-butylphenyl)ethynyl]benzyl}(pent-4-ynoyl)amino]methyl}phenoxy)acetate and NaOH 1N in the presence of MeOH/THF as a yellow oil (87%). $^1$H NMR (DMSO-$d_6$, 300 MHz) δ 7.49 (m, 4H), 7.25-7.11 (m, 6H), 6.87 (m, 2H), 4.65 (s, 1H), 4.64 (s, 1H), 4.54 (s, 1H), 4.50 (s, 1H), 4.46 (s, 1H), 4.44 (s, 1H) 2.77-2.42 (m, 7H), 1.55 (m, 2H), 1.30 (m, 2H), 0.89 (t, J=7.3 Hz, 3H). M$^-$ (ESI): 506.4; M$^+$ (ESI): 508.4. HPLC, Rt: 5.05 min (Purity: 99.1%).

Example 43

[4-({{4-[(4-butylphenyl)ethynyl]benzyl}[(6-hydroxypyridin-3-yl)carbonyl]amino}methyl)phenoxy] acetic acid Step a) Formation of methyl [4-({{4-[(4-butylphenyl)ethynyl]benzyl}[(6-hydroxypyridin-3-yl)carbonyl]amino}methyl)phenoxy]acetate

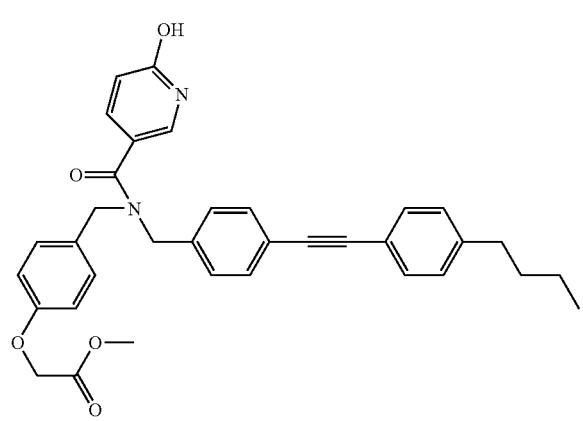

The titled compound was prepared following the procedure H using methyl {4-[({4-[(4-butylphenyl)ethynyl]benzyl}amino)methyl]phenoxy}acetate and 6-hydroxynicotinic acid as a colorless oil (95%). HPLC, Rt: 4.86 min (Purity: 88%).

Step b) Formation of [4-({{4-[(4-butylphenyl)ethynyl]benzyl}[(6-hydroxypyridin-3-yl)carbonyl]amino}methyl)phenoxy]acetic acid

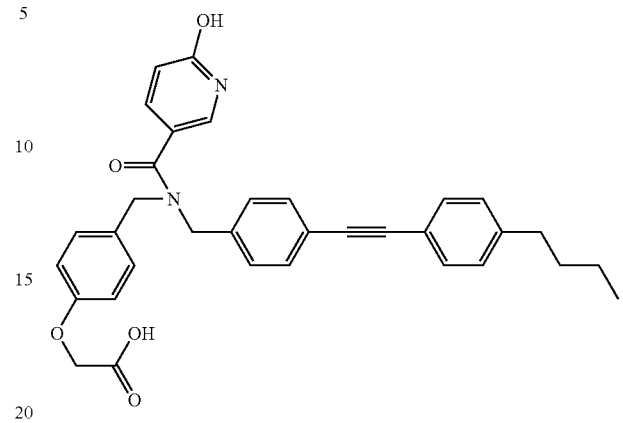

The titled compound was prepared following the procedure F using methyl [4-({{4-[(4-butylphenyl)ethynyl]benzyl}[(6-hydroxypyridin-3-yl)carbonyl]amino}methyl)phenoxy]acetate and NaOH 1N in the presence of MeOH/THF as a white powder (47%). $^1$H NMR (DMSO-$d_6$, 300 MHz) δ 7.57-7.43 (m, 6H), 7.26-7.09 (m, 6H), 6.89 (d, J=8.7 Hz, 2H), 6.33 (d, J=9.4 Hz, 1H), 4.65 (s, 2H), 4.52 (2H), 4.48 (s, 2H), 2.60 (t, J=7.5 Hz, 2H), 1.55 (m, 2H), 1.30 (m, 2H), 0.89 (t, J=7.3 Hz, 3H). M$^-$ (ESI): 547.3; M$^+$ (ESI): 549.4. HPLC, Rt: 4.48 min (Purity: 76.9%).

Example 44

[4-({{4-[(4-butylphenyl)ethynyl]benzyl}[(2-methoxyethoxy)acetyl]amino}methyl)phenoxy]acetic acid Step a) Formation of methyl [4-({{4-[(4-butylphenyl)ethynyl]benzyl}[(2-methoxyethoxy)acetyl]amino}methyl)phenoxy]acetate

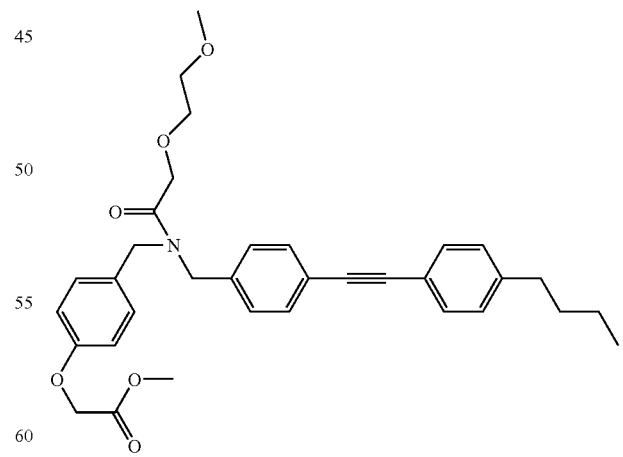

The titled compound was prepared following the procedure H using methyl {4-[({4-[(4-butylphenyl)ethynyl]benzyl}amino)methyl]phenoxy}acetate and (2-methoxyethoxy)acetic acid as a yellow oil (96%). HPLC, Rt: 5.17 min (Purity: 94.8%).

Step b) Formation of [4-({{4-[(4-butylphenyl)ethynyl]benzyl}[(2-methoxyethoxy)acetyl]amino}methyl)phenoxy]acetic acid

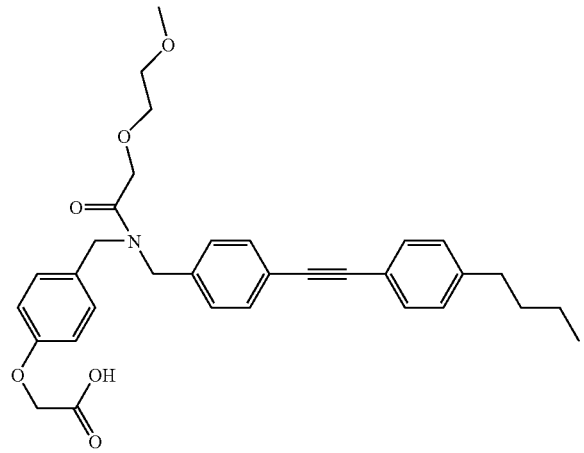

The titled compound was prepared following the procedure F using methyl [4-({{4-[(4-butylphenyl)ethynyl]benzyl}[(2-methoxyethoxy)acetyl]amino}methyl)phenoxy]acetate and NaOH 1N in the presence of MeOH/THF as a yellow oil (94%). $^1$H NMR (DMSO-$d_6$, 300 MHz) δ 7.54-7.43 (m, 4H), 7.24 (m, 4H), 7.14 (d, J=8.3 Hz, 2H), 6.86 (m, 2H), 4.62 (s, 2H), 4.41 (m, 4H), 4.28 (s, 1H), 4.20 (s, 1H), 3.59 (m, 2H), 3.42 (m, 2H), 3.21 (s, 1.5H), 3.19 (s, 1.5H), 2.60 (t, J=7.5 Hz, 2H), 1.55 (m, 2H), 1.30 (m, 2H), 0.89 (t, J=7.2 Hz, 3H). M$^-$ (ESI): 542.4; M$^+$ (ESI): 544.4. HPLC, Rt: 4.82 min (Purity: 90.8%).

Example 45

(4-{[{4-[4-butylphenyl)ethynyl]benzyl}(1H-pyrazol-4-ylcarbonyl)amino]methyl}phenoxy)acetic acid Step a) Formation of methyl (4-{[{4-[(4-butylphenyl)ethynyl]benzyl}(1H-pyrazol-4-ylcarbonyl)amino]methyl}phenoxy)acetate

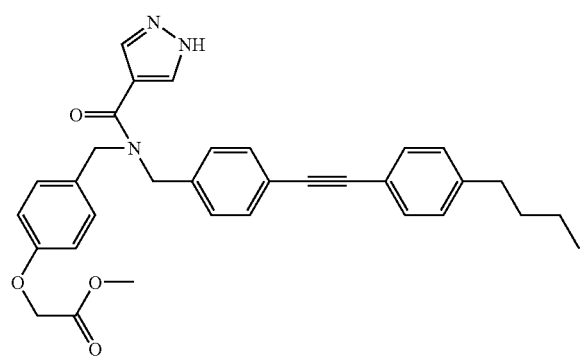

The titled compound was prepared following the procedure H using methyl {4-[({4-[(4-butylphenyl)ethynyl]benzyl}amino)methyl]phenoxy}acetate and 1H-pyrazole-4-carboxylic acid as a colorless oil (95%). HPLC, Rt: 5.15 min (Purity: 69.2%).

Step b) Formation of (4-{[{4-[(4-butylphenyl)ethynyl]benzyl}(1H-pyrazol-4-ylcarbonyl)amino]methyl}phenoxy)acetic acid

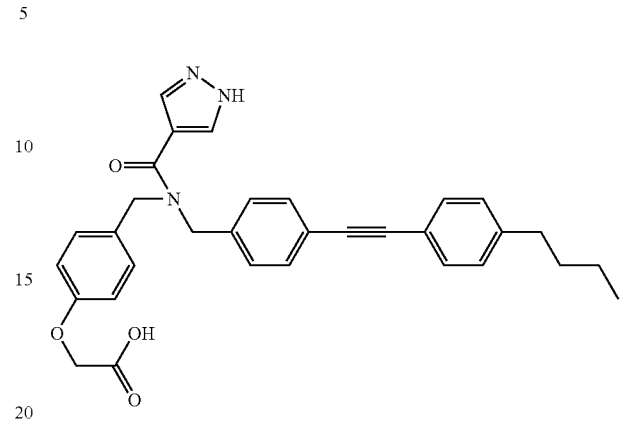

The titled compound was prepared following the procedure F using methyl (4-{[{4-[(4-butylphenyl)ethynyl]benzyl}(1H-pyrazol-4-ylcarbonyl)amino]methyl}phenoxy)acetate and NaOH 1N in the presence of MeOH/THF as a white powder (30%). $^1$H NMR (MeOD, 300 MHz) δ 7.76 (m, 2H), 7.45 (m, 4H), 7.17 (m, 6H), 6.88 (m, 2H), 4.64 (s, 2H), 3.94 (s, 4H), 2.59 (t J=7.7 Hz, 2H), 1.57 (m, 2H), 1.33 (m, 2H), 0.90 (t, J=7.3 Hz, 3H). HPLC, Rt: 4.62 min (Purity: 88%).

Example 46

3-[(3-cyclopentylpropanoyl)(4-dec-1-ylbenzylamino]benzoic acid, N-methyl-D-glucamine (i.e. 1-deoxy-1-(methylamino)glucitol) salt Step a) Formation of methyl 3-[(4-dec-1-yn-1-ylbenzyl)amino]benzoate hydrochloride

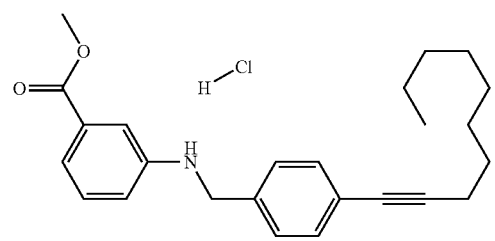

The titled compound was prepared following the procedure A using methyl 3-aminobenzoate and 4-dec-1-yn-1-ylbenzaldehyde as a yellow powder (41%). $^1$H NMR (MeOD, 300 MHz) δ 7.33 (s, 4H), 7.28 (m, 2H), 7.19 (m, 1H), 6.84 (m, 1H), 4.36 (s, 2H). 3.87 (s, 3H), 2.41 (t, J=7.0 Hz, 2H), 1.61 (m, 2H), 1.49 (m, 2H), 1.35 (m, 8H), 0.93 (t, J=6.8 Hz, 3H). HPLC, Rt: 5.63 min (Purity: 98.7%).

Step b) Formation of methyl 3-[(3-cyclopentylpropanoyl)(4-dec-1-yn-1-ylbenzyl)amino]benzoate

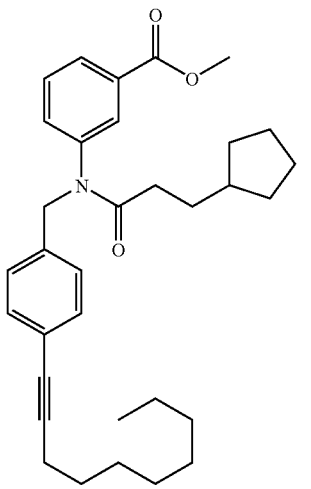

The titled compound was prepared following the procedure G using methyl 3-[(4-dec-1-yn-1-ylbenzyl)amino]benzoate hydrochloride and 3-cyclopentylpropanoyl chloride as a pale yellow oil (76%). $^1$H NMR (CDCl$_3$, 300 MHz) δ 7.99 (d, J=7.9 Hz, 1H), 7.73 (s, 1H), 7.38 (m, 1H), 7.29 (d, J=8.3 Hz, 2H), 7.09 (m, 3H), 4.88 (s, 2H), 3.93 (s, 3H), 2.39 (t, J=7.0 Hz, 2H), 2.06 (m, 2H), 1.61-1.30 (m, 21H), 0.95 (m, 2H), 0.89 (t, J=6.8 Hz, 3H). M$^+$ (ESI): 502.4. HPLC, Rt: 6.32 min (Purity: 99.9%).

Step c) Formation of 3-[(3-cyclopentylpropanoyl)(4-dec-1-yn-1-ylbenzyl)amino]benzoic acid

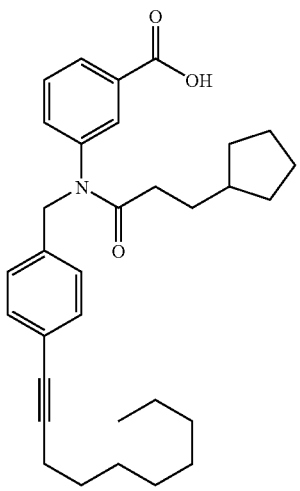

The titled compound was prepared following the procedure F using methyl 3-[(3-cyclopentylpropanoyl)(4-dec-1-yn-1-ylbenzyl)amino]benzoate and NaOH 5N aq in the presence of MeOH as a pale yellow oil (86%). $^1$H NMR (CDCl$_3$, 300 MHz) δ 8.07 (d, J=7.5 Hz, 1H), 7.83 (s, 1H), 7.43 (m, 1H), 7.31 (d, J=7.9 Hz, 2H), 7.12 (m, 3H), 4.90 (s, 2H), 2.39 (t, J=7.0 Hz, 2H), 2.09 (m, 21H), 1.62-1.30 (m, 21H), 0.96 (m, 2H), 0.89 (t, J=6.6 Hz, 3H). M$^-$ (ESI): 486.6; M$^+$ (ESI): 488.5. HPLC, Rt: 5.8 min (Purity: 100%).

Step d) Formation of 3-[(3-cyclopentylpropanoyl)(4-dec-1-yn-1-ylbenzyl)amino]benzoic acid, N-methyl-D-glucamine (i.e. 1-deoxy-1-(methylamino)glucitol) salt The titled compound was prepared following the procedure D using 3-[(3-cyclopentylpropanoyl)(4-dec-1-yn-1-ylbenzyl)amino]benzoic acid and N-methyl-D-glucamine as a white gummy solid (93%). M$^-$ (ESI): 486.4; M$^+$ (ESI): 488. HPLC, Rt: 5.99 min (Purity: 99.8%).

Example 47

3-[(4-dec-1-yn-1-ylbenzyl)(hexanoyl)amino]benzoic acid

Step a) Formation of methyl 3-[(4-dec-1-yn-1-ylbenzyl)(hexanoyl)amino]benzoate

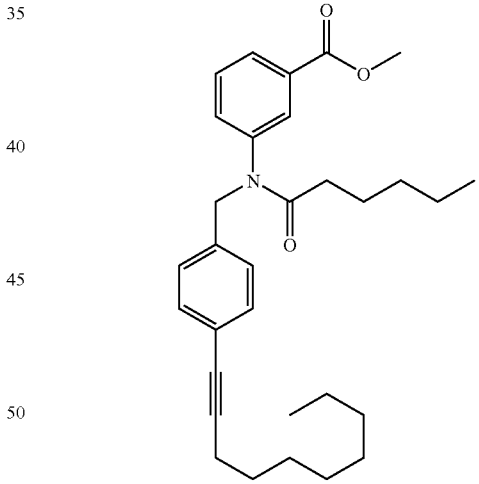

The titled compound was prepared following the procedure G using methyl 3-[(4-dec-1-yn-1-ylbenzyl)amino]benzoate hydrochloride and hexanoyl chloride as a pale yellow oil (74%). $^1$H NMR (CDCl$_3$, 300 MHz) δ 7.98 (d, J=7.6 Hz, 1H), 7.73 (s, 1H), 7.38 (m, 1H), 7.30 (d, J=7.9 Hz, 2H), 7.08 (m, 3H), 4.88 (s, 2H), 3.93 (s, 3H), 2.39 (t, J=7.0 Hz, 2H), 2.04 (t, J=7.2 Hz, 2H), 1.60 (m, 4H); 1.44 (m, 2H), 1.35-1.15 (m, 12H), 0.89 (t, J=6.8 Hz, 3H), 0.84 (t, J=7.0 Hz, 3H), M$^1$(ESI): 476.5. HPLC, Rt: 6.17 min (Purity: 100%).

Step b) Formation of 3-[(4-dec-1-yn-1-ylbenzyl)(hexanoyl)amino]benzoic acid

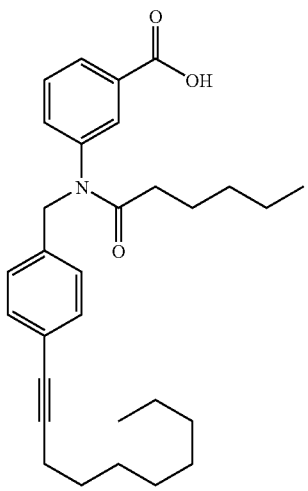

The titled compound was prepared following the procedure F using methyl 3-[(4-dec-1-yn-1-ylbenzyl)(hexanoyl)amino]benzoate and NaOH 5N aq in the presence of MeOH as a pale yellow oil (89%). $^1$H NMR (CDCl$_3$, 300 MHz) δ 8.06 (d, J=7.5 Hz, 1H), 7.82 (s, 1H), 7.43 (m, 1H), 7.31 (d, J=8.3 Hz, 2H), 7.12 (m, 3H), 4.91 (s, 2H), 2.39 (t. J=7.0 Hz, 2H), 2.07 (m, 2H), 1.60 (m, 4H), 1.44 (m, 2H), 1.35-1.17 (m, 12H), 0.86 (m, 6H). M$^-$ (ESI): 460.6; M$^+$ (ESI): 462.5. HPLC, Rt: 5.65 min (Purity: 99.5%).

Example 48

4-{[{4-[(4-butylphenyl)ethynyl]benzyl}(3-cyclopentylpropanoyl)amino]methyl}benzoic acid Step) a) Formation of methyl 4-[({4-[(4-butylphenyl)ethynyl]benzyl}amino)methyl]benzoate

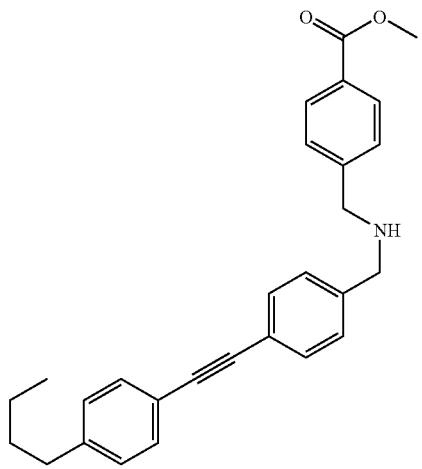

The titled compound was prepared following the procedure A using methyl 4-(aminomethyl)benzoate hydrochloride and 4-[(4-butylphenyl)ethynyl]benzaldehyde as a white solid (54%). $^1$H NMR (CDCl$_3$, 300 MHz) δ 8.02 (d, J=8.3 Hz, 2H), 7.51 (d, J=7.9 Hz, 2H), 7.44 (m, 4H), 7.33 (d, J=7.9 Hz, 2H), 7.17 (d, J=7.9 Hz, 2H), 3.92 (s, 3H), 3.87 (s, 2H), 3.82 (s, 2H), 2.63 (t, J=7.7 Hz, 2H), 1.61 (m, 2H), 1.37 (m, 2H), 0.94 (t, J=7.3 Hz, 3H). M$^+$ (ESI): 412.4. HPLC, Rt: 4.28 min (Purity: 99.4%).

Step b) Formation of methyl 4-{[{4-[(4-butylphenyl)ethynyl]benzyl}(3-cyclopentylpropanoyl)amino]methyl}benzoate

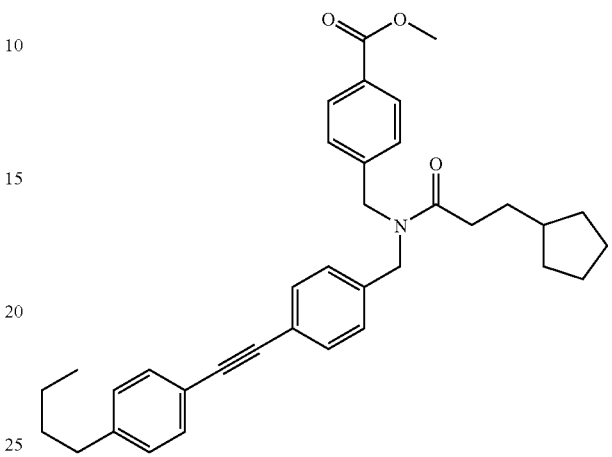

The titled compound was prepared following the procedure E using methyl 4-[({4-[(4-butylphenyl)ethynyl]benzyl}amino)methyl]benzoate and 3-cyclopentylpropanoyl chloride as a colorless oil (71%). $^1$H NMR (CDCl$_3$, 300 MHz) δ 8.02 (d, J=8.3 Hz, 1H), 7.97 (d, J=8.3 Hz, 1H), 7.54-7.39 (m, 4H), 7.30-7.06 (m, 6H), 4.61 (d, J=11.3 Hz, 2H), 4.48 (d, J=11.7 Hz, 2H), 3.91 (m, 3H), 2.61 (t, J=7.7 Hz, 2H), 2.41 (m, 2H), 1.79-1.66 (m, 4H), 1.65-1.43 (m, 7H), 1.40-1.28 (m, 2H), 1.14-1.00 (m, 2H), 0.92 (t, J=7.3 Hz, 3H). M$^+$ (ESI): 536.4. HPLC, Rt: 6.42 min (Purity: 99%).

Step c) Formation of 4-{[{4-[(4-butylphenyl)ethynyl]benzyl}(3-cyclopentylpropanoyl)amino]methyl}benzoic acid

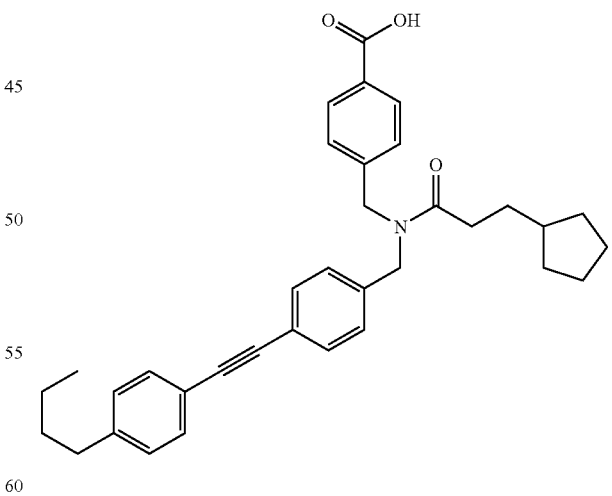

The titled compound was prepared following the procedure F using methyl 4-{[{4-[(4-butylphenyl)ethynyl]benzyl}(3-cyclopentylpropanoyl)amino]methyl}benzoate and NaOH 1M as a yellow foam (77%). $^1$H NMR (CDCl$_3$, 300 MHz) δ 8.15-8.02 (m, 2H), 7.56-7.40 (m, 4H), 7.33-7.22 (m, 2H), 7.21-7.08 (m, 4H), 4.69-4.58 (m, 2H), 4.54-4.43 (m, 2H), 2.61 (t, J=7.7 Hz, 2H), 2.49-2.35 (m, 2), 1.81-1.0 (m, 15H), 0.93 (t, J=7.3 Hz, 3H). M⁻ (ESI): 520.4; M¹(ESI): 522.3. HPLC, Rt: 5.71 min (Purity: 99.2%).

Example 49

4-{[{4-[(4-butylphenyl)ethynyl]benzyl}(hexanoyl)amino]methyl}benzoic acid

Step a) Formation of methyl 4-{[{4-[(4-butylphenyl)ethynyl]benzyl}(hexanoyl)amino]methyl}benzoate

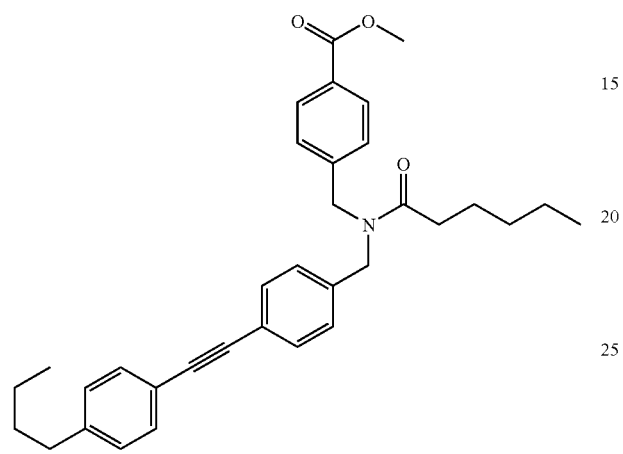

The titled compound was prepared following the procedure E using methyl 4-[({4-[(4-butylphenyl)ethynyl]benzyl}amino)methyl]benzoate and hexanoyl chloride as a colorless oil (69%). ¹H NMR (CDCl₃, 300 MHz) δ 8.03 (d, 1H), 7.97 (d, 1H), 7.54-7.40 (m, 4H). 7.27-7.09 (m, 6H), 4.62 (m, 2H), 4.46 (m, 2H), 3.92 (m, 3H), 2.62 (t, 2H), 2.40 (m, 2H), 1.77-1.54 (m, 4H), 1.43-1.23 (m, 6H), 0.96-0.83 (m, 6H). M⁺ (ESI): 510.4. HPLC, Rt: 6.25 min (Purity: 100%).

Step b) Formation of 4-{[{4-[(4-butylphenyl)ethynyl]benzyl}(hexanoyl)amino]methyl}benzoic acid

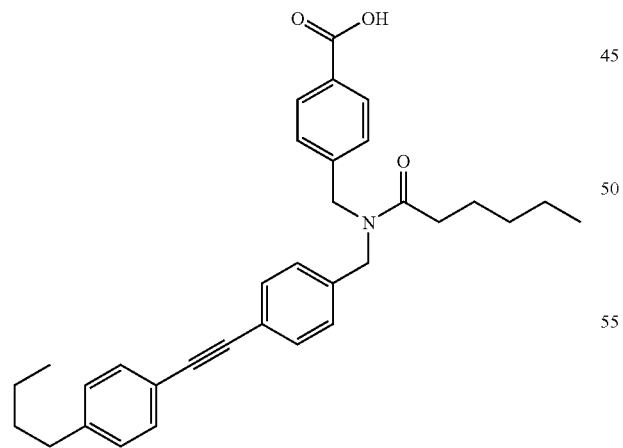

The titled compound was prepared following the procedure F using methyl 4-{[{4-[(4-butylphenyl)ethynyl]benzyl}(hexanoyl)amino]methyl}benzoate and NaOH 1M as a brown oil (95%). ¹HNMR (CDCl₃, 300 MHz) δ 8.14-8.01 (m, 2H), 7.56-7.40 (m, 4H), 7.34-7.22 (m, 4H), 7.21-7.07 (m, 4H), 4.69-4.58 (m, 2H), 4.54-4.43 (m, 2H), 2.62 (m, 2H), 2.48-2.33 (m, 2H), 1.80-1.53 (m, 4H), 1.43-1.15 (m, 6H), 0.97-0.78 (m, 6H). M⁻ (ESI): 494.4; M⁺ (ESI): 496.4. HPLC, Rt: 5.54 min (Purity: 98%).

Example 50

4-[((4-tert-butylbenzoyl){4-[(4-butylphenyl)ethynyl]benzyl}amino)-methyl]benzoic acid Step a) Formation of methyl 4-[((4-tert-butylbenzoyl){4-[(4-butylphenyl)ethynyl]benzyl}amino)-methyl]benzoate

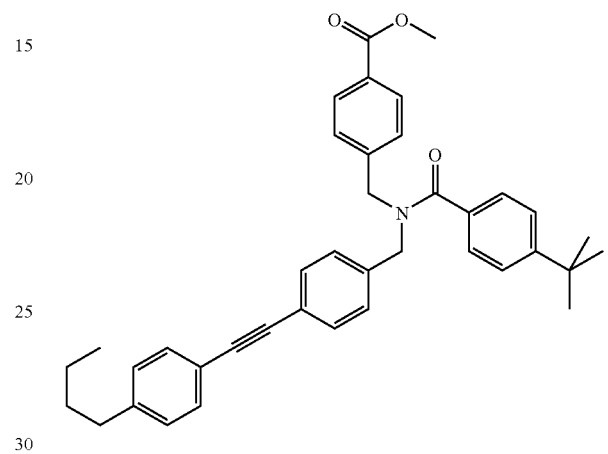

The titled compound was prepared following the procedure E using methyl 4-[({4-[(4-butylphenyl)ethynyl]benzyl}amino)methyl]benzoate and 4-tert-butylbenzoyl chloride as a colorless oil (63%). ¹H NMR (CDCl₃, 300 MHz) δ 8.02 (d, J=8.3 Hz, 2H), 7.50 (d, J=8.3 Hz, 2H), 7.48-7.29 (m, 7H), 7.28-7.07 (m, 5H), 4.80-4.62 (m, 2H), 4.55-4.40 (m, 2H), 3.92 (s, 3H), 2.61 (t, J=7.7 Hz, 2H), 1.66-1.53 (m, 2H), 1.40-1.23 (m, 11H), 0.92 (t, J=7.4 Hz, 3H). M⁺ (ESI): 572.5. HPLC, Rt: 6.22 min (Purity: 99.5%).

Step b) Formation of 4-[((4-tert-butylbenzoyl){4-[(4-butylphenyl)ethynyl]benzyl}amino)methyl]benzoic acid

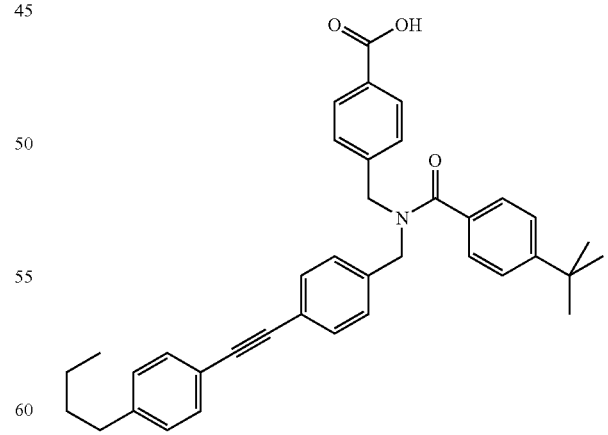

The titled compound was prepared following the procedure F using methyl 4-[((4-tert-butylbenzoyl){4-[(4-butylphenyl)ethynyl]benzyl}amino)methyl]benzoate and NaOH 5M in the presence of MeOH/THF 1/1, as a brown solid (95%). ¹H NMR (CDCl₃, 300 MDz) δ 8.09 (d, 2H, J=7.9

Hz), 7.54-7.32 (m, 6H), 7.22-7.09 (m, 4H), 4.79-4.42 (m, 4H), 2.62 (t, 2H, J=7.7 Hz), 1.70-1.05 (m, 14H), 0.97-0.75 (m, 6H). M⁻ (ESI): 556.3; M⁺ (ESI): 558.4. HPLC, Rt: 6.03 min (Purity: 98.8%).

Example 51

4-[{4-[(4-butylphenyl)ethynyl]benzyl}(hexanoyl)amino]benzoic acid

Step a) Formation of ethyl 4-({4-[(4-butylphenyl)ethynyl]benzyl}amino)benzoate

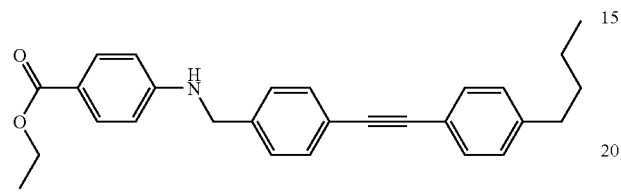

The titled compound was prepared following the procedure A using 4-[(4-butylphenyl)ethynyl]benzaldehyde and ethyl 3-aminobenzoate as a white solid (48%). ¹H NMR (CDCl₃, 300 MHz) δ 7.86 (d, J=8.6 Hz, 2H), 7.48 (d, J=8.3 Hz, 2H), 7.42 (d, J=8.3 Hz, 2H), 7.30 (d, J=8.3 Hz, 2H), 7.15 (d, J=7.9 Hz, 2H), 6.57 (d, J=9.1 Hz, 2H), 4.51 (m, 1H), 4.40 (s, 2H), 4.30 (q, J=7.2 Hz, 2H), 2.61 (t, J=7.5 Hz, 2H), 1.66-1.52 (m, 3H), 1.42-1.25 (m, 4H), 0.93 (t, J=7.3 Hz, 3H). M⁻ (ESI): 410.3; M⁺ (ESI): 412.7. HPLC, Rt: 5.96 min (Purity: 98.6%).

Step b) Formation of ethyl 4-[{4-[(4-butylphenyl)ethynyl]benzyl}(hexanoyl)amino]benzoate

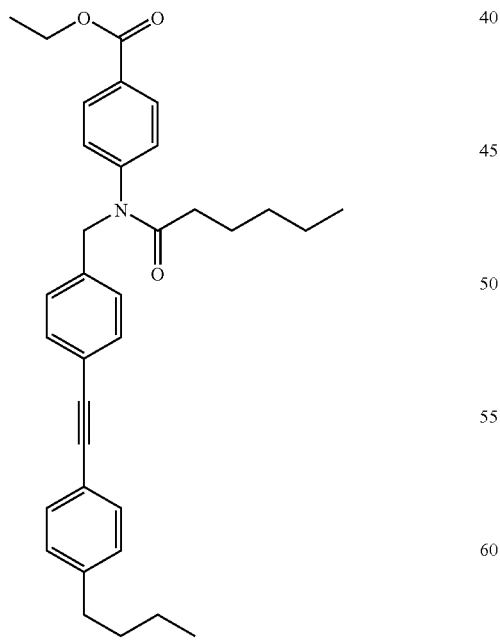

The titled compound was prepared following the procedure B using ethyl 4-({4-[(4-butylphenyl)ethynyl]benzyl}amino)benzoate and hexanoyl chloride as a yellow oil (92%). ¹H NMR (CDCl₃, 300 MHz) δ 8.00 (d, J=8.3 Hz, 2H), 7.41 (m, 4H), 7.14 (m, 4H), 7.03 (d, J=8.7 Hz, 2H), 4.89 (s, 2H), 4.37 (q, J=7.2 Hz, 2H), 2.60 (t, J=7.5 Hz, 2H), 2.06 (t, J=7.5 Hz, 2H), 1.67-1.55 (m, 4H), 1.43-1.10 (m, 9H), 0.91 (t, J=7.2 Hz, 3H), 0.82 (t, J=7.0 Hz, 3H). M⁺ (ESI): 510.5. HPLC, Rt: 6.14 min (Purity: 98.2%).

Step c) Formation of 4-[{4-[(4-butylphenyl)ethynyl]benzyl}(hexanoyl)amino]benzoic acid

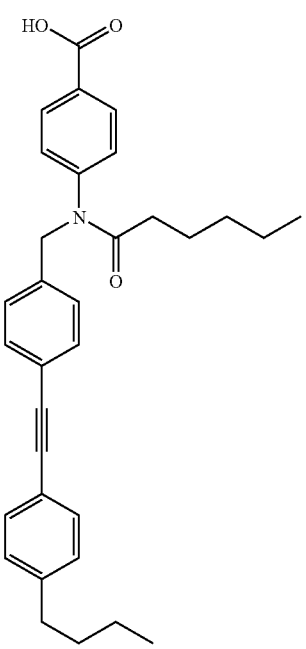

The titled compound was prepared following the procedure F using ethyl 4-[{4-[(4-butylphenyl)ethynyl]benzyl}(hexanoyl)amino]benzoate and NaOH 5M as a yellow powder (75%). ¹H NMR (CDCl₃, 300 MHz) δ 8.06 (d, J=8.7 Hz, 2H). 7.42 (s, 2H), 7.40 (s, 2H), 7.16 (s, 2H), 7.13 (s, 21), 4.91 (s, 2H), 2.61 (t, J=7.7 Hz, 2H), 2.09 (t, J=7.5 Hz, 2H), 1.68-1.52 (m, 5H), 1.42-1.29 (m, 2H), 1.27-1.11 (m, 5H), 0.91 (t, J=7.3 Hz, 3H), 0.82 (t, J=7.1 Hz, 3H). M⁻ (ESI): 480.5; M⁺ (ESI): 482.4. HPLC, Rt: 5.76 min (Purity: 99%).

Example 52

4-[{4-[(4-butylphenyl)ethynyl]benzyl}(3-cyclopentylpropanoyl)-amino]benzoic acid Step a) Formation of ethyl 4-[{4-[(4-butylphenyl)ethynyl]benzyl}(3-cyclopentylpropanoyl)amino]benzoate

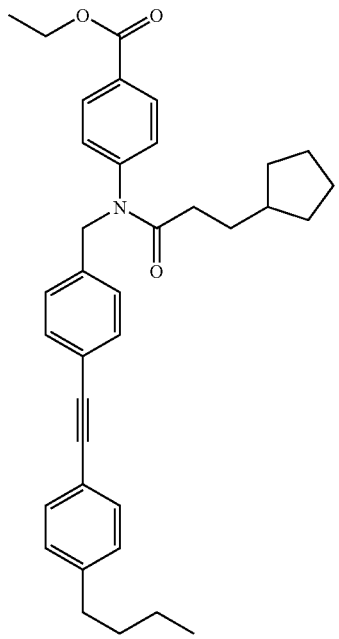

The titled compound was prepared following the procedure B using ethyl 4-({4-[(4-butylphenyl)ethynyl]benzyl}amino)benzoate and 3-cyclopentylpropanoyl chloride as a yellow oil (79%). $^1$H NMR (CDCl$_3$, 300 MHz) δ 8.01 (d, J=8.3 Hz, 2H), 7.41 (m, 4H), 7.14 (m, 4H), 7.04 (d, J=8.3 Hz, 2H), 4.89 (s, 2H), 4.39 (q, J=6.8 Hz, 2H), 2.61 (t, J=7.7 Hz, 2H), 2.09 (m, 2H), 1.80-1.25 (m, 16H), 1.00-0.88 (m, 5H). M$^+$ (ESI): 536.9. HPLC, Rt: 6.58 min (Purity: 98.7%).

Step b) Formation of 4-[{4-[(4-butylphenyl)ethynyl]benzyl}(3-cyclopentylpropanoyl)amino]-benzoic acid

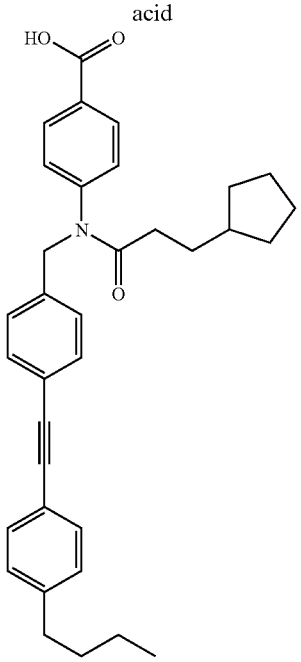

The titled compound was prepared following the procedure F using ethyl 4-[{4-[(4-butylphenyl)ethynyl]benzyl}(3-cyclopentylpropanoyl)amino]benzoate and LiOH.H$_2$O in the presence of dioxane as a yellow powder (79%). $^1$H NMR (CDCl$_3$, 300 MHz) δ 8.08 (m, 2H), 7.49-7.35 (m, 4H), 7.23-7.02 (m, 6H), 4.91 (br s, 2H), 2.66-2.53 (m, 2H), 2.18-2.05 (m, 2H), 1.70-1.20 (m, 13H), 1.30-0.82 (m, 5H). M$^-$ (ESI): 506.4; M$^+$ (ESI): 508.4. HPLC, Rt: 5.67 min (Purity: 98.5%).

Example 53

8-[{4-[(4-butylphenyl)ethynyl]benzyl}(3-cyclopentylpropanoyl)amino]-5,6,7,8-tetrahydronaphthalene-2-carboxylic acid, N-methyl-D-glucamine (i.e. 1-deoxy-1-(methylamino)glucitol) salt Step a) Formation of methyl 8-({4-[(4-butylphenyl)ethynyl]benzyl}amino)-5,6,7,8-tetrahydronaphthalene-2-carboxylate

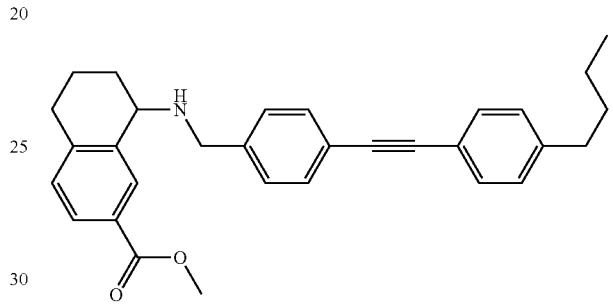

The titled compound was prepared following the procedure L using 4-[(4-butylphenyl)ethynyl]benzaldehyde and methyl 8-amino-5,6,7,8-tetrahydronaphthalene-2-carboxylate as a yellow oil (95%). $^1$H NMR (CDCl$_3$, 300 MHz) δ 7.96 (d, J=1.7 Hz, 1H), 7.72 (dd, J=7.9, 1.7 Hz, 1H), 7.29-7.42 (m, 5H), 7.17 (d, J=2.8 Hz, 1H), 7.07 (m, 3H), 3.82 (m, 5H), 3.75 (m, 1H), 2.67-2.82 (m, 2H), 2.50 (m, 2H), 1.92 (m, 1H), 1.82 (m, 2H), 1.62 (m, 1H), 1.51 (m, 2H), 1.28 (m, 2H), 0.83 (m, 3H). M$^+$ (ESI): 452.2. HPLC, Rt: 4.37 min (Purity: 60.1%).

Step b) Formation of methyl 8-[{4-[(4-butylphenyl)ethynyl]benzyl}(3-cyclopentylpropanoyl)amino]-5,6,7,8-tetrahydro-2-7-naphthalenecarboxylate

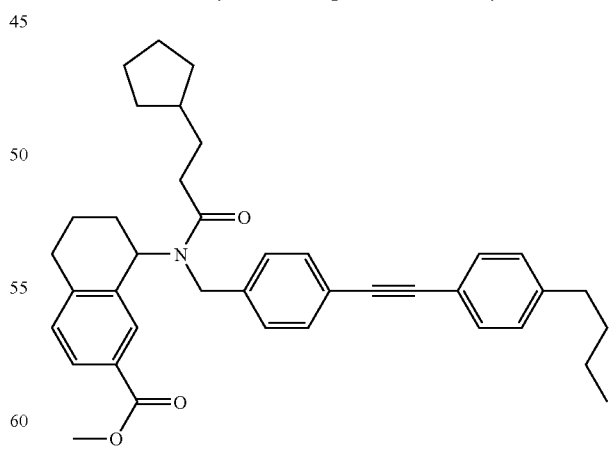

The titled compound was prepared following the procedure B using methyl 8-({4-[(4-butylphenyl)ethynyl]benzyl}amino)-5,6,7,8-tetrahydronaphthalene-2-carboxylate and 3-cyclopentylpropanoyl chloride as a colorless oil (63%). $^1$H NMR (CDCl$_3$, 300 MHz) δ 7.81 (m, 1H), 7.67 (d, J=7.6 Hz, 1H), 7.47 (d, J=8.3 Hz, 2H), 7.35-7.42 (m, 2H), 7.11-7.15 (m, 5H), 6.08 (m, 0.5H), 5.10 (m, 0.5H), 4.84 (d, J=16 Hz, 0.5H), 4.49 (d, J=16 Hz, 0.5H), 4.10 (m, 1H), 3.87 (s, 3H), 2.77 (m, 2H), 2.60 (t, J=7.7 Hz, 2H), 1.22-2.35 (m, 21H), 0.91 (t, J=7.3 Hz, 3H). M$^1$(ESI): 576.2. HPLC, Rt: 6.4 min (Purity: 98.9%).

Step c) Formation of 8-[{4-[(4-butylphenyl)ethynyl]benzyl}(3-cyclopentylpropanoyl)amino]-5,6,7,8-tetrahydronaphthalene-2-carboxylic acid

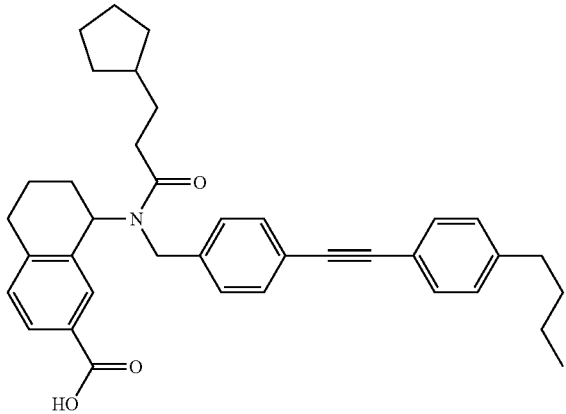

The titled compound was prepared following the procedure F using methyl 8-[{4-[(4-butylphenyl)ethynyl]benzyl}(3-cyclopentylpropanoyl)amino]-5,6,7,8-tetrahydro-2-naphthalenecarboxylate and LiOH.H$_2$O, as a white solid (94%). $^1$H NMR (MeOD, 300 MHz) δ 7.80 (m, 1H), 7.71 (d, J=5.5 Hz. 1H), 7.47 (d, J=7.5 Hz, 1H), 7.38 (m, 3H), 7.18 (m, 5H), 5.94 (m, 0.5H), 5.30 (m, 0.5H), 4.80 (m, 1H), 4.63 (d, J=18.3 Hz, 0.5H), 4.21 (d, J=18.3 Hz, 0.5H), 2.81 (m, 2H), 2.62 (m, 2H), 2.45 (m, 1H), 2.27 (m, 1H), 2.10-1.06 (m, 19H), 0.93 (t, J=7.2 Hz, 3H). M$^-$ (ESI): 560.3; M$^+$ (ESI): 562.2. HPLC, Rt: 5.97 min (Purity: 99.2%).

Step d) Formation of 8-[{4-[(4-butylphenyl)ethynyl]benzyl}(3-cyclopentylpropanoyl)amino]-5,6,7,8-tetrahydronaphthalene-2-carboxylic acid, N-methyl-D-glucamine (i.e. 1-deoxy-1-(methylamino)glucitol) salt The titled compound was prepared following the procedure D using 8-[{4-[(4-butylphenyl)ethynyl]benzyl}(3-cyclopentylpropanoyl)amino]-5,6,7,8-tetrahydronaphthalene-2-carboxylic acid and N-methyl-D-glucamine as a white powder (87%). M$^-$ (ESI): 560; M$^+$ (ESI): 562.3. HPLC, Rt: 5.95 min (Purity: 100%).

Example 54

5-[{4-[(4-chlorophenyl)ethynyl]benzyl}(3-cyclopentylpropanoyl)amino]-2-hydroxybenzoic acid, N-methyl-D-glucamine (i.e. 1-deoxy-1-(methylamino)glucitol) salt Step a) Formation of 6-({4-[(4-chlorophenyl)ethynyl]benzyl}amino)-2,2-dimethyl-4H-1,3-benzodioxin-4-one

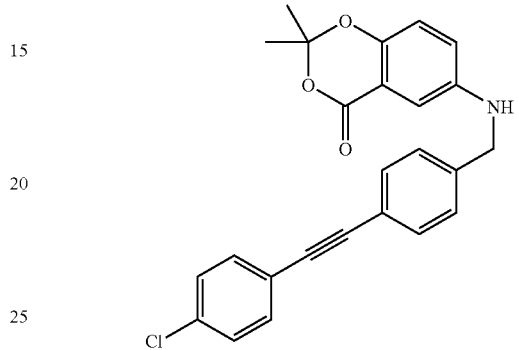

The titled compound was prepared following the procedure A using 4-[(4-chlorophenyl)ethynyl]benzaldehyde (intermediate which may be obtained according to methods disclosed in EP03103780.7) and 6-amino-2,2-dimethyl-4H-1,3-benzodioxin-4-one as a yellow powder (62%). $^1$H NMR (CDCl$_3$, 300 MHz) δ 7.52-7.41 (m, 4H), 7.38-7.28 (m, 4H), 7.16 (d, J=2.7 Hz, 1H), 6.87-6.76 (m, 2H), 4.34 (s, 2H), 1.68 (s, 6H). M$^-$ (ESI): 416.1. HPLC, Rt: 5.45 min (Purity: 96%).

Step b) Formation of N-{4-[(4-chlorophenyl)ethynyl]benzyl}-3-cyclopentyl-N-(2,2-dimethyl-4-oxo-4H-1,3-benzodioxin-6-yl)propanamide

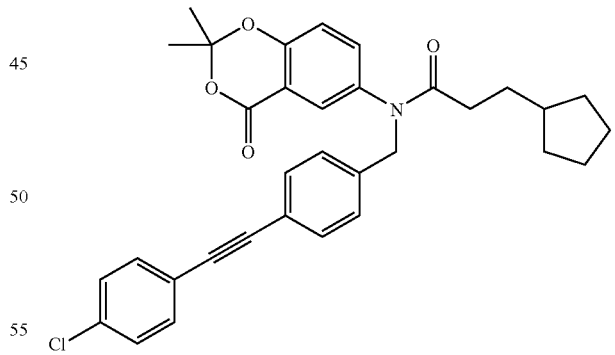

The titled compound was prepared following the procedure B using 6-({4-[(4-chlorophenyl)ethynyl]benzyl}amino)-2,2-dimethyl-4H-1,3-benzodioxin-4-one and 3-cyclopentylpropanoyl chloride as a white foam (80%). $^1$H NMR (CDCl$_3$, 300 MHz) δ 7.67 (m, 1H), 7.42 (m, 4H), 7.31 (m, 2H), 7.17 (d, J=7.9 Hz, 2H), 7.06 (m, 1H), 6.89 (d, J=8.7 Hz, 1H), 4.86 (s, 2H), 2.06 (m, 2H), 1.73 (s, 6H), 1.66-1.39 (m, 9H), 0.95 (m, 2H). M$^+$ (ESI): 542.1. HPLC, Rt: 5.83 min (Purity: 97.3%).

Step c) Formation of 5-[{4-[(4-chlorophenyl)ethynyl]benzyl}(3-cyclopentylpropanoyl)amino]-2-hydroxybenzoic acid

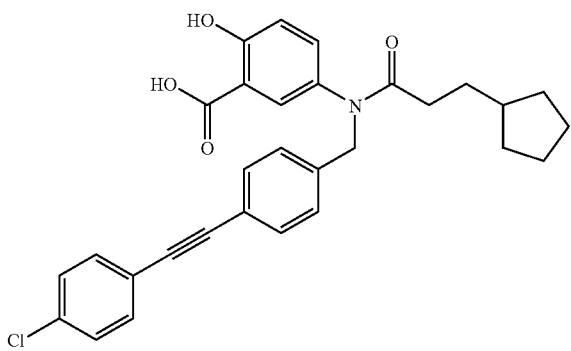

The titled compound was prepared following the procedure C using N-{4-[(4-chlorophenyl)ethynyl]benzyl}-3-cyclopentyl-N-(2,2-dimethyl-4-oxo-4H-1,3-benzodioxin-6-yl)propanamide and NaOH as a white powder (95%). $^1$H NMR (DMSO-d$_6$, 300 MHz) δ 7.56 (m, 2H), 7.48 (m, 5H), 7.30-7.19 (m, 3H), 6.93 (m, 1H), 4.82 (brs, 2H). 2.08-1.99 (m, 2H), 1.69-1.33 (m, 9H), 0.99-0.82 (m, 3H). HPLC, Rt: 5.76 min (Purity: 88.5%).

Step d) Formation of 5-[{4-[(4-chlorophenyl)ethynyl]benzyl}(3-cyclopentylpropanoyl)amino]-2-hydroxybenzoic acid, N-methyl-D-glucamine (i.e. 1-deoxy-1-(methylamino)glucitol) salt The titled compound was prepared following the procedure D using 5-[{4-[(4-chlorophenyl)ethynyl]benzyl}(3-cyclopentylpropanoyl)amino]-2-hydroxybenzoic acid and N-methyl-D-glucamine as a white powder (88%). M$^-$ (ESI): 500.5. HPLC, Rt: 5.41 min (Purity: 99.8%).

Example 55

5-[{4-[(4-chlorophenyl)ethynyl]benzyl}(4-heptylbenzoyl)amino]-2-hydroxybenzoic acid Step a) Formation of N-{4-[(4-chlorophenyl)ethynyl]benzyl}-N-(2,2-dimethyl-4-oxo-4H-1,3-benzodioxin-6-yl)-4-heptylbenzamide

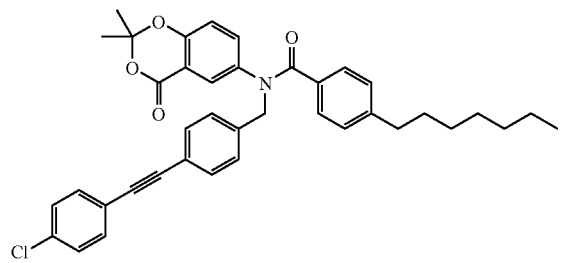

The titled compound was prepared following the procedure E using 6-({4-[(4-chlorophenyl)ethynyl]benzyl}amino)-2,2-dimethyl-4H-1,3-benzodioxin-4-one and 4-heptylbenzoyl chloride as a yellow oil (94%). HPLC, Rt: 6.8 min (Purity: 96.4%).

Step b) Formation of 5-[{4-[(4-chlorophenyl)ethynyl]benzyl}(4-heptylbenzoyl)amino]-2-hydroxybenzoic acid

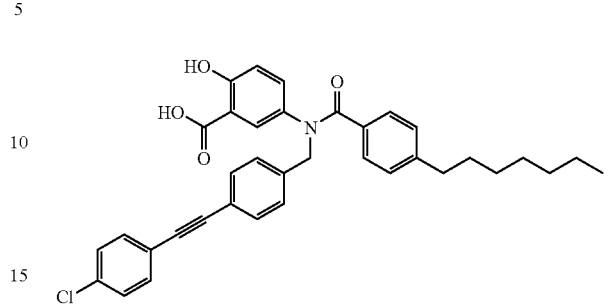

The titled compound was prepared following the procedure C using N-{4-[(4-chlorophenyl)ethynyl]benzyl}-N-(2,2-dimethyl-4-oxo-4H-1,3-benzodioxin-6-yl)-4-heptylbenzamide and NaOH as a white solid (67%). M$^-$ (ESI): 577.8; M$^+$ (ESI): 580.1. HPLC, Rt: 5.89 min (Purity: 92.3%).

Example 56

5-[{4-[(4-chlorophenyl)ethynyl]benzyl}(isoxazol-5-ylcarbonyl)amino]-2-hydroxybenzoic acid Step a) Formation of N-{4-[(4-chlorophenyl)ethynyl]benzyl}-N-(2,2-dimethyl-4-oxo-4H-1,3-benzodioxin-6-yl)isoxazole-5-carboxamide

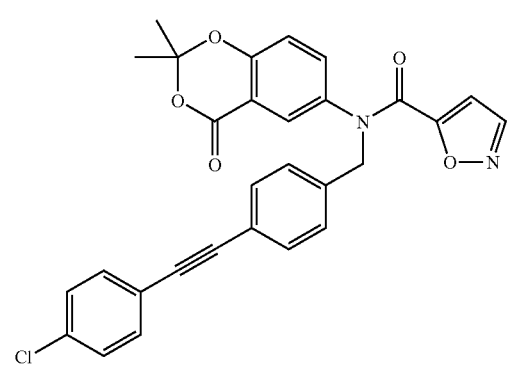

The titled compound was prepared following the procedure E using 6-({4-[(4-chlorophenyl)ethynyl]benzyl}amino)-2,2-dimethyl-4H-1,3-benzodioxin-4-one and isoxazole-5-carbonyl chloride as a yellow oil (72%). M$^-$ (ESI): 511.5; M$^+$ (ESI): 513.1. HPLC, Rt: 5.38 min (Purity: 99.1%).

Step b) Formation of 5-[{4-[(4-chlorophenyl)ethynyl]benzyl}(isoxazol-5-ylcarbonyl)amino]-2-hydroxybenzoic acid

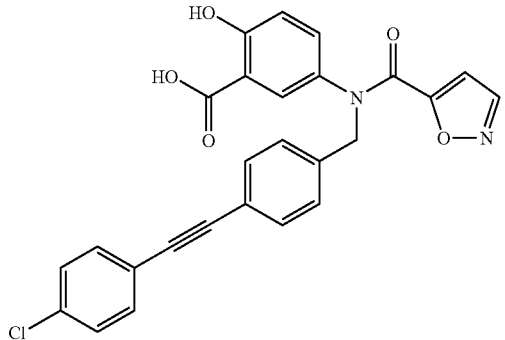

The titled compound was prepared following the procedure C using N-{4-[(4-chlorophenyl)ethynyl]benzyl}-N-(2,2-dimethyl-4-oxo-4H-1,3-benzodioxin-6-yl)isoxazole-5-carboxamide and NaOH as a yellow solid (55%). M⁻ (ESI): 470.7; M⁺ (ESI): 472.6. HPLC, Rt: 4.56 min (Purity: 71.3%).

Step b) Formation of 5-[{4-[(4-chlorophenyl)ethynyl]benzyl}(2-thienylacetyl)amino]-2-hydroxybenzoic acid

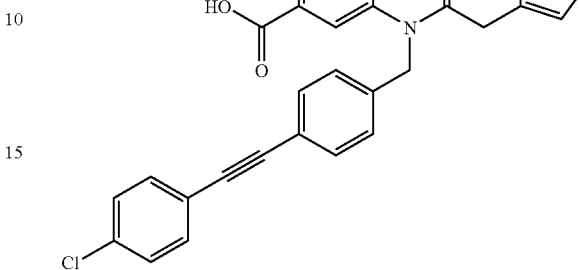

The titled compound was prepared following the procedure C using N-{4-[(4-chlorophenyl)ethynyl]benzyl}-N-(2,2-dimethyl-4-oxo-4H-1,3-benzodioxin-6-yl)-2-(2-thienyl)acetamide and NaOH as a brown solid (42%). M⁻ (ESI): 499.7; M⁺ (ESI): 502.3. HPLC, Rt: 4.92 min (Purity: 88.5%).

Example 57

5-[{4-[(4-chlorophenyl)ethynyl]benzyl}(2-thienylacetyl)amino]-2-hydroxybenzoic acid Step a) Formation of N-{4-[(4-chlorophenyl)ethynyl]benzyl}-N-(2,2-dimethyl-1-oxo-4H-1,3-benzodioxin-6-yl)-2-(2-thienyl)acetamide

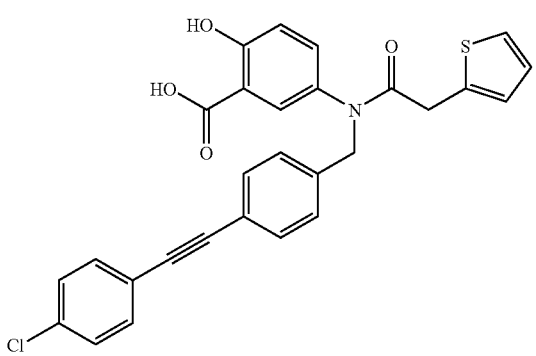

The titled compound was prepared following the procedure E using 6-({4-[(4-chlorophenyl)ethynyl]benzyl}amino)-2,2-dimethyl-4H-1,3-benzodioxin-4-one and 2-thienylacetyl chloride as a yellow oil (71%). M⁺ (ESI): 542.2. HPLC, Rt: 5.71 min (Purity: 88.2%).

Example 58

5-[{4-[(4-chlorophenyl)ethynyl]benzyl}(3-phenylpropanoyl)amino]-2-hydroxybenzoic acid N-methyl-D-glucamine (i.e. 1-deoxy-1-(methylamino)glucitol) salt Step a) Formation of N-{4-[(4-chlorophenyl)ethynyl]benzyl}-N-(2,2-dimethyl-4-oxo-4H-1,3-benzodioxin-6-yl)-3-phenylpropanamide

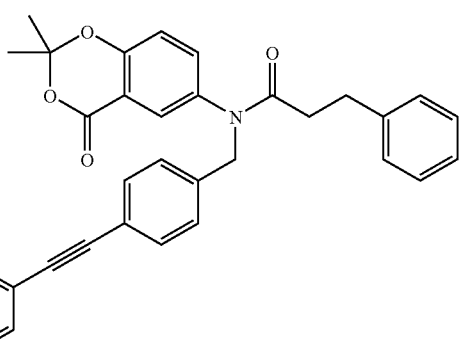

The titled compound was prepared following the procedure using 6-({4-[(4-chlorophenyl)ethynyl]benzyl}amino)-2,2-dimethyl-4H-1,3-benzodioxin-4-one and 3-phenylpropanoyl chloride as an oil (77%). HPLC, Rt: 5.9 min (Purity: 97.3%).

Step b) Formation of 5-[{4-[(4-chlorophenyl)ethynyl]benzyl}(3-phenylpropanoyl)amino]-2-hydroxybenzoic acid

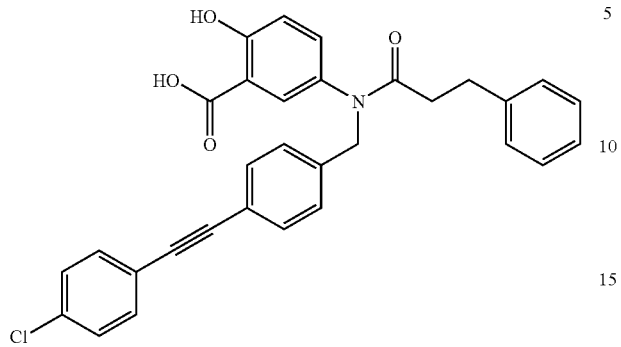

The titled compound was prepared following the procedure C using N-{4-[(4-chlorophenyl)ethynyl]benzyl}-N-(2,2-dimethyl-4-oxo-4H-1,3-benzodioxin-6-yl)-3-phenylpropanamide mid NaOH as a white powder (35%). $^1$H NMR (MeOD, 300 MHz) δ 7.53 (m, 2H), 7.44 (m, 4H), 7.35 (m, 1H), 7.31-7.20 (m, 3H), 7.11 (m, 4H), 6.98-6.77 (m, 2H), 4.86 (br s, 2H), 2.94 (t, 2H), 2.46 (t, J=7.2 Hz, 2H). M$^-$ (ESI): 508.4; M$^+$ (ESI): 509.9. HPLC, Rt: 5.09 min (Purity: 96.9%).

Step c) Formation of 5-[{4-[(4-chlorophenyl)ethynyl]benzyl}(3-phenylpropanoyl)amino]-2-hydroxybenzoic acid, N-methyl-D-glucamine (i.e. 1-deoxy-1-(methylamino)glucitol) salt The titled compound was prepared following the procedure D using 5-[{4-[(4-chlorophenyl)ethynyl]benzyl}(3-phenylpropanoyl)amino]-2-hydroxybenzoic acid and N-methyl-D-glucamine as a white powder (50%). M$^-$ (ESI): 508; M$^+$ (ESI): 509.9. HPLC, Rt: 5.17 min (Purity: 98.2%).

Example 59

5-[{4-[(4-chlorophenyl)ethynyl]benzyl}(4-methoxybenzoyl)amino]-2-hydroxybenzoic acid N-methyl-D-glucamine (i.e. 1-deoxy-1-(methylamino)glucitol) salt Step a) Formation of N-{4-[(4-chlorophenyl)ethynyl]benzyl}-N-(2,2-dimethyl-4-oxo-4H-1,3-benzodioxin-6-yl)-4-methoxybenzamide

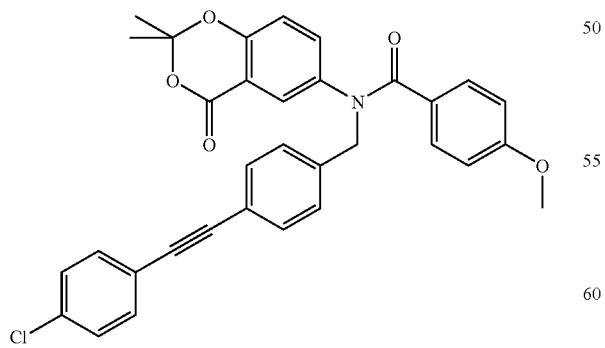

The titled compound was prepared following the procedure E using 6-({4-[(4-chlorophenyl)ethynyl]benzyl}amino)-2,2-dimethyl-4H-1,3-benzodioxin-4-one and 4-methoxybenzoyl chloride as a yellow oil (91%). M$^+$ (ESI): 552. HPLC, Rt: 5.65 min (Purity: 98.5%).

Step b) Formation of 5-[{4-[(4-chlorophenyl)ethynyl]benzyl}(4-methoxybenzoyl)amino]-2-hydroxybenzoic acid

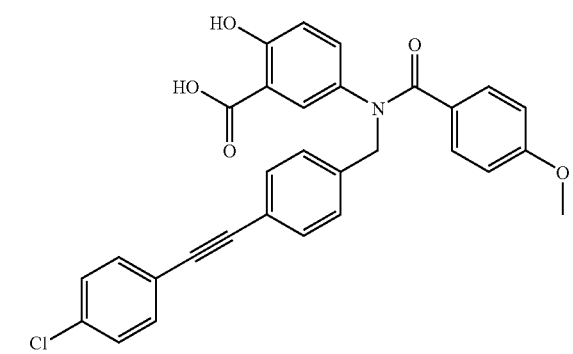

The titled compound was prepared following the procedure C using N-{4-[(4-chlorophenyl)ethynyl]benzyl}-N-(2,2-dimethyl-4-oxo-4H-1,3-benzodioxin-6-yl)-4-methoxybenzamide and NaOH as a white powder (45%). $^1$H NMR (MeOD, 300 MHz) δ 7.53-7.42 (m, 5H), 7.41-7.28 (m, 6H), 7.09 (m, 1H), 6.77 (m, 3H), 5.11 (s, 2H), 3.73 (s, 3H). M$^-$ (ESI): 510; M$^+$ (ESI): 511.9. HPLC, Rt: 4.89 min (Purity: 97.6%).

Step c) Formation of 5-[{4-[(4-chlorophenyl)ethynyl]benzyl}(4-methoxybenzoyl)amino]-2-hydroxybenzoic acid, N-methyl-D-glucamine (i.e. 1-deoxy-1-(methylamino)glucitol) salt The titled compound was prepared following the procedure D using 5-[{4-[(4-chlorophenyl)ethynyl]benzyl}(4-methoxybenzoyl)amino]-2-hydroxybenzoic acid and N-methyl-D-glucamine as a white powder (47%). M$^-$ (ESI): 509.8. M$^+$ (ESI): 512.4. HPLC, Rt: 4.94 min (Purity: 98.7%).

Example 60

5-[{4-[(4-chlorophenyl)ethynyl]benzyl}(3-fluorobenzoyl)amino]-2-hydroxybenzoic acid N-methyl-D-glucamine (i.e. 1-deoxy-1-(methylamino)glucitol) salt Step a) Formation of N-{4-[(4-chlorophenyl)ethynyl]benzyl}-N-(2,2-dimethyl-4-oxo-4H-1,3-benzodioxin-6-yl)-3-fluorobenzamide

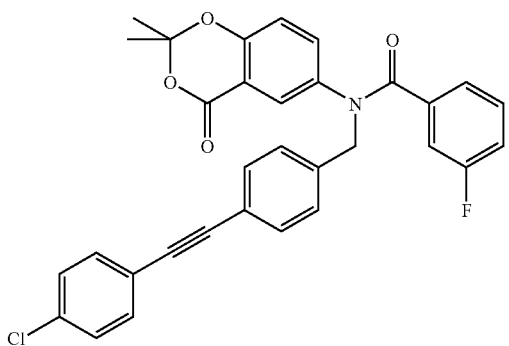

The titled compound was prepared following the procedure E using 6-({4-[(4-chlorophenyl)ethynyl]

benzyl}amino)-2,2-dimethyl-4H-1,3-benzodioxin-4-one and 3-fluorobenzoyl chloride as a yellow oil (96%). M⁺ (ESI): 540.2. HPLC, Rt: 5.71 min (Purity: 97.4%).

Step b) Formation of 5-[{4-[(4-chlorophenyl)ethynyl]benzyl}(3-fluorobenzoyl)amino]-2-hydroxybenzoic acid

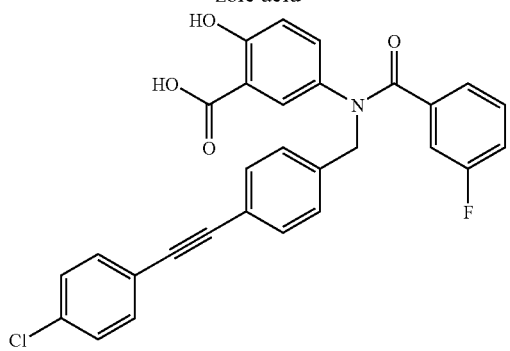

The titled compound was prepared following the procedure C using N-{4-[(4-chlorophenyl)ethynyl]benzyl}-N-(2,2-dimethyl-4-oxo-4H-1,3-benzodioxin-6-yl)-3-fluorobenzamide and NaOH as a white powder (56%). ¹H NMR (MeOD, 300 MHz) δ 7.51 (m, 5H), 7.45-7.22 (m, 5H), 7.20-7.02 (m, 4H), 6.79 (d, J=9 Hz, 1H), 5.15 (s, 2H) M⁻ (ESI): 497.9. HPLC. Rt: 4.92 min (Purity: 97.9%).

Step d) Formation of 5-[{4-[(4-chlorophenyl)ethynyl]benzyl}(3-fluorobenzoyl)amino]-2-hydroxybenzoic acid, N-methyl-D-glucamine (i.e. 1-deoxy-1-(methylamino)glucitol) salt The titled compound was prepared following the procedure D using 5-[{4-[(4-chlorophenyl)ethynyl]benzyl}(3-fluorobenzoyl)amino]-2-hydroxybenzoic acid and N-methyl-D-glucamine as a white powder (37%). M⁻ (ESI): 497.9. HPLC, Rt: 4.93 min (Purity: 99.2%).

Example 61

5-[{4-[(4-chlorophenyl)ethynyl]benzyl}(cyclohexylcarbonyl)amino]-2-hydroxybenzoic acid N-methyl-D-glucamine (i.e. 1-deoxy-1-(methylamino)glucitol) salt Step a) Formation of N-{4-[(4-chlorophenyl)ethynyl]benzyl}-N-(2,2-dimethyl-4-oxo-4H-1,3-benzodioxin-6-yl)cyclohexanecarboxamide

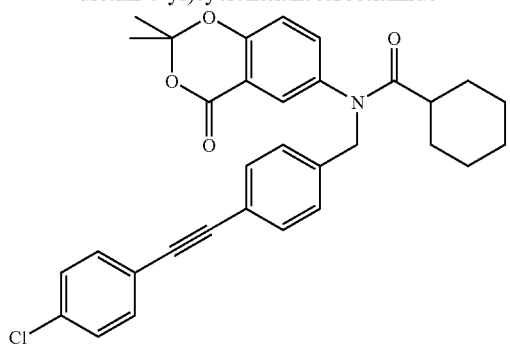

The titled compound was prepared following the procedure E using 6-({4-[(4-chlorophenyl)ethynyl]benzyl}amino)-2,2-dimethyl-4H-1,3-benzodioxin-4-one and cyclohexanecarbonyl chloride as a yellow oil (79%). HPLC, Rt: 6.01 min (Purity: 98.2%).

Step b) Formation of 5-[{4-[(4-chloroplenyl)ethynyl]benzyl}(cyclohexylcarbonyl)amino]-2-hydroxybenzoic acid

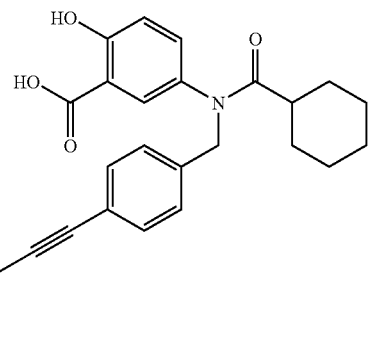

The titled compound was prepared following the procedure C using N-{4-[(4-chlorophenyl)ethynyl]benzyl}-N-(2,2-dimethyl-4-oxo-4H-1,3-benzodioxin-6-yl)cyclohexanecarboxamide and NaOH as a white powder (47%). ¹H NMR (MeOD, 300 MHz) δ 7.56-7.39 (m, 7H), 7.26-7.16 (m, 3H), 6.97 (d, J=9 Hz, 1H), 4.87 (m, 2H), 2.35-2.20 (m, 1H), 1.79-0.95 (m, 10H). M⁻ (ESI): 486; M⁺ (ESI): 488.1. HPLC, Rt: 5.16 min (Purity: 97.7%).

Step c) Formation of 5-[{4-[(4-chlorophenyl)ethynyl]benzyl}(cyclohexycarbonyl)amino]-2-hydroxybenzoic acid, N-methyl-D-glucamine (i.e. 1-deoxy-1-(methylamino)glucitol) salt The titled compound was prepared following the procedure D using 5-[{4-[(4-chlorophenyl)ethynyl]benzyl}(cyclohexylcarbonyl)amino]-2-hydroxybenzoic acid and N-methyl-D-glucamine as a white powder (36%). M⁻ (ESI): 486.1; M⁺ (ESI): 488.1. HPLC, Rt: 5.25 min (Purity: 98.8%).

Example 62

5-(acetyl{4-[(4-chlorophenyl)ethynyl]benzyl}amino)-2-hydroxybenzoic acid, N-methyl-D-glucamine (i.e. 1-deoxy-1-(methylamino)glucitol) salt Step a) Formation of N-{4-[(4-chlorophenyl)ethynyl]benzyl}-N-(2,2-dimethyl-1-4-oxo-4H-1,3-benzodioxin-6-yl)acetamide

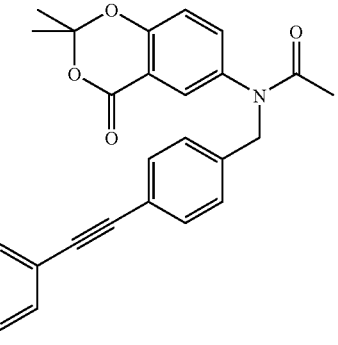

The titled compound was prepared following the procedure using 6-({4-[(4-chlorophenyl)ethynyl]benzyl}amino)-2,2-dimethyl-4H-1,3-benzodioxin-4-one and acetyl chloride as an oil (95%). M⁺ (ESI): 460.2. HPLC, Rt: 5.26 min (Purity: 91.8%).

Step b) Formation of 5-(acetyl{4-[(4-chlorophenyl)ethynyl]benzyl}amino)-2-hydroxybenzoic acid

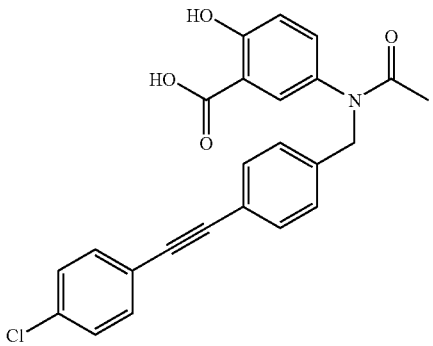

The titled compound was prepared following the procedure C using N-{4-[(4-chlorophenyl)ethynyl]benzyl}-N-(2,2-dimethyl-4-oxo-4H-1,3-benzodioxin-6-yl)acetamide and NaOH as a pale yellow powder (74%). $^1$H NMR (MeOD, 300 MHz) δ 7.60 (m, 1H), 7.56-7.45 (m, 4H), 7.41 (m, 2H), 7.29-7.19 (m, 3H), 6.96 (d, 1H), 4.92 (br s, 2H), 1.93 (s, 3H). M$^-$ (ESI): 418.1; M$^+$ (ESI): 420.1. HPLC, Rt: 4.5 min (Purity: 96.6%).

Step c) Formation of 5-(acetyl{4-[(4-chlorophenyl)ethynyl]benzyl}amino)-2-hydroxybenzoic acid, N-methyl-D-glucamine (i.e. 1-deoxy-1-(methylamino)glucitol) salt The titled compound was prepared following the procedure D using 5-(acetyl{4-[(4-chlorophenyl)ethynyl]benzyl}amino)-2-hydroxybenzoic acid and N-methyl-D-glucamine as a pale yellow powder (52%). M$^-$ (ESI): 418. HPLC, Rt: 4.71 min (Purity: 99.1%).

Example 63

5-[{4-[(4-butylphenyl)ethynyl]-2-fluorobenzyl}(3-cyclopentylpropanoyl)amino]-2-hydroxybenzoic acid, N-methyl-D-glucamine (i.e. 1-deoxy-1-(methylamino)glucitol) salt Step a) Formation of 4-[(4-butylphenyl)ethynyl]-2-fluorobenzaldehyde

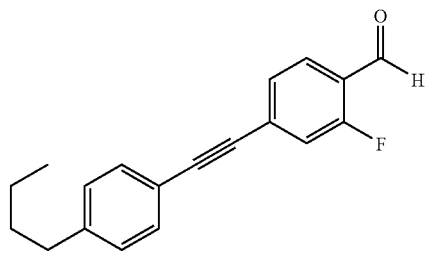

To a solution of 4-bromo-2-fluoro-benzaldehyde (10.0 g, 49.3 mmol), 1-butyl-4-ethynyl-benzene (8.57 g, 54.2 mmol), CuI (94 mg, 0.49 mmol) and of Et$_3$N (9.9 g) in anhydrous THF (120 mL) were added PPh$_3$ (258 mg, 1 mmol) and Pd(OAc)$_2$ (221 mg). The reaction mixture was heated under argon for 3 hours. After cooling to rt, the salts were filtered off, then charcoal and silica gel were added to the solution. After filtration, the solution was concentrated under reduced pressure and the residual oil was dissolved in petroleum ether (100 mL) and stored in the freezer. The solids were filtered off and washed with cold petroleum ether to give the title compound as a white powder (5.53 g, 40%). $^1$H NMR (CDCl$_3$) δ 10.33 (s, 1H), 7.82 (t, J=7.7 Hz, 1H), 7.45 (d, J=7.9 Hz, 2H), 7.38 (d, J=8.3 Hz, 1H), 7.30 (d, J=10.9 Hz, 1H), 7.18 (d, J=8.3 Hz, 2H), 2.62 (t, J=7.7 Hz, 2H), 1.58 (m, 2H), 1.36 (m, 2H), 0.92 (t, J=7.3 Hz, 3H). HPLC, Rt: 5.26 min (purity: 99.4%).

Step b) Formation of 6-({4-[(4-butylphenyl)ethynyl]-2-fluorobenzyl}amino)-2,2-dimethyl-4H-1,3-benzodioxin-4-one

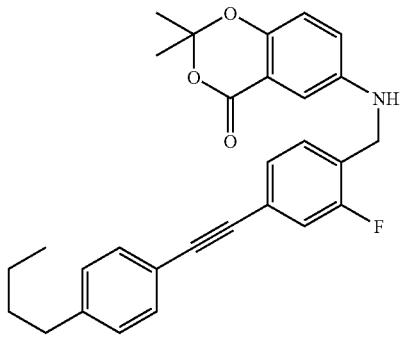

The titled compound was prepared following the procedure A using 4-[(4-butylphenyl)ethynyl]-2-fluorobenzaldehyde and 6-amino-2,2-dimethyl-4H-1,3-benzodioxin-4-one as a yellow powder (66%). $^1$H NMR (CDCl$_3$, 300 MHz) δ 7.41 (d, J=7.9 Hz, 2H), 7.38-7.12 (m, 6H), 6.90-6.76 (m, 2H), 4.39 (s, 2H), 2.61 (t, J=7.7 Hz, 2H), 1.68 (s, 6H), 1.65-1.52 (m, 2H). 1.41-1.17 (m, 2H), 0.92 (t, J=7.3 Hz, 3H). M$^-$ (ESI): 456.1 HPLC, Rt: 5.66 min (Purity: 97.9%).

Step c) Formation of N-{4-[(4-butylphenyl)ethynyl]-2-fluorobenzyl}-3-cyclopentyl-N-(2,2-dimethyl-4-oxo-4H-1,3-benzodioxin-6-yl)propanamide

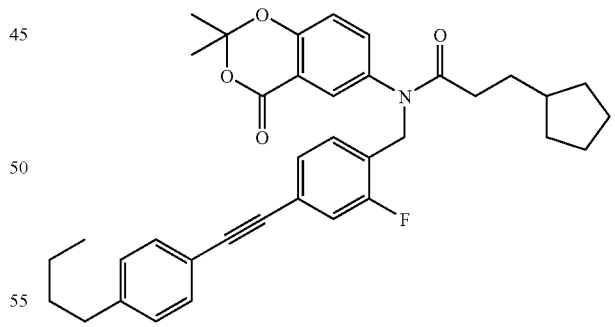

The titled compound was prepared following the procedure B using 6-({4-[(4-butylphenyl)ethynyl]-2-fluorobenzyl}amino)-2,2-dimethyl-4H-1,3-benzodioxin-4-one and 3-cyclopentylpropanoyl chloride as a colorless oil (73%). $^1$H NMR (CDCl$_3$, 300 MHz) δ 7.69 (m, 1H), 7.43-7.30 (m, 3H), 7.28-7.20 (m, 1H), 7.19-7.03 (m, 4H), 6.92 (d, J=8.7 Hz, 1H), 4.87 (s, 2H), 2.61 (t, J=7.7 Hz, 2H), 2.06 (m, 2H), 1.73 (s, 6H), 7.70-1.26 (m, 13H), 1.00-0.85 (m, 5H). M$^+$ (ESI): 582. HPLC, Rt: 6.63 min (Purity: 100%).

Step d) Formation of 5-[{4-[(4-butylphenyl)ethynyl]-2-fluorobenzyl}(3-cyclopentypropanoyl)amino]-2-hydroxybenzoic acid

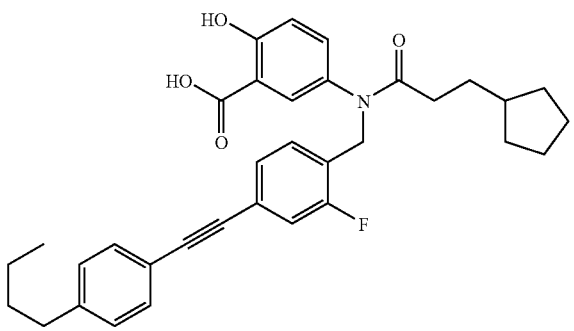

The titled compound was prepared following the procedure C using N-{4-[(4-butylphenyl)ethynyl]-2-fluorobenzyl}-3-cyclopentyl-N-(2,2-dimethyl-4-oxo-4H-1,3-benzodioxin-6-yl)propanamide and NaOH as a beige powder (81%). $^1$H NMR (MeOD, 300 MHz) δ 7.58 (m, 1H), 7.45 (d, J=8.3 Hz, 2H), 7.39-7.29 (m, 2H), 7.29-7.16 (m, 4H), 6.97 (d, J=8.7 Hz, 1H), 4.99 (s, 2H), 2.67 (t, J=7.5 Hz, 2H), 2.17 (t, J=7.5 Hz, 2H), 1.76-1.25 (m, 13H), 0.97 (m, 5H). M$^-$ (ESI): 540; M+(ESI): 542. HPLC, Rt: 6.19 min (Purity: 98.7%).

Step e) Formation of 5-[{4-[(4-butylphenyl)ethynyl]-2-fluorobenzyl}(3-cyclopentylpropanoyl)amino]-2-hydroxybenzoic acid, N-methyl-D-glucamine (i.e. 1-deoxy-1-(methylamino)glucitol) salt The titled compound was prepared following the procedure D using 5-[{4-[(4-butylphenyl)ethynyl]-2-fluorobenzyl}(3-cyclopentylpropanoyl)amino]-2-hydroxybenzoic acid and N-methyl-D-glucamine as a white powder (97%). M$^-$ (ESI): 540.2; M$^+$ (ESI): 542.1. HPLC, Rt: 5.88 min (Purity: 99.1%).

Example 64

8-((3-cyclopentylpropanoyl){4-[(4-fluorophenyl)ethynyl]benzyl}amino)-5,6,7,8-tetrahydronaphthalene-2-carboxylic acid, N-methyl-D-glucamine (i.e. 1-deoxy-1-(methylamino)glucitol) salt

Step a) Formation of methyl 8-({4-[(4-fluorophenyl)ethynyl]benzyl}amino)-5,6,7,8-tetrahydro-2-naphthalenecarboxylate

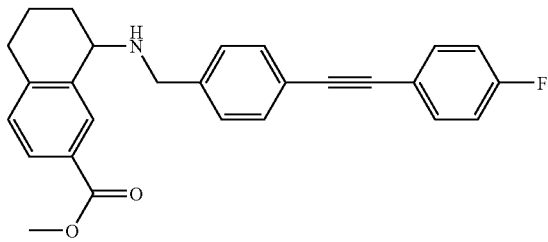

The titled compound was prepared following the procedure L using 4-[(4-fluorophenyl)-ethynyl]benzaldehyde (intermediate which may be obtained according to methods disclosed in EP03 103780.7) and methyl-8-amino-5,6,7,8-tetrahydronaphthalene as a brown oil (76%). $^1$H NMR (CDCl$_3$, 300 MHz) δ 8.03 (d, J=1.8 Hz, 1H), 7.78 (dd, J=7.9, 1.9 Hz, 1H), 7.37-7.51 (m, 6H), 7.13 (d, J=8.1 Hz, 1H), 7.02 (m, 2H), 3.71-3.95 (m, 7H), 2.84 (m, 2H), 1.67 (m, 1H), 2.07 (m, 2H), 1.52 (m, 1H). M$^+$ (ESI): 414.2. HPLC, Rt: 3.67 min (Purity: 72.4%).

Step b) Formation of methyl 8-((3-cyclopentylpropanoyl){4-[(4-fluorophenyl)ethynyl]-benzyl}amino)-5,6,7,8-tetrahydro-2-naphthalenecarboxylate

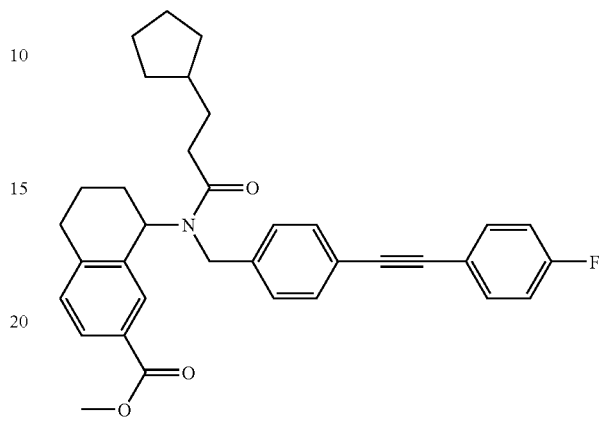

The titled compound was prepared following the procedure B using methyl 8-({4-[(4-fluorophenyl)ethynyl]benzyl}amino)-5,6,7,8-tetrahydro-2-naphthalenecarboxylate and 3-cyclopentylpropionyl chloride as a white powder (80%). $^1$H NMR (CDCl$_3$, 300 MHz) δ 1.06 (m, 2H), 1.41-2.10 (m, 11H), 2.27-2.60 (m, 2H), 2.77 (m, 2H), 3.87 (s, 3.4H), 4.07 (d, J=17.9 Hz, 0.6H), 4.52 (d, J=18.5 Hz, 0.6H), 4.86 (d, J=15.6 Hz, 0.4H), 5.10 (m, 0.4H), 6.06 (m, 0.6H), 7.00-7.20 (m, 5H), 7.36 (d, J=8.1 Hz, 1H), 7.48 (m, 3H), 7.66 (d, J=10.4 Hz, 1H), 7.78 (m, 1H). HPLC, Rt: 5.83 min (Purity: 99.4%).

Step c) Formation of 8-((3-cyclopentylpropanoyl){4-[(4-fluorophenyl)ethynyl]-benzyl}amino)-5,6,7,8-tetrahydro-2-naphthalenecarboxylic acid

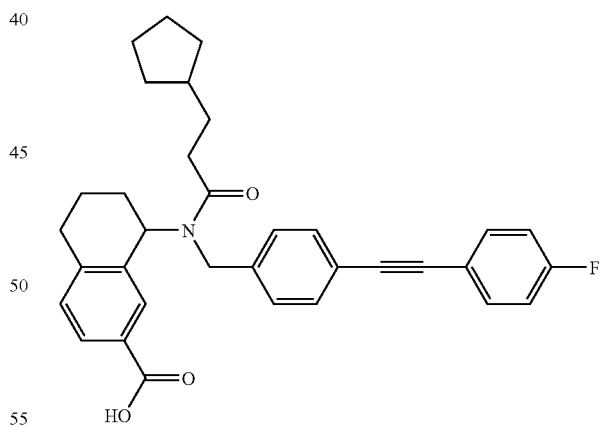

The titled compound was prepared following the procedure F using methyl 8-((3-cyclopentylpropanoyl){4-[(4-fluorophenyl)ethynyl]benzyl}amino)-5,6,7,8-tetrahydro-2-naphthalenecarboxylate in the presence of LiOH as a white powder (87%). $^1$H NMR (MeOD, 300 MHz) δ 1.07 (m, 2H), 1.59-2.26 (m, 12H), 2.28 (qt, J=7.6 Hz, 1H), 2.48 (m, 1H), 2.61 (m, 1H), 2.83 (m, 2H), 4.21 (d, J=18.5 Hz, 0.6H), 4.64 (d, J=18.3 Hz, 0.4H), 4.80 (m, 1H), 5.29 (m, 0.4H) 5.95 (m, 0.6H), 7.10 (m, 3H), 7.24 (d, J=8.5 Hz, 2H), 7.38 (d, J=7.9 Hz, 1H), 7.55 (m, 3H), 7.70 (d, J=6.8 Hz, 1H), 7.80 (d, J=6.7 Hz, 1H) M$^-$ (ESI): 522.0; M$^+$ (ESI): 524.1 HPLC, Rt: 5.33 min (Purity: 100%).

Step d) Formation of 8-((3-cyclopentylpropanoyl){4-[(4-fluorophenyl)ethynyl]benzyl}-amino)-5,6,7,8-tetrahydronaphthalene-2-carboxylic acid, N-methyl-D-glucamine (i.e. 1-deoxy-1-(methylamino)glucitol) salt The titled compound was prepared following the procedure D using 8-((3-cyclopentylpropanoyl){4-[(4-fluorophenyl)ethynyl]benzyl}amino)-5,6,7,8-tetrahydronaphthalene-2-carboxylic acid as a white powder (84.6%). M⁻ (ESI): 522.1; M⁺ (ESI): 524.0. HPLC, Rt: 5.36 min (Purity: 98.8%).

Example 65

5-[({6-[(4-butylphenyl)ethynyl]pyridin-3-yl}methyl)(3-cyclopentyl-propanoyl)amino]-2-hydroxybenzoic acid, N-methyl-D-glucamine (i.e. 1-deoxy-1-(methylamino)glucitol) salt Step a) Formation of 6-[(4-butylphenyl)ethynyl]nicotinaldehyde

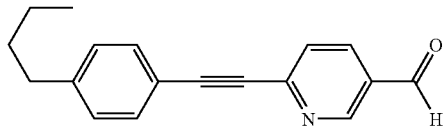

To a solution of 6-bromo-nicotinaldehyde (9.3 g, 50 mmol), Et₃N (15.2 g, 150 mmol), CuI (190 mg, 1.0 mmol) and PPh₃ (1.05 g, 4.0 mmol) in anhydrous degassed THF (250 mL) was added Pd(OAc)₂ (225 mg, 1 mmol). The mixture was heated at 70° C. for 30 min. Then, a solution of 1-butyl-4-eth-1-ynylbenzene (11.9 g, 75 mmol) in anhydrous degassed THF (1M) was added dropwise. The reaction mixture was stirred at 70° C. for 15 h. Then, an aqueous solution of HCl 1N was added and the resulting mixture was extracted with Et₂O (3×). The combined organic layers were washed with brine, dried over MgSO₄, filtered and concentrated under reduced pressure to give an orange oil. Purification by chromatography on silica gel (c-Hex/EtOAc 85/15) gave 4.5 g of the title compound as an orange oil (34%). M⁺ (ESI): 264.3. HPLC, Rt: 4.87 min (purity: 96.7%).

Step b) Formation of 6-[({6-[(4-butylphenyl)ethynyl]-3-pyridinyl}methyl)amino]-2,2-dimethyl-4H-1,3-benzodioxin-4-one

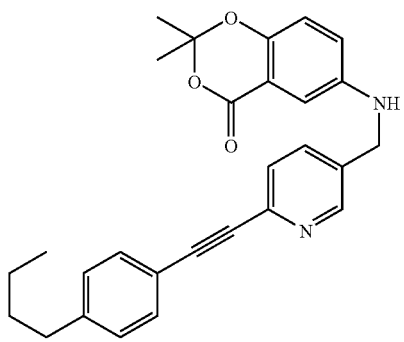

The titled compound was prepared following the procedure A using 6-[(4-butylphenyl)ethynyl]nicotinaldehyde and 6-amino-2,2-dimethyl-benzo[1,3]dioxin-4-one as a yellow powder (22%). ¹H NMR (CDCl₃, 300 MHz) δ 8.61 (s, 1H), 7.66 (m, 1H), 7.48 (m, 3H), 7.16 (m, 3H), 6.87-6.76 (m, 2H), 4.36 (s, 2H), 2.61 (t, J=7.7 Hz, 2H), 1.69 (s, 6H), 1.66-1.54 (m, 2H), 1.41-1.28 (m, 2H), 0.92 (t, J=7.2 Hz, 3H). M⁻ (ESI): 439.1; M⁺ (ESI): 441.4. HPLC, Rt: 4.55 min (Purity: 85.3%).

Step c) Formation of N-({6-[(4-butylphenyl)ethynyl]-3-pyridinyl}methyl)-3-cyclopentyl-N-(2,2-dimethyl-4-oxo-4H-1,3-benzodioxin-6-yl)propanamide

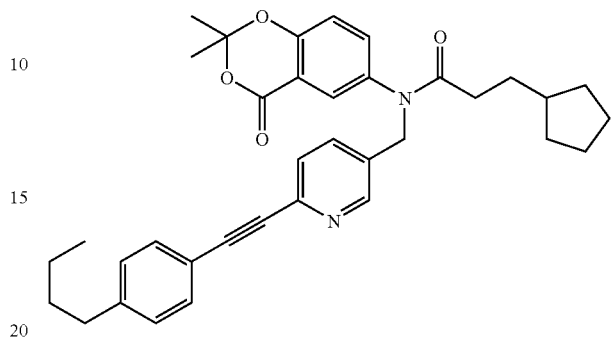

The titled compound was prepared following the procedure B using 6-[({6-[(4-butylphenyl)ethynyl]-3-pyridinyl}methyl)amino]-2,2-dimethyl-4H-1,3-benzodioxin-4-one and 3-cyclopentylpropionyl chloride as a yellow oil (73%). ¹H NMR (CDCl₃, 300 MHz) δ 8.28 (s, 1H), 7.77 (m, 2H), 7.48 (m, 3H), 7.16 (d, J=8.3 Hz, 2H), 7.05 (m, 1H), 6.93 (d, J=8.7 Hz, 1H), 4.87 (s, 2H), 2.61 (t, J=7.5 Hz, 2H), 2.05 (m, 2H), 1.74 (s, 6H), 1.68-1.29 (m, 13H), 0.92 (m, 5H). M⁺ (ESI): 565.3. HPLC, Rt: 5.43 min (Purity: 97.6%).

Step d) Formation of 5-[({6-[(4-butylphenyl)ethynyl]-3-pyridinyl}methyl)(3-cyclopentylpropanoyl)amino]-2-hydroxybenzoic acid

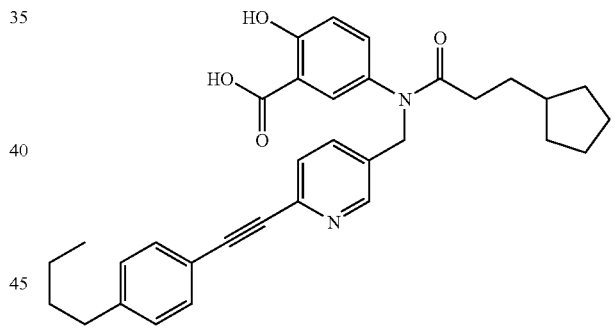

The titled compound was prepared following the procedure C using of N-({6-[(4-butylphenyl)ethynyl]-3-pyridinyl}methyl)-3-cyclopentyl-N-(2,2-dimethyl-4-oxo-4H-1,3-benzodioxin-6-yl)propanamide as a yellow foam (80%). ¹H NMR (MeOD, 300 MHz) δ 8.37 (m, 1H), 7.76 (m, 1H), 7.60 (m, 2H), 7.52 (d, J=8.3 Hz, 2H), 7.26 (m, 3H), 7.01 (d, J=9.0 Hz, 1H), 4.95 (s, 2H), 2.68 (t, J=7.5 Hz, 2H), 2.18 (t, J=7.3 Hz, 2H), 1.73-1.30 (m, 13H), 0.98 (m, 5H). M⁻ (ESI): 523.3; M⁺ (ESI): 525.2. HPLC, Rt: 5.00 min (Purity: 98.4%).

Step e) Formation of 5-[({6-[(4-butylphenyl)ethynyl]pyridin-3-yl}methyl)(3-cyclopentylpropanoyl)amino]-2-hydroxybenzoic acid, N-methyl-D-glucamine (i.e. 1-deoxy-1-(methylamino)glucitol) salt The titled compound was prepared following the procedure D using 5-[({6-[(4-butylphenyl)ethynyl]-3-pyridinyl}methyl)(3-cyclopentylpropanoyl)amino]-2-hydroxybenzoic acid and N-methyl-D-glucamine as a pale yellow powder (92%). M⁻ (ESI): 523.2; M⁺ (ESI): 525.2. HPLC, Rt: 5.01 min (Purity: 98.7%).

Example 66

5-[{4-[(4-butylphenyl)ethynyl]benzyl}(3-cyclopentylpropanoyl)amino]-2-fluorobenzoic acid. N-methyl-D-glucamine (i.e. 1-deoxy-1-(methylamino)glucitol) salt Step a) Formation of methyl 5-({4-[(4-butylphenyl)ethynyl]benzyl}amino)-2-fluorobenzoate

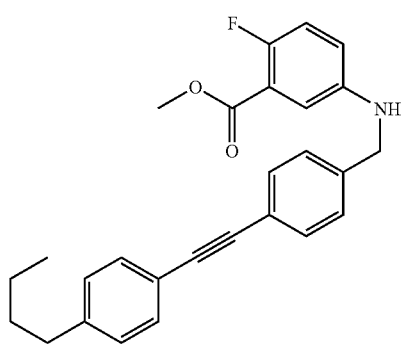

The titled compound was prepared following the procedure A using 4-[(4-butylphenyl)ethynyl]benzaldehyde and methyl 5-amino-2-fluorobenzoate as a white powder (74%). ¹HNMR (CDCl₃, 300 MHz) δ 7.51 (d, J=7.9 Hz, 2H), 7.45 (d, J=8.0 Hz, 2H), 7.34 (d, J=8.0 Hz, 2H), 7.17 (m, 3H), 6.97 (m, 1H), 6.76 (m, 1H), 4.35 (s, 2H), 3.92 (s, 3H), 2.63 (t, J=7.8 Hz, 2H), 1.61 (m, 2H), 1.37 (m, 2H), 0.94 (t, J=7.4 Hz, 3H). M⁺ (ESI): 414.0. HPLC, Rt: 5.78 min (Purity: 98.2%).

Step b) Formation of methyl 5-[{4-[(4-butylphenyl)ethynyl]benzyl}(3-cyclopentyl-propanoyl)amino]-2-fluorobenzoate

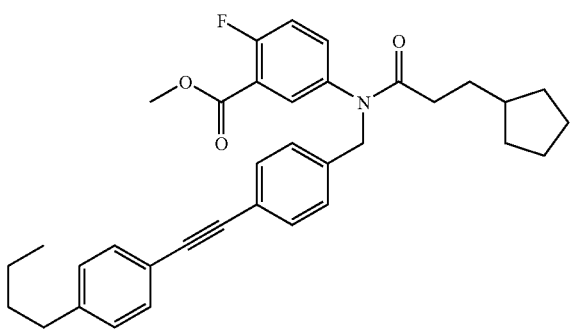

The titled compound was prepared following the procedure B using methyl 5-({4-[(4-butylphenyl)ethynyl]benzyl}amino)-2-fluorobenzoate and 3-cyclopentylpropionyle chloride as a colorless oil (99%). ¹H NMR (CDCl₃, 300 MHz) δ 7.65 (dd, J=6.0, 2.3 Hz, 1H), 7.44 (m, 4H), 7.18-7.00 (m, 6H), 4.88 (s, 2H), 3.94 (s, 3H), 2.63 (t, J=7.7 Hz, 2H), 2.06 (t, J=6.8 Hz, 2H), 1.66-1.30 (m, 13H), 0.96 (m, 2H), 0.94 (t, J=7.4 Hz, 3H). M⁺ (ESI): 540.1. HPLC, Rt: 6.09 min (Purity: 99.0%).

Step c) Formation of 5-[{4-[(4-butylphenyl)ethynyl]benzyl}(3-cyclopentylpropanoyl)amino]-2-fluorobenzoic acid

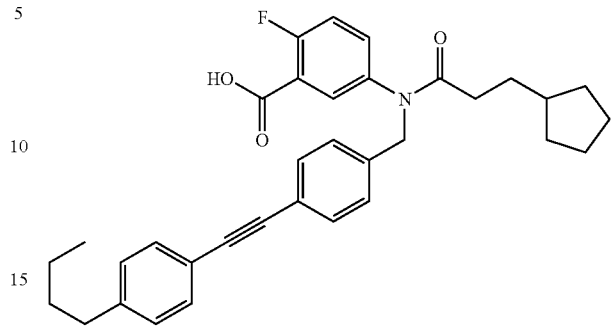

The titled compound was prepared following the procedure F using methyl 5-[{4-[(4-butylphenyl)ethynyl]benzyl}(3-cyclopentylpropanoyl)amino]-2-fluorobenzoate as a white powder (79%). ¹H NMR (CDCl₃, 300 MHz) δ 7.55 (dd, J=6.4, 2.3 Hz, 1H), 7.44 (m, 4H), 7.15 (m, 6H), 4.90 (s, 2H), 2.62 (t, J=7.8 Hz, 2H), 2.08 (t, J=6.8 Hz, 2H), 1.65-1.30 (m, 13H), 0.96 (m, 2H), 0.93 (t, J=7.4 Hz, 3H). M⁻ (ESI): 523.9; M⁺ (ESI): 526.3. HPLC, Rt: 5.69 min (Purity: 99.9%).

Step a) Formation of 5-[{4-[(4-butylphenyl)ethynyl]benzyl}(3-cyclopentylpropanoyl)amino]-2-fluorobenzoic acid, N-methyl-D-glucamine (i.e. 1-deoxy-1-(methylamino)glucitol) salt The titled compound was prepared following the procedure D using 5-[{4-[(4-butylphenyl)ethynyl]benzyl}(3-cyclopentylpropanoyl)amino]-2-fluorobenzoic acid and N-methyl-D-glucamine as a white powder (97%). M⁻ (ESI): 524.3. HPLC, Rt: 5.63 min (Purity: 99.8%).

Example 67

5-[{4-[(4-butylphenyl)ethynyl]benzyl}(3,3-dimethylbutanoyl)amino]-2-fluorobenzoic acid N-methyl-D-glucamine (i.e. 1-deoxy-1-(methylamino)-glucitol) salt Step a) Formation of methyl 5-[{4-[(4-butylphenyl)ethynyl]benzyl}(3,3-dimethylbutanoyl)amino]-2-fluorobenzoate

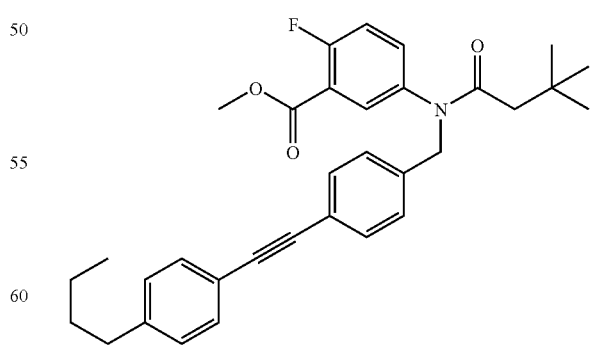

The titled compound was prepared following the procedure B using methyl 5-({4-[(4-butylphenyl)ethynyl]benzyl}amino)-2-fluorobenzoate and tert-butylacetyl chloride as a pale yellow oil (97%). ¹H NMR (CDCl₃, 300 MHz)

δ 7.61 (dd, J=6.0, 1.9 Hz, 1H), 7.44 (m, 4H), 7.16 (m, 4H), 7.08 (m, 1H), 6.99 (m, 1H), 4.88 (s, 2H), 3.94 (s, 3H), 2.63 (t, J=7.7 Hz, 2H), 2.00 (s, 2H), 1.61 (m, 2H), 1.37 (m, 2H), 0.99 (s, 9H), 0.94 (t, J=7.3 Hz, 3H). M⁺ (ESI): 514.0, HPLC, Rt: 5.92 min (Purity: 100.0%).

Step b) Formation of 5-[{4-[(4-butylphenyl)ethynyl] benzyl}(3,3-dimethylbutanoyl)amino]-2-fluorobenzoic acid

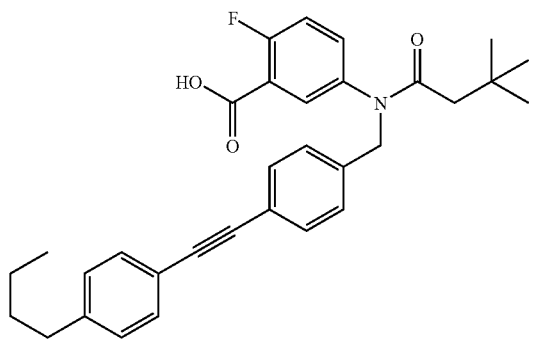

The titled compound was prepared following the procedure F using methyl 5-[{4-[(4-butylphenyl)ethynyl]benzyl} (3,3-dimethylbutanoyl)amino]-2-fluorobenzoate as a white powder (80%). ¹H NMR (CDCl₃, 300 MHz) δ 7.71 (d, J=4.9 Hz, 1H), 7.44 (m, 4H), 7.17-7.06 (m, 6H), 4.90 (s, 2H), 2.62 (t, J=7.7 Hz, 2H), 2.02 (s, 2H), 1.60 (m, 2H), 1.36 (m, 2H), 1.00 (s, 9H), 0.93 (t, J=7.2 Hz, 3H). M⁻ (ESI): 498.1. HPLC, Rt: 5.47 min (Purity: 100%).

Step c) Formation of 5-[{4-[(4-butylphenyl)ethynyl] benzyl}(3,3-dimethylbutanoyl)amino]-2-fluorobenzoic acid, N-methyl-D-glucamine (i.e. 1-deoxy-1-(methylamino)glucitol) salt The titled compound was prepared following the procedure D using 5-[{4-[(4-butylphenyl)ethynyl]benzyl}(3,3-dimethylbutanoyl)amino]-2-fluorobenzoic acid and N-methyl-D-glucamine as a white powder (90%). M⁻ (ESI): 498.0; M⁺ (ESI): 500.4. HPLC, Rt: 5.48 min (Purity: 99.3%).

Example 68

5-[{4-[(4-butylphenyl)ethynyl]benzyl}(2-thienylacetyl)amino]-2-fluorobenzoic acid, N-methyl-D-glucamine (i.e. 1-deoxy-1-(methylamino)glucitol) salt Step a) Formation of methyl 5-[{4-[(4-butylphenyl) ethynyl]benzyl}(2-thienylacetyl)amino]-2 fluorobenzoate

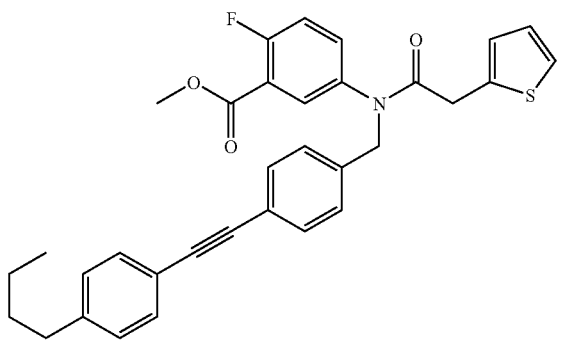

The titled compound was prepared following the procedure B using methyl 5-({4-[(4-butylphenyl)ethynyl] benzyl}amino)-2-fluorobenzoate and 2-thiophenacetyl chloride as a pink oil (92%). ¹H NMR (CDCl₃, 300 MHz) δ 7.61 (dd, J=6.2, 2.5 Hz, 1H), 7.44 (m, 4H), 7.17 (m, 5H), 7.07 (m, 1H), 6.97-6.88 (m, 2H), 6.70 (d, J=3.0 Hz, 1H), 4.90 (s, 2H), 3.94 (s, 3I), 3.65 (s, 2H), 2.63 (t, J=7.5 Hz, 2H), 1.61 (m, 2H), 1.37 (m, 2H), 0.94 (t, J=7.4 Hz, 3H). M¹(ESI): 540.1. HPLC, Rt: 5.72 min (Purity: 99.2%).

Step b) Formation of 5-[{4-[(4-butylphenyl)ethynyl] benzyl}(2-thienylacetyl)amino]-2-fluorobenzoic acid

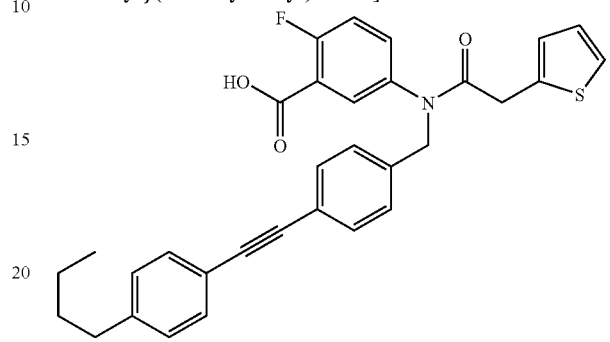

The titled compound was prepared following the procedure F using methyl 5-[{4-[(4-butylphenyl)ethynyl]benzyl} (2-thienylacetyl)amino]-2-fluorobenzoate as a beige powder (79%). ¹H HNMR (CDCl₃, 300 MHz) δ 7.72 (dd. J=5.8, 2.1 Hz, 1H), 7.43 (m, 4H), 7.16 (m, 5H), 7.10 (m, 1H), 7.01 (m, 1H), 6.90 (m, 1H), 6.71 (m, 1H), 4.92 (s, 2H), 3.69 (s, 2H), 2.62 (t, J=7.7 Hz, 2H), 1.60 (m, 2H), 1.36 (m, 2H), 0.93 (t, J=7.4 Hz, 3H). M⁻ (ESI): 523.8. HPLC, Rt: 5.27 min (Purity: 99.5%).

Step c) Formation of 5-[{4-[(4-butylphenyl)ethynyl] benzyl}(2-thienylacetyl)amino]-2-fluorobenzoic acid, N-methyl-D-glucamine (i.e. 1-deoxy-1-(methylamino)glucitol) salt The titled compound was prepared following the procedure D using 5-[{4-[(4-butylphenyl)ethynyl]benzyl}(2-thienylacetyl)amino]-2-fluorobenzoic acid and N-methyl-D-glucamine as a beige powder (84%). M⁻ (ESI): 523.9; M⁺ (ESI): 526.3. HPLC, Rt: 5.24 min (Purity: 99.7%).

Example 69

4-[{4-[(4-butylphenyl)ethynyl]benzyl}(3,3-dimethylbutanoyl)amino]-2-hydroxybenzoic acid, N-methyl-D-glucamine (i.e. 1-deoxy-1-(methylamino) glucitol) salt Step a) Formation of N-{4-[(4-butylphenyl)ethynyl] benzyl}-N-(2,2-dimethyl-4-oxo-4H-1,3-benzodioxin-7-yl)-3,3-dimethylbutanamide

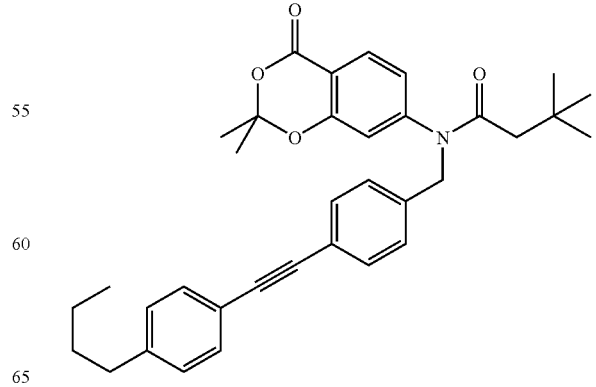

The titled compound was prepared following the procedure M using 7-({4-[(4-butylphenyl)ethynyl]benzyl}amino)-

2,2-dimethyl-4H-1,3-benzodioxin-4-one and tert-butyl acetyl chloride as an orange solid (71%). $^1$HNMR (CDCl$_3$, 300 MHz) δ: 7.91 (d, J=8.3 Hz, 1H), 7.43 (m, 2H), 7.39 (m, 2H), 7.16 (m, 2H), 7.14 (m, 2H), 6.76 (m, 0.5H), 6.73 (m, 0.5H), 6.55 (m, 1H), 4.88 (s, 2H), 2.61 (t, J=7.7 Hz, 2H), 2.09 (s, 2H), 1.71 (s, 6H), 1.67-1.54 (m, 2H), 1.41-1.27 (m, 2H), 1.00 (s, 9H), 0.92 (t, J=7.4 Hz, 3H). HPLC, Rt: 6.02 min, (Purity: 98.9%).

Step b) Formation of 4-[{4-[(4-butylphenyl)ethynyl]benzyl}(3,3-dimethylbutanoyl)amino]-2-hydroxybenzoic acid

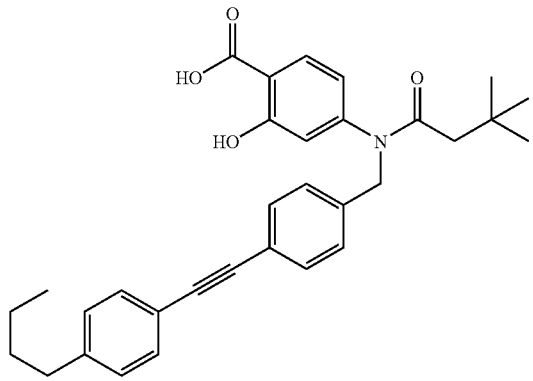

The titled compound was prepared following the procedure C using N-{4-[(4-butylphenyl)ethynyl]benzyl}-N-(2,2-dimethyl-4-oxo-4H-1,3-benzodioxin-7-yl)-3,3-dimethylbutanamide as an oil (80%). $^1$H NMR (MeOD, 300 MHz) δ 7.87 (d, J=8.7 Hz, 1H), 7.41 (m, 4H), 7.26-7.16 (m, 4H), 6.69 (m, 1H), 6.63 (m, 1H), 4.94 (s, 1H), 2.64 (t, J=7.5 Hz, 2H), 2.19 (s, 2H), 1.67-1.56 (m, 2H), 1.44-1.30 (m, 2H), 1.00 (s, 9H), 0.95 (t, J=7.3 Hz, 3H). M$^-$ (ESI): 496.6. HPLC, Rt: 5.56 min (Purity: 99.7%).

Step c) Formation of 4-[{4-[(4-butylphenyl)ethynyl]benzyl}(3,3-dimethylbenzyl)amino]-2-hydroxybenzoic acid, N-methyl-D-glucamine (i.e. 1-deoxy-1-(methylamino)glucitol) salt The titled compound was prepared following the procedure D using 4-[{4-[(4-butylphenyl)ethynyl]benzyl}(3,3-dimethylbutanoyl)amino]-2-hydroxybenzoic acid and N-methyl-D-glucamine as a white powder (94%). M$^-$ (ESI): 496.0; M$^+$ (ESI): 498.2 HPLC, Rt: 5.56 min (Purity: 98.6%).

Example 70

3-[{4-[(4-butylphenyl)ethynyl]benzyl}(3-cyclopentylpropanoyl)amino]-4-fluorobenzoic acid Step a) Formation of ethyl 3-({4-[(4-butylphenyl)ethynyl]benzyl}amino)-4-fluorobenzoate

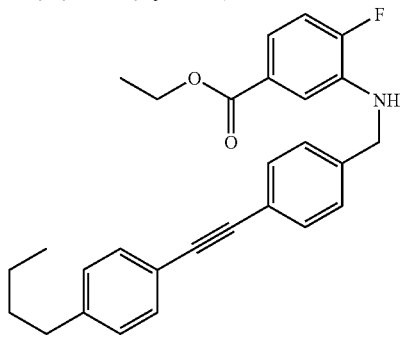

The titled compound was prepared following the procedure A using 4-[(4-butylphenyl)ethenyl]benzaldehyde and ethyl 3-amino-4-fluorobenzoate as a pale yellow oil (61%). $^1$H NMR (CDCl$_3$, 300 MHz) δ 7.49 (d, J=8.3 Hz, 2H), 7.42 (d, J=7.9 Hz, 2H), 7.35 (m, 4H), 7.14 (d, J=7.9 Hz, 2H), 7.00 (dd, J=11.0, 8.7 Hz, 1H), 4.41 (brs, 2H), 4.30 (q, J=7.2 Hz, 2H), 2.60 (t, J=7.7 Hz, 2H), 1.69-1.53 (m, 4H), 1.34 (t, J=7.2 Hz, 3H), 0.91 (t, J=7.4 Hz, 3H). HPLC, Rt: 5.87 min (Purity: 94.3%).

Step b) Formation of ethyl 3-[{4-[(4-butylphenyl)ethynyl]benzyl}(3-cyclopentylpropanoyl)amino]-4-fluorobenzoate

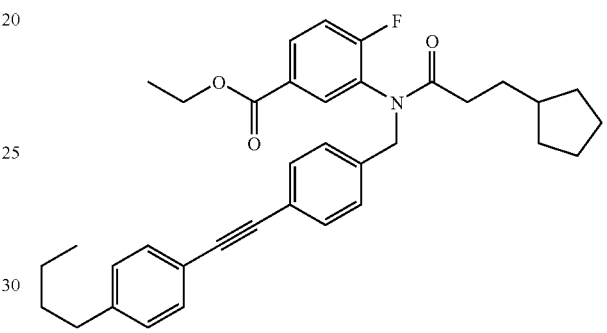

The titled compound was prepared following the procedure B using ethyl 3-({4-[(4-butylphenyl)ethynyl]benzyl}amino)-4-fluorobenzoate and 3-cyclopentylpropionyl chloride in the presence of DMAP as a colorless oil (15%). M$^+$ (ESI): 553.9. HPLC, Rt: 6.39 min (Purity: 93.6%).

Step c) Formation of 3-[{4-[(4-butylphenyl)ethynyl]benzyl}(3-cyclopentylpropanoyl)amino]-4-fluorobenzoic acid

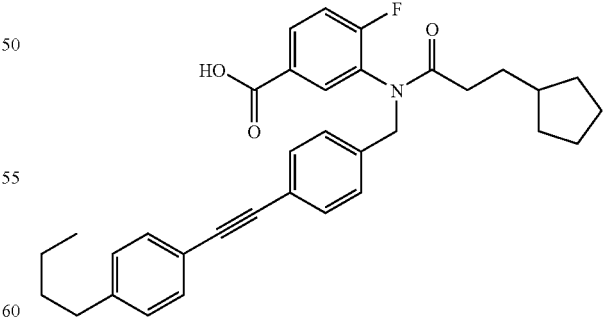

The titled compound was prepared following the procedure F using ethyl 3-[{4-[(4-butylphenyl)ethynyl]benzyl}(3cyclopentylpropanoyl)amino]-4-fluorobenzoate as a pale yellow powder (67%). M$^-$ (ESI): 524.0. HPLC, Rt: 5.75 min (Purity: 94.8%). -

Example 71

4-[{4-[(4-chlorophenyl)ethynyl]benzyl}(3-cyclopentylpropanoyl)amino]-2-hydroxybenzoic acid, N-methyl-D-glucamine (i.e. 1-deoxy-1-(methylamino)glucitol) salt Step a) Formation of 7-[((E)-{4-[(4-chlorophenyl)ethynyl]phenyl}methylidene)amino]-2,2-dimethyl-4H-1,3-benzodioxin-4-one

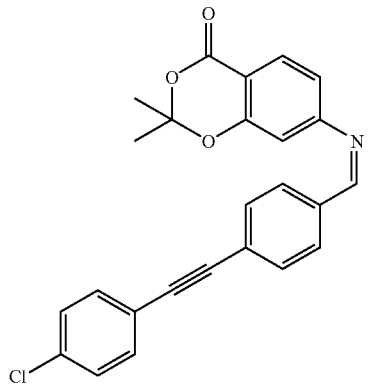

A solution of 4-[(4-chlorophenyl)ethynyl]benzaldehyde (1.31 g, 5.43 mmol) and 7-amino-2,2-dimethyl-4H-1,3-benzodioxin-4-one (1.00 g, 5.18 mmol) in toluene (20 ml) was heated at reflux for 18 h with azeotropic removal of water. Then the reaction mixture was cooled to rt and MeOH (20 ml) was added. The precipitate was filtered off, washed with MeOH and dried under reduced pressure to give 1.95 g of the titled compound as a yellow powder (91%). $^1$H NMR (CDCl$_3$, 300 MHz) δ 8.42 (s, 1H), 7.99 (d, J=8.3 Hz, 1H), 7.91 (d, J=8.2 Hz, 2H), 7.65 (d, J=8.2 Hz, 2H), 7.50 (d, J=8.7 Hz, 2H), 7.37 (d, J=8.7 Hz, 2H), 6.91 (dd, J=8.3, 1.9 Hz, 1H), 6.74 (d, J=1.9 Hz, 1H), 1.77 (s, 6H).

Step b) Formation of 7-({4-[(4-chlorophenyl)ethynyl]benzyl}amino)-2,2-dimethyl-1H-1,3-benzodioxin-4-one

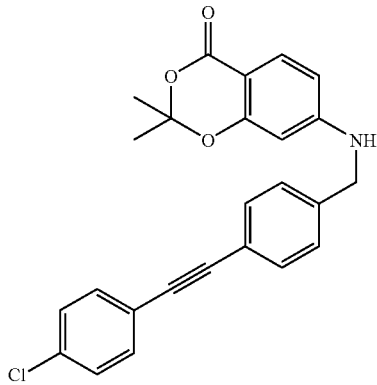

A mixture of 7-[((E)-{4-[(4-chlorophenyl)ethynyl]phenyl}methylidene)amino]-2,2-dimethyl-4H-1,3-benzodioxin-4-one (1.65 g, 3.97 mmol), sodium triacetoxyborohydride (2.52 g, 11.9 mmol) and acetic acid (0.34 mL, 5.95 mmol) in anhydrous DCE (100 mL) was heated at 50° C. for 3 h. Then the reaction mixture was diluted with H$_2$O (100 mL) and a saturated aqueous solution of NaHCO$_3$ (100 mL) and extracted with DCM (3×200 mL). The combined organic layers were dried over MgSO$_4$ and the solvents were removed under reduced pressure. Precipitation by addition of pentane and filtration gave 1.30 g of the titled compound as a pale yellow powder (77%). M$^-$ (ESI): 415.9. HPLC, Rt: 5.05 min (Purity: 98.0%).

Step c) Formation of N-{4-[(4-chlorophenyl)ethynyl]benzyl}-3-cyclopentyl-N-(2,2-dimethyl-4-oxo-4H-1,3-benzodioxin-7-yl)propanamide

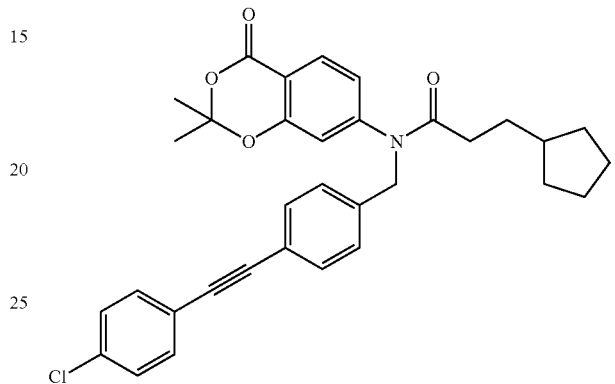

The titled compound was prepared following the procedure M using 7-({4-[(4-chlorophenyl)ethynyl]benzyl}amino)-2,2-dimethyl-4H-1,3-benzodioxin-4-one and 3-cyclopentylpropionyle chloride as a white powder (69%). M$^+$ (ESI): 542.0. HPLC, Rt: 6.14 min (Purity: 99.8%).

Step d) Formation of 4-[{4-[(4-chlorophenyl)ethynyl]benzyl}(3-cyclopentylpropanoyl)amino]-2-hydroxybenzoic acid

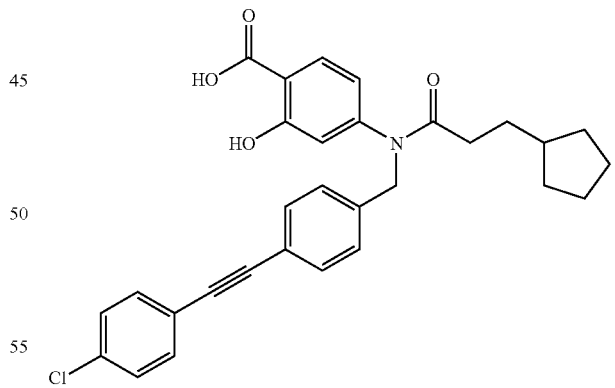

The titled compound was prepared following the procedure C using N-{4-[(4-chlorophenyl)ethynyl]benzyl}-3-cyclopentyl-N-(2,2-dimethyl-4-oxo-4H-1,3-benzodioxin-7-yl)propanamide as a white powder (93%). $^1$H NMR (CDCl$_3$, 300 MFz) δ 10.65 (s, 1H), 7.89 (d, J=8.3 Hz, 1H), 7.45 (m, 4H), 7.33 (d, J=8.3 Hz, 2H), 7.20 (d, J=7.9 Hz, 2H), 6.72 (s, 1H), 6.58 (d, J=8.3 Hz, 1H), 4.93 (s, 2H), 2.22 (t, J=6.8 Hz, 2H), 1.70-1.35 (m, 9H), 1.00 (m, 2H). M$^-$ (ESI): 500.5; M$^+$ (ESI): 502.2. HPLC, Rt: 5.66 min (Purity: 99.8%).

Step e) Formation of 4-[{4-[(4-chlorophenyl)ethynyl]benzyl}(3-cyclopentylpropanoyl)amino]-2-hydroxybenzoic acid, N-methyl-D-glucamine (i.e. 1-deoxy)-1-(methylamino)glucitol) salt The titled compound was prepared following the procedure D using 4-[{4-[(4-chlorophenyl)ethynyl]benzyl}(3-cyclopentylpropanoyl)amino]-2-hydroxybenzoic acid and N-methyl-D-glucamine as a white powder (98%). M⁻ (ESI): 499.9; M⁺ (ESI): 502.1. HPLC, Rt: 5.65 min (Purity: 99.7%).

Example 72

4-(acetyl{4-[(4-butylphenyl)ethynyl]benzyl}amino)-2-hydroxybenzoic acid, N-methyl-D-glucamine (i.e. 1-deoxy-1-(methylamino)glucitol) salt Step a) Formation of N-{4-[(4-butylphenyl)ethynyl)]benzyl}-N-(2,2-dimethyl-4-oxo-4H-1,3-benzodioxin-7-yl)acetamide

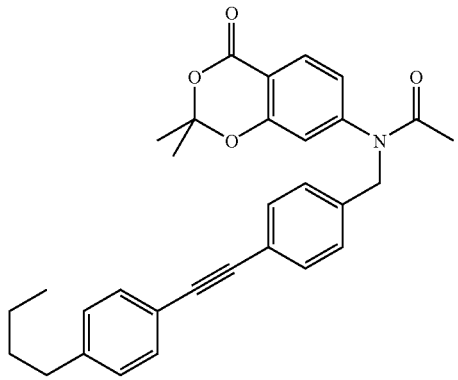

The titled compound was prepared following the procedure B using 7-({4-[(4-butylphenyl)ethynyl]benzyl}amino)-2,2-dimethyl-4H-1,3-benzodioxin-4-one and acetyl chloride in the presence of dry THF for 15 h at reflux as an oil (77%). ¹H NMR (CDCl₃, 300 MHz) δ 7.93 (d, J=8.3 Hz, 1H), 7.42 (m, 4H), 7.14 (m, 4H), 6.81 (m, 0.5H), 6.79 (m, 0.5H), 6.62 (m, 1H), 4.90 (s, 2H), 2.61 (t, J=7.7 Hz, 2H), 1.99 (s, 3H), 1.71 (s, 6H), 1.65-1.54 (m, 2H), 1.41-1.27 (m, 2H), 0.91 (t, J=7.3 Hz, 3H). M⁺ (ESI): 481.9. HPLC, Rt: 5.72 min (Purity: 99.4%).

Step b) Formation of 4-(acetyl{4-[(4-butylphenyl)ethynyl]benzyl}amino)-2-hydroxybenzoic acid

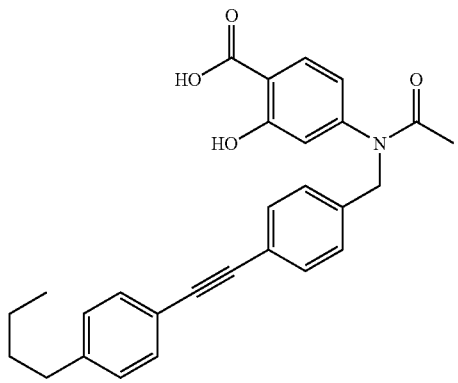

The titled compound was prepared following the procedure C using N-{4-[(4-butylphenyl)ethynyl]benzyl}-N-(2,2-dimethyl-4-oxo-4H-1,3-benzodioxin-7-yl)acetamide as a pale yellow solid (68%). ¹HNMR (DMSO-d6, 300 MHz) δ 7.76 (d, J=8.7 Hz, 1H), 7.45 (m, 4H), 7.25 (m, 4H), 6.89 (m, 1H), 6.82 (m, 0.5H), 6.79 (m, 0.5H), 4.93 (s, 2H), 2.61 (t, J=7.5 Hz, 2H), 1.96 (s, 3H), 1.54 (m, 2H), 1.27 (m, 2H), 0.89 (t, J=7.3 Hz, 3H). M⁻ (ESI): 440.3. HPLC, Rt: 5.25 min (Purity: 98.5%).

Step c) Formation of 4-(acetyl{4-[(4-butylphenyl)ethynyl]benzyl}amino)-2-hydroxybenzoic acid, N-methyl-D-glucamine (i.e. 1-deoxy-1-(methylamino)glucitol) salt The titled compound was prepared following the procedure D using 4-(acetyl{4-[(4-butylphenyl)ethynyl]benzyl}amino)-2-hydroxybenzoic acid and N-methyl-D-glucamine as a white powder (97%). M⁻ (ESI): 440.7; M⁺ (ESI): 441.8. HPLC, Rt: 5.26 min (Purity: 98.1%).

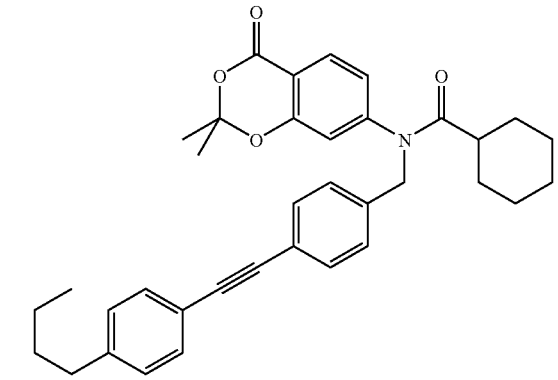

Example 73

4-[{4-[(4-butylphenyl)ethynyl]benzyl}(cyclohexylcarbonyl)amino]-2-hydroxybenzoic acid, N-methyl-D-glucamine (i.e. 1-deoxy-1-(methylamino)glucitol) salt Step a) Formation of N-{4-[(4-butylphenyl)ethynyl]benzyl}-N-(2,2-dimethyl-4-oxo-4H-1,3-benzodioxin-7-yl)cyclohexanecarboxamide The titled compound was prepared following the procedure M using 7-({4-[(4-butylphenyl)ethynyl]benzyl}amino)-2,2-dimethyl-4H-1,3-benzodioxin-4-one and cyclohexanecarbonyl chloride as an orange oil (52%). ¹H NMR (CDCl₃, 300 MHz) δ 7.92 (d, J=8.3 Hz, 1H), 7.41 (m, 4H), 7.14 (m, 4H), 6.77 (m, 0.5H), 6.75 (m, 0.5H), 6.57 (m, 1H), 4.87 (s, 2H), 2.60 (t, J=7.5 Hz, 2H), 2.2 (m, 1H), 1.71 (s, 6H), 1.69-1.52 (m, 8H), 1.39-0.97 (m, 6H), 0.91 (t, J=7.3 Hz, 3H). M⁺ (ESI): 550.1. HPLC, Rt: 6.35 min (Purity: 97.5%).

Step b) Formation of 4-[{4-[(4-butylphenyl)ethynyl] benzyl}(cyclohexylcarbonyl)amino]-2-hydroxybenzoic acid

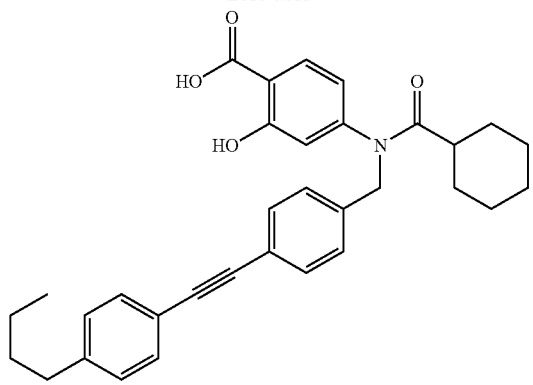

The titled compound was prepared following the procedure C using N-{4-[(4-butylphenyl)ethynyl]benzyl}-N-(2,2-dimethyl-4-oxo-4H-1,3-benzodioxin-7-yl)cyclohexanecarboxamide in the presence of THF as a brown powder (78%). $^1$H NMR (CDCl$_3$, 300 MHz) δ 10.64 (s, 1H), 7.85 (d, J=8.7 Hz, 1H), 7.41 (m, 4H), 7.14 (m, 4H), 6.68 (m, 1H), 6.52 (d, J=8.7 Hz, 1H), 4.87 (s, 2H), 2.60 (t, J=7.1 Hz, 2H), 2.25 (m, 1H), 1.80-1.50 (m, 8H), 1.41-0.95 (m, 6H), 0.91 (t, J=7.3 Hz, 3H). M$^-$ (ESI): 507.9. M$^+$ (ESI): 510.0. HPLC, Rt: 5.92 min (Purity: 100%).

Step c) Formation of 4-[{4-[(4-butylphenyl)ethynyl)] benzyl}(cyclohexylcarbonyl)amino]-2-hydroxybenzoic acid, N-methyl-D-glucamine (i.e. 1-deoxy-1-(methylamino)glucitol) salt The titled compound was prepared following the procedure D using 4-[{4-[(4-butylphenyl)ethynyl]benzyl}(cyclohexylcarbonyl)amino]-2-hydroxybenzoic acid and N-methyl-D-glucamine as a white powder (95%). M$^-$ (ESI): 508.8; M$^+$ (ESI): 510.2. HPLC, Rt: 5.90 min (Purity: 100%).

Example 74

4-[{4-[(4-butylphenyl)ethynyl]benzyl}(hexanoyl) amino]-2-hydroxybenzoic acid, N-methyl-D-glucamine (i.e. 1-deoxy-1-(methylamino)glucitol) salt Step a) Formation of N-{4-[(4-butylphenyl)ethynyl] benzyl}-N-(2,2-dimethyl-4-oxo-4H-1,3-benzodioxin-7-yl)hexanamide

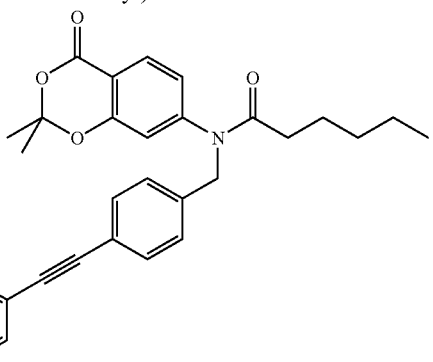

The titled compound was prepared following the procedure M using 7-({4-[(4-butylphenyl)ethynyl]benzyl}amino)-2,2-dimethyl-4H-1,3-benzodioxin-4-one and hexanoyl chloride as all orange oil (69%). $^1$H NMR (CDCl$_3$, 300 MHz) δ 7.92 (d, J=8.3 Hz, 1H), 7.41 (m, 4H), 7.14 (m, 4H), 6.78 (d, J=8.3 Hz, 1H), 6.59 (s, 1H), 4.89 (s, 2H), 2.60 (t, J=7.7 Hz, 2H), 2.14 (t, J=7.3 Hz, 2H), 1.71 (s, 6H), 1.66-1.51 (m, 4H), 1.43-1.12 (m, 8H), 0.91 (t, J=7.3 Hz, 3H). 0.84 (t, J=6.7 Hz, 3H). M$^+$ (ESI): 538.2. HPLC, Rt: 6.34 min (Purity: 99.4%).

Step b) Formation of 4-[{4-[(4-butylphenyl)ethynyl] benzyl}(hexanoyl)amino]-2-hydroxybenzoic acid

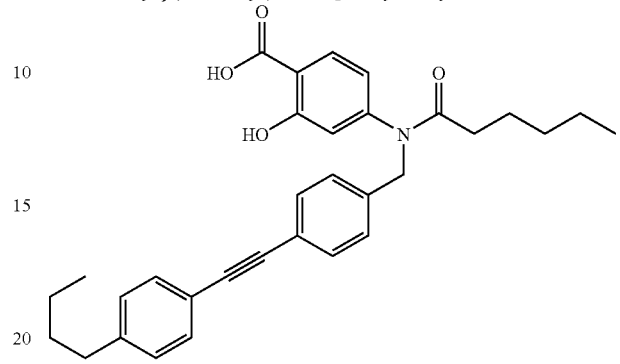

The titled compound was prepared following the procedure C using N-{4-[(4-butylphenyl)ethynyl]benzyl}-N-(2,2-dimethyl-4-oxo-4H-1,3-benzodioxin-7-yl)hexanamide in the presence of THF as a pale yellow powder (81%). $^1$H NMR (CDCl$_3$, 300 MHz) δ 10.62 (s, 1H), 7.86 (d, J=8.3 Hz, 1H), 7.41 (m, 4H), 7.15 (m, 4H), 6.69 (m, 1H), 6.55 (m, 0.5H), 6.53 (m, 0.5H), 4.90 (s, 2H), 2.60 (t, J=7.6 Hz, 2H), 2.17 (t, J=7.6 Hz, 2H), 1.68-1.52 (m, 4H), 1.40-1.28 (m, 2H), 1.27-1.13 (m, 4H), 0.93 (t, J=7.3 Hz, 3H), 0.91 (t, J=6.8 Hz, 3H). M$^-$ (ESI): 496.7; M$^1$(ESI): 498.1. HPLC, Rt: 5.92 min (Purity: 97.5%).

Step c) Formation of 4-[{4-[(4-butylphenyl)ethynyl] benzyl}(hexanoyl)amino]-2-hydroxybenzoic acid, N-methyl-D-glucamine (i.e. 1-deoxy-1-(methylamino)glucitol) salt The titled compound was prepared following the procedure D using 4-[{4-[(4-butylphenyl)ethynyl]benzyl}(hexanoyl)amino]-2-hydroxybenzoic acid and N-methyl-D-glucamine as a white powder (95%). M$^-$ (ESI): 496.6; M$^+$ (ESI): 498.1. HPLC, Rt: 5.91 min (Purity: 99.8%).

Example 75

4-[{4-[(4-butylphenyl)ethynyl]benzyl}(3-cyclopentylpropanoyl)amino]-2-fluorobenzoic acid, N-methyl-D-glucamine (i.e. 1-deoxy-1-(methylamino) glucitol) salt Step a) Formation of methyl 4-({4-[(4-butylphenyl) ethynyl]benzyl}amino)-2-fluorobenzoate

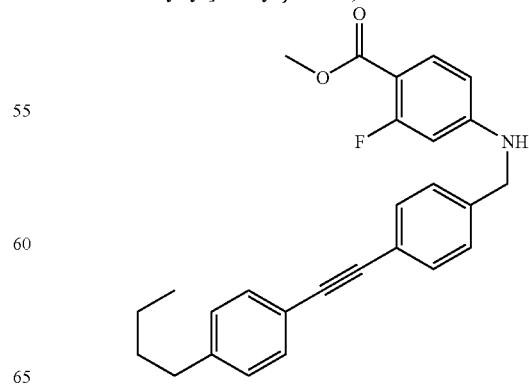

The titled compound was prepared following the procedure A using 4-[(4-butylphenyl)ethynyl]benzaldehyde and methyl 4-amino-2-fluorobenzoate as a beige powder (63%). M⁻ (ESI): 414.1; M⁺ (ESI): 416.9. HPLC, Rt: 5.58 min (Purity: 96.9%).

Step b) Formation of methyl 4-[{4-[(4-butylphenyl)ethynyl]benzyl}(3-cyclopentylpropanoyl)amino]-2-fluorobenzoate

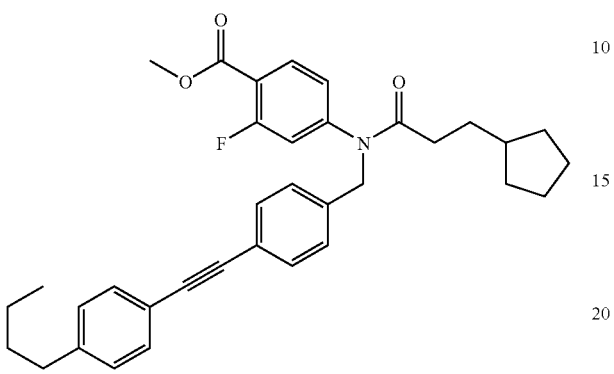

The titled compound was prepared following the procedure B using methyl 4-({4-[(4-butylphenyl)ethynyl]benzyl}amino)-2-fluorobenzoate and 3-cyclopentylpropionyl chloride as a pale yellow oil (54%). M⁺ (ESI): 540.1. HPLC, Rt: 6.35 min (Purity: 98.2%).

Step c) Formation of 4-[{4-[(4-buthylphenyl)ethynyl]benzyl}(3-cyclopentylpropanoyl)amino]-2-fluorobenzoic acid

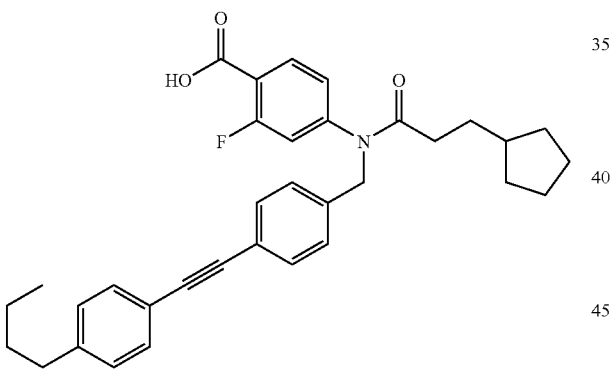

The titled compound was prepared following the procedure F using methyl 4-[{4-[(4-butylphenyl)ethynyl]benzyl}(3-cyclopentylpropanoyl)amino]-2-fluorobenzoate as a white powder (63%). ¹H NMR (DMSO-d₆, 300 MHz) δ 7.71 (m, 1H), 7.43 (m, 4H), 7.23 (m, 5H), 7.04 (d, J=7.9 Hz, 1H), 4.91 (s, 2H), 2.59 (t, J=7.5 Hz, 2H), 2.17 (t, J=7.3 Hz, 2H), 1.65-1.20 (m, 13H), 0.92 (m, 2H), 0.88 (t, J=7.3 Hz, 3H). HPLC, Rt: 5.85 min (Purity: 94.3%).

Step d) Formation of 4-[{4-[(4-butylphenyl)ethynyl]benzyl}(3-cyclopentylpropanoyl)amino]-2-fluorobenzoic acid, N-methyl-D-glucamine (i.e. 1-deoxy-1-(methylamino)glucitol) salt The titled compound was prepared following the procedure D using 4-[{4-[(4-butylphenyl)ethynyl]benzyl}(3-cyclopentylpropanoyl)amino]-2-fluorobenzoic acid and N-methyl-D-glucamine as a white powder (81%). M⁻ (ESI): 524.4; M⁺ (ESI): 526.6. HPLC, Rt: 5.94 min (Purity: 97.1%).

Example 76

4-[{4-[(4-butylphenyl)ethynyl]benzyl}(2,2-dimethylpropanoyl)amino]-2-hydroxybenzoic acid, N-methyl-D-glucamine (i.e. 1-deoxy-1-(methylamino)glucitol) salt Step a) Formation of N-{4-[(4-butylphenyl)ethynyl]benzyl}-N-(2,2-dimethyl-4-oxo-4H-1,3-benzodioxin-7-yl)-2,2-dimethylpropanamide

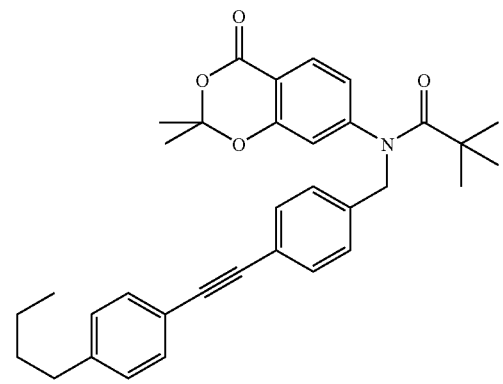

The titled compound was prepared following the procedure M using 7-({4-[(4-butylphenyl)ethynyl]benzyl}amino)-2,2-dimethyl-4H-1,3-benzodioxin-4-one and 2,2'-dimethylpropionyl chloride as a pale yellow oil (53%). ¹H NMR (CDCl₃, 300 MHz) δ 7.90 (d, J=8.3 Hz, 1H), 7.41 (m, 4H), 7.14 (m, 4H), 6.81 (m, 0.5H) 6.78 (m, 0.5H), 6.56 (m, 1H), 4.83 (s, 2H), 2.61 (t, J=7.5 Hz, 2H) 1.71 (s, 6H), 1.56 (m, 2H), 1.35 (m, 2H), 1.08 (s, 9H), 0.92 (t, J=7.3 Hz, 3H). HPLC, Rt: 6.21 min (Purity: 98.0%).

Step b) Formation of 4-[{4-[(4-butylphenyl)ethynyl]benzyl}(2,2-dimethylpropanoyl)amino]-2-hydroxybenzoic acid

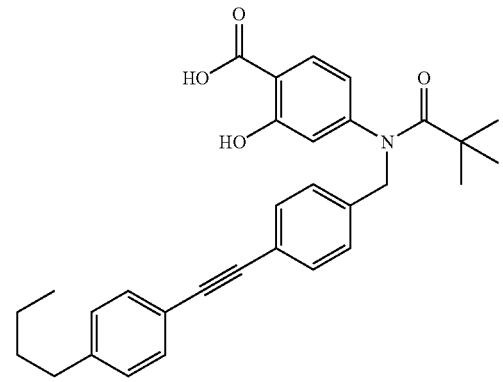

The titled compound was prepared following the procedure C using N-{4-[(4-butylphenyl)ethynyl]benzyl}-N-(2,2-dimethyl-4-oxo-4H-1,3-benzodioxin-7-yl)-2,2-dimethylpropanamide as a white solid (84%). ¹H NMR (CDCl₃, 300 MHz) δ 10.54 (s, 1H), 7.83 (d, J=8.3 Hz, 1H), 7.41 (m, 4H), 7.14 (m, 4H), 6.71 (m, 1H), 6.57 (m, 0.5H), 6.55 (m, 0.5H), 4.84 (s, 2H), 2.60 (t, J=7.7 Hz, 2H), 1.58 (m, 2H), 1.38 (m, 2H), 1.10 (s, 9H), 0.91 (t, J37.3 Hz, 3H). M⁻ (ESI): 482.3; M⁺ (ESI): 484.6. HPLC, Rt: 5.61 min (Purity: 97.9%).

Step c) Formation of 4-[{4-[(4-butylphenyl)ethynyl]benzyl}(2,2-dimethylpropanoyl)amino]-2-hydroxybenzoic acid, N-methyl-D-glucamine (i.e. 1-deoxy-1-(methylamino)glucitol) salt The titled compound was prepared following the procedure D using 4-[{4-[(4-butylphenyl)ethynyl]benzyl}(2,2-dimethylpropanoyl)amino]-2-hydroxybenzoic acid and N-methyl-D-glucamine as a white powder (89%). M⁻ (ESI): 482.1; M⁺ (ESI): 484.1. HPLC, Rt: 5.69 min (purity: 99.6%).

Example 77

4-((3-cyclopentylpropanoyl){4-[(4-methoxyphenyl)ethynyl]-benzyl}amino)-2-hydroxybenzoic acid, N-methyl-D-glucamine (i.e. 1-deoxy-1-(methylamino)glucitol) salt

Step a) Formation of 7-({4-[(4-methoxyphenyl)ethynyl]benzyl}amino)-2,2-dimethyl-4H-1,3-benzodioxin-4-one

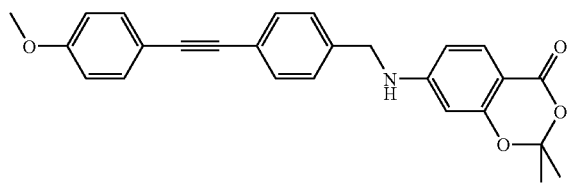

The title compound was prepared following the procedure A using 4-[(4-methoxyphenyl)-ethynyl]benzaldehyde (intermediate which may be obtained according to methods disclosed in EP03103780.7) and 7-amino-2,2-dimethyl-4H-1,3-benzodioxin-4-one as a brown powder (%). ¹H NMR (CDCl₃) δ 7.70 (d, J=8.7 Hz, 1H), 7.48 (d, J=8.3 Hz, 2H), 7.44 (d, J=8.9 Hz, 2H), 7.28 (d, J=8.1 Hz, 2H), 6.86 (d, J=8.9 Hz, 2H), 6.30 (m, 1H), 6.01 (s, 1H), 4.37 (s, 2H), 3.81 (s, 3H), 1.67 (s, 6H). M⁺ (ESI): 414.1, M⁻ (ESI): 412.1. HPLC, Rt: 4.90 min (purity: 92.8%).

Step b) Formation of 3-cyclopentyl-N-(2,2-dimethyl-4-oxo-4H-1,3-benzodioxin-7-yl)-N-{4-[(4-methoxyphenyl)ethynyl]benzyl}propanamide

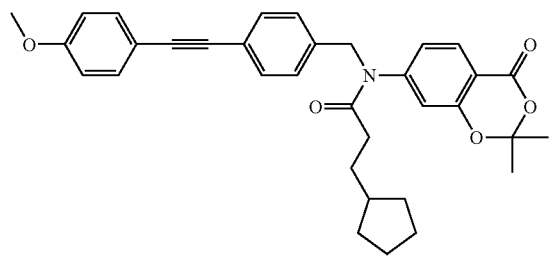

The title compound was prepared following the procedure B using 7-({4-[(4-methoxyphenyl)ethynyl]benzyl}amino)-2,2-dimethyl-4H-1,3-benzodioxin-4-one and 3-cyclopentylpropionyl chloride as a beige solid (63%). ¹H NMR (CDCl₃) δ 7.91 (d, J=8.3 Hz, 1H), 7.41 (m, 4H), 7.12 (d, J=8.1 Hz, 2H), 6.85 (d, J=8.5 Hz, 2H), 6.76 (d, J=8.1 Hz, 1H), 6.59 (s, 1H), 4.87 (s, 2H), 3.80 (s, 3H), 2.15 (t, J=6.9 Hz, 2H), 1.70 (s, 6H), 1.40-1.61 (m, 9H), 0.95 (m, 2H). HPLC, Rt: 5.78 min (purity: 99.3%).

Step c) Formation of 4-((3-cyclopentylpropanoyl){4-[(4-methoxyphenyl)ethynyl]-benzyl}amino)-2-hydroxybenzoic acid

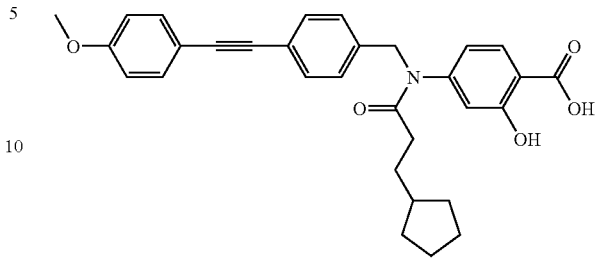

The title compound was prepared following the procedure C using 3-cyclopentyl-N-(2,2-dimethyl-4-oxo-4H-1,3-benzodioxin-7-yl)-N-{4-[(4-methoxyphenyl)ethynyl]benzyl}-propanamide as a beige solid (77%). ¹H NMR (CDCl₃) δ: 7.84 (d, J=8.7 Hz, 1H), 7.43 (t, J=9.0 Hz, 4H), 7.40 (d, J=8.3 Hz, 2H), 7.14 (d, J=8.3 Hz, 2H), 6.68 (d, J=1.9 Hz, 1H), 6.53 (dd, J=8.7, 1.9 Hz, 1H), 4.88 (s, 2H), 3.81 (s, 3H), 2.17 (t, J=7.2 Hz, 2H), 1.40-1.62 (m, 9H), 0.97 (m, 2H). M⁺ (ESI): 498.2, M⁻ (ESI): 496.03. HPLC, Rt: 5.3 min (purity: 99.1%).

Step d) Formation of 4-((3-cyclopentylpropanoyl){4-[(4-methoxyphenyl)ethynyl]-benzyl}amino)-2-hydroxybenzoic acid, N-methyl-D-glucamine (i.e. 1-deoxy-1-(methylamino)glucitol) salt The title compound was prepared following the procedure D using 4-((3-cyclopentylpropanoyl){4-[(4-methoxyphenyl)ethynyl]benzyl}amino)-2-hydroxybenzoic acid and N-methyl-D-glucamine as a white powder (96%). M⁺ (ESI): 498.1; M⁻ (ESI): 496.1. HPLC, Rt: 5.3 min (purity: 100%), Analysis calculated for C₃₁H₃₁NO₅·C₇H₁₇NO₅·H₂O: C, 64.21; H, 7.09; N, 3.94%. Found: C, 64.57; H, 6.83; N, 3.87%.

Example 78

4-[{4-[(4-tert-butylphenyl)ethynyl]benzyl}(3-cyclopentylpropanoyl)amino]-2-hydroxybenzoic acid, N-methyl-D-glucamine (i.e. 1-deoxy-1-(methylamino)glucitol) salt

Step a) Formation of 7-[(4-bromobenzyl)amino]-2,2-dimethyl-4H-1,3-benzodioxin-4-one

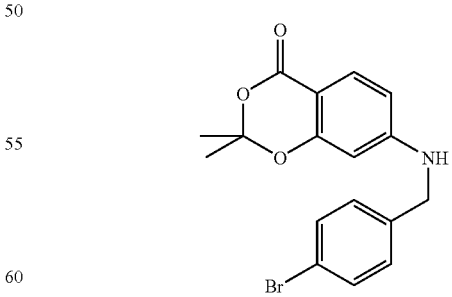

The titled compound was prepared following the procedure A using 7-amino-2,2-dimethyl-4H-1,3-benzodioxin-4-one and 4-bromobenzyldehyde as a beige powder (76%). M⁻ (ESI): 360.0; M⁻ (ESI): 362.0. HPLC, Rt: 4.42 min (Purity: 95.3%).

Step b) Formation of N-(4-bromobenzyl)-3-cyclopentyl-N-(2,2-dimethyl-4-oxo-4H-1,3-benzodioxin-7-yl)propanamide

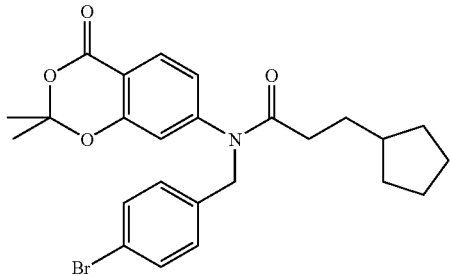

The titled compound was prepared following the procedure M using 7-[(4-bromobenzyl)amino]-2,2-dimethyl-4H-1,3-benzodioxin-4-one and 3-cyclopentylpropionyl chloride as a white powder (86%). M⁺ (ESI): 488.0. HPLC, Rt: 5.41 min (Purity: 99.9%).

Step c) Formation of N-{4-[(4-tert-butylphenyl)ethynyl]benzyl}-3-cyclopentyl-N-(2,2-dimethyl-4-oxo-4H-1,3-benzodioxin-7-yl)propanamide

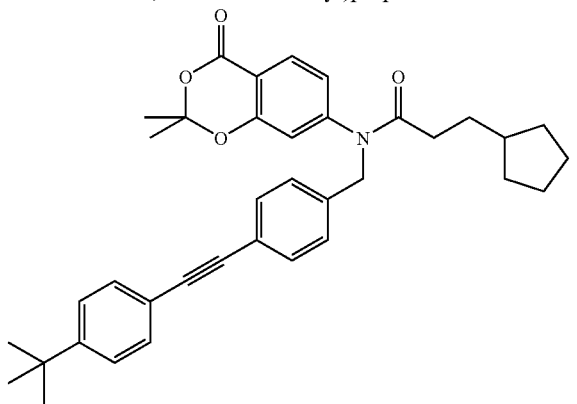

The titled compound was prepared following the procedure N using N-(4-bromobenzyl)-3-cyclopentyl-N-(2,2-dimethyl-4-oxo-4H-1,3-benzodioxin-7-yl)propanamide and 4-(tert-butyl)-phenylacetylene as a beige powder (65%). M¹(ESI): 564.2. HPLC, Rt: 6.39 min (Purity: 98.9%).

Step d) Formation of 4-[{4-[(4-tert-butylphenyl)ethynyl]benzyl}(3-cyclopentylpropanoyl-)amino]-2-hydroxybenzoic acid

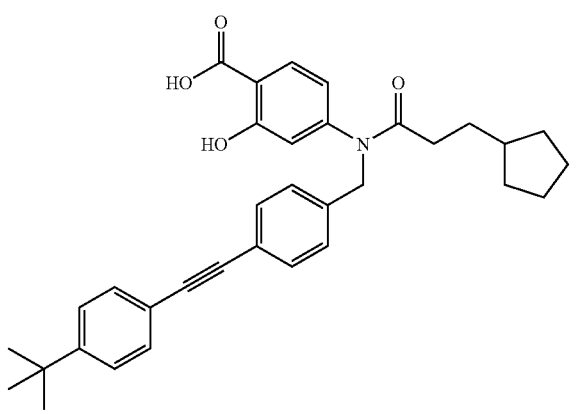

The titled compound was prepared following the procedure C using N-{4-[(4-tert-butylphenyl)ethynyl]benzyl}-3-cyclopentyl-N-(2,2-dimethyl-4-oxo-4H-1,3-benzodioxin-7-yl)propanamide as a pale yellow powder (66%). ¹H NMR (CDCl₃, 300 MHz) δ 10.67 (s, 1H), 7.89 (d, J=8.3 Hz, 1H) 7.45 (m, 4H), 7.37 (d, J=8.6 Hz, 2H), 7.19 (d, J=8.3 Hz, 2H), 6.73 (d, J=1.9 Hz, 1H), 6.57 (dd, J=8.3, 1.9 Hz, 1H), 4.93 (s, 2H), 2.22 (t, J=7.4 Hz, 2H), 1.70-1.40 (m, 9H), 1.33 (s, 9H), 1.00 (m, 2H). M⁻ (ESI): 522.2; M⁺ (ESI): 524.2. HPLC, Rt: 5.99 min (Purity: 99.1%).

Step e) Formation of 4-[{4-[(4-tert-butylphenyl)ethynyl]benzyl}(3-cyclopentylpropanoyl)-amino]-2-hydroxybenzoic acid, N-methyl-D-glucamine (i.e. 1-deoxy-1-(methylamino)glucitol) salt The titled compound was prepared following the procedure D using 4-[{4-[(4-tert-butylphenyl)ethynyl]benzyl}(3-cyclopentylpropanoyl)amino]-2-hydroxybenzoic acid and N-methyl-D-glucamine as a white powder (89%). M⁻ (ESI): 522.1; M⁺ (ESI): 524.2. HPLC, Rt: 5.94 min (Purity: 97.7%).

Example 79

4-((3-cyclopentylpropanoyl){4-[(4-propoxyphenyl)ethynyl]benzyl}amino)-2-hydroxybenzoic acid, N-methyl-D-glucamine (i.e. 1-deoxy-1-(methylamino)glucitol) salt Step a) Formation of 3-cyclopentyl-N-(2,2-dimethyl-4-oxo-4H-1,3-benzodioxin-7-yl)-N-{4-[(4-propoxyphenyl)ethynyl]benzyl}propanamide

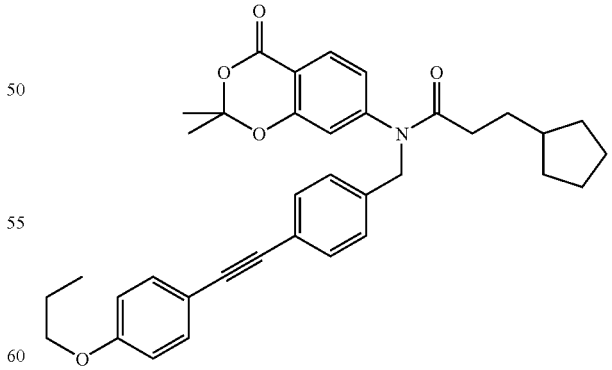

The titled compound was prepared following the procedure N using N-(4-bromobenzyl)-3-cyclopentyl-N-(2,2-dimethyl-4-oxo-4H-1,3-benzodioxin-7-yl)propanamide and 4-(propoxy)-phenylacetylene as a beige powder (59%). M⁺ (ESI): 566.2. HPLC, Rt: 6.17 min (Purity: 97.7%).

Step b) Formation of 4-((3-cyclopentylpropanoyl){4-[(4-propoxyphenyl)ethynyl]benzyl}-amino)-2-hydroxybenzoic acid

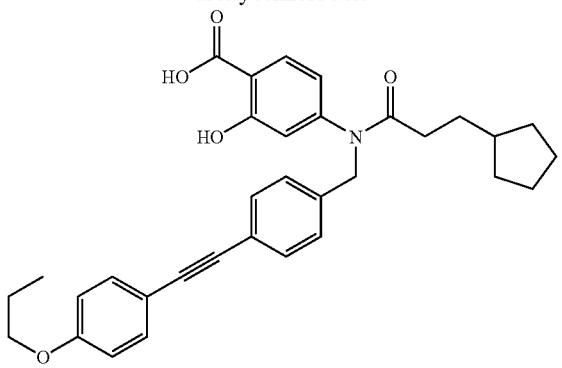

The titled compound was prepared following the procedure C using 3-cyclopentyl-N-(2,2-dimethyl-4-oxo-4H-1,3-benzodioxin-7-yl)-N-{4-[(4-propoxyphenyl)ethynyl]benzyl}propanamide as a beige powder (60%). $^1$H NMR (CDCl$_3$, 300 MHz) δ 10.66 (s, 1H), 7.89 (d, J=8.3 Hz, 1H), 7.44 (m, 4H), 7.18 (d, J=7.9 Hz, 2H), 6.87 (d, J=8.7 Hz, 2H), 6.72 (d, J=1.9 Hz, 1H), 6.57 (dd, J=8.3, 1.9 Hz, 1H), 4.92 (s, 2H), 3.94 (t, J=6.6 Hz, 2H), 2.22 (t, J=7.0 Hz, 2H), 1.83 (m, 2H), 1.70-1.40 (m, 9H), 1.05 (t, J=7.5 Hz, 3H), 1.02 (m, 2H). M$^-$ (ESI): 524.6; M$^+$ (ESI): 526.2. HPLC, Rt: 5.71 min (Purity: 99.1%).

Step c) Formation of 4-((3-cyclopentylpropanoyl){4-[(4-propoxyphenyl)ethynyl]benzyl}-amino)-2-hydroxybenzoic acid, N-methyl-D-glucamine (i.e. 1-deoxy-1-(methylamino)-glucitol) salt The titled compound was prepared following the procedure D using 4-((3-cyclopentyl-propanoyl){4-[(4-propoxyphenyl)ethynyl]benzyl}amino)-2-hydroxybenzoic acid and N-methyl-D-glucamine as a beige powder (84%). M$^-$ (ESI): 524.0; M$^+$ (ESI): 526.0. HPLC, Rt: 5.74 min (Purity: 98.0%).

Example 80

4-((3-cyclopentylpropanoyl){4-[(4-propylphenyl)ethynyl]benzyl}amino)-2-hydroxybenzoic acid, N-methyl-D-glucamine (i.e. 1-deoxy-1-(methylamino)glucitol) salt Step a) Formation of N-{4-[(4-propylphenyl)ethynyl]benzyl}-3-cyclopentyl-N-(2,2-dimethyl-4-oxo-4H-1,3-benzodioxin-7-yl)propanamide

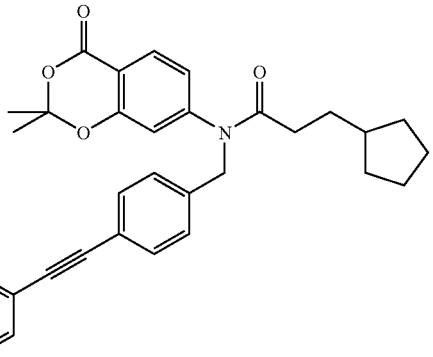

The titled compound was prepared following the procedure N using N-(4-bromobenzyl)-3-cyclopentyl-N-(2,2-dim-ethyl-4-oxo-4H-1,3-benzodioxin-7-yl)propanamide and 4-propylphenylacetylene as a white powder (40%). M$^+$ (ESI): 550.1. HPLC, Rt: 6.33 min (Purity: 100%).

Step b) Formation of 4-((3-cyclopentylpropanoyl){4-[(4-propylphenyl)ethynyl]benzyl}-amino)-2-hydroxybenzoic acid

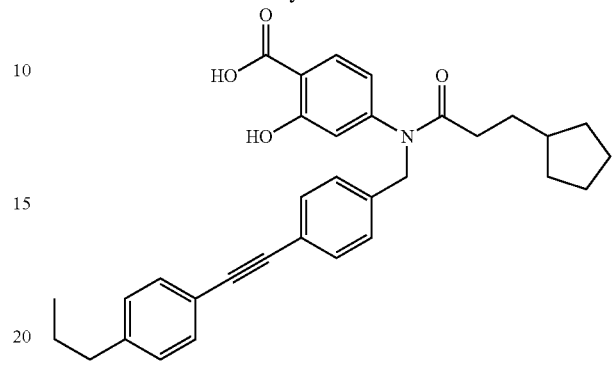

The titled compound was prepared following the procedure C using N-{4-[(4-propylphenyl)ethynyl]benzyl}-3-cyclopentyl-N-(2,2-dimethyl-4-oxo-4H-1,3-benzodioxin-7-yl) propanamide as a beige powder (91%). $^1$H NMR (CDCl$_3$, 300 MHz) δ 10.65 (s, 1H), 7.89 (d, J=8.3 Hz, 1H), 7.44 (m, 4H), 7.17 (m, 4H), 6.72 (d, J=1.9 Hz, 1H), 6.57 (dd, J=8.3, 1.9 Hz, 1H), 4.92 (s, 2H), 2.60 (t, J=7.6 Hz, 2H), 2.22 (t, J=7.0 Hz 2H), 1.75-1.40 (m, 11H), 1.00 (m, 2H), 0.95 (t, J=7.4 Hz, 3H). M$^-$ (ESI): 508.1; M$^+$ (ESI): 510.0. HPLC, Rt: 5.89 min (Purity: 99.8%).

Step c) Formation of 4-((3-cyclopentyproponoyl){4-[(4-propylphenyl)ethynyl]benzyl}-amino)-2-hydroxybenzoic acid, N-methyl-D-glucamine (i.e. 1-deoxy-1-(methylamino)glucitol) salt The titled compound was prepared following the procedure D using 4-((3-cyclopentylpropanoyl){4-[(4-propylphenyl)ethynyl]benzyl}amino)-2-hydroxybenzoic acid and N-methyl-D-glucamine as a pale beige powder (90%). M$^-$ (ESI): 508.2; M$^+$ (ESI): 510.2. HPLC, Rt: 5.86 min (Purity: 100%).

Example 81

4-{(3-cyclopentylpropanoyl)[4-(5-phenylpent-1-yn-1-yl)benzyl]amino}-2-hydroxybenzoic acid N-methyl-D-glucamine (i.e. 1-deoxy-1-(methylamino) glucitol) salt Step a) Formation of 3-cyclopentyl-N-(2,2-dimethyl-4-oxo-4H-1,3-benzodioxin-7-yl)-N-[4-(5-phenyl-1-pentynyl)benzyl]propanamide

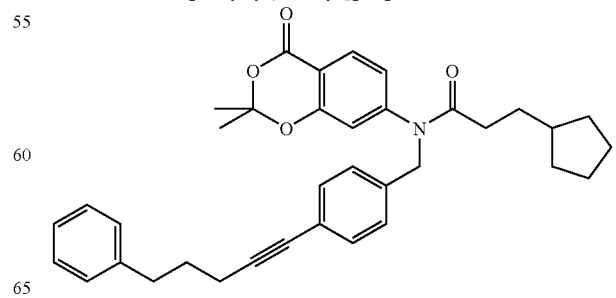

The titled compound was prepared following the procedure N using N-(4-bromobenzyl)-3-cyclopentyl-N-(2,2-dim ethyl-4-oxo-4H-1,3-benzodioxin-7-yl)propanamide and 5-phenyl-1-pentyne as a yellow oil (54%). M+ (ESI): 550.2. HPLC, Rt: 5.96 min (Purity: 94.9%).

Step b) Formation of 4-{3-cyclopentylpropanoyl)[4-(5-phenylpent-1-yn-1-yl)benzyl]amino}-2-hydroxybenzoic acid

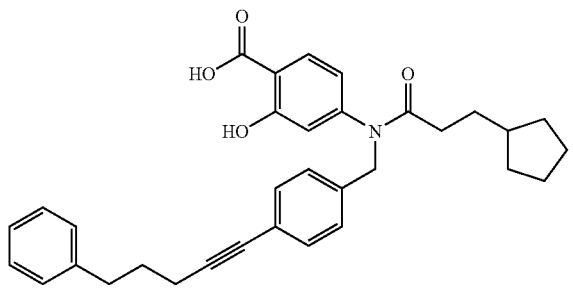

The titled compound was prepared following the procedure C using 3-cyclopentyl-N-(2,2-dimethyl-4-oxo-4H-1,3-benzodioxin-7-yl)-N-[4-(5-phenyl-1-pentynyl)benzyl]propanamide as a yellow solid (76%). $^1$H NMR (DMSO-d$_6$, 300 MHz) δ 7.74 (d, J=8.3 Hz, 1H), 7.32-7.13 (m, 9H), 6.81 (d, J=2.3 Hz, 1H), 6.73 (dd, J=8.3, 2.3 Hz, 1H), 4.87 (s, 2H), 2.70 (t, J=7.7 Hz, 2H), 2.38 (t, J=7.0 Hz, 2H), 2.18 (t, J=7.3 Hz, 2H), 1.81 (m, 2H), 1.65-1.34 (m, 9H), 0.93 (m, 2H). M⁻ (ESI): 508.4; M+ (ESI): 510.1. HPLC, Rt: 5.57 min (Purity: 96.1%).

Step c) Formation of 4-{(3-cyclopentylpropanoyl)[4-(5-phenylpent-1-yn-1-yl)benzyl]amino}-2-hydroxybenzoic acid, N-methyl-D-glucamine (i.e. 1-deoxy-1-(methylamino)glucitol) salt The titled compound was prepared following the procedure D using 4-{(3-cyclopentylpropanoyl)[4-(5-phenylpent-1-yn-1-yl)benzyl]amino}-2-hydroxybenzoic acid and N-methyl-D-glucamine as a beige powder (86%). M⁻ (ESI): 508.3. M+ (ESI): 510.4. HPLC, Rt: 5.57 min (Purity: 98.8%).

Example 82

Preparation of a Pharmaceutical Formulation

Formulation 1—Tablets

An alkynyl aryl carboxamide of formula (I) or (I') is admixed as a dry powder with a dry gelatin binder in an approximate 1:2 weight ration. A minor amount of magnesium stearate is added as a lubricant. The mixture is formed into 240-270 mg tablets (80-90 mg of active piperazine-2-carboxamide compound per tablet) in a tablet press.

Formulation 2—Capsules

An alkynyl aryl carboxamide of formula (I) or (I') is admixed as a dry powder with a starch diluent in an approximate 1:1 weight ratio. The mixture is filled into 250 mg capsules (125 mg of active piperazine-2-carboxamide compound per capsule).

Formulation 3—Liquid

An alkynyl aryl carboxamide of formula (I) or (I'), sucrose and xanthan gum are blended, passed through a No. 10 mesh U.S. sieve, and then mixed with a previously prepared solution of microcrystalline cellulose and sodium carboxymethyl cellulose (11:89) in water. Sodium benzoate, flavor, and color are diluted with water and added with stirring. Sufficient water is then added.

Formulation 4—Tablets

An alkynyl aryl carboxamide of formula (I) or (I'), is admixed as a dry powder with a dry gelatin binder in an approximate 1:2 weight ratio. A minor amount of magnesium stearate is added as a lubricant. The mixture is formed into 300-600 mg tablets (150-300 mg of active alkynyl aryl carboxamide derivative) in a tablet press.

Formulation 5—Injection

An alkynyl aryl carboxamide of formula (I) or (I'), is dissolved in a buffered sterile saline injectable aqueous medium to a concentration of approximately 5 mg/ml.

Example 83

Biological Assays

The compounds of formula (I) or (I'), may be subjected to the following assays:
(1) The PTP Enzyme Assay
(2) The in vivo assay in db/db mice (1) The PTP Enzyme Assay (In Vitro Assay)

Assays for the determination of the PTP inhibitory activity of test compounds are well known to a person skilled in the art. An example of such an assay is described below:

The PTP Enzyme Assay aims at determining the extent of inhibition of PTPs, e.g. of PTP1B, SHP-1, SHP-2, GLEPP-1 or PTP-H1 in the presence of a test compound of formula (I) or (I'). The inhibition is illustrated by IC$_{50}$ values which denote the concentration of test compound necessary to achieve an inhibition of 50% of said PTP's using the following concentration of the PTP substrate DiFMUP:

5 µM DiFMUP for PTP1B and PTP-H1;
20 µM DiFMUP for SHP-1 and SHP-2.
30 µM DiFMUP for GLEPP-1.

a) PTPs Cloning

The cloning and expression of the catalytic domain e.g. of PTP1B, may be performed as described in *J. Biol. Chem.* 2000, 275(13), pp 9792-9796.

b) Materials and Methods

The DiFMUP assay allows to follow the dephosphorylation of DiFMUP (6,8-DiFluoro-4-MethylUmbelliferyl Phosphate)—which is the PTP substrate—mediated by PTP into its stable hydrolysis product, i.e. DiFMU (6,8-difluoro-7-hydroxy coumarin). Due to its rather low pKa and its high quantum yield, DiFMU allows to measure both acidic and alkaline phosphatase activities with a great sensitivity.

Assays were performed in a 96 well plate format, using the catalytic core of a human recombinant PTP as the enzyme and 6,8-DiFluoro-4-MethylUmbelliferyl Phosphate (DiFMUP, Molecular Probes, D-6567) as a substrate. Compounds to be tested were dissolved in 100% DMSO at a concentration of 2 mM. Subsequent dilutions of the test compounds (to yield a concentration of 100, 30, 10, 3, 1, 0.3, 0.1, 0.03, 0.01, 0.001 µM) wore performed in 60% DMSO manually. 8 µl of diluted compound or vehicle (60% DMSO=control) was distributed to a black Costar 96 well plate. 42 µl of human recombinant PTP enzyme diluted in assay buffer (20 mM Tris HCl pH 7.5, 0.01% IGEPAL CA-630, 0.1 mM ethylenediaminetetracetic acid, 1 mM DL-Dithiothreitol) can be added to the dilutions of compound or vehicle (distributed to a black Costar 96 well plate), followed by 50 µl of DiFMUP diluted in the assay buffer. The reaction ran for 30 minutes at room temperature before reading the fluorescence intensity (integral or intensity) on a Perkin-Elmer Victor 2 spectrofluorimeter (excitation of 6,8-difluoro-7-hydroxy coumarin is at 355 nm, the emission at 460 nm, for 0.1 s). The percentage of inhibition is determined by measuring the relative fluorescence ion absence of a test compound (PTP inhibitor), i.e. with the solvent alone (5% DMSO). The $IC_{50}$ values for inhibition were determined in triplicates.

The tested compounds according to formula (I) or (I') display an inhibition (illustrated by $IC_{50}$ values) with regard to PTP of preferably less than 20 µM, more preferred less than 5 µM.

For instance the compound of example 2 displays an $IC_{50}$ value of 0.49 µM in respect of PTP1B and an $IC_{50}$ value of 0.61 µm in respect of GLEPP-1, an $IC_{50}$ value of 1.2, 0.49 and 3.37 µM in respect of SHP-1, SHP-2 and PTP-H1.

The compound of example 16 displays an $IC_{50}$ value of 0.29 µM in respect of PTP1B and an $IC_{50}$ value of 0.21 µM in respect of GLEPP-1, an $IC_{50}$ value of 1.6, 1.4 and 5.70 µM in respect of SHP-1, SHP-2 and PTP-H1.

The compound of example 68 displays an $IC_{50}$ value of 0.49 µM in respect of PTPL1B and an $IC_{50}$ value of 1.58 µM in respect of GLEPP-1, an $IC_{50}$ value of 3.7, 1.9 and 9.9 µM in respect of SHP-1, SHP-2 and PTP-H1.

The compound of example 76 displays an $IC_{50}$ value of 0.97 µM in respect of PTP1B and an $IC_{50}$ value of 0.99 µM in respect of GLEPP-1, an $IC_{50}$ value of 3.0, 2.2 and 6.3 µM in respect of SHP-1, SHP-2 and PTP-H1.

(2) In Vivo Assay in db/db Mice

The following assay aims at determining the anti-diabetic effect of the test compounds of formula (I) or (I') in a model of postprandial glycemia in db/db mice, in vivo.

The assay was performed as follows:

A total of 18 db/db mice (about 8-9 weeks; obtained from IFFACREDO, l'Arbreste, France) were fasted during 20 hours.

3 groups, each consisting of 6 animals were formed:

Group 1: The animals were administered (per os) a dose of 10 mL/kg of vehicle (control).

Group 2: The animals were administered (per os) a dose of 30 mg/kg of the test compound according to formula (I) solubilized in the vehicle.

Group 3: The animals were administered (per os) a dose of 100 mg/kg of the test compound according to formula (I) solubilized in the vehicle.

After oral administration of the compounds of formula (I) or (I') solubilized or suspended in CarboxyMethylCellulose (0.5%), Tween 20 (0.25%) in water as vehicle, the animals had access to commercial food (D04, UAR, Villemoisson/Orge, France) ad libitum. The diabetic state of the mice was verified by determining the blood glucose level before fasting. Blood glucose and serum insulin levels were then determined 4 hrs after drug administration.

The determination of the blood glucose level was performed using a glucometer (Ascensia Dex², Bayer, ref 3956C).

The determination of the Insulin level was performed using an ELISA kit (Mercodia, ref 10-1149-10).

Changes in blood glucose and serum insulin of drug treated mice were expressed as a percentage of control (group 1: vehicle treated mice).

Treatment (per os) of the animals with alkynyl aryl carboxamide compounds of formula (I) & (1'), at a dosage of 30 mg/kg, decreased the blood glucose level induced by food intake by about 20-40%.

For instance, upon using the compound of example 2, i.e. 5-[(3-cyclopentylpropanoyl)(4-dec-1-ynylbenzyl)amino]-2-hydroxybenzoic acid, N-methyl-D-glucamine salt, the following decrease in blood glucose level as well as insulin level was determined (difference in insulin & glucose levels compared to Group 1 animals):

| Animal Group | Decrease in blood glucose | ±SEM | Decrease in serum insulin | ±SEM |
| --- | --- | --- | --- | --- |
| Group 2 | 28 | 14 | 84 | 2 |
| Group 3 | 58 | 8 | 88 | 2 |

(SEM = Standard Error of the Mean)

(3) In Vivo Assay for Inflammatory Diseases: Thioglycollate-Induced Peritoneal Recruitment of Macrophages in Mice To assess the compounds of the present invention for their suitability in the treatment of inflammatory diseases they may be subjected to the following assay:

C3H mice (Elevage Janvier) (8 week old, n=6) are treated with Thioglycollate (1.5%, 40 ml/kg, ip) 15 min after administration of the test molecules and a second administration of the test molecules 24 h later. Forty-eight hours after the challenge, the animals are sacrificed and the lavage of the peritoneal cavity is conducted using 2×5 ml PBS-1 mM EDTA (+4° C.). After centrifugation (10 min at 3000 rpm), the pellet is resuspended in 1 ml PBS. The peritoneal cells are counted using a Beckman/Coulter counter. The test compounds of formula (I) & (I') are solubilized or suspended in 0.5% carboxymethylcellulose (CMC)/0.25% Tween-20 and orally administered. Dexamethasone (1 mg/kg, po) is used as reference compound.

The invention claimed is:

1. A method of treating at least one disease, in a mammal in need thereof, wherein the at least one disease is selected from the group consisting of diabetes, inadequate glucose tolerance, hyperlipidemia, hypertriglyceridemia, hypercholerstrolemia, obesity, and polycystic ovary syndrome, comprising administering at least one alkynyl aryl carboxamide of Formula (I')

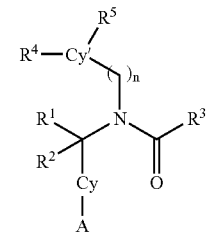

(I')

as well as its geometrical isomers, its optically active forms as enantiomers, diastereomers and its racemate forms, as well as pharmaceutically acceptable salts thereof, wherein A is a $C_2$-$C_{15}$ alkynyl, or $C_2$-$C_6$-alkynyl aryl;

Cy is an aryl;

Cy' is an aryl, which may optionally be fused by a 3-8 membered cycloalkyl;

n is 0 or 1;

$R_1$ and $R_2$ are independently from each other selected from the group consisting of hydrogen and $C_1$-$C_6$-alkyl;

$R_3$ is selected from the group consisting of $C_1$-$C_6$-alkyl, $C_2$-$C_6$-alkenyl, $C_2$-$C_6$-alkynyl, $C_1$-$C_6$-alkoxy, $C_1$-$C_6$-alkyl amine, $C_1$-$C_6$-alkyl alkoxy, $C_1$-$C_6$-alkyl carboxy, aryl, heteroaryl, saturated or unsaturated 3-8-membered cycloalkyl, 3-8-membered heterocycloalkyl, $C_1$-$C_6$-alkyl aryl, $C_1$-$C_6$-alkyl heteroaryl, $C_2$-$C_6$-alkenyl aryl, $C_2$-$C_6$-alkenyl heteroaryl, $C_2$-$C_6$-alkynyl aryl; $C_2$-$C_6$-alkynyl heteroaryl, $C_1$-$C_6$-alkyl cycloalkyl, $C_1$-$C_6$-alkyl heterocycloalkyl, $C_2$-$C_6$-alkenyl cycloalkyl, $C_2$-$C_6$-alkenyl heterocycloalkyl, $C_2$-$C_6$-alkynyl cycloalkyl, and $C_2$-$C_6$-alkynyl heterocycloalkyl;

$R^4$ and $R^5$ are independently from each other selected from the group consisting of H, hydroxy, fluoro, $C_1$-$C_6$ alkyl, carboxy, $C_1$-$C_6$ alkoxy, $C_1$-$C_3$ alkyl carboxy, $C_2$-$C_3$ alkenyl carboxy, and $C_2$-$C_3$ alkynyl carboxy, wherein at least one of $R^4$ or $R^5$ is neither a hydrogen nor a $C_1$-$C_6$ alkyl; to the mammal in an amount sufficient to treat or prevent the at least one disease.

2. A method of treating at least one disease in a mammal in need thereof, wherein the at least one disease is selected from the group consisting of diabetes, inadequate glucose tolerance, hyperlipidemia, hypertriglyceridemia, hypercholerstrolemia, obesity, and polycystic ovary syndrome, comprising
administering at least one alkynyl aryl carboxamide of Formula (I)

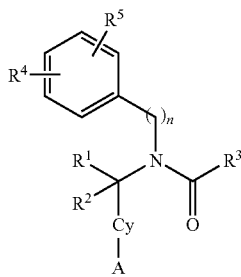

(I)

as well as its geometrical isomers, its optically active forms as enantiomers, diastereomers and its racemate forms, as well as pharmaceutically acceptable salts thereof, wherein
A is a $C_2$-$C_{15}$ alkynyl, or $C_2$-$C_6$-alkynyl aryl;
Cy is an aryl;
n is 0 or 1;
$R^1$ and $R^2$ are independently from each other selected from the group consisting of hydrogen and $C_1$-$C_6$-alkyl;
$R^3$ is selected from the group consisting of $C_1$-$C_6$-alkyl, $C_2$-$C_6$-alkenyl, $C_2$-$C_6$-alkynyl, $C_1$-$C_6$-alkoxy, $C_1$-$C_6$-alkyl amine, $C_1$-$C_6$-alkyl alkoxy, aryl, heteroaryl, saturated 3-8-membered cycloalkyl, unsaturated 3-8 membered cycloalkyl, 3-8-membered heterocycloalkyl, an acyl moiety, $C_1$-$C_6$-alkyl aryl, $C_1$-$C_6$-alkyl heteroaryl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, $C_1$-$C_6$-alkyl cycloalkyl, $C_1$-$C_6$-alkyl heterocycloalkyl, $C_2$-$C_6$-alkenyl cycloalkyl, $C_2$-$C_6$-alkenyl heterocycloalkyl, $C_2$-$C_6$-alkynyl cycloalkyl, and $C_2$-$C_6$-alkynyl heterocycloalkyl;
$R^4$ and $R^5$ are each independently from each other selected from the group consisting of H, hydroxy, $C_1$-$C_6$ alkyl, carboxy, $C_1$-$C_6$ alkoxy, $C_1$-$C_3$ alkyl carboxy, $C_2$-$C_3$ alkenyl carboxy, $C_2$-$C_3$ alkynyl carboxy, and amino, or $R^4$ and $R^5$ may form an unsaturated or saturated heterocyclic ring, wherein at least one of $R^4$ or $R^5$ is not a hydrogen or $C_1$-$C_6$ alkyl; to the mammal in an amount sufficient to treat or prevent the at least one disease.

3. A method of treating at least one disease in a mammal in need thereof, wherein the at least one disease is selected from the group consisting of metabolic disorders mediated by insulin resistance or hyperglycemia, inflammatory diseases, and combinations thereof, comprising
administering at least one alkynyl aryl carboxamide of Formula (I')

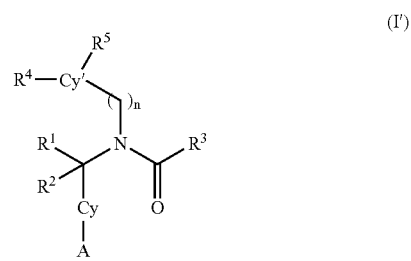

(I')

as well as its geometrical isomers, its optically active forms as enantiomers, diastereomers and its racemate forms, as well as pharmaceutically acceptable salts thereof, wherein
A is a $C_2$-$C_{15}$ alkynyl, or $C_2$-$C_6$-alkynyl aryl;
Cy is an aryl;
Cy' is an aryl, which may optionally be fused by a 3-8 membered cycloalkyl;
n is 0 on;
$R_1$ and $R_2$ are independently from each other selected from the group consisting of hydrogen and $C_1$-$C_6$-alkyl;
$R_3$ is selected from the group consisting of $C_1$-$C_6$-alkyl, $C_2$-$C_6$-alkenyl, $C_2$-$C_6$-alkynyl, $C_1$-$C_6$-alkoxy, $C_1$-$C_6$-alkyl amine, $C_1$-$C_6$-alkyl alkoxy, $C_1$-$C_6$-alkyl carboxy, aryl, heteroaryl, saturated or unsaturated 3-8-membered cycloalkyl, 3-8-membered heterocycloalkyl, $C_1$-$C_6$-alkyl aryl, $C_1$-$C_6$-alkyl heteroaryl, $C_2$-$C_6$-alkenyl aryl, $C_2$-$C_6$-alkenyl heteroaryl, $C_2$-$C_6$-alkynyl aryl; $C_2$-$C_6$-alkynyl heteroaryl, $C_1$-$C_6$-alkyl cycloalkyl, $C_1$-$C_6$-alkyl heterocycloalkyl, $C_2$-$C_6$-alkenyl cycloalkyl, $C_2$-$C_6$-alkenyl heterocycloalkyl, $C_2$-$C_6$-alkynyl cycloalkyl, and $C_2$-$C_6$-alkynyl heterocycloalkyl;
$R^4$ and $R^5$ are independently from each other selected from the group consisting of H, hydroxy, fluoro, $C_1$-$C_6$ alkyl, carboxy, $C_1$-$C_6$ alkoxy, $C_1$-$C_3$ alkyl carboxy, $C_2$-$C_3$ alkenyl carboxy, and $C_2$-$C_3$ alkynyl carboxy, wherein at least one of $R^4$ or $R^5$ is neither a hydrogen nor a $C_1$-$C_6$ alkyl; to the mammal in an amount sufficient to treat or prevent the at least one disease.

4. The method of claim 1, wherein the method is a method of treating.

5. The method of claim 2, wherein the method is a method of treating.

6. The method of claim 3, wherein the method is a method of treating.

7. The method of claim 1, wherein $R^1$ and $R^2$ are each H.

8. The method of claim 1, wherein Cy is a phenyl group.

9. The method of claim 1, wherein A is a moiety of the formula —C≡C—$R^6$, and wherein $R^6$ is $C_6$-$C_{12}$ alkyl, a 3-8 membered cycloalkyl, $C_1$-$C_6$ alkyl-(3-8 membered) cycloalkyl, $C_2$-$C_6$-alkenyl, $C_2$-$C_6$-alkynyl, phenyl, $C_1$-$C_{12}$ alkyl phenyl, $C_2$-$C_6$-alkenyl phenyl, or a $C_2$-$C_6$-alkynyl phenyl.

10. An alkynyl aryl carboxamide or its salt according to any of formulae (Ia), (Ib), (Ic) or (It):

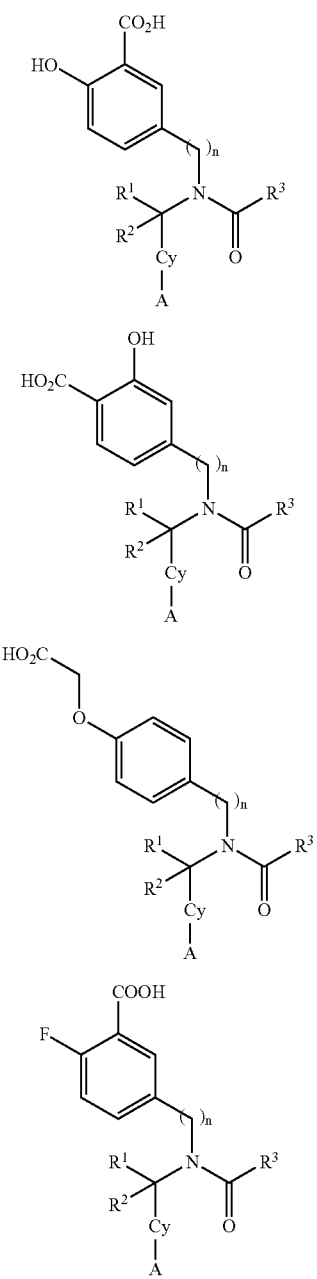

wherein
A is a $C_2$-$C_{15}$ alkynyl, or $C_2$-$C_6$-alkynyl aryl;
Cy is an aryl;
n is 0 or 1;
$R^1$ and $R^2$ are independently from each other is selected from the group consisting of hydrogen and $C_1$-$C_6$-alkyl; and wherein
$R^3$ is selected from the group consisting of H, hydroxy, $C_1$-$C_6$-alkyl, $C_2$-$C_6$-alkenyl, $C_2$-$C_6$-alkynyl, $C_1$-$C_6$-alkoxy, $C_1$-$C_6$-alkyl amine, $C_1$-$C_6$-alkyl alkoxy, aryl, heteroaryl, saturated or unsaturated 3-8-membered cycloalkyl, 3-8-membered heterocycloalkyl, an acyl moiety, $C_1$-$C_6$-alkyl aryl, $C_1$-$C_6$-alkyl heteroaryl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, $C_1$-$C_6$-alkyl cycloalkyl, $C_1$-$C_6$-alkyl heterocycloalkyl, $C_2$-$C_6$-alkenyl cycloalkyl, $C_2$-$C_6$-alkenyl heterocycloalkyl, $C_2$-$C_6$-alkynyl cycloalkyl, and $C_2$-$C_6$-alkynyl heterocycloalkyl.

11. An alkynyl aryl carboxamide or its salt according to claim 10 having the formula (Ib)

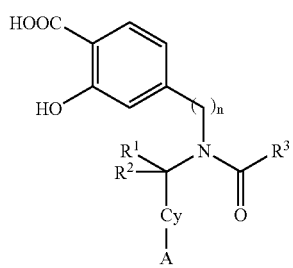

wherein
A is a $C_2$-$C_{15}$ alkynyl, or $C_2$-$C_6$-alkynyl;
Cy is an aryl;
n is 0 or 1;
$R^1$ and $R^2$ are independently from each other is selected from the group consisting of hydrogen and $C_1$-$C_6$-alkyl; and wherein
$R^3$ is selected from the group consisting of H, hydroxy, $C_1$-$C_6$-alkyl, $C_2$-$C_6$-alkenyl, $C_2$-$C_6$-alkynyl, $C_1$-$C_6$-alkoxy, $C_1$-$C_6$-alkyl amine, $C_1$-$C_6$-alkyl alkoxy, aryl, heteroaryl, saturated or unsaturated 3-8-membered cycloalkyl, 3-8-membered heterocycloalkyl, an acyl moiety, $C_1$-$C_6$-alkyl aryl, $C_1$-$C_6$-alkyl heteroaryl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, $C_1$-$C_6$-alkyl cycloalkyl, $C_1$-$C_6$-alkyl heterocycloalkyl, $C_2$-$C_6$-alkenyl cycloalkyl, $C_2$-$C_6$-alkenyl heterocycloalkyl, $C_2$-$C_6$-alkynyl cycloalkyl, and $C_2$-$C_6$-alkynyl heterocycloalkyl.

12. An alkynyl aryl carboxamide or its salt according to any of formulae (Id) or (Ie):

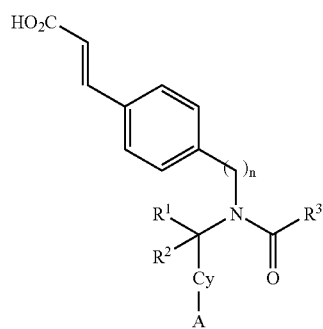

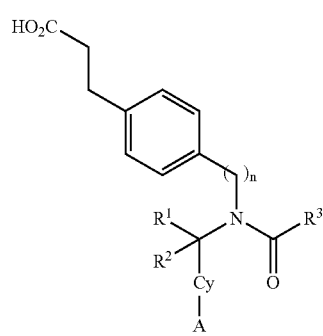

wherein
A is a $C_2$-$C_{15}$ alkynyl, or $C_2$-$C_6$-alkynyl aryl;
Cy is an aryl;
n is 0 or 1;
$R^1$ and $R^2$ are independently from each other is selected from the group consisting of hydrogen and $C_1$-$C_6$-alkyl;
$R^3$ is selected from the group consisting of $C_1$-$C_6$-alkyl, $C_2$-$C_6$-alkenyl, $C_2$-$C_6$-alkynyl, $C_1$-$C_6$-alkoxy, $C_1$-$C_6$-alkyl amine, $C_1$-$C_6$-alkyl alkoxy, aryl, heteroaryl, saturated 3-8-membered cycloalkyl, unsaturated 3-8 membered cycloalkyl, 3-8-membered heterocycloalkyl, an acyl moiety, $C_1$-$C_6$-alkyl aryl, $C_1$-$C_6$-alkyl heteroaryl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, $C_1$-$C_6$-alkyl cycloalkyl, $C_1$-$C_6$-alkyl heterocycloalkyl, $C_2$-$C_6$-alkenyl cycloalkyl, $C_2$-$C_6$-alkenyl heterocycloalkyl, $C_2$-$C_6$-alkynyl cycloalkyl, and $C_2$-$C_6$-alkynyl heterocycloalkyl.

13. The alkynyl aryl carboxamide or its salt of claim 10, wherein $R^1$ and $R^2$ are each H, Cy is a phenyl group, and A is a moiety of the formula —C≡C— $R^6$; wherein $R^6$ is $C_6$-$C_{12}$ alkyl, a 3-8 membered cycloalkyl, $C_1$-$C_6$ alkyl-(3-8 membered) cycloalkyl, $C_2$-$C_6$-alkenyl, $C_2$-$C_6$-alkynyl, phenyl, $C_1$-$C_{12}$ alkyl phenyl, $C_2$-$C_6$-alkenyl phenyl, or $C_2$-$C_6$-alkynyl phenyl.

14. The alkynyl aryl carboxamide or its salt claim 10, selected from the group consisting of:
  5-[(3-Cyclopentylpropanoyl)(4-dec-1-ynylbenzyl)amino]-2-hydroxybenzoic acid;
  5-[(3-Cyclopentylpropanoyl)(4-dec-1-ynylbenzyl)amino]-2-hydroxybenzoic acid, N-methyl-D-glucamine;
  5-[{4-[(4-Butylphenyl)ethynyl]benzyl}(3-cyclopentylpropanoyl)amino]-2-hydroxybenzoic acid;
  5-[(4-[(4-Butylphenyl)ethynyl]benzyl}(3-cyclopentylpropanoyl)amino]-2-hydroxybenzoic acid, N-methyl-D-glucamine;
  5-[Acetyl(4-dec-1-ynylbenzyl)amino]-2-hydroxybenzoic acid;
  5-[(4-Dec-1-ynylbenzyl)(pyridin-3-ylcarbonyl)amino]-2-hydroxybenzoic acid;
  5-[(4-Dec-1-ynylbenzyl)(isonicotinoyl)amino]-2-hydroxybenzoic acid;
  5-((4-Dec-1-ynylbenzyl)[(2E)-3-phenylprop-2-enoyl]amino)-2-hydroxybenzoic acid;
  5-[(4-Dec-1-ynylbenzyl)(thien-2-ylacetyl)amino]-2-hydroxybenzoic acid;
  5-((4-Dec-1-ynylbenzyl){(2E)-3-[3-(trifluoromethyl)phenyl]prop-2-enoyl}amino)-2-hydroxybenzoic acid;
  5-[(4-Dec-1-ynylbenzyl)(phenoxyacetyl)amino]-2-hydroxybenzoic acid;
  [4-({(4-Dec-1-ynylbenzyl)[(2E)-3-phenylprop-2-enoyl]amino}methyl)phenoxy]acetic acid;
  (4-{[(3-Cyclopentylpropanoyl)(4-dec-1-ynylbenzyl)amino]methyl}phenoxy)acetic acid;
  (4-{[(4-Dec-1-ynylbenzyl)(hexanoyl)amino]methyl}phenoxy)acetic acid;
  (4-{[Acetyl(4-dec-1-ynylbenzyl)amino]methyl}phenoxy)acetic acid;
  2-(Carboxymethoxy)-5-({(4-dec-1-ynylbenzyl) [(2E)-3-phenylprop-2-enoyl]amino}methyl)benzoic acid;
  2-(Carboxymethoxy)-5-{[(3-cyclopentylpropanoyl)(4-dec-1-ynylbenzyl)amino]methyl}benzoic acid;
  5-{[Acetyl(4-dec-1-ynylbenzyl)amino]methyl}-2-(carboxymethoxy)benzoic acid (2E)-3-(4-{[(4-Dec-1-ynylbenzyl)(3-phenylpropanoyl)amino]methyl)phenyl}acrylic acid;
  (2E)-3-(4-[(4-Dec-1-ynylbenzyl)(3-phenylpropanoyl)amino]phenyl}acrylic acid;
  (2E)-3-{4-[Acetyl(4-dec-1-ynylbenzyl)amino]phenyl}acrylic acid;
  3-(4-{[(3-Cyclopentylpropanoyl)(4-dec-ynylbenzyl)amino]methyl}phenyl)propanoic acid;
  5-[{4-[(4-Butylphenyl)ethynyl]benzyl})(cyclohexylcarbonyl)amino]-2-hydroxybenzoic acid;
  5-[{4-[(4-Butylphenyl)ethynyl]benzyl}(hexanoyl)amino]-2-hydroxybenzoic acid, N-methyl-D-glucamine;
  5-((4-tert-Butylbenzoyl){4-[(4-butylphenyl)ethynyl]benzyl}amino)-2-hydroxybenzoic acid, N-methyl-D-glucamine;
  5-((Biphenyl-4-ylcarbonyl){4-[(4-butylphenyl)ethynyl]benzyl}amino)-2-hydroxybenzoic acid;
  5-[{4-[(4-Butylphenyl)ethynyl]benzyl}(3,3-dimethylbutanoyl)amino]-2-hydroxybenzoic acid;
  5-[{4-[(4-Butylphenyl)ethynyl]benzyl}(2,3-dihydro-1-benzofuran-5-ylcarbonyl)amino]-2-hydroxybenzoic acid;
  5-[{4-[(4-Butylphenyl)ethynyl]benzyl}(7-carboxyheptanoyl)amino]-2-hydroxybenzoic acid;
  5-((1,3-Benzodioxol-5-ylcarbonyl) {4-[(4-butylphenyl)ethynyl]benzyl}amino)-2-hydroxybenzoic acid;
  5-[{4-[(4-Butylphenyl)ethynyl]benzyl}(2,2-dimethylpropanoyl)amino]-2-hydroxybenzoic acid;
  5-([(Benzyloxy)acetyl]{4-[(4-butylphenyl)ethynyl]benzyl}amino)-2-hydroxybenzoic acid;
  5-[{4-[(4-Butylphenyl)ethynyl]benzyl}(4-hexylbenzoyl)amino]-2-hydroxybenzoic acid;
  5-[{4-[(4-Butylphenyl)ethynyl]benzyl}(2-naphthoyl)amino]-2-hydroxybenzoic acid;
  5-((1-Benzothien-2-ylcarbonyl) {4-[(4-butylphenyl)ethynyl]benzyl}amino)-2-hydroxybenzoic acid, N-methyl-D-glucamine;
  4-[{4-[(4-Butylphenyl)ethynyl]benzyl}(3-cyclopentylpropanoyl)amino]-2-hydroxybenzoic acid, N-methyl-D-glucamine;
  5-{[{4-[(4-Butylphenyl)ethynyl]benzyl}(3-cyclopentylpropanoyl)amino]methyl}-2-hydroxybenzoic acid, N-methyl-D-glucamine;
  5-{[{4-[(4-Butylphenyl)ethynyl]benzyl}(hexanoyl)amino]methyl}-2-hydroxybenzoic acid;
  (4-{[{4-[(4-Butylphenyl)ethynyl]benzyl}(hexanoyl)amino]methyl}phenoxy)acetic acid, N-methyl-D-glucamine;
  (4-{[{4-[(4-Butylphenyl)ethynyl]benzyl}(cyanoacetyl)amino]methyl}phenoxy)acetic acid;
  (4-{[{4-[(4-Butylphenyl)ethynyl]benzyl}(1H-indazol-3-ylcarbonyl)amino]methyl}-phenoxy)acetic acid;
  (4-{[{4-[(4-Butylphenyl)ethynyl]benzyl}(pent-4-ynoyl)amino]methyl}phenoxy)-acetic acid;
  [4-({4-[(4-Butylphenyl)ethynyl]benzyl}[(6-hydroxypyridin-3-yl)carbonyl]amino)-methyl-phenoxy]acetic acid;
  [4-({{4-[(4-Butylphenyl)ethynyl]benzyl}[(2-methoxyethoxy)acetyl]amino}methyl)-phenoxy]acetic acid;
  (4-{[{4-[(4-Butylphenyl)ethynyl]benzyl}(1H-pyrazol-4-ylcarbonyl)amino]-methyl)phenoxy)acetic acid 3-[(3-Cyclopentylpropanoyl)(4-dec-1-yn-1-ylbenzyl)amino]benzoic acid, N-methyl-D-glucamine;
  3-[(4-Dec-1-yn-1-ylbenzyl)(hexanoyl)amino]benzoic acid;
  4-{[{4-[(4-Butylphenyl)ethynyl]benzyl}(3-cyclopentylpropanoyl)amino]methyl}-benzoic acid;
  4-[{4-[(4-Butylphenyl)ethynyl]benzyl)(hexanoyl)amino]methyl}benzoic acid;

4-[((4-tert-Butylbenzoyl){4-[(4-butylphenyl)ethynyl]benzyl}amino)methyl]benzoic acid;
4-[{4-[(4-Butylphenyl)ethynyl]benzyl}(hexanoyl)amino]benzoic acid;
4-[{4-[(4-Butylphenyl)ethynyl]benzyl}(3-cyclopentylpropanoyl)amino]benzoic acid;
8-[{4-[(4-Butylphenyl)ethynyl]benzyl}(3-cyclopentylpropanoyl)amino]-5,6,7,8-tetrahydronaphthalene-2-carboxylic acid, N-methyl-D-glucamine;
5-[{4-[(4-Chlorophenyl)ethynyl]benzyl}(3-cyclopentylpropanoyl)amino]-2-hydroxybenzoic acid, N-methyl-D-glucamine;
5-[f4-[(4-Chlorophenyl)ethynyl]benzyl}(4-heptylbenzoyl)amino]-2-hydroxybenzoic acid;
5-[{4-[(4-Chlorophenyl)ethynyl]benzyl}(isoxazol-5-ylcarbonyl)amino]-2-hydroxy-benzoic acid;
5-[{4-[(4-Chlorophenyl)ethynyl]benzyl}(2-thienylacetyl)amino]-2-hydroxybenzoic acid;
5-[{4-[(4-Chlorophenyl)ethynyl]benzyl}(3-phenylpropanoyl)amino]-2-hydroxy-benzoic acid, N-methyl-D-glucamine;
5-[{4-[(4-Chlorophenyl)ethynyl]benzyl}(4-methoxybenzoyl)amino]-2-hydroxy-benzoic acid, N-methyl-D-glucamine;
5-[{4-[(4-Chlorophenyl)ethynyl]benzyl}(3-fluorobenzoyl)amino]-2-hydroxybenzoic acid, N-methyl-D-glucamine;
5-[{4-[(4-Chlorophenyl)ethynyl]benzyl}(cyclohexylcarbonyl)amino]-2-hydroxybenzoic acid, N-methyl-D-glucamine;
5-(acetyl {4-[(4-Chlorophenyl)ethynyl]benzyl}amino)-2-hydroxybenzoic acid, N-methyl-D-glucamine;
5-[{4-[(4-Butylphenyl)ethynyl]-2-fluorobenzyl)(3-cyclopentylpropanoyl)amino]-2-hydroxybenzoic acid, N-methyl-D-glucamine;
8-((3-Cyclopentylpropanoyl) {4-[(4-fluorophenyl)ethynyl]benzyl}amino)-5,6,7,8-tetrahydronaphthalene-2-carboxylic acid, N-methyl-D-glucamine;
5-[f4-[(4-Butylphenyl)ethynyl]benzyl}(3-cyclopentylpropanoyl)amino]-2-fluorobenzoic acid, N-methyl-D-glucamine;
5-[{4-[(4-Butylphenyl)ethynyl]benzyl)(3,3-dimethylbutanoyl)amino]-2-fluorobenzoic acid, N-methyl-D-glucamine;
5-[{4-[(4-Butylphenyl)ethynyl]benzyl)(2-thienylacetyl)amino]-2-fluorobenzoic acid, N-methyl-D-glucamine;
4-[{4-[(4-Butylphenyl)ethynyl]benzyl)(3,3-dimethylbutanoyl)amino]-2-hydroxybenzoic acid, N-methyl-D-glucamine;
3-[{4-[(4-Butylphenyl)ethynyl]benzyl)(3-cyclopentylpropanoyl)amino]-4-fluorobenzoic acid;
4-[{4-[(4-Chlorophenyl)ethynyl]benzyl}(3-cyclopentylpropanoyl)amino]-2-hydroxybenzoic acid, N-methyl-D-glucamine;
4-(Acetyl{4-[(4-butylphenyl)ethynyl]benzyl}amino)-2-hydroxybenzoic acid, N-methyl-D-glucamine;
4-[{4-[(4-Butylphenyl)ethynyl]benzyl)(cyclohexylcarbonyl)amino]-2-hydroxybenzoic acid, N-methyl-D-glucamine;
4-[{4-[(4-Butylphenyl)ethynyl]benzyl)(hexanoyl)amino]-2-hydroxybenzoic acid, N-methyl-D-glucamine;
4-[{4-[(4-Butylphenyl)ethynyl]benzyl)(3-cyclopentylpropanoyl)amino]-2-fluorobenzoic acid, N-methyl-D-glucamine;
4-[{4-[(4-Butylphenyl)ethynyl]benzyl)(2,2-dimethylpropanoyl)amino]-2-hydroxybenzoic acid, N-methyl-D-glucamine;
4-((3-Cyclopentylpropanoyl)(4-[(4-methoxyphenyl)ethynyl]benzyl}amino)-2-hydroxybenzoic acid, N-methyl-D-glucamine;
4-[{4-[(4-tert-Butylphenyl)ethynyl]benzyl}(3-cyclopentylpropanoyl)amino]-2-hydroxybenzoic acid, N-methyl-D-glucamine;
4-((3-Cyclopentylpropanoyl) {4-[(4-propoxyphenyl)ethynyl]benzyl}amino)-2-hydroxybenzoic acid, N-methyl-D-glucamine
4-((3-Cyclopentylpropanoyl) {4-[(4-propylphenyl)ethynyl]benzyl}amino)-2-hydroxybenzoic acid, N-methyl-D-glucamine, and
4-{(3-Cyclopentylpropanoyl)[4-(5-phenylpent-1-yn-1-yl)benzyl]amino)-2-hydroxybenzoic acid, N-methyl-D-glucamine.

15. A composition comprising at least one alkynyl aryl carboxamide of claim 10 or its salt and a pharmaceutically acceptable carrier, diluent, excipient, or combination thereof.

16. A pharmaceutical composition comprising at least one alkynyl aryl carboxamide of claim 11 or its salt and a pharmaceutically acceptable carrier, diluent excipient, or combination thereof.

17. The pharmaceutical composition of claim 16, further comprising at least one supplementary drug selected from the group consisting of insulin, aldose reductase inhibitors, alpha-glucosidase inhibitors, sulfonyl urea agents, biguanides thiazolidindiones, PPARs agonists, c-Jun Kinase and GSK-3 inhibitors.

18. The pharmaceutical composition of claim 17 wherein the at least one supplementary drug is selected from the group consisting of a rapid acting insulin, an intermediate acting insulin, a long acting insulin, a combination of intermediate and rapid acting insulins, Minalrestat, Tolrestat, Sorbinil, Methosorbinil, Zopolrestat, Epalrestat, Zenarestat, Imirestat, Ponalrestat, ONO-2235, GP-1447, CT-112, BAL-ARI 8, AD-5467, ZD5522, M-16209, NZ-314, M-79175, SPR-210, ADN 138, SNK-860, Miglitol, Acarbose, Glipizide, Glyburide, Chlorpropamide, Tolbutamide, Tolazamide, and Glimepriride.

19. A method of preparing the alkynyl aryl carboxamide of claim 10, comprising deprotecting, transforming, or deprotecting and transforming the compound of formula (Z) to form the alkynyl aryl carboxamide of formula (I)

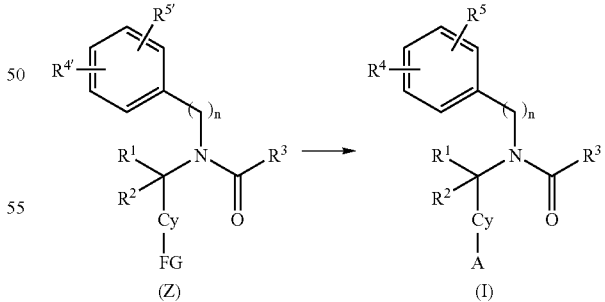

wherein FG is A or a leaving group.

20. The method of claim 2, wherein $R^1$ and $R^2$ are each H.
21. The method of claim 3, wherein $R^1$ and $R^2$ are each H.
22. The method of claim 2, wherein Cy is a phenyl group.
23. The method of claim 3, wherein Cy is a phenyl group.
24. The method of claim 2, wherein A is a moiety of the formula —C≡C—$R^6$, and wherein $R^6$ is $C_6$-$C_2$ alkyl, a 3-8 membered cycloalkyl, $C_1$-$C_6$ alkyl-(3-8 membered) cycloalkyl, $C_2$-$C_6$-alkenyl, $C_2$-$C_6$-alkynyl, phenyl, $C_1$-$C_{12}$ alkyl phenyl, $C_2$-$C_6$-alkenyl phenyl, or a $C_2$-$C_6$-alkynyl phenyl.

25. The method of claim 3, wherein A is a moiety of the formula —C≡C—$R^6$, and wherein $R^6$ is $C_6$-$C_{12}$ alkyl, a 3-8 membered cycloalkyl, $C_1$-$C_6$ alkyl-(3-8 membered) cycloalkyl, $C_2$-$C_6$-alkenyl, $C_2$-$C_6$-alkynyl, phenyl, $C_1$-$C_{12}$ alkyl phenyl, $C_2$-$C_6$-alkenyl phenyl, or a $C_2$-$C_6$-alkynyl phenyl.

* * * * *